United States Patent
Brucher et al.

(10) Patent No.: US 11,066,659 B2
(45) Date of Patent: Jul. 20, 2021

(54) GLUCOSE ISOMERASE

(71) Applicants: C-LEcta GmbH, Leipzig (DE); New Matterhorn, LLC, Wilmington, DE (US)

(72) Inventors: Birgit Brucher, Leipzig (DE); Andreas Vogel, Leipzig (DE); Hanna Maria Dudek, Leipzig (DE); Rico Czaja, Leipzig (DE)

(73) Assignees: NEW MATTERHORN, LLC, Wilmington, DE (US); C-LEcta GmbH, Leipzig (DE)

( * ) Notice: Subject to any disclaimer, the term of this patent is extended or adjusted under 35 U.S.C. 154(b) by 53 days.

(21) Appl. No.: 16/610,373

(22) PCT Filed: May 4, 2018

(86) PCT No.: PCT/EP2018/061573
§ 371 (c)(1),
(2) Date: Nov. 1, 2019

(87) PCT Pub. No.: WO2018/202880
PCT Pub. Date: Nov. 8, 2018

(65) Prior Publication Data
US 2020/0224187 A1 Jul. 16, 2020

(30) Foreign Application Priority Data
May 5, 2017 (EP) ..................... 17000785

(51) Int. Cl.
*C12N 9/92* (2006.01)
*C12P 19/02* (2006.01)
*C12P 19/24* (2006.01)

(52) U.S. Cl.
CPC ............... *C12N 9/92* (2013.01); *C12P 19/02* (2013.01); *C12P 19/24* (2013.01)

(58) Field of Classification Search
None
See application file for complete search history.

(56) References Cited
U.S. PATENT DOCUMENTS

| 5,310,665 | A | 5/1994 | Lambeir et al. |
| 5,340,738 | A | 8/1994 | Lambeir et al. |
| 5,376,536 | A | 12/1994 | Quax et al. |
| 5,384,257 | A | 1/1995 | Lambeir et al. |
| 7,704,719 | B2 | 4/2010 | Wang et al. |
| 2011/0318801 | A1 | 12/2011 | Kahsay et al. |

OTHER PUBLICATIONS

Borgi, et al., Involvement of Alanine 103 Residue in Kinetic and Physicochemical Properties of Glucose Isomerases From Streptomyces Species, Biotechnology Journal, 2007, 2:2:254-259.
Borgi, et al., Involvement of Cysteine 306 and Alanine 63 in the Thermostability and Oligomeric Organization of Glucose Isomerase From *Streptomyces* sp. SK, Biologia, 2009, 64:5: 845-851.
Ben Hilma, et al, Identification of Critical Residues for the Activity and Thermostability of Streptomycessp. SK glucose isomerase, Applied Microbiology and Biotechnology, Springer, DE, 2013, 97:22:9715-9726.
Ben Hilma, et al., Engineered Glucose Isomerase Fromsp. SK is Resistant to Cainhibition and Coindependent, Journal of Industrial Microbiology Biotechnology Official Journal of & The Society for Industrial Microbiology, 2012, 39:4:537-546.
Ben Hilma, et al., Probing the Role of Helix [alpha]1 in the Acid-Tolerance and Thermal Stability of the Streptomycessp. SK Glucose Isomerase by Site-Directed Mutagen, Journal of Biotechnology, 2014, 173:15:1-6.
International Search Report issued in PCT/EP2018/061573, dated Sep. 12, 2018.
Bhosale, Microbiol Reviews, 1996, 60, 280-300.
Smith et al., D-Xylose (D-glucose) Isomerase from Arthrobacter Strain N.R.R.L. B3728, Biochem J, 1991, 277, 255-261.

*Primary Examiner* — Suzanne M Noakes
*Assistant Examiner* — Jae W Lee
(74) *Attorney, Agent, or Firm* — Blank Rome LLP

(57) ABSTRACT

The present invention relates to polypeptide, preferably to a glucose isomerase, comprising an amino acid sequence, wherein the amino acid sequence of the polypeptide, preferably the glucose isomerase, is at least 95% identical to an amino acid sequence of SEQ ID NO:1, wherein the amino acid sequence of the polypeptide, preferably the glucose isomerase, comprises an amino acid substitution at one or more amino acid positions, wherein the one or more amino acid positions is/are each and independently selected from the group consisting of SEQ ID NO: 1 amino acid positions 89, 90, 95, 0, 33, 34, 35, and 59. The present invention further relates to methods preparing glucose including the use of the polypeptides of the invention for preparing glucose.

32 Claims, No Drawings
Specification includes a Sequence Listing.

SEQUENCE LISTING

<160> NUMBER OF SEQ ID NOS: 23

<210> SEQ ID NO 1
<211> LENGTH: 388
<212> TYPE: PRT
<213> ORGANISM: Streptomyces sp. SK

<400> SEQUENCE: 1

Met Asn Tyr Gln Pro Thr Pro Glu Asp Arg Phe Thr Phe Gly Leu Trp
1               5                   10                  15

Thr Val Gly Trp Gln Gly Arg Asp Pro Phe Gly Asp Ala Thr Arg Pro
            20                  25                  30

Ala Leu Asp Pro Val Glu Ala Val Gln Arg Leu Ala Glu Leu Gly Ala
        35                  40                  45

Tyr Gly Val Thr Phe His Asp Asp Leu Ile Pro Phe Gly Ala Ser
    50                  55                  60

Asp Thr Glu Arg Glu Ala His Val Lys Arg Phe Arg Gln Ala Leu Asp
65                  70                  75                  80

Ala Thr Gly Met Thr Val Pro Met Ala Thr Thr Asn Leu Phe Thr His
                85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Lys Val Tyr Val Ala Trp Gly Gly Arg Glu Gly Ala Glu
    130                 135                 140

Ser Gly Ala Ala Lys Asp Val Arg Ala Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Ile Gly His Ala Leu Ala Phe Ile Glu Arg Leu Glu Arg
        195                 200                 205

Pro Glu Leu Tyr Gly Val Asn Pro Glu Val Gly His Glu Gln Met Ala
    210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

```
Asp Leu Arg Phe Gly Ala Gly Asp Leu Arg Ala Ala Phe Trp Leu Val
            260                 265                 270

Asp Leu Leu Glu Ser Ala Gly Trp Glu Gly Pro Arg His Phe Asp Phe
        275                 280                 285

Lys Pro Pro Arg Thr Glu Asp Ile Asp Gly Val Trp Ala Ser Ala Ala
    290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ala Arg Leu Asp
                325                 330                 335

Gln Leu Ala Glu Pro Thr Ala Ala Asp Gly Leu Gln Ala Leu Leu Ala
            340                 345                 350

Asp Arg Thr Ala Tyr Glu Asp Phe Asp Val Asp Ala Ala Ala Ala Arg
        355                 360                 365

Gly Met Ala Phe Glu Arg Leu Asp Gln Leu Ala Met Asp His Leu Leu
    370                 375                 380

Gly Ala Arg Gly
385

<210> SEQ ID NO 2
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Asn Tyr Gln Pro Thr Pro Glu Asp Arg Phe Thr Phe Gly Leu Trp
1               5                   10                  15

Thr Val Gly Trp Gln Gly Arg Asp Pro Phe Gly Asp Ala Thr Arg Pro
            20                  25                  30

Ile Leu Asp Pro Val Glu Ala Val Gln Arg Leu Ala Glu Leu Gly Ala
        35                  40                  45

Tyr Gly Val Thr Phe His Asp Asp Leu Ile Pro Phe Gly Ala Ser
    50                  55                  60

Asp Thr Glu Arg Glu Ala His Val Lys Arg Phe Arg Gln Ala Leu Asp
65                  70                  75                  80

Ala Thr Gly Met Thr Val Pro Met Ala Thr Thr Asn Leu Phe Thr His
                85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Lys Val Tyr Val Ala Trp Gly Gly Arg Glu Gly Ala Glu
    130                 135                 140

Ser Gly Ala Ala Lys Asp Val Arg Ala Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Ile Gly His Ala Leu Ala Phe Ile Glu Arg Leu Glu Arg
        195                 200                 205

Pro Glu Leu Tyr Gly Val Asn Pro Glu Val Gly His Glu Gln Met Ala
    210                 215                 220
```

```
Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
            245                 250                 255

Asp Leu Arg Phe Gly Ala Gly Asp Leu Arg Ala Ala Phe Trp Leu Val
        260                 265                 270

Asp Leu Leu Glu Ser Ala Gly Trp Glu Gly Pro Arg His Phe Asp Phe
    275                 280                 285

Lys Pro Pro Arg Thr Glu Asp Ile Asp Gly Val Trp Ala Ser Ala Ala
290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ala Arg Leu Asp
            325                 330                 335

Gln Leu Ala Glu Pro Thr Ala Ala Asp Gly Leu Gln Ala Leu Leu Ala
        340                 345                 350

Asp Arg Thr Ala Tyr Glu Asp Phe Asp Val Asp Ala Ala Ala Ala Arg
    355                 360                 365

Gly Met Ala Phe Glu Arg Leu Asp Gln Leu Ala Met Asp His Leu Leu
370                 375                 380

Gly Ala Arg Gly
385

<210> SEQ ID NO 3
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Asn Tyr Gln Pro Thr Pro Glu Asp Arg Phe Thr Phe Gly Leu Trp
1               5                   10                  15

Thr Val Gly Trp Gln Gly Arg Asp Pro Phe Gly Asp Ala Thr Arg Pro
            20                  25                  30

Asn Leu Asp Pro Val Glu Ala Val Gln Arg Leu Ala Glu Leu Gly Ala
        35                  40                  45

Tyr Gly Val Thr Phe His Asp Asp Leu Ile Pro Phe Gly Ala Ser
    50                  55                  60

Asp Thr Glu Arg Glu Ala His Val Lys Arg Phe Arg Gln Ala Leu Asp
65                  70                  75                  80

Ala Thr Gly Met Thr Val Pro Met Ala Thr Thr Asn Leu Phe Thr His
                85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Lys Val Tyr Val Ala Trp Gly Gly Arg Glu Gly Ala Glu
    130                 135                 140

Ser Gly Ala Ala Lys Asp Val Arg Ala Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
```

```
            180                 185                 190
Leu Pro Thr Ile Gly His Ala Leu Ala Phe Ile Glu Arg Leu Glu Arg
            195                 200                 205

Pro Glu Leu Tyr Gly Val Asn Pro Glu Val Gly His Glu Gln Met Ala
        210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Glu Ser Ala Gly Trp Glu Gly Pro Arg His Phe Asp Phe
        275                 280                 285

Lys Pro Pro Arg Thr Glu Asp Ile Asp Gly Val Trp Ala Ser Ala Ala
            290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ala Arg Leu Asp
                325                 330                 335

Gln Leu Ala Glu Pro Thr Ala Ala Asp Gly Leu Gln Ala Leu Leu Ala
            340                 345                 350

Asp Arg Thr Ala Tyr Glu Asp Phe Asp Val Asp Ala Ala Ala Ala Arg
                355                 360                 365

Gly Met Ala Phe Glu Arg Leu Asp Gln Leu Ala Met Asp His Leu Leu
        370                 375                 380

Gly Ala Arg Gly
385

<210> SEQ ID NO 4
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Asn Tyr Gln Pro Thr Pro Glu Asp Arg Phe Thr Phe Gly Leu Trp
1               5                   10                  15

Thr Val Gly Trp Gln Gly Arg Asp Pro Phe Gly Asp Ala Thr Arg Pro
            20                  25                  30

Ala Phe Asp Pro Val Glu Ala Val Gln Arg Leu Ala Glu Leu Gly Ala
        35                  40                  45

Tyr Gly Val Thr Phe His Asp Asp Asp Leu Ile Pro Phe Gly Ala Ser
    50                  55                  60

Asp Thr Glu Arg Glu Ala His Val Lys Arg Phe Arg Gln Ala Leu Asp
65                  70                  75                  80

Ala Thr Gly Met Thr Val Pro Met Ala Thr Thr Asn Leu Phe Thr His
                85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Lys Val Tyr Val Ala Trp Gly Gly Arg Glu Gly Ala Glu
    130                 135                 140
```

Ser Gly Ala Ala Lys Asp Val Arg Ala Ala Leu Asp Arg Met Lys Glu
145                 150                 155                 160

Ala Phe Asp Leu Leu Gly Glu Tyr Val Thr Ser Gln Gly Tyr Asp Ile
            165                 170                 175

Arg Phe Ala Ile Glu Pro Lys Pro Asn Glu Pro Arg Gly Asp Ile Leu
        180                 185                 190

Leu Pro Thr Ile Gly His Ala Leu Ala Phe Ile Glu Arg Leu Glu Arg
    195                 200                 205

Pro Glu Leu Tyr Gly Val Asn Pro Glu Val Gly His Glu Gln Met Ala
210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
            245                 250                 255

Asp Leu Arg Phe Gly Ala Gly Asp Leu Arg Ala Ala Phe Trp Leu Val
        260                 265                 270

Asp Leu Leu Glu Ser Ala Gly Trp Glu Gly Pro Arg His Phe Asp Phe
    275                 280                 285

Lys Pro Pro Arg Thr Glu Asp Ile Asp Gly Val Trp Ala Ser Ala Ala
290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ala Arg Leu Asp
            325                 330                 335

Gln Leu Ala Glu Pro Thr Ala Ala Asp Gly Leu Gln Ala Leu Leu Ala
        340                 345                 350

Asp Arg Thr Ala Tyr Glu Asp Phe Asp Val Asp Ala Ala Ala Ala Arg
    355                 360                 365

Gly Met Ala Phe Glu Arg Leu Asp Gln Leu Ala Met Asp His Leu Leu
370                 375                 380

Gly Ala Arg Gly
385

<210> SEQ ID NO 5
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Asn Tyr Gln Pro Thr Pro Glu Asp Arg Phe Thr Phe Gly Leu Trp
1               5                   10                  15

Thr Val Gly Trp Gln Gly Arg Asp Pro Phe Gly Asp Ala Thr Arg Pro
            20                  25                  30

Ala Leu Cys Pro Val Glu Ala Val Gln Arg Leu Ala Glu Leu Gly Ala
        35                  40                  45

Tyr Gly Val Thr Phe His Asp Asp Leu Ile Pro Phe Gly Ala Ser
    50                  55                  60

Asp Thr Glu Arg Glu Ala His Val Lys Arg Phe Arg Gln Ala Leu Asp
65                  70                  75                  80

Ala Thr Gly Met Thr Val Pro Met Ala Thr Thr Asn Leu Phe Thr His
            85                  90                  95

Pro Val Phe Lys Asp Gly Ala Phe Thr Ala Asn Asp Arg Asp Val Arg
        100                 105                 110

-continued

```
Arg Tyr Ala Leu Arg Lys Thr Ile Arg Asn Ile Asp Leu Ala Val Glu
            115                 120                 125

Leu Gly Ala Lys Val Tyr Val Ala Trp Gly Gly Arg Glu Gly Ala Glu
        130                 135                 140

Ser Gly Ala Ala Lys Asp Val Arg Ala Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Ile Gly His Ala Leu Ala Phe Ile Glu Arg Leu Glu Arg
        195                 200                 205

Pro Glu Leu Tyr Gly Val Asn Pro Glu Val Gly His Glu Gln Met Ala
    210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Ser Ala Gly Trp Glu Gly Pro Arg His Phe Asp Phe
        275                 280                 285

Lys Pro Pro Arg Thr Glu Asp Ile Asp Gly Val Trp Ala Ser Ala Ala
    290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ala Arg Leu Asp
                325                 330                 335

Gln Leu Ala Glu Pro Thr Ala Ala Asp Gly Leu Gln Ala Leu Leu Ala
            340                 345                 350

Asp Arg Thr Ala Tyr Glu Asp Phe Asp Val Asp Ala Ala Ala Ala Arg
        355                 360                 365

Gly Met Ala Phe Glu Arg Leu Asp Gln Leu Ala Met Asp His Leu Leu
    370                 375                 380

Gly Ala Arg Gly
385
```

<210> SEQ ID NO 6
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Asn Tyr Gln Pro Thr Pro Glu Asp Arg Phe Thr Phe Gly Leu Trp
1               5                   10                  15

Thr Val Gly Trp Gln Gly Arg Asp Pro Phe Gly Asp Ala Thr Arg Pro
            20                  25                  30

Ala Leu Asp Pro Val Glu Ala Val Gln Arg Leu Ala Glu Leu Gly Ala
        35                  40                  45

Tyr Gly Val Thr Leu His Asp Asp Asp Leu Ile Pro Phe Gly Ala Ser
    50                  55                  60

Asp Thr Glu Arg Glu Ala His Val Lys Arg Phe Arg Gln Ala Leu Asp
```

```
            65                  70                  75                  80
Ala Thr Gly Met Thr Val Pro Met Ala Thr Thr Asn Leu Phe Thr His
                85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Lys Val Tyr Val Ala Trp Gly Gly Arg Glu Gly Ala Glu
130                 135                 140

Ser Gly Ala Ala Lys Asp Val Arg Ala Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Ile Gly His Ala Leu Ala Phe Ile Glu Arg Leu Glu Arg
        195                 200                 205

Pro Glu Leu Tyr Gly Val Asn Pro Glu Val Gly His Glu Gln Met Ala
210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Ser Ala Gly Trp Glu Gly Pro Arg His Phe Asp Phe
        275                 280                 285

Lys Pro Pro Arg Thr Glu Asp Ile Asp Gly Val Trp Ala Ser Ala Ala
290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ala Arg Leu Asp
                325                 330                 335

Gln Leu Ala Glu Pro Thr Ala Ala Asp Gly Leu Gln Ala Leu Leu Ala
            340                 345                 350

Asp Arg Thr Ala Tyr Glu Asp Phe Asp Val Ala Ala Ala Ala Ala Arg
        355                 360                 365

Gly Met Ala Phe Glu Arg Leu Asp Gln Leu Ala Met Asp His Leu Leu
370                 375                 380

Gly Ala Arg Gly
385

<210> SEQ ID NO 7
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Asn Tyr Gln Pro Thr Pro Glu Asp Arg Phe Thr Phe Gly Leu Trp
1               5                   10                  15

Thr Val Gly Trp Gln Gly Arg Asp Pro Phe Gly Asp Ala Thr Arg Pro
            20                  25                  30
```

```
Ala Leu Asp Pro Val Glu Ala Val Gln Arg Leu Ala Glu Leu Gly Ala
         35                  40                  45

Tyr Gly Val Thr Phe His Asp Asp Leu Ile Pro Phe Gly Ala Ser
 50                  55                  60

Asp Thr Glu Arg Glu Ala His Val Lys Arg Phe Arg Gln Ala Leu Asp
 65                  70                  75                  80

Ala Thr Gly Met Thr Val Pro Met Val Thr Thr Asn Leu Phe Thr His
                 85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Lys Val Tyr Val Ala Trp Gly Gly Arg Glu Gly Ala Glu
130                 135                 140

Ser Gly Ala Ala Lys Asp Val Arg Ala Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Ile Gly His Ala Leu Ala Phe Ile Glu Arg Leu Glu Arg
        195                 200                 205

Pro Glu Leu Tyr Gly Val Asn Pro Glu Val Gly His Glu Gln Met Ala
    210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Ser Ala Gly Trp Glu Gly Pro Arg His Phe Asp Phe
        275                 280                 285

Lys Pro Pro Arg Thr Glu Asp Ile Asp Gly Val Trp Ala Ser Ala Ala
    290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ala Arg Leu Asp
                325                 330                 335

Gln Leu Ala Glu Pro Thr Ala Ala Asp Gly Leu Gln Ala Leu Leu Ala
            340                 345                 350

Asp Arg Thr Ala Tyr Glu Asp Phe Asp Val Asp Ala Ala Ala Ala Arg
        355                 360                 365

Gly Met Ala Phe Glu Arg Leu Asp Gln Leu Ala Met Asp His Leu Leu
    370                 375                 380

Gly Ala Arg Gly
385

<210> SEQ ID NO 8
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8
```

Met Asn Tyr Gln Pro Thr Pro Glu Asp Arg Phe Thr Phe Gly Leu Trp
1               5                   10                  15

Thr Val Gly Trp Gln Gly Arg Asp Pro Phe Gly Asp Ala Thr Arg Pro
            20                  25                  30

Ala Leu Asp Pro Val Glu Ala Val Gln Arg Leu Ala Glu Leu Gly Ala
        35                  40                  45

Tyr Gly Val Thr Phe His Asp Asp Leu Ile Pro Phe Gly Ala Ser
    50                  55                  60

Asp Thr Glu Arg Glu Ala His Val Lys Arg Phe Arg Gln Ala Leu Asp
65                  70                  75                  80

Ala Thr Gly Met Thr Val Pro Met Ala Ser Thr Asn Leu Phe Thr His
                85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Lys Val Tyr Val Ala Trp Gly Gly Arg Glu Gly Ala Glu
    130                 135                 140

Ser Gly Ala Ala Lys Asp Val Arg Ala Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Ile Gly His Ala Leu Ala Phe Ile Glu Arg Leu Glu Arg
        195                 200                 205

Pro Glu Leu Tyr Gly Val Asn Pro Glu Val Gly His Glu Gln Met Ala
210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Ser Ala Gly Trp Glu Gly Pro Arg His Phe Asp Phe
        275                 280                 285

Lys Pro Pro Arg Thr Glu Asp Ile Asp Gly Val Trp Ala Ser Ala Ala
    290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ala Arg Leu Asp
                325                 330                 335

Gln Leu Ala Glu Pro Thr Ala Ala Asp Gly Leu Gln Ala Leu Leu Ala
            340                 345                 350

Asp Arg Thr Ala Tyr Glu Asp Phe Asp Val Asp Ala Ala Ala Ala Arg
        355                 360                 365

Gly Met Ala Phe Glu Arg Leu Asp Gln Leu Ala Met Asp His Leu Leu
    370                 375                 380

Gly Ala Arg Gly
385

<210> SEQ ID NO 9
<211> LENGTH: 388

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

Met Asn Tyr Gln Pro Thr Pro Glu Asp Arg Phe Thr Phe Gly Leu Trp
1               5                   10                  15

Thr Val Gly Trp Gln Gly Arg Asp Pro Phe Gly Asp Ala Thr Arg Pro
            20                  25                  30

Ala Leu Asp Pro Val Glu Ala Val Gln Arg Leu Ala Glu Leu Gly Ala
        35                  40                  45

Tyr Gly Val Thr Phe His Asp Asp Leu Ile Pro Phe Gly Ala Ser
    50                  55                  60

Asp Thr Glu Arg Glu Ala His Val Lys Arg Phe Arg Gln Ala Leu Asp
65                  70                  75                  80

Ala Thr Gly Met Thr Val Pro Met Ala Thr Thr Asn Leu Phe Arg His
                85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Lys Val Tyr Val Ala Trp Gly Gly Arg Glu Gly Ala Glu
130                 135                 140

Ser Gly Ala Ala Lys Asp Val Arg Ala Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Ile Gly His Ala Leu Ala Phe Ile Glu Arg Leu Glu Arg
        195                 200                 205

Pro Glu Leu Tyr Gly Val Asn Pro Glu Val Gly His Glu Gln Met Ala
210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Ser Ala Gly Trp Glu Gly Pro Arg His Phe Asp Phe
        275                 280                 285

Lys Pro Pro Arg Thr Glu Asp Ile Asp Gly Val Trp Ala Ser Ala Ala
290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ala Arg Leu Asp
                325                 330                 335

Gln Leu Ala Glu Pro Thr Ala Ala Asp Gly Leu Gln Ala Leu Leu Ala
            340                 345                 350

Asp Arg Thr Ala Tyr Glu Asp Phe Asp Val Asp Ala Ala Ala Ala Arg
        355                 360                 365

Gly Met Ala Phe Glu Arg Leu Asp Gln Leu Ala Met Asp His Leu Leu
370                 375                 380

Gly Ala Arg Gly
385

<210> SEQ ID NO 10
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Asn Tyr Gln Pro Thr Pro Glu Asp Arg Phe Thr Phe Gly Leu Trp
1               5                   10                  15

Thr Val Gly Trp Gln Gly Arg Asp Pro Phe Gly Asp Ala Thr Arg Pro
            20                  25                  30

Ala Leu Asp Pro Val Glu Ala Val Gln Arg Leu Ala Glu Leu Gly Ala
        35                  40                  45

Tyr Gly Val Thr Phe His Asp Asp Leu Ile Pro Phe Gly Ala Ser
    50                  55                  60

Asp Thr Glu Arg Glu Ala His Val Lys Arg Phe Arg Gln Ala Leu Asp
65                  70                  75                  80

Ala Thr Gly Met Thr Val Pro Met Ala Thr Thr Asn Leu Phe Tyr His
                85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Lys Val Tyr Val Ala Trp Gly Gly Arg Glu Gly Ala Glu
    130                 135                 140

Ser Gly Ala Ala Lys Asp Val Arg Ala Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Ile Gly His Ala Leu Ala Phe Ile Glu Arg Leu Glu Arg
        195                 200                 205

Pro Glu Leu Tyr Gly Val Asn Pro Glu Val Gly His Glu Gln Met Ala
    210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Ser Ala Gly Trp Glu Gly Pro Arg His Phe Asp Phe
        275                 280                 285

Lys Pro Pro Arg Thr Glu Asp Ile Asp Gly Val Trp Ala Ser Ala Ala
    290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ala Arg Leu Asp
                325                 330                 335

Gln Leu Ala Glu Pro Thr Ala Ala Asp Gly Leu Gln Ala Leu Leu Ala

```
                    340                 345                 350
Asp Arg Thr Ala Tyr Glu Asp Phe Asp Val Asp Ala Ala Ala Arg
            355                 360                 365

Gly Met Ala Phe Glu Arg Leu Asp Gln Leu Ala Met Asp His Leu Leu
        370                 375                 380

Gly Ala Arg Gly
385

<210> SEQ ID NO 11
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Asn Tyr Gln Pro Thr Pro Glu Asp Lys Phe Thr Phe Gly Leu Trp
1               5                   10                  15

Thr Val Gly Trp Gln Gly Arg Asp Pro Phe Gly Asp Ala Thr Arg Pro
            20                  25                  30

Ala Leu Asp Pro Val Glu Ala Val Gln Arg Leu Ala Glu Leu Gly Ala
        35                  40                  45

Tyr Gly Val Thr Phe His Asp Asp Leu Ile Pro Phe Gly Ala Ser
    50                  55                  60

Asp Thr Glu Arg Glu Ala His Val Lys Arg Phe Arg Gln Ala Leu Asp
65                  70                  75                  80

Ala Thr Gly Met Thr Val Pro Met Ala Thr Thr Asn Leu Phe Thr His
                85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Lys Val Tyr Val Ala Trp Gly Gly Arg Glu Gly Ala Glu
    130                 135                 140

Ser Gly Ala Ala Lys Asp Val Arg Ala Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Ile Gly His Ala Leu Ala Phe Ile Glu Arg Leu Glu Arg
        195                 200                 205

Pro Glu Leu Tyr Gly Val Asn Pro Glu Val Gly His Glu Gln Met Ala
    210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Ser Ala Gly Trp Glu Gly Pro Arg His Phe Asp Phe
        275                 280                 285

Lys Pro Pro Arg Thr Glu Asp Ile Asp Gly Val Trp Ala Ser Ala Ala
    290                 295                 300
```

```
Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ala Arg Leu Asp
                325                 330                 335

Gln Leu Ala Glu Pro Thr Ala Ala Asp Gly Leu Gln Ala Leu Leu Ala
            340                 345                 350

Asp Arg Thr Ala Tyr Glu Asp Phe Asp Val Asp Ala Ala Ala Ala Arg
        355                 360                 365

Gly Met Ala Phe Glu Arg Leu Asp Gln Leu Ala Met Asp His Leu Leu
    370                 375                 380

Gly Ala Arg Gly
385

<210> SEQ ID NO 12
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Asn Tyr Gln Pro Thr Pro Glu Asp Arg Phe Thr Phe Gly Leu Trp
1               5                   10                  15

Thr Val Gly Trp Gln Gly Arg Asp Pro Phe Gly Asp Ala Thr Arg Pro
            20                  25                  30

Ala Leu Asp Pro Val Glu Ala Val Gln Arg Leu Ala Glu Leu Gly Ala
        35                  40                  45

Tyr Gly Val Thr Phe His Asp Asp Leu Phe Pro Phe Gly Ala Ser
    50                  55                  60

Asp Thr Glu Arg Glu Ala His Val Lys Arg Phe Arg Gln Ala Leu Asp
65                  70                  75                  80

Ala Thr Gly Met Thr Val Pro Met Ala Thr Thr Asn Leu Phe Thr His
                85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Lys Val Tyr Val Ala Trp Gly Gly Arg Glu Gly Ala Glu
    130                 135                 140

Ser Gly Ala Ala Lys Asp Val Arg Ala Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Ile Gly His Ala Leu Ala Phe Ile Glu Arg Leu Glu Arg
        195                 200                 205

Pro Glu Leu Tyr Gly Val Asn Pro Glu Val Gly His Glu Gln Met Ala
    210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270
```

```
Asp Leu Leu Glu Ser Ala Gly Trp Glu Gly Pro Arg His Phe Asp Phe
            275                 280                 285

Lys Pro Pro Arg Thr Glu Asp Ile Asp Gly Val Trp Ala Ser Ala Ala
        290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ala Arg Leu Asp
                325                 330                 335

Gln Leu Ala Glu Pro Thr Ala Ala Asp Gly Leu Gln Ala Leu Leu Ala
            340                 345                 350

Asp Arg Thr Ala Tyr Glu Asp Phe Asp Val Asp Ala Ala Ala Ala Arg
        355                 360                 365

Gly Met Ala Phe Glu Arg Leu Asp Gln Leu Ala Met Asp His Leu Leu
370                 375                 380

Gly Ala Arg Gly
385

<210> SEQ ID NO 13
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Asn Tyr Gln Pro Thr Pro Glu Asp Lys Phe Thr Phe Gly Leu Trp
1               5                   10                  15

Thr Val Gly Trp Gln Gly Arg Asp Pro Phe Gly Asp Ala Thr Arg Pro
            20                  25                  30

Ala Leu Asp Pro Val Glu Ala Val Gln Arg Leu Ala Glu Leu Gly Ala
        35                  40                  45

Tyr Gly Val Thr Leu His Asp Asp Leu Ile Pro Phe Gly Ala Ser
    50                  55                  60

Asp Thr Glu Arg Glu Ala His Val Lys Arg Phe Arg Gln Ala Leu Asp
65                  70                  75                  80

Ala Thr Gly Met Thr Val Pro Met Ala Thr Thr Asn Leu Phe Tyr His
                85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Lys Val Tyr Val Ala Trp Gly Gly Arg Glu Gly Ala Glu
    130                 135                 140

Ser Gly Ala Ala Lys Asp Val Arg Ala Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Ile Gly His Ala Leu Ala Phe Ile Glu Arg Leu Glu Arg
        195                 200                 205

Pro Glu Leu Tyr Gly Val Asn Pro Glu Val Gly His Glu Gln Met Ala
    210                 215                 220

Gly Leu Asn Phe Pro His Gly Ile Ala Gln Ala Leu Trp Ala Gly Lys
```

```
            225                 230                 235                 240
Leu Phe His Ile Asp Leu Asn Gly Gln Ser Gly Ile Lys Tyr Asp Gln
                    245                 250                 255

Asp Leu Arg Phe Gly Ala Gly Asp Leu Arg Ala Ala Phe Trp Leu Val
                260                 265                 270

Asp Leu Leu Glu Ser Ala Gly Trp Glu Gly Pro Arg His Phe Asp Phe
            275                 280                 285

Lys Pro Pro Arg Thr Glu Asp Ile Asp Gly Val Trp Ala Ser Ala Ala
290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Arg Leu Asp
                325                 330                 335

Gln Leu Ala Glu Pro Thr Ala Ala Asp Gly Leu Gln Ala Leu Leu Ala
                340                 345                 350

Asp Arg Thr Ala Tyr Glu Asp Phe Asp Val Asp Ala Ala Ala Ala Arg
                355                 360                 365

Gly Met Ala Phe Glu Arg Leu Asp Gln Leu Ala Met Asp His Leu Leu
            370                 375                 380

Gly Ala Arg Gly
385

<210> SEQ ID NO 14
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Asn Tyr Gln Pro Thr Pro Glu Asp Lys Phe Thr Phe Gly Leu Trp
1               5                   10                  15

Thr Val Gly Trp Gln Gly Arg Asp Pro Phe Gly Asp Ala Thr Arg Pro
            20                  25                  30

Ala Leu Asp Pro Val Glu Ala Val Gln Arg Leu Ala Glu Leu Gly Ala
        35                  40                  45

Tyr Gly Val Thr Leu His Asp Asp Asp Leu Ile Pro Phe Gly Ala Ser
    50                  55                  60

Asp Thr Glu Arg Glu Ala His Val Lys Arg Phe Arg Gln Ala Leu Asp
65                  70                  75                  80

Ala Thr Gly Met Thr Val Pro Met Ala Ser Thr Asn Leu Phe Tyr His
                85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Lys Val Tyr Val Ala Trp Gly Gly Arg Glu Gly Ala Glu
    130                 135                 140

Ser Gly Ala Ala Lys Asp Val Arg Ala Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190
```

-continued

```
Leu Pro Thr Ile Gly His Ala Leu Ala Phe Ile Glu Arg Leu Glu Arg
            195                 200                 205

Pro Glu Leu Tyr Gly Val Asn Pro Glu Val Gly His Glu Gln Met Ala
        210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Ser Ala Gly Trp Glu Gly Pro Arg His Phe Asp Phe
        275                 280                 285

Lys Pro Pro Arg Thr Glu Asp Ile Asp Gly Val Trp Ala Ser Ala Ala
290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ala Arg Leu Asp
                325                 330                 335

Gln Leu Ala Glu Pro Thr Ala Ala Asp Gly Leu Gln Ala Leu Leu Ala
            340                 345                 350

Asp Arg Thr Ala Tyr Glu Asp Phe Asp Val Asp Ala Ala Ala Ala Arg
        355                 360                 365

Gly Met Ala Phe Glu Arg Leu Asp Gln Leu Ala Met Asp His Leu Leu
370                 375                 380

Gly Ala Arg Gly
385

<210> SEQ ID NO 15
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Asn Tyr Gln Pro Thr Pro Glu Asp Lys Phe Thr Phe Gly Leu Trp
1               5                   10                  15

Thr Val Gly Trp Gln Gly Arg Asp Pro Phe Gly Asp Ala Thr Arg Pro
            20                  25                  30

Asn Leu Asp Pro Val Glu Ala Val Gln Arg Leu Ala Glu Leu Gly Ala
        35                  40                  45

Tyr Gly Val Thr Leu His Asp Asp Leu Ile Pro Phe Gly Ala Ser
    50                  55                  60

Asp Thr Glu Arg Glu Ala His Val Lys Arg Phe Arg Gln Ala Leu Asp
65                  70                  75                  80

Ala Thr Gly Met Thr Val Pro Met Ala Ser Thr Asn Leu Phe Tyr His
                85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Lys Val Tyr Val Ala Trp Gly Gly Arg Glu Gly Ala Glu
    130                 135                 140

Ser Gly Ala Ala Lys Asp Val Arg Ala Ala Leu Asp Arg Met Lys Glu
145                 150                 155                 160
```

```
Ala Phe Asp Leu Leu Gly Glu Tyr Val Thr Ser Gln Gly Tyr Asp Ile
            165                 170                 175

Arg Phe Ala Ile Glu Pro Lys Pro Asn Glu Pro Arg Gly Asp Ile Leu
            180                 185                 190

Leu Pro Thr Ile Gly His Ala Leu Ala Phe Ile Glu Arg Leu Glu Arg
            195                 200                 205

Pro Glu Leu Tyr Gly Val Asn Pro Glu Val Gly His Glu Gln Met Ala
        210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
            245                 250                 255

Asp Leu Arg Phe Gly Ala Gly Asp Leu Arg Ala Ala Phe Trp Leu Val
            260                 265                 270

Asp Leu Leu Glu Ser Ala Gly Trp Glu Gly Pro Arg His Phe Asp Phe
            275                 280                 285

Lys Pro Pro Arg Thr Glu Asp Ile Asp Gly Val Trp Ala Ser Ala Ala
        290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ala Arg Leu Asp
            325                 330                 335

Gln Leu Ala Glu Pro Thr Ala Ala Asp Gly Leu Gln Ala Leu Leu Ala
            340                 345                 350

Asp Arg Thr Ala Tyr Glu Asp Phe Asp Val Asp Ala Ala Ala Ala Arg
            355                 360                 365

Gly Met Ala Phe Glu Arg Leu Asp Gln Leu Ala Met Asp His Leu Leu
        370                 375                 380

Gly Ala Arg Gly
385

<210> SEQ ID NO 16
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Asn Tyr Gln Pro Thr Pro Glu Asp Lys Phe Thr Phe Gly Leu Trp
1               5                   10                  15

Thr Val Gly Trp Gln Gly Arg Asp Pro Phe Gly Asp Ala Thr Arg Pro
            20                  25                  30

Ala Leu Asp Pro Val Glu Ala Val Gln Arg Leu Ala Glu Leu Gly Ala
        35                  40                  45

Tyr Gly Val Thr Leu His Asp Asp Leu Ile Pro Phe Gly Ala Ser
    50                  55                  60

Asp Thr Glu Arg Glu Ala His Val Lys Arg Phe Arg Gln Ala Leu Asp
65                  70                  75                  80

Ala Thr Gly Met Thr Val Pro Met Ala Ser Thr Asn Leu Phe Thr His
            85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
```

```
            115                 120                 125
Leu Gly Ala Lys Val Tyr Val Ala Trp Gly Gly Arg Glu Gly Ala Glu
        130                 135                 140
Ser Gly Ala Ala Lys Asp Val Arg Ala Ala Leu Asp Arg Met Lys Glu
145                 150                 155                 160
Ala Phe Asp Leu Leu Gly Glu Tyr Val Thr Ser Gln Gly Tyr Asp Ile
                165                 170                 175
Arg Phe Ala Ile Glu Pro Lys Pro Asn Glu Pro Arg Gly Asp Ile Leu
            180                 185                 190
Leu Pro Thr Ile Gly His Ala Leu Ala Phe Ile Glu Arg Leu Glu Arg
        195                 200                 205
Pro Glu Leu Tyr Gly Val Asn Pro Glu Val Gly His Glu Gln Met Ala
    210                 215                 220
Gly Leu Asn Phe Pro His Gly Ile Ala Gln Ala Leu Trp Ala Gly Lys
225                 230                 235                 240
Leu Phe His Ile Asp Leu Asn Gly Gln Ser Gly Ile Lys Tyr Asp Gln
                245                 250                 255
Asp Leu Arg Phe Gly Ala Gly Asp Leu Arg Ala Ala Phe Trp Leu Val
            260                 265                 270
Asp Leu Leu Glu Ser Ala Gly Trp Glu Gly Pro Arg His Phe Asp Phe
        275                 280                 285
Lys Pro Pro Arg Thr Glu Asp Ile Asp Gly Val Trp Ala Ser Ala Ala
    290                 295                 300
Gly Cys Met Arg Asn Tyr Leu Ile Leu Lys Glu Arg Ala Ala Ala Phe
305                 310                 315                 320
Arg Ala Asp Pro Glu Val Gln Glu Ala Leu Arg Ala Arg Leu Asp
                325                 330                 335
Gln Leu Ala Glu Pro Thr Ala Ala Asp Gly Leu Gln Ala Leu Leu Ala
            340                 345                 350
Asp Arg Thr Ala Tyr Glu Asp Phe Asp Val Asp Ala Ala Ala Arg
        355                 360                 365
Gly Met Ala Phe Glu Arg Leu Asp Gln Leu Ala Met Asp His Leu Leu
    370                 375                 380
Gly Ala Arg Gly
385

<210> SEQ ID NO 17
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Asn Tyr Gln Pro Thr Pro Glu Asp Lys Phe Thr Phe Gly Leu Trp
1               5                   10                  15
Thr Val Gly Trp Gln Gly Arg Asp Pro Phe Gly Asp Ala Thr Arg Pro
                20                  25                  30
Ala Leu Asp Pro Val Glu Ala Val Gln Arg Leu Ala Glu Leu Gly Ala
            35                  40                  45
Tyr Gly Val Thr Phe His Asp Asp Leu Ile Pro Phe Gly Ala Ser
        50                  55                  60
Asp Thr Glu Arg Glu Ala His Val Lys Arg Phe Arg Gln Ala Leu Asp
65                  70                  75                  80
```

Ala Thr Gly Met Thr Val Pro Met Val Ser Thr Asn Leu Phe Tyr His
            85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
            115                 120                 125

Leu Gly Ala Lys Val Tyr Val Ala Trp Gly Gly Arg Glu Gly Ala Glu
            130                 135                 140

Ser Gly Ala Ala Lys Asp Val Arg Ala Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Ile Gly His Ala Leu Ala Phe Ile Glu Arg Leu Glu Arg
            195                 200                 205

Pro Glu Leu Tyr Gly Val Asn Pro Glu Val Gly His Glu Gln Met Ala
            210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Ser Ala Gly Trp Glu Gly Pro Arg His Phe Asp Phe
            275                 280                 285

Lys Pro Pro Arg Thr Glu Asp Ile Asp Gly Val Trp Ala Ser Ala Ala
290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ala Arg Leu Asp
            325                 330                 335

Gln Leu Ala Glu Pro Thr Ala Ala Asp Gly Leu Gln Ala Leu Leu Ala
            340                 345                 350

Asp Arg Thr Ala Tyr Glu Asp Phe Asp Val Asp Ala Ala Ala Ala Arg
            355                 360                 365

Gly Met Ala Phe Glu Arg Leu Asp Gln Leu Ala Met Asp His Leu Leu
            370                 375                 380

Gly Ala Arg Gly
385

<210> SEQ ID NO 18
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Asn Tyr Gln Pro Thr Pro Glu Asp Lys Phe Thr Phe Gly Leu Trp
1               5                   10                  15

Thr Val Gly Trp Gln Gly Arg Asp Pro Phe Gly Asp Ala Thr Arg Pro
            20                  25                  30

Ile Leu Asp Pro Val Glu Ala Val Gln Arg Leu Ala Glu Leu Gly Ala
            35                  40                  45

Tyr Gly Val Thr Leu His Asp Asp Leu Ile Pro Phe Gly Ala Ser
    50                  55                  60

Asp Thr Glu Arg Glu Ala His Val Lys Arg Phe Arg Gln Ala Leu Asp
 65                  70                  75                  80

Ala Thr Gly Met Thr Val Pro Met Ala Ser Thr Asn Leu Phe Tyr His
                 85                  90                  95

Pro Val Phe Lys Asp Gly Ala Phe Thr Ala Asn Asp Arg Asp Val Arg
                100                 105                 110

Arg Tyr Ala Leu Arg Lys Thr Ile Arg Asn Ile Asp Leu Ala Val Glu
            115                 120                 125

Leu Gly Ala Lys Val Tyr Val Ala Trp Gly Arg Glu Gly Ala Glu
    130                 135                 140

Ser Gly Ala Ala Lys Asp Val Arg Ala Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Ile Gly His Ala Leu Ala Phe Ile Glu Arg Leu Glu Arg
    195                 200                 205

Pro Glu Leu Tyr Gly Val Asn Pro Glu Val Gly His Glu Gln Met Ala
210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Ser Ala Gly Trp Glu Gly Pro Arg His Phe Asp Phe
    275                 280                 285

Lys Pro Pro Arg Thr Glu Asp Ile Asp Gly Val Trp Ala Ser Ala Ala
290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ala Arg Leu Asp
                325                 330                 335

Gln Leu Ala Glu Pro Thr Ala Ala Asp Gly Leu Gln Ala Leu Leu Ala
            340                 345                 350

Asp Arg Thr Ala Tyr Glu Asp Phe Asp Val Asp Ala Ala Ala Ala Arg
    355                 360                 365

Gly Met Ala Phe Glu Arg Leu Asp Gln Leu Ala Met Asp His Leu Leu
370                 375                 380

Gly Ala Arg Gly
385

<210> SEQ ID NO 19
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Asn Tyr Gln Pro Thr Pro Glu Asp Lys Phe Thr Phe Gly Leu Trp

```
  1               5                   10                  15
Thr Val Gly Trp Gln Gly Arg Asp Pro Phe Gly Asp Ala Thr Arg Pro
                 20                  25                  30
Ala Leu Ser Pro Val Glu Ala Val Gln Arg Leu Ala Glu Leu Gly Ala
                 35                  40                  45
Tyr Gly Val Thr Leu His Asp Asp Leu Ile Pro Phe Gly Ala Ser
         50                  55                  60
Asp Thr Glu Arg Glu Ala His Val Lys Arg Phe Arg Gln Ala Leu Asp
 65                  70                  75                  80
Ala Thr Gly Met Thr Val Pro Met Ala Ser Thr Asn Leu Phe Tyr His
                 85                  90                  95
Pro Val Phe Lys Asp Gly Ala Phe Thr Ala Asn Asp Arg Asp Val Arg
                100                 105                 110
Arg Tyr Ala Leu Arg Lys Thr Ile Arg Asn Ile Asp Leu Ala Val Glu
                115                 120                 125
Leu Gly Ala Lys Val Tyr Val Ala Trp Gly Gly Arg Glu Gly Ala Glu
                130                 135                 140
Ser Gly Ala Ala Lys Asp Val Arg Ala Ala Leu Asp Arg Met Lys Glu
145                 150                 155                 160
Ala Phe Asp Leu Leu Gly Glu Tyr Val Thr Ser Gln Gly Tyr Asp Ile
                165                 170                 175
Arg Phe Ala Ile Glu Pro Lys Pro Asn Glu Pro Arg Gly Asp Ile Leu
                180                 185                 190
Leu Pro Thr Ile Gly His Ala Leu Ala Phe Ile Glu Arg Leu Glu Arg
                195                 200                 205
Pro Glu Leu Tyr Gly Val Asn Pro Glu Val Gly His Glu Gln Met Ala
                210                 215                 220
Gly Leu Asn Phe Pro His Gly Ile Ala Gln Ala Leu Trp Ala Gly Lys
225                 230                 235                 240
Leu Phe His Ile Asp Leu Asn Gly Gln Ser Gly Ile Lys Tyr Asp Gln
                245                 250                 255
Asp Leu Arg Phe Gly Ala Gly Asp Leu Arg Ala Ala Phe Trp Leu Val
                260                 265                 270
Asp Leu Leu Glu Ser Ala Gly Trp Glu Gly Pro Arg His Phe Asp Phe
                275                 280                 285
Lys Pro Pro Arg Thr Glu Asp Ile Asp Gly Val Trp Ala Ser Ala Ala
                290                 295                 300
Gly Cys Met Arg Asn Tyr Leu Ile Leu Lys Glu Arg Ala Ala Ala Phe
305                 310                 315                 320
Arg Ala Asp Pro Glu Val Gln Glu Ala Leu Arg Ala Arg Leu Asp
                325                 330                 335
Gln Leu Ala Glu Pro Thr Ala Ala Asp Gly Leu Gln Ala Leu Leu Ala
                340                 345                 350
Asp Arg Thr Ala Tyr Glu Asp Phe Asp Val Asp Ala Ala Ala Arg
                355                 360                 365
Gly Met Ala Phe Glu Arg Leu Asp Gln Leu Ala Met Asp His Leu Leu
                370                 375                 380
Gly Ala Arg Gly
385

<210> SEQ ID NO 20
<211> LENGTH: 388
<212> TYPE: PRT
<213> ORGANISM: Artificial Sequence
```

<220> FEATURE:
<223> OTHER INFORMATION: Description of Artificial Sequence: Synthetic polypeptide

<400> SEQUENCE: 20

```
Met Asn Tyr Gln Pro Thr Pro Glu Asp Lys Phe Thr Phe Gly Leu Trp
1               5                   10                  15
Thr Val Gly Trp Gln Gly Arg Asp Pro Phe Gly Asp Ala Thr Arg Pro
            20                  25                  30
Asn Leu Asp Pro Val Glu Ala Val Gln Arg Leu Ala Glu Leu Gly Ala
        35                  40                  45
Tyr Gly Val Thr Phe His Asp Asp Leu Phe Pro Phe Gly Ala Ser
    50                  55                  60
Asp Thr Glu Arg Glu Ala His Val Lys Arg Phe Arg Gln Ala Leu Asp
65                  70                  75                  80
Ala Thr Gly Met Thr Val Pro Met Ala Ser Thr Asn Leu Phe Thr His
                85                  90                  95
Pro Val Phe Lys Asp Gly Ala Phe Thr Ala Asn Asp Arg Asp Val Arg
            100                 105                 110
Arg Tyr Ala Leu Arg Lys Thr Ile Arg Asn Ile Asp Leu Ala Val Glu
        115                 120                 125
Leu Gly Ala Lys Val Tyr Val Ala Trp Gly Gly Arg Glu Gly Ala Glu
    130                 135                 140
Ser Gly Ala Ala Lys Asp Val Arg Ala Ala Leu Asp Arg Met Lys Glu
145                 150                 155                 160
Ala Phe Asp Leu Leu Gly Glu Tyr Val Thr Ser Gln Gly Tyr Asp Ile
                165                 170                 175
Arg Phe Ala Ile Glu Pro Lys Pro Asn Glu Pro Arg Gly Asp Ile Leu
            180                 185                 190
Leu Pro Thr Ile Gly His Ala Leu Ala Phe Ile Glu Arg Leu Glu Arg
        195                 200                 205
Pro Glu Leu Tyr Gly Val Asn Pro Glu Val Gly His Glu Gln Met Ala
    210                 215                 220
Gly Leu Asn Phe Pro His Gly Ile Ala Gln Ala Leu Trp Ala Gly Lys
225                 230                 235                 240
Leu Phe His Ile Asp Leu Asn Gly Gln Ser Gly Ile Lys Tyr Asp Gln
                245                 250                 255
Asp Leu Arg Phe Gly Ala Gly Asp Leu Arg Ala Ala Phe Trp Leu Val
            260                 265                 270
Asp Leu Leu Glu Ser Ala Gly Trp Glu Gly Pro Arg His Phe Asp Phe
        275                 280                 285
Lys Pro Pro Arg Thr Glu Asp Ile Asp Gly Val Trp Ala Ser Ala Ala
    290                 295                 300
Gly Cys Met Arg Asn Tyr Leu Ile Leu Lys Glu Arg Ala Ala Ala Phe
305                 310                 315                 320
Arg Ala Asp Pro Glu Val Gln Glu Ala Leu Arg Ala Ala Arg Leu Asp
                325                 330                 335
Gln Leu Ala Glu Pro Thr Ala Ala Asp Gly Leu Gln Ala Leu Leu Ala
            340                 345                 350
Asp Arg Thr Ala Tyr Glu Asp Phe Asp Val Asp Ala Ala Ala Ala Arg
        355                 360                 365
Gly Met Ala Phe Glu Arg Leu Asp Gln Leu Ala Met Asp His Leu Leu
    370                 375                 380
Gly Ala Arg Gly
```

<210> SEQ ID NO 21
<211> LENGTH: 388
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

```
Met Asn Tyr Gln Pro Thr Pro Glu Asp Lys Phe Thr Phe Gly Leu Trp
1               5                   10                  15

Thr Val Gly Trp Gln Gly Arg Asp Pro Phe Gly Asp Ala Thr Arg Pro
            20                  25                  30

Ile Leu Ser Pro Val Glu Ala Val Gln Arg Leu Ala Glu Leu Gly Ala
        35                  40                  45

Tyr Gly Val Thr Phe His Asp Asp Leu Phe Pro Phe Gly Ala Ser
    50                  55                  60

Asp Thr Glu Arg Glu Ala His Val Lys Arg Phe Arg Gln Ala Leu Asp
65                  70                  75                  80

Ala Thr Gly Met Thr Val Pro Met Ala Ser Thr Asn Leu Phe Thr His
                85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Lys Val Tyr Val Ala Trp Gly Gly Arg Glu Gly Ala Glu
    130                 135                 140

Ser Gly Ala Ala Lys Asp Val Arg Ala Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Ile Gly His Ala Leu Ala Phe Ile Glu Arg Leu Glu Arg
        195                 200                 205

Pro Glu Leu Tyr Gly Val Asn Pro Glu Val Gly His Glu Gln Met Ala
    210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Ser Ala Gly Trp Glu Gly Pro Arg His Phe Asp Phe
        275                 280                 285

Lys Pro Pro Arg Thr Glu Asp Ile Asp Gly Val Trp Ala Ser Ala Ala
    290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ala Arg Leu Asp
                325                 330                 335

Gln Leu Ala Glu Pro Thr Ala Ala Asp Gly Leu Gln Ala Leu Leu Ala
            340                 345                 350
```

```
Asp Arg Thr Ala Tyr Glu Asp Phe Asp Val Asp Ala Ala Ala Ala Arg
            355                 360                 365
Gly Met Ala Phe Glu Arg Leu Asp Gln Leu Ala Met Asp His Leu Leu
    370                 375                 380
Gly Ala Arg Gly
385

<210> SEQ ID NO 22
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Asn Tyr Gln Pro Thr Pro Glu Asp Lys Phe Thr Phe Gly Leu Trp
1               5                   10                  15
Thr Val Gly Trp Gln Gly Arg Asp Pro Phe Gly Asp Ala Thr Arg Pro
            20                  25                  30
Ala Leu Asp Pro Val Glu Ala Val Gln Arg Leu Ala Glu Leu Gly Ala
        35                  40                  45
Tyr Gly Val Thr Phe His Asp Asp Leu Ile Pro Phe Gly Ala Ser
    50                  55                  60
Asp Thr Glu Arg Glu Ala His Val Lys Arg Phe Arg Gln Ala Leu Asp
65                  70                  75                  80
Ala Thr Gly Met Thr Val Pro Met Ala Ser Thr Asn Leu Phe Tyr His
                85                  90                  95
Pro Val Phe Lys Asp Gly Ala Phe Thr Ala Asn Asp Arg Asp Val Arg
            100                 105                 110
Arg Tyr Ala Leu Arg Lys Thr Ile Arg Asn Ile Asp Leu Ala Val Glu
        115                 120                 125
Leu Gly Ala Lys Val Tyr Val Ala Trp Gly Gly Arg Glu Gly Ala Glu
    130                 135                 140
Ser Gly Ala Ala Lys Asp Val Arg Ala Ala Leu Asp Arg Met Lys Glu
145                 150                 155                 160
Ala Phe Asp Leu Leu Gly Glu Tyr Val Thr Ser Gln Gly Tyr Asp Ile
                165                 170                 175
Arg Phe Ala Ile Glu Pro Lys Pro Asn Glu Pro Arg Gly Asp Ile Leu
            180                 185                 190
Leu Pro Thr Ile Gly His Ala Leu Ala Phe Ile Glu Arg Leu Glu Arg
        195                 200                 205
Pro Glu Leu Tyr Gly Val Asn Pro Glu Val Gly His Glu Gln Met Ala
    210                 215                 220
Gly Leu Asn Phe Pro His Gly Ile Ala Gln Ala Leu Trp Ala Gly Lys
225                 230                 235                 240
Leu Phe His Ile Asp Leu Asn Gly Gln Ser Gly Ile Lys Tyr Asp Gln
                245                 250                 255
Asp Leu Arg Phe Gly Ala Gly Asp Leu Arg Ala Ala Phe Trp Leu Val
            260                 265                 270
Asp Leu Leu Glu Ser Ala Gly Trp Glu Gly Pro Arg His Phe Asp Phe
        275                 280                 285
Lys Pro Pro Arg Thr Glu Asp Ile Asp Gly Val Trp Ala Ser Ala Ala
    290                 295                 300
Gly Cys Met Arg Asn Tyr Leu Ile Leu Lys Glu Arg Ala Ala Ala Phe
305                 310                 315                 320
```

Arg Ala Asp Pro Glu Val Gln Glu Ala Leu Arg Ala Ala Arg Leu Asp
            325                 330                 335

Gln Leu Ala Glu Pro Thr Ala Ala Asp Gly Leu Gln Ala Leu Leu Ala
            340                 345                 350

Asp Arg Thr Ala Tyr Glu Asp Phe Asp Val Asp Ala Ala Ala Ala Arg
            355                 360                 365

Gly Met Ala Phe Glu Arg Leu Asp Gln Leu Ala Met Asp His Leu Leu
        370                 375                 380

Gly Ala Arg Gly
385

<210> SEQ ID NO 23
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Asn Tyr Gln Pro Thr Pro Glu Asp Lys Phe Thr Phe Gly Leu Trp
1               5                   10                  15

Thr Val Gly Trp Gln Gly Arg Asp Pro Phe Gly Asp Ala Thr Arg Pro
            20                  25                  30

Ala Leu Asp Pro Val Glu Ala Val Gln Arg Leu Ala Glu Leu Gly Ala
        35                  40                  45

Tyr Gly Val Thr Phe His Asp Asp Leu Ile Pro Phe Gly Ala Ser
    50                  55                  60

Asp Thr Glu Arg Glu Ala His Val Lys Arg Phe Arg Gln Ala Leu Asp
65                  70                  75                  80

Ala Thr Gly Met Thr Val Pro Met Ala Ser Thr Asn Leu Phe Arg His
                85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Lys Val Tyr Val Ala Trp Gly Gly Arg Glu Gly Ala Glu
    130                 135                 140

Ser Gly Ala Ala Lys Asp Val Arg Ala Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Ile Gly His Ala Leu Ala Phe Ile Glu Arg Leu Glu Arg
        195                 200                 205

Pro Glu Leu Tyr Gly Val Asn Pro Glu Val Gly His Glu Gln Met Ala
    210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Ser Ala Gly Trp Glu Gly Pro Arg His Phe Asp Phe

```
                275                 280                 285
Lys Pro Pro Arg Thr Glu Asp Ile Asp Gly Val Trp Ala Ser Ala Ala
        290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ala Arg Leu Asp
                325                 330                 335

Gln Leu Ala Glu Pro Thr Ala Ala Asp Gly Leu Gln Ala Leu Leu Ala
            340                 345                 350

Asp Arg Thr Ala Tyr Glu Asp Phe Asp Val Asp Ala Ala Ala Ala Arg
        355                 360                 365

Gly Met Ala Phe Glu Arg Leu Asp Gln Leu Ala Met Asp His Leu Leu
    370                 375                 380

Gly Ala Arg Gly
385
```

US 11,066,659 B2

GLUCOSE ISOMERASE

This application is the U.S. national stage of International Patent Application No. PCT/EP2018/061573, filed May 4, 2018, which claims the benefit of European Patent Application 17000785.0, filed May 5, 2017.

The instant application contains a Sequence Listing which has been filed electronically in ASCII format and is hereby incorporated by reference in its entirety. Said ASCII copy, created on Mar. 24, 2020, is named 155646_01300_SL.txt and is 79,709 bytes in size.

FIELD OF THE INVENTION

The present invention is related to an isomerase, preferably a glucose isomerase, a method for reacting a ketose or an aldose molecule, a method for converting fructose to glucose, the use of the isomerase for producing glucose, a method for increasing the activity of a glucose isomerase, a method for reducing the $K_M$ value of a glucose isomerase for fructose, and a method for increasing the soluble expression of a glucose isomerase.

BACKGROUND OF THE INVENTION

Isomerases are enzymes which convert a molecule from one isomer to another isomer. Glucose isomerases specifically catalyse the isomerization of aldoses to ketoses, or vice versa. Glucose isomerase enzymes of this kind are also called D-xylose aldose-ketose-isomerases, D-xylose isomerases, D-xylose ketoisomerases, or fructose isomerases.

Glucose isomerases that convert glucose to fructose and D-xylose to D-xylulose belong to the EC subclass of EC 5.3.1.5 as defined by the International Union of Biochemistry and Molecular Biology. The natural standard reaction catalysed by glucose isomerases is the isomerization of the substrate xylose to xylulose with high affinity and high specific activity. As a side activity, and usually with much lower affinity and low specific activity, conversion of glucose to fructose, ribose to ribulose, arabinose to ribulose, or rhamnose to a so far uncharacterized product are described.

The reactions catalyzed by glucose isomerases are reversible equilibrium reactions and may undergo substrate or product inhibition, depending on the specific direction of the reaction. In order to obtain industrially relevant amounts of a desired product, glucose isomerases are required that catalyze the conversion of substrates with high specific activity. In addition, other kinetic factors of the glucose isomerases, such as substrate selectivity and $K_M$ may play an important role for product yields. Other relevant aspects may include but are not limited to regioselectivity, inhibition by other factors such as, e.g. crude extract components, substrate contaminants or side products, and recombinant soluble expression in suitable hosts.

A major shortcoming of wild type glucose isomerases when used in industrial processes is their specific reaction equilibrium status, which results in incomplete substrate conversion and insufficient product yields. Glucose isomerases were identified from various microorganisms (see, for example, the review article of Bhosale, Microbiol Reviews, 1996, 60, 280-300). For example, U.S. Pat. No. 6,372,476 describes the glucose isomerase activity of *Streptomyces* sp. SK.

Wild type glucose isomerases usually exhibit high $K_M$ values for substrates other than xylose such as, e.g., glucose or fructose, no specifically high activities for conversions of such substrates, and high temperature optima, whereas certain industrial processes require low temperature profiles and efficient conversion of glucose or fructose substrates. See, for example, Smith et al., Biochem J, 1991, 277, 255-261.

There is thus a need for glucose isomerases the reaction characteristics of which meet the requirements of technical processes such as high specific activity at moderate temperatures and low substrate, i.e. glucose or fructose, concentrations. Additionally, a higher activity yield of the glucose isomerase from expression culture is advantageous for industrial application. Among others, improvements in terms of one or more of these characteristics lead to lower enzyme costs.

Engineered glucose isomerases are disclosed in U.S. Pat. Nos. 5,376,536, 7,704,719, 5,340,738, 5,384,257, 5,310,665, and US 2011/0318801. Ben Hlima (J Ind Microbiol Biotechnol, 2012, 39, 537-546) discloses variants of a *Streptomyces* sp. SK glucose isomerase which have mutations F53L and/or G219D. The wild type glucose isomerase according to this publication has a $K_M$ value of 200 mM for glucose, which is too high for industrial applications. The variants containing F53L, G219D or both mutations F53L/G219D showed an even higher $K_M$ value for glucose. Variants with mutations at positions 33, 34, 35, 59, 89, 90 and/or 95 are not described. Apart from variants containing the mutations F53L and/or D219A, all variants described in the art show lower specific activity with glucose as the substrate and lower thermal stability. None of the references cites mutations that influence the $K_M$ value for fructose in catalyzing the conversion to glucose; in particular no reference indicates mutations that contribute to a lower $K_M$ value of the enzymes.

In light of the above it is evident that both wild type glucose isomerase and engineered glucose isomerases of the prior art are not satisfying the needs for their use in industrial processes. Such insufficiency arises from the catalyzed reaction being reversible and the glucose isomerases of the prior art showing low enzyme activity at low substrate concentrations and at typical reaction conditions such as moderate temperatures such as 30-50° C. There is a need for glucose isomerases which are advantageous compared to wild type glucose isomerases, in particular glucose isomerases which are enzymatically active at low fructose concentrations and show high activity at comparatively moderate temperatures such as 30-50° C., for the industrial production of glucose from fructose. Accordingly, an objective of the present invention is a glucose isomerase which is suitable for use in industrial production of glucose from fructose.

Another objective is a glucose isomerase which has a higher specific activity, preferably the specific Activity, for converting fructose to glucose of at least 1.1-fold, preferably at least 1.4-fold, more preferably at least 1.6-fold, and most preferably at least 1.7-fold higher at a fructose concentration of 50 mM compared to a wild type glucose isomerase.

Yet another objective is a glucose isomerase which has a higher specific activity, preferably the specific Activity, for converting fructose to glucose of at least 1.2-fold, preferably at least 1.3-fold, more preferably of at least 1.4-fold, and most preferably at least 1.5-fold higher at a fructose concentration of 200 mM compared to a wild type glucose isomerase.

Yet another objective is a mutant glucose isomerase which is thermostable, where the mutant glucose isomerase shows improved activity, preferably the Activity, for converting fructose to glucose compared to the underlying wild type glucose isomerase, no, or a minor decrease in thermal stability compared to the underlying wild type glucose isomerase, and a Residual Activity of at least 30%, preferably of at least 40%, and most preferably of at least 60%.

Yet another objective is a glucose isomerase with a $K_M$ value of 190 mM or less, preferably with a $K_M$ value of 170 mM or less, more preferably with a $K_M$ value of 160 mM or less, and most preferably with a $K_M$ value of 152 mM and less.

These and other problems are solved by the present invention as described below and in the claims.

SUMMARY OF THE INVENTION

The problem underlying the present invention is solved in a first aspect, which is also a first embodiment of the first aspect, by a polypeptide, preferably a glucose isomerase, comprising an amino acid sequence, wherein the amino acid sequence of the polypeptide, preferably the glucose isomerase, is at least 95% identical to and/or at least 95% homologous to an amino acid sequence of SEQ ID NO:1, wherein the amino acid sequence of the polypeptide, preferably the glucose isomerase, comprises an amino acid substitution at one or more amino acid positions, wherein the one or more amino acid positions is/are each and independently selected from the group consisting of SEQ ID NO: 1 amino acid positions 10, 33, 34, 35, 53, 59, 89, 90, and 95.

In a preferred embodiment, the problem underlying the present invention is solved by a polypeptide, preferably a glucose isomerase, comprising an amino acid sequence, wherein the amino acid sequence of the polypeptide, preferably the glucose isomerase, is at least 95% identical to an amino acid sequence of SEQ ID NO: 1, wherein the amino acid sequence of the polypeptide, preferably the glucose isomerase, comprises an amino acid substitution at one or more amino acid positions, wherein the one or more amino acid positions is/are each and independently selected from the group consisting of SEQ ID NO: 1 amino acid positions 89, 90, 95, 10, 33, 34, 35, and 59.

In a preferred embodiment of the first aspect, which is also an embodiment of any one of the other embodiments of the first aspect, the polypeptide, preferably the glucose isomerase comprises an additional amino acid substitution at SEQ ID NO: 1 amino acid position 53.

In a second embodiment of the first aspect, which is also an embodiment of the first embodiment of the first aspect, the one or more amino acid positions is/are selected from the group consisting of SEQ ID NO: 1 amino acid positions R10, A33, L34, D35, F53, I59, A89, T90, and T95.

In a third embodiment of the first aspect, which is also an embodiment of the first and second embodiment of the first aspect, the one or more amino acid positions is/are selected from the group consisting of SEQ ID NO: 1 amino acid positions 10, 33, 34, 35, 59, 89, 90, and 95.

In a fourth embodiment of the first aspect, which is also an embodiment of the first, second and third embodiment of the first aspect, preferably of the third embodiment of the first aspect, the one or more amino acid positions is/are selected from the group consisting of SEQ ID NO: 1 amino acid positions R10, A33, L34, D35, I59, A89, T90, and T95.

In a fifth embodiment of the first aspect, which is also an embodiment of the first, second, third and fourth embodiment of the first aspect, the one or more amino acid positions is/are selected from the group consisting of SEQ ID NO: 1 amino acid positions 10, 33, 34, 35, and 59.

In a sixth embodiment of the first aspect, which is also an embodiment of the first, second, third, fourth and fifth embodiment of the first aspect, preferably of the fifth embodiment of the first aspect, the one or more amino acid positions is/are selected from the group consisting of SEQ ID NO: 1 amino acid positions R10, A33, L34, D35, and I59.

In a seventh embodiment of the first aspect, which is also an embodiment of the first, second, third, fourth, fifth and sixth embodiment of the first aspect, the one or more amino acid positions is/are selected from the group consisting of SEQ ID NO: 1 amino acid positions 10, 33, and 35.

In an eighth embodiment of the first aspect, which is also an embodiment of the first, second, third, fourth, fifth, sixth and seventh embodiment of the first aspect, the one or more amino acid positions is/are selected from the group consisting of SEQ ID NO: 1 amino acid positions R10, A33, and D35.

In a ninth embodiment of the first aspect, which is also an embodiment of the first, second, third and fourth embodiment of the first aspect, the polypeptide, preferably the glucose isomerase, comprises an amino acid substitution at one or more amino acid positions, wherein the one or more amino acid positions is/are selected from the group consisting of SEQ ID NO: 1 amino acid positions 10, 90 and 95; preferably, the one or more amino acid positions is/are selected from the group consisting of SEQ ID NO: 1 amino acid positions R10, T90 and T95; and more preferably, the polypeptide, preferably the glucose isomerase comprises an amino acid sequence, wherein the amino acid sequence comprises one or more of the amino acid substitutions selected from the group consisting of R10K, T90S and T95Y.

In a tenth embodiment of the first aspect, which is also an embodiment of the first, second, third, fourth, fifth, sixth, seventh, eighth and ninth embodiment of the first aspect, the one amino acid position is SEQ ID NO: 1 amino acid position 10, preferably the one amino acid position is SEQ ID NO: 1 amino acid position R10.

In an eleventh embodiment of the first aspect, which is also an embodiment of the first, second, third, fourth, fifth, sixth, seventh, eighth, ninth and tenth embodiment of the first aspect, the one or more amino acid positions is two or more amino acid positions.

In a twelfth embodiment of the first aspect, which is also an embodiment of the first, second, third, fourth, fifth, sixth, seventh, eighth, ninth, tenth and eleventh embodiment of the first aspect, preferably of the eleventh embodiment of the first aspect, the one or more amino acid positions is three or more amino acid positions.

In a $13^{th}$ embodiment of the first aspect, which is also an embodiment of the first, second, third, fourth, fifth, sixth, seventh, eighth, ninth, tenth, eleventh and twelfth embodiment of the first aspect, preferably of the twelfth embodiment of the first aspect, the one or more amino acid positions is four or more amino acid positions.

In a $14^{th}$ embodiment of the first aspect, which is also an embodiment of the first, second, third, fourth, fifth, sixth, seventh, eighth, ninth, tenth, eleventh, twelfth and $13^{th}$ embodiment of the first aspect, preferably of the $13^{th}$ embodiment of the first aspect, the one or more amino acid positions is five or more amino acid positions.

In another preferred embodiment, which is also an embodiment of any one of the other embodiments of the first aspect, the one or more amino acid positions is four or more or five or more amino acid positions.

In a $15^{th}$ embodiment of the first aspect, which is also an embodiment of the first, second, third, fourth, fifth, sixth, seventh, eighth, ninth, tenth, eleventh, twelfth, $13^{th}$, and $14^{th}$ embodiment of the first aspect, preferably of any one of the eleventh, twelfth, $13^{th}$ and $14^{th}$ of the first aspect, each and any of the amino acid positions is independently and individually selected from the group consisting of SEQ ID NO: 1 amino acid positions 10, 33, 34, 35, 53, 59, 89, 90, and 95.

In a 16$^{th}$ embodiment of the first aspect, which is also an embodiment of the 15$^{th}$ embodiment of the first aspect, each and any of the amino acid positions is independently and individually selected from the group consisting of SEQ ID NO: 1 amino acid positions R10, A33, L34, D35, F53, I59, A89, T90, and T95.

In a 17$^{th}$ embodiment of the first aspect, which is also an embodiment of the 15$^{th}$ embodiment of the first aspect, each and any of the amino acid positions is independently and individually selected from the group consisting of SEQ ID NO: 1 amino acid positions 10, 33, 34, 35, 59, 89, 90, and 95.

In an 18$^{th}$ embodiment of the first aspect, which is also an embodiment of the 17$^{th}$ embodiment of the first aspect, each and any of the amino acid positions is independently and individually selected from the group consisting of SEQ ID NO: 1 amino acid positions R10, A33, L34, D35, I59, A89, T90, and T95.

In a 19$^{th}$ embodiment of the first aspect, which is also an embodiment of the 17$^{th}$ embodiment of the first aspect, each and any of the amino acid positions is independently and individually selected from the group consisting of SEQ ID NO: 1 amino acid positions 10, 33, 34, 35, and 59.

In a 20$^{th}$ embodiment of the first aspect, which is also an embodiment of the 19$^{th}$ embodiment of the first aspect, each and any of the amino acid positions is independently and individually selected from the group consisting of SEQ ID NO: 1 amino acid positions R10, A33, L34, D35, and I59.

In a 21$^{st}$ embodiment of the first aspect, which is also an embodiment of the 19$^{th}$ embodiment of the first aspect, each and any of the amino acid positions is independently and individually selected from the group consisting of SEQ ID NO: 1 amino acid positions 10, 33, and 35.

In a 22$^{nd}$ embodiment of the first aspect, which is also an embodiment of the 21$^{st}$ embodiment of the first aspect, each and any of the amino acid positions is independently and individually selected from the group consisting of SEQ ID NO: 1 amino acid positions R10, A33, and D35.

In a 23$^{th}$ embodiment of the first aspect, which is also an embodiment of the eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$ and 22$^{nd}$ embodiment of the first aspect, the two or more amino acid positions comprise a pair of two amino acid positions, wherein the pair of two amino acid positions is selected from the group consisting of SEQ ID NO: 1 amino acid positions R10 and A33, R10 and L34, R10 and D35, R10 and F53, R10 and I59, R10 and A89, R10 and T90, R10 and T95, A33 and L34, A33 and D35, A33 and F53, A33 and I59, A33 and A89, A33 and T90, A33 and T95, L34 and D35, L34 and F53, L34 and I59, L34 and A89, L34 and T90, L34 and T95, D35 and F53, D35 and I59, D35 and A89, D35 and T90, D35 and T95, F53 and I59, F53 and A89, F53 and T90, F53 and T95, I59 and A89, I59 and T90, I59 and T95, A89 and T90, A89 and T95, and T90 and T95.

In a 24$^{th}$ embodiment of the first aspect, which is also an embodiment of the 23$^{rd}$ embodiment of the first aspect, the two or more amino acid positions comprise a pair of two amino acid positions, wherein the pair of two amino acid positions is selected from the group consisting of SEQ ID NO: 1 amino acid positions R10 and A33, R10 and L34, R10 and D35, R10 and I59, R10 and A89, R10 and T90, R10 and T95, A33 and L34, A33 and D35, A33 and I59, A33 and A89, A33 and T90, A33 and T95, L34 and D35, L34 and I59, L34 and A89, L34 and T90, L34 and T95, D35 and I59, D35 and A89, D35 and T90, D35 and T95, I59 and A89, I59 and T90, I59 and T95, A89 and T90, A89 and T95, and T90 and T95.

In a 25$^{th}$ embodiment of the first aspect, which is also an embodiment of the 24$^{th}$ embodiment of the first aspect, the two or more amino acid positions comprise a pair of two amino acid positions, wherein the pair of two amino acid positions is selected from the group consisting of SEQ ID NO: 1 amino acid positions R10 and A33, R10 and L34, R10 and D35, R10 and I59, A33 and L34, A33 and D35, A33 and I59, L34 and D35, L34 and I59, and D35 and I59.

In a 26$^{th}$ embodiment of the first aspect, which is also an embodiment of the 25$^{th}$ embodiment of the first aspect, the two or more amino acid positions comprise a pair of two amino acid positions, wherein the pair of two amino acid positions is selected from the group consisting of SEQ ID NO: 1 amino acid positions R10 and A33, R10 and D35, R10 and I59, A33 and D35, A33 and I59, and D35 and I59.

In a 27$^{th}$ embodiment of the first aspect, which is also an embodiment of the 26$^{th}$ embodiment of the first aspect, the two or more amino acid positions comprises a pair of two amino acid positions, wherein the pair of two amino acid positions is selected from the group consisting of SEQ ID NO: 1 amino acid positions R10 and A33, R10 and D35, and A33 and D35.

For the purpose of this invention, it is understood that an amino acid sequence of the polypeptide, preferably the glucose isomerase, that comprises an amino acid substitution at two amino acid positions of SEQ ID NO: 1 selected from a specific group, contains a pair of two amino acid substitutions, and may contain, in addition to such pair, one or more additional substitutions at other amino acid position. Similarly, it shall be understood, that an amino acid sequence of the polypeptide, preferably the glucose isomerase, that comprises amino acid substitutions at three, four, or five, amino acid positions of SEQ ID NO: 1 selected from a specific group, respectively, contains a triple, a quadruple, or a quintuple substitution, respectively, and may contain, in addition, one or more additional substitutions at other amino acid positions.

Alternatively, such a variant of the amino acid sequence of the polypeptide, preferably the glucose isomerase, herein may be referred to as an amino acid sequence of the polypeptide, preferably the glucose isomerase, which comprises an amino acid substitution at two or more amino acid positions, wherein the two or more amino acid positions comprise a pair of two amino acid positions, wherein the pair of two amino acid positions is selected from a specific group. Similarly, it shall be understood, that an amino acid sequence of the polypeptide, preferably the glucose isomerase, that comprises an amino acid substitution at three or more, four or more, or five or more amino acid positions, respectively, of SEQ ID NO: 1 selected from a specific group, contains a triple, quadruple, or quintuple of amino acid substitutions, respectively, and in addition may comprise one or more additional substitution at other amino acid positions.

In a 28$^{th}$ embodiment of the first aspect, which is also an embodiment of the eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$ and 27$^{th}$ embodiment of the first aspect, preferably of any one of the 23$^{rd}$, 24$^{th}$, 25$^{th}$, 26$^{th}$, and 27$^{th}$ embodiment of the first aspect, in addition to the substitution at the two amino acid positions, the amino acid sequence of the polypeptide, preferably the glucose isomerase, comprises an amino acid substitution at at least one or more additional amino acid positions, wherein the one or more additional amino acid position is independently and individually selected from the group consisting of SEQ ID NO: 1 amino acid positions 10, 33, 34, 35, 53, 59, 89, 90, and 95.

In a 29th embodiment of the first aspect, which is also an embodiment of the 28th embodiment of the first aspect, the one or more additional amino acid position is independently and individually selected from the group consisting of SEQ ID NO: 1 amino acid positions R10, A33, L34, D35, F53, I59, A89, T90, and T95.

In a 30th embodiment of the first aspect, which is also an embodiment of the 28th embodiment of the first aspect, the one or more additional amino acid position is independently and individually selected from the group consisting of SEQ ID NO:1 amino acid positions 10, 33, 34, 35, 59, 89, 90, and 95.

In a 31st embodiment of the first aspect, which is also an embodiment of the 30th embodiment of the first aspect, the one or more additional amino acid position is independently and individually selected from the group consisting of SEQ ID NO:1 amino acid positions R10, A33, L34, D35, I59, A89, T90, and T95.

In a 32nd embodiment of the first aspect, which is also an embodiment of the 28th embodiment of the first aspect, the one or more additional amino acid position is independently and individually selected from the group consisting of SEQ ID NO:1 amino acid positions 10, 33, 34, 35, and 59.

In a 33rd embodiment of the first aspect, which is also an embodiment of the 32nd embodiment of the first aspect, the one or more additional amino acid position is independently and individually selected from the group consisting of SEQ ID NO:1 amino acid positions R10, A33, L34, D35, and I59.

In a 34th embodiment of the first aspect, which is also an embodiment of the eleventh, twelfth, 13th, 14th, 15th, 16th, 17th, 18th, 19th, 20th, 21st, 22nd, 23rd, 24th, 25th, 26th, 27th, 28th, 29th, 30th, 31st, 32nd and 33rd embodiment of the first aspect, preferably of any one of the 23rd, 24th, 25th, 26th, 27th, 28th, 29th, 30th, 31st, 32nd and 33rd embodiment of the first aspect, more preferably of any one of the 28th, 29th, 30th, 31st, 32nd and 33rd embodiment of the first aspect, the two or more amino acid positions comprise three amino acid positions, wherein the three amino acid positions are selected from the group consisting of SEQ ID NO:1 amino acid positions R10 and A33 and L34, R10 and A33 and D35, R10 and A33 and F53, R10 and A33 and I59, R10 and A33 and A89, R10 and A33 and T90, R10 and A33 and T95, R10 and L34 and D35, R10 and L34 and F53, R10 and L34 and I59, R10 and L34 and A89, R10 and L34 and T90, R10 and L34 and T95, R10 and D35 and F53, R10 and D35 and I59, R10 and D35 and A89, R10 and D35 and T90, R10 and D35 and T95, R10 and F53 and I59, R10 and F53 and A89, R10 and F53 and T90, R10 and F53 and T95, R10 and I59 and A89, R10 and I59 and T90, R10 and I59 and T95, R10 and A89 and T90, R10 and A89 and T95, R10 and T90 and T95, A33 and L34 and D35, A33 and L34 and F53, A33 and L34 and I59, A33 and L34 and A89, A33 and L34 and T90, A33 and L34 and T95, A33 and D35 and F53, A33 and D35 and I59, A33 and D35 and A89, A33 and D35 and T90, A33 and D35 and T95, A33 and F53 and I59, A33 and F53 and A89, A33 and F53 and T90, A33 and F53 and T95, A33 and I59 and A89, A33 and I59 and T90, A33 and I59 and T95, A33 and A89 and T90, A33 and A89 and T95, A33 and T90 and T95, L34 and D35 and F53, L34 and D35 and I59, L34 and D35 and A89, L34 and D35 and T90, L34 and D35 and T95, L34 and F53 and I59, L34 and F53 and A89, L34 and F53 and T90, L34 and F53 and T95, L34 and I59 and A89, L34 and I59 and T90, L34 and I59 and T95, L34 and A89 and T90, L34 and A89 and T95, L34 and T90 and T95, D35 and F53 and I59, D35 and F53 and A89, D35 and F53 and T90, D35 and F53 and T95, D35 and I59 and A89, D35 and I59 and T90, D35 and I59 and T95, D35 and A89 and T90, D35 and A89 and T95, D35 and T90 and T95, F53 and I59 and A89, F53 and I59 and T90, F53 and I59 and T95, F53 and A89 and T90, F53 and A89 and T95, F53 and T90 and T95, I59 and A89 and T90, I59 and A89 and T95, I59 and T90 and T95, and A89 and T90 and T95.

In a 35th embodiment of the first aspect, which is also an embodiment of the 34th embodiment of the first aspect, the two or more amino acid positions comprise three amino acid positions, wherein the three amino acid positions are selected from the group consisting of SEQ ID NO:1 amino acid positions R10 and A33 and L34, R10 and A33 and D35, R10 and A33 and I59, R10 and A33 and A89, R10 and A33 and T90, R10 and A33 and T95, R10 and L34 and D35, R10 and L34 and I59, R10 and L34 and A89, R10 and L34 and T90, R10 and L34 and T95, R10 and D35 and I59, R10 and D35 and A89, R10 and D35 and T90, R10 and D35 and T95, R10 and A89 and T90, R10 and A89 and T95, R10 and T90 and T95, A33 and L34 and D35, A33 and L34 and I59, A33 and L34 and A89, A33 and L34 and T90, A33 and L34 and T95, A33 and D35 and I59, A33 and D35 and A89, A33 and D35 and T90, A33 and D35 and T95, A33 and I59 and A89, A33 and I59 and T90, A33 and I59 and T95, A33 and A89 and T90, A33 and A89 and T95, A33 and T90 and T95, L34 and D35 and I59, L34 and D35 and A89, L34 and D35 and T90, L34 and D35 and T95, L34 and I59 and A89, L34 and I59 and T90, L34 and I59 and T95, L34 and A89 and T90, L34 and A89 and T95, L34 and T90 and T95, D35 and I59 and A89, D35 and I59 and T90, D35 and I59 and T95, D35 and A89 and T90, D35 and A89 and T95, D35 and T90 and T95, I59 and A89 and T90, I59 and A89 and T95, I59 and T90 and T95, and A89 and T90 and T95.

In a 36th embodiment of the first aspect, which is also an embodiment of the 35th embodiment of the first aspect, the two or more amino acid positions comprise three amino acid positions, wherein the three amino acid positions are selected from the group consisting of SEQ ID NO:1 amino acid positions R10 and A33 and L34, R10 and A33 and D35, R10 and A33 and I59, R10 and L34 and D35, R10 and L34 and I59, R10 and D35 and I59, A33 and L34 and D35, A33 and L34 and I59, A33 and D35 and I59, and L34 and D35 and I59.

In a 37th embodiment of the first aspect, which is also an embodiment of the 36th embodiment of the first aspect, the two or more amino acid positions comprise three amino acid positions, wherein the three amino acid positions are selected from the group consisting of SEQ ID NO:1 amino acid positions R10 and A33 and D35, R10 and A33 and I59, and R10 and D35 and I59.

In a 38th embodiment of the first aspect, which is also an embodiment of the 37th embodiment of the first aspect, the two or more amino acid positions comprise three amino acid positions, wherein the three amino acid positions are R10 and A33 and D35 of SEQ ID NO: 1, or R10 and A33 and I59 of SEQ ID NO: 1.

In a 39th embodiment of the first aspect, which is also an embodiment of the eleventh, twelfth, 13th, 14th, 15th, 16th, 17th, 18th, 19th, 20th, 21st, 22nd, 23rd, 24th, 25th, 26th, 27th, 28th, 29th, 30th, 31st, 32nd, 33rd 34th, 35th, 36th, 37th and 38th embodiment of the first aspect, preferably of any one of the 28th, 29th, 30th, 31st, 32nd, 33rd, 34th, 35th, 36th, 37th and 38th embodiment of the first aspect, more preferably of any one of the 34th, 35th, 36th, 37th and 38th embodiment of the first aspect, in addition to the substitution at the three amino acid positions, the amino acid sequence of the polypeptide, preferably the glucose isomerase, comprises an amino acid substitution at at least one or more additional amino acid positions, wherein the one or more additional amino acid position is independently and individually selected from the group consisting of SEQ ID NO:1 amino acid positions 10, 33, 34, 35, 53, 59, 89, 90, and 95.

In a 40$^{th}$ embodiment of the first aspect, which is also an embodiment of the 39$^{th}$ embodiment of the first aspect, the one or more additional amino acid position is independently and individually selected from the group consisting of SEQ ID NO:1 amino acid positions of SEQ ID NO:1 R10, A33, L34, D35, F53, I59, A89, T90, and T95.

In a 41$^{st}$ embodiment of the first aspect, which is also an embodiment of the 39$^{th}$ embodiment of the first aspect, the one or more additional amino acid position is independently and individually selected from the group consisting of SEQ ID NO:1 amino acid positions 10, 33, 34, 35, 59, 89, 90, and 95.

In a 42$^{nd}$ embodiment of the first aspect, which is also an embodiment of the 41$^{st}$ embodiment of the first aspect, the one or more additional amino acid position is independently and individually selected from the group consisting of SEQ ID NO:1 amino acid positions R10, A33, L34, D35, I59, A89, T90, and T95.

In a 43$^{rd}$ embodiment of the first aspect, which is also an embodiment of the 39$^{th}$ embodiment of the first aspect, the one or more additional amino acid position is independently and individually selected from the group consisting of SEQ ID NO:1 amino acid positions 10, 33, 34, 35, and 59.

In a 44$^{th}$ embodiment of the first aspect, which is also an embodiment of the 43$^{rd}$ embodiment of the first aspect, the one or more additional amino acid position is independently and individually selected from the group consisting of SEQ ID NO:1 amino acid positions R10, A33, L34, D35, and I59.

In a 45$^{th}$ embodiment of the first aspect, which is also an embodiment of the eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{th}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{th}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$ and 44$^{th}$ embodiment of the first aspect, preferably of any one of the 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$ and 44$^{th}$ embodiment of the first aspect, preferably of any of the 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$ and 44$^{th}$ embodiment of the first aspect, more preferably any one of the 39$^{th}$, 40$^{th}$, 41$^{st}$, 42$^{nd}$, 43$^{rd}$, 44$^{th}$ embodiment of the first aspect, the two or more amino acid positions comprise four amino acid positions, wherein the four amino acid positions are selected from the group consisting of SEQ ID NO:1 amino acid positions R10 and A33 and L34 and D35, R10 and A33 and L34 and F53, R10 and A33 and L34 and I59, R10 and A33 and L34 and A89, R10 and A33 and L34 and T90, R10 and A33 and L34 and T95, R10 and A33 and D35 and F53, R10 and A33 and D35 and I59, R10 and A33 and D35 and A89, R10 and A33 and D35 and T90, R10 and A33 and D35 and T95, R10 and A33 and F53 and I59, R10 and A33 and F53 and A89, R10 and A33 and F53 and T90, R10 and A33 and F53 and T95, R10 and A33 and I59 and A89, R10 and A33 and I59 and T90, R10 and A33 and I59 and T95, R10 and A33 and A89 and T90, R10 and A33 and A89 and T95, R10 and A33 and T90 and T95, R10 and L34 and D35 and F53, R10 and L34 and D35 and I59, R10 and L34 and D35 and A89, R10 and L34 and D35 and T90, R10 and L34 and D35 and T95, R10 and L34 and F53 and I59, R10 and L34 and F53 and A89, R10 and L34 and F53 and T90, R10 and L34 and F53 and T95, R10 and L34 and I59 and A89, R10 and L34 and I59 and T90, R10 and L34 and I59 and T95, R10 and L34 and A89 and T90, R10 and L34 and A89 and T95, R10 and L34 and T90 and T95, R10 and D35 and F53 and I59, R10 and D35 and F53 and A89, R10 and D35 and F53 and T90, R10 and D35 and F53 and T95, R10 and D35 and I59 and A89, R10 and D35 and I59 and T90, R10 and D35 and I59 and T95, R10 and D35 and A89 and T90, R10 and D35 and A89 and T95, R10 and D35 and T90 and T95, R10 and F53 and I59 and A89, R10 and F53 and I59 and T90, R10 and F53 and I59 and T95, R10 and F53 and A89 and T90, R10 and F53 and A89 and T95, R10 and F53 and T90 and T95, R10 and I59 and A89 and T90, R10 and I59 and A89 and T95, R10 and I59 and T90 and T95, R10 and A89 and T90 and T95, A33 and L34 and D35 and F53, A33 and L34 and D35 and I59, A33 and L34 and D35 and A89, A33 and L34 and D35 and T90, A33 and L34 and D35 and T95, A33 and L34 and F53 and I59, A33 and L34 and F53 and A89, A33 and L34 and F53 and T90, A33 and L34 and F53 and T95, A33 and L34 and I59 and A89, A33 and L34 and I59 and T90, A33 and L34 and I59 and T95, A33 and L34 and A89 and T90, A33 and L34 and A89 and T95, A33 and L34 and T90 and T95, A33 and D35 and F53 and I59, A33 and D35 and F53 and A89, A33 and D35 and F53 and T90, A33 and D35 and F53 and T95, A33 and D35 and I59 and A89, A33 and D35 and I59 and T90, A33 and D35 and I59 and T95, A33 and D35 and A89 and T90, A33 and D35 and A89 and T95, A33 and D35 and T90 and T95, A33 and F53 and I59 and A89, A33 and F53 and I59 and T90, A33 and F53 and I59 and T95, A33 and F53 and A89 and T90, A33 and F53 and A89 and T95, A33 and F53 and T90 and T95, A33 and I59 and A89 and T90, A33 and I59 and A89 and T95, A33 and I59 and T90 and T95, A33 and A89 and T90 and T95, L34 and D35 and F53 and I59, L34 and D35 and F53 and A89, L34 and D35 and F53 and T90, L34 and D35 and F53 and T95, L34 and D35 and I59 and A89, L34 and D35 and I59 and T90, L34 and D35 and I59 and T95, L34 and D35 and A89 and T90, L34 and D35 and A89 and T95, L34 and D35 and T90 and T95, L34 and F53 and I59 and A89, L34 and F53 and I59 and T90, L34 and F53 and I59 and T95, L34 and F53 and A89 and T90, L34 and F53 and A89 and T95, L34 and F53 and T90 and T95, L34 and I59 and A89 and T90, L34 and I59 and A89 and T95, L34 and I59 and T90 and T95, L34 and A89 and T90 and T95, D35 and F53 and I59 and A89, D35 and F53 and I59 and T90, D35 and F53 and I59 and T95, D35 and F53 and A89 and T90, D35 and F53 and A89 and T95, D35 and F53 and T90 and T95, D35 and I59 and A89 and T90, D35 and I59 and A89 and T95, D35 and I59 and T90 and T95, D35 and A89 and T90 and T95, F53 and I59 and A89 and T90, F53 and I59 and A89 and T95, F53 and I59 and T90 and T95, F53 and A89 and T90 and T95, and I59 and A89 and T90 and T95.

In a 46$^{th}$ embodiment of the first aspect, which is also an embodiment of the 45$^{rd}$ embodiment of the first aspect, the two or more amino acid positions comprise four amino acid positions, wherein the four amino acid positions are selected from the group consisting of SEQ ID NO: 1 amino acid positions R10 and A33 and L34 and D35, R10 and A33 and L34 and I59, R10 and A33 and L34 and A89, R10 and A33 and L34 and T90, R10 and A33 and L34 and T95, R10 and A33 and D35 and I59, R10 and A33 and D35 and A89, R10 and A33 and D35 and T90, R10 and A33 and D35 and T95, R10 and A33 and I59 and A89, R10 and A33 and I59 and T90, R10 and A33 and I59 and T95, R10 and A33 and A89 and T90, R10 and A33 and A89 and T95, R10 and A33 and T90 and T95, R10 and L34 and D35 and I59, R10 and L34 and D35 and A89, R10 and L34 and D35 and T90, R10 and L34 and D35 and T95, R10 and L34 and I59 and A89, R10 and L34 and I59 and T90, R10 and L34 and I59 and T95, R10 and L34 and A89 and T90, R10 and L34 and A89 and T95, R10 and L34 and T90 and T95, R10 and D35 and I59 and A89, R10 and D35 and I59 and T90, R10 and D35 and I59 and T95, R10 and D35 and A89 and T90, R10 and D35 and A89 and T95, R10 and D35 and T90 and T95, R10 and I59 and A89 and T90, R10 and I59 and A89 and T95, R10 and I59 and T90 and T95, R10 and A89 and T90 and T95, A33 and L34 and D35 and I59, A33 and L34 and D35 and A89, A33 and L34 and D35 and T90, A33 and L34 and D35 and T95, A33 and L34 and I59 and A89, A33 and L34 and I59 and T90, A33 and L34 and I59 and T95, A33 and L34 and A89 and T90, A33 and L34 and A89 and T95, A33 and L34 and T90 and T95, A33 and D35 and I59 and A89, A33 and D35 and I59 and T90, A33 and D35 and I59 and T95, A33 and D35 and A89 and T90, A33 and D35 and A89 and T95, A33 and D35 and T90 and T95, A33 and I59 and A89 and T90, A33 and I59 and A89 and T95, A33 and I59 and T90 and T95, A33 and A89 and T90 and T95, L34 and D35 and I59 and A89, L34 and D35 and I59 and T90, L34 and D35 and I59 and T95, L34 and D35 and A89 and T90, L34 and D35 and A89 and T95, L34 and D35 and T90 and T95, L34 and I59 and A89 and T90, L34 and I59 and A89 and T95, L34 and I59 and T90 and T95, L34 and A89 and T90 and T95, and I59 and A89 and T90 and T95.

In a 47$^{th}$ embodiment of the first aspect, which is also an embodiment of the 46$^{th}$ embodiment of the first aspect, the two or more amino acid positions comprise four amino acid positions, wherein the four amino acid positions are selected from the group consisting of SEQ ID NO: 1 amino acid positions R10 and A33 and L34 and D35, R10 and A33 and L34 and I59, R10 and A33 and D35 and I59.

In a 48$^{th}$ embodiment of the first aspect, which is also an embodiment of the 47$^{th}$ embodiment of the first aspect, the two or more amino acid positions comprise four amino acid positions, wherein the four amino acid positions are R10 and A33 and D35 and I59 of SEQ ID NO: 1.

In a 49$^{th}$ embodiment of the first aspect, which is also an embodiment of the eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$ and 48$^{th}$ embodiment of the first aspect, preferably of any one of the 23$^{th}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{th}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$ and 48$^{th}$ embodiment of the first aspect, more preferably of any one of the 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$ and 48$^{th}$ embodiment of the first aspect, even more preferably of any one of the 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$ embodiment of the first aspect and most preferably of any one of the 45$^{th}$, 46$^{th}$, 47$^{th}$ and 48$^{th}$ embodiment of the first aspect, in addition to the substitution at the four amino acid positions, the amino acid sequence of the polypeptide, preferably the glucose isomerase, comprises an amino acid substitution at at least one or more additional amino acid positions, wherein the one or more additional amino acid position is independently and individually selected from the group consisting of SEQ ID NO: 1 amino acid positions 10, 33, 34, 35, 53, 59, 89, 90, and 95.

In a 50$^{th}$ embodiment of the first aspect, which is also an embodiment of the 49$^{th}$ embodiment of the first aspect, the one or more additional amino acid position is independently and individually selected from the group consisting of SEQ ID NO: 1 amino acid positions R10, A33, L34, D35, F53, I59, A89, T90, and T95.

In a 51$^{st}$ embodiment of the first aspect, which is also an embodiment of the 49$^{th}$ embodiment of the first aspect, the one or more additional amino acid position is independently and individually selected from the group consisting of SEQ ID NO: 1 amino acid positions 10, 33, 34, 35, 59, 89, 90, and 95.

In a 52$^{nd}$ embodiment of the first aspect, which is also an embodiment of the 51$^{st}$ embodiment of the first aspect, the one or more additional amino acid position is independently and individually selected from the group consisting of SEQ ID NO: 1 amino acid positions R10, A33, L34, D35, I59, A89, T90, and T95.

In a 53$^{rd}$ embodiment of the first aspect, which is also an embodiment of the 49$^{th}$ embodiment of the first aspect, the one or more additional amino acid position is independently and individually selected from the group consisting of SEQ ID NO: 1 amino acid positions 10, 33, 34, 35, and 59.

In a 54$^{th}$ embodiment of the first aspect, which is also an embodiment of the 53$^{rd}$ embodiment of the first aspect, the one or more additional amino acid position is independently and individually selected from the group consisting of SEQ ID NO:1 amino acid positions R10, A33, L34, D35, and I59.

In a 55$^{th}$ embodiment of the first aspect, which is also an embodiment of any one of the 3$^{rd}$, 17$^{th}$, 30$^{th}$, 41$^{st}$ and 51$^{st}$ embodiment of the first aspect, in addition to the substitution at the one or more amino acid positions, the amino acid sequence of the polypeptide, preferably the glucose isomerase, comprises an amino acid substitution at one more additional amino acid position, wherein the one more additional amino acid position is SEQ ID NO: 1 amino acid position 53.

In a 56$^{th}$ embodiment of the first aspect, which is also an embodiment of any one of the 4$^{th}$, 18$^{th}$, 31$^{st}$, 42$^{nd}$ and 52$^{nd}$ embodiment of the first aspect, in addition to the substitution at the one or more amino acid positions, the amino acid sequence of the polypeptide, preferably the glucose isomerase, comprises an amino acid substitution at one more additional amino acid position, wherein the one more additional amino acid position is of SEQ ID NO:1 amino acid positions F53.

In a preferred embodiment of the first aspect, which is also an embodiment of any one of the other embodiments of the first aspect, the amino acid sequence of the polypeptide, preferably the glucose isomerase, comprises an amino acid substitution at one or more amino acid positions, wherein the one or more amino acid positions is/are each and independently selected from the group consisting of SEQ ID NO: 1 amino acid positions 10, 33, 34, 35, 59, 89, 90, and 95, and wherein the polypeptide, preferably the glucose isomerase, comprises in addition an amino acid substitution at one more additional amino acid position at SEQ ID NO: 1 amino acid position 53.

In a preferred embodiment of the first aspect, which is also an embodiment of any one of the other embodiments of the first aspect, the amino acid sequence of the polypeptide, preferably the glucose isomerase, comprises an amino acid substitution at one or more amino acid positions, wherein the one or more amino acid positions is/are each and independently selected from the group consisting of SEQ ID NO: 1 amino acid positions R10, A33, L34, D35, I59, A89, T90, and T95, and wherein the polypeptide, preferably the glucose isomerase, comprises in addition an amino acid at one more additional amino acid position at SEQ ID NO: 1 amino acid position F53.

In a 57$^{th}$ embodiment of the first aspect, which is also an embodiment of any one of the 5$^{th}$, 19$^{th}$, 32$^{nd}$, 43$^{rd}$ and 53$^{rd}$ embodiment of the first aspect, in addition to the substitution at the one or more amino acid positions, the amino acid sequence of the polypeptide, preferably the glucose isomerase, comprises an amino acid substitution at at least one or more additional amino acid positions, wherein the one or more additional amino acid positions are independently and individually selected from the group consisting of SEQ ID NO: 1 amino acid positions 53, 89, 90, and 95.

In a 58$^{th}$ embodiment of the first aspect, which is also an embodiment of any one of the 6$^{th}$, 20$^{th}$, 33$^{rd}$, 44$^{th}$ and 54$^{th}$ embodiment of the first aspect, in addition to the substitution at the one or more amino acid positions, the amino acid sequence of the polypeptide, preferably the glucose isomerase, comprises an amino acid substitution at at least one or more additional amino acid positions, wherein the one or more additional amino acid positions are independently and individually selected from the group consisting of SEQ ID NO: 1 amino acid positions of SEQ ID NO: 1 F53, A89, T90, and T95.

In a 59$^{th}$ embodiment of the first aspect, which is also an embodiment of any one of the 7$^{th}$ and 21$^{st}$ embodiment of the first aspect, in addition to the substitution at the one or more amino acid positions, the amino acid sequence of the polypeptide, preferably the glucose isomerase, comprises an amino acid substitution at at least one or more additional amino acid positions, wherein the one or more additional amino acid positions are independently and individually selected from the group consisting of SEQ ID NO: 1 amino acid positions 34, 53, 59, 89, 90, and 95.

In a 60$^{th}$ embodiment of the first aspect, which is also an embodiment of any one of the 8$^{th}$ and 22$^{nd}$ embodiment of the first aspect, in addition to the substitution at the one or more amino acid positions, the amino acid sequence of the polypeptide, preferably the glucose isomerase, comprises an amino acid substitution at at least one or more additional amino acid positions, wherein the one or more additional amino acid positions are independently and individually selected from the group consisting of SEQ ID NO: 1 amino acid positions L34, F53, I59, A89, T90, and T95.

In a 61$^{st}$ embodiment of the first aspect, which is also an embodiment of the 9$^{th}$ embodiment of the first aspect, in addition to the substitution at the one amino acid position, the amino acid sequence of the polypeptide, preferably the glucose isomerase, comprises an amino acid substitution at at least one or more additional amino acid positions, wherein the one or more additional amino acid positions are independently and individually selected from the group consisting of SEQ ID NO: 1 amino acid positions 33, 34, 35, 53, 59, 89, 90, and 95.

In a 62$^{nd}$ embodiment of the first aspect, which is also an embodiment of the 10$^{th}$ embodiment of the first aspect, in addition to the substitution at the one amino acid position, the amino acid sequence of the polypeptide, preferably the glucose isomerase, comprises an amino acid substitution at at least one or more additional amino acid positions, wherein the one or more additional amino acid positions are independently and individually selected from the group consisting of SEQ ID NO: 1 amino acid positions A33, L34, D35, F53, I59, A89, T90, and T95.

In a 63$^{rd}$ embodiment of the first aspect, which is also an embodiment of any one of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$ and 62$^{nd}$, embodiment or of any one of the other embodiments of the first aspect, preferably of any of the eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$ and 62$^{nd}$, embodiment of the first aspect, more preferably of any one of the 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$. 59$^{th}$, 60$^{th}$, 61$^{st}$ and 62$^{nd}$ embodiment of the first aspect, even more preferably of any one of the 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, and 62$^{nd}$ embodiment of the first aspect, also even more preferably of any one of the 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$ and 62$^{nd}$ embodiment of the first aspect, also even more preferably of any one of the 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$. 59$^{th}$, 60$^{th}$, 61$^{st}$ and 62$^{nd}$ embodiment of the first aspect, and most preferably of the first aspect, the amino acid sequence of the polypeptide, preferably the glucose isomerase, comprises an amino acid substitution at one amino acid position of SEQ ID NO: 1, preferably at two amino acid positions of SEQ ID NO: 1, preferably at three amino acid positions of SEQ ID NO: 1, preferably at four amino acid positions of SEQ ID NO: 1, and more preferably at five amino acid positions of SEQ ID NO: 1, wherein each and any of the amino acid positions of SEQ ID NO: 1 is independently and individually selected from the group consisting of SEQ ID NO: 1 amino acid positions 10, 33, 35, 53, 59, 89, 90, and 95.

In a 64$^{th}$ embodiment of the first aspect, which is also an embodiment of the 63$^{rd}$ embodiment of the first aspect, the amino acid sequence of the polypeptide, preferably the glucose isomerase, comprises an amino acid substitution at two amino acid positions of SEQ ID NO: 1, preferably at three amino acid positions of SEQ ID NO: 1, preferably at four amino acid positions of SEQ ID NO: 1, more preferably at five amino acid positions of SEQ ID NO: 1, and most preferably at six amino acid positions of SEQ ID NO: 1, wherein each and any of the amino acid positions of SEQ ID NO: 1 is independently and individually selected from the group consisting of SEQ ID NO: 1 amino acid positions R10, A33, D35, F53, I59, A89, T90, and T95.

In a 65$^{th}$ embodiment of the first aspect, which is also an embodiment of any one of the 63$^{rd}$ and 64$^{th}$ embodiment of the first aspect, the amino acid sequence of the polypeptide, preferably the glucose isomerase, comprises an amino acid substitution at two amino acid positions of SEQ ID NO: 1, wherein each and any of the amino acid positions of SEQ ID NO: 1 is independently and individually selected from the group consisting of SEQ ID NO: 1 amino acid positions 10, 33, 35, 53, 59, 89, 90, and 95.

In a 66$^{th}$ embodiment of the first aspect, which is also an embodiment of any one of the 63$^{rd}$ and 64$^{th}$ embodiment of the first aspect, the amino acid sequence of the polypeptide, preferably the glucose isomerase, comprises an amino acid substitution at two amino acid positions of SEQ ID NO: 1, wherein each and any of the amino acid positions of SEQ ID NO: 1 is independently and individually selected from the group consisting of SEQ ID NO: 1 amino acid positions R10, A33, D35, F53, I59, A89, T90, and T95.

In a 67$^{th}$ embodiment of the first aspect, which is also an embodiment of any one of the 63$^{rd}$, 64$^{th}$, 65$^{th}$ and 66$^{th}$ embodiment of the first aspect, the amino acid sequence of the polypeptide, preferably the glucose isomerase, comprises an amino acid substitution at three amino acid positions of SEQ ID NO: 1, wherein each and any of the amino acid positions of SEQ ID NO: 1 is independently and individually selected from the group consisting of SEQ ID NO: 1 amino acid positions 10, 33, 35, 53, 59, 89, 90, and 95.

In a 68$^{th}$ embodiment of the first aspect, which is also an embodiment of any one of the 63$^{rd}$, 64$^{th}$, 65$^{th}$ and 66$^{th}$ embodiment of the first aspect, the amino acid sequence of the polypeptide, preferably the glucose isomerase, comprises an amino acid substitution at three amino acid positions of SEQ ID NO: 1, wherein each and any of the amino acid positions of SEQ ID NO: 1 is independently and individually selected from the group consisting of SEQ ID NO: 1 amino acid positions R10, A33, D35, F53, I59, A89, T90, and T95.

In a 69$^{th}$ embodiment of the first aspect, which is also an embodiment of any one of the 63$^{rd}$, 64$^{th}$, 65$^{th}$, 66$^{th}$, 67$^{th}$ and 68$^{th}$ embodiment of the first aspect, the amino acid sequence of the polypeptide, preferably the glucose isomerase, comprises an amino acid substitution at four amino acid positions of SEQ ID NO: 1, wherein each and any of the amino acid positions of SEQ ID NO: 1 is independently and individually selected from the group consisting of SEQ ID NO: 1 amino acid positions 10, 33, 35, 53, 59, 89, 90, and 95.

In a 70$^{th}$ embodiment of the first aspect, which is also an embodiment of any one of the 63$^{rd}$, 64$^{th}$, 65$^{th}$, 66$^{th}$, 67$^{th}$ and 68$^{th}$ embodiment of the first aspect, the amino acid sequence of the polypeptide, preferably the glucose isomerase, comprises an amino acid substitution at four amino acid positions of SEQ ID NO: 1, wherein each and any of the amino acid positions of SEQ ID NO: 1 is independently and individually selected from the group consisting of SEQ ID NO: 1 amino acid positions R10, A33, D35, F53, I59, A89, T90, and T95.

In a 71$^{st}$ embodiment of the first aspect, which is also an embodiment of any one of the 63$^{rd}$, 64$^{th}$, 65$^{th}$, 66$^{th}$, 67$^{th}$, 68$^{th}$, 69$^{th}$ and 70$^{th}$ embodiment of the first aspect, the amino acid sequence of the polypeptide, preferably the glucose isomerase, comprises an amino acid substitution at five amino acid positions of SEQ ID NO: 1, wherein each and any of the amino acid positions of SEQ ID NO: 1 is independently and individually selected from the group consisting of SEQ ID NO: 1 amino acid positions 10, 33, 35, 53, 59, 89, 90, and 95.

In a 72$^{nd}$ embodiment of the first aspect, which is also an embodiment of any one of the 63$^{th}$, 64$^{th}$, 65$^{th}$, 66$^{th}$, 67$^{th}$, 68$^{th}$, 69$^{th}$ and 70$^{th}$ embodiment of the first aspect, the amino acid sequence of the polypeptide, preferably the glucose isomerase, comprises an amino acid substitution at five amino acid positions of SEQ ID NO: 1, wherein each and any of the amino acid positions of SEQ ID NO: 1 is independently and individually selected from the group consisting of SEQ ID NO: 1 amino acid positions R10, A33, D35, F53, I59, A89, T90, and T95.

In a preferred embodiment of the first aspect, which is also an embodiment of any one of the 63$^{rd}$, 64$^{th}$, 65$^{th}$, 66$^{th}$, 67$^{th}$, 68$^{th}$, 69$^{th}$, 70$^{th}$, 71$^{st}$, and 72$^{nd}$ embodiment or any other embodiment of the first aspect, the amino acid sequence of the polypeptide, preferably the glucose isomerase, comprises an amino acid substitution at one amino acid position of SEQ ID NO: 1, preferably at two amino acid positions of SEQ ID NO: 1, preferably at three amino acid positions of SEQ ID NO: 1, preferably at four amino acid positions of SEQ ID NO: 1, and more preferably at five amino acid positions of SEQ ID NO: 1, wherein each and any of the amino acid positions of SEQ ID NO: 1 is independently and individually selected from the group consisting of SEQ ID NO: 1 amino acid positions 10, 33, 89, 90, and 95.

In a preferred embodiment of the first aspect, which is also an embodiment of any one of the other embodiments of the first aspect, the one amino acid position is selected from the group consisting of SEQ ID NO: 1 amino acid positions 89, 90, 95, 10, and 33, wherein the polypeptide, preferably the glucose isomerase, in addition comprises an amino acid substitution at SEQ ID NO: 1 amino acid position 53.

In a preferred embodiment of the first aspect, which is also an embodiment of any one of the 63$^{rd}$, 64$^{th}$, 65$^{th}$, 66$^{th}$, 67$^{th}$, 68$^{th}$, 69$^{th}$, 70$^{th}$, 71$^{st}$, and 72$^{nd}$ embodiment or any other embodiment of the first aspect, the amino acid sequence of the polypeptide, preferably the glucose isomerase, comprises an amino acid substitution at one amino acid position of SEQ ID NO: 1, preferably at two amino acid positions of SEQ ID NO: 1, preferably at three amino acid positions of SEQ ID NO: 1, preferably at four amino acid positions of SEQ ID NO: 1, and more preferably at five amino acid positions of SEQ ID NO: 1, wherein each and any of the amino acid positions of SEQ ID NO: 1 is independently and individually selected from the group consisting of SEQ ID NO: 1 amino acid positions R10, A33, A89, T90, and T95.

In a preferred embodiment of the first aspect, which is also an embodiment of any one of the 63$^{rd}$, 64$^{th}$, 65$^{th}$, 66$^{th}$, 67$^{th}$, 68$^{th}$, 69$^{th}$, 70$^{th}$, 71$^{st}$, and 72$^{nd}$ embodiment or any other embodiment of the first aspect, the amino acid sequence of the polypeptide, preferably the glucose isomerase, comprises an amino acid substitution at one amino acid position of SEQ ID NO: 1, preferably at two amino acid positions of SEQ ID NO: 1, preferably at three amino acid positions of SEQ ID NO: 1, preferably at four amino acid positions of SEQ ID NO: 1, and more preferably at five amino acid positions of SEQ ID NO: 1, wherein each and any of the amino acid positions of SEQ ID NO: 1 is independently and individually selected from the group consisting of SEQ ID NO: 1 amino acid positions 10, 33, 89, 90, and 95, and wherein the polypeptide, preferably the glucose isomerase, in addition comprises one or more amino acid substitution at SEQ ID NO: 1 amino acid positions selected from the group consisting of SEQ ID NO: 1 amino acid position 35, 53, and/or 59.

In a preferred embodiment of the first aspect, which is also an embodiment of any one of the 63$^{th}$, 64$^{th}$, 65$^{th}$, 66$^{th}$, 67$^{th}$, 68$^{th}$, 69$^{th}$, 70$^{th}$, 71$^{st}$, and 72$^{nd}$ embodiment or any other embodiment of the first aspect, the amino acid sequence of the polypeptide, preferably the glucose isomerase, comprises an amino acid substitution at one amino acid position of SEQ ID NO: 1, preferably at two amino acid positions of SEQ ID NO: 1, preferably at three amino acid positions of SEQ ID NO: 1, preferably at four amino acid positions of SEQ ID NO: 1, and more preferably at five amino acid positions of SEQ ID NO: 1, wherein each and any of the amino acid positions of SEQ ID NO: 1 is independently and individually selected from the group consisting of SEQ ID NO: 1 amino acid positions R10, A33, A89, T90, and T95, and wherein the polypeptide, preferably the glucose isomerase, in addition comprises one or more amino acid substitution at SEQ ID NO: 1 amino acid positions selected from the group consisting of SEQ ID NO: 1 amino acid position D35, F53, and/or I59.

In a 73$^{rd}$ embodiment of the first aspect, which is also an embodiment of any one of the 63$^{th}$, 64$^{th}$, 65$^{th}$, 66$^{th}$, 67$^{th}$, 68$^{th}$, 69$^{th}$, 70$^{th}$, 71$^{st}$, and 72$^{nd}$ embodiment or of any one of the other embodiments of the first aspect, the amino acid sequence of the polypeptide, preferably the glucose isomerase, comprises an amino acid substitution at two or more amino acid positions of SEQ ID NO: 1, wherein the two amino acid positions are selected from the group consisting of SEQ ID NO: 1 amino acid positions 10 and 33, 10 and 35, 10 and 53, 10 and 59, 10 and 89, 10 and 90, 10 and 95, 33 and 35, 33 and 53, 33 and 59, 33 and 90, 33 and 95, 35 and 53, 35 and 59, 35 and 90, 35 and 95, 53 and 89, 53 and 90, 53 and 95, 59 and 90, 89 and 90, 89 and 95, and 90 and 95, preferably SEQ ID NO: 1 amino acid positions 10 and 33, 10 and 53, 10 and 89, 10 and 90, 10 and 95, 33 and 90, 53 and 90, 53 and 95, 89 and 90, 89 and 95, and 90 and 95.

In a preferred embodiment of the first aspect, which is also an embodiment of any one of the other embodiments of the first aspect, the amino acid sequence of the polypeptide, preferably the glucose isomerase, comprises an amino acid substitution at two or more amino acid positions of SEQ ID NO: 1, wherein the two amino acid positions are selected from the group consisting of SEQ ID NO: 1 amino acid positions 10 and 53, 33 and 53, 35 and 53, 53 and 89, 53 and 90, and 53 and 95.

In a preferred embodiment of the first aspect, which is also an embodiment of any one of the other embodiments of the first aspect, the amino acid sequence of the polypeptide, preferably the glucose isomerase, comprises an amino acid substitution at two or more amino acid positions of SEQ ID NO: 1, wherein the two amino acid positions are SEQ ID NO: 1 amino acid positions 53 and 90.

In a preferred embodiment of the first aspect, which is also an embodiment of any one of the other embodiments of the first aspect, the amino acid sequence of the polypeptide, preferably the glucose isomerase, comprises an amino acid substitution at two or more amino acid positions of SEQ ID NO: 1, wherein the two amino acid positions are SEQ ID NO: 1 amino acid positions 53 and 95.

In a 74$^{th}$ embodiment of the first aspect, which is also an embodiment of any one of the 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$ and 73$^{rd}$ embodiment or of any one of the other embodiments of the first aspect, the amino acid sequence of the polypeptide, preferably the glucose isomerase, comprises an amino acid substitution at two amino acid positions of SEQ ID NO: 1 selected from the group consisting of SEQ ID NO: 1 amino acid positions R10 and A33, R10 and D35, R10 and F53, R10 and I59, R10 and A89, R10 and T90, R10 and T95, A33 and D35, A33 and F53, A33 and I59, A33 and T90, A33 and T95, D35 and F53, D35 and I59, D35 and T90, D35 and T95, F53 and T90, F53 and T95, I59 and T90, A89 and T90, A89 and T95, and T90 and T95, preferably SEQ ID NO: 1 amino acid positions R10 and A33, R10 and F53, R10 and A89, R10 and T90, R10 and T95, A33 and T90, F53 and T90, F53 and T95, A89 and T90, A89 and T95, and T90 and T95.

In a 75$^{th}$ embodiment of the first aspect, which is also an embodiment of any one of the 73$^{rd}$ and 74$^{th}$ embodiment of the first aspect or of any one of the other embodiments, one, two or three additional amino acid positions are independently and individually selected from the group consisting of SEQ ID NO: 1 amino acid positions 10, 33, 34, 35, 53, 59, 89, 90, and 95.

In a 76$^{th}$ embodiment of the first aspect, which is also an embodiment of the 75$^{th}$ embodiment of the first aspect, the one, two or three additional amino acid positions are independently and individually selected from the group consisting of SEQ ID NO: 1 amino acid positions R10, A33, L34, D35, F53 I59, A89, T90, and T95.

In a 77$^{th}$ embodiment of the first aspect, which is also an embodiment of any one of the 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$ and 76$^{th}$ embodiment or of any one of the other embodiments of the first aspect, the amino acid sequence of the polypeptide, preferably the glucose isomerase, comprises an amino acid substitution at two amino acid positions of SEQ ID NO: 1 selected from the group consisting of SEQ ID NO: 1 amino acid positions (i) 10 and 33, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions 34, 35, 53, 59, 89, 90, and 95, preferably SEQ ID NO: 1 amino acid positions 35, 53, 59, 90 or 95; and (ii) 10 and 35, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions 33, 34, 53, 59, 89, 90, and 95, preferably SEQ ID NO: 1 amino acid positions 33, 53, 59, or 90; and (iii) 10 and 53, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions 33, 34, 35, 59, 89, 90, and 95, preferably SEQ ID NO: 1 amino acid positions 33, 35, 90 or 95; and (iv) 10 and 59, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions 33, 34, 35, 53, 89, 90, and 95, preferably SEQ ID NO: 1 amino acid positions 33, 35, or 90; and (v) 10 and 89, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions 33, 34, 35, 53, 59, 90, and 95, preferably 90 or 95; and (vi) 10 and 90, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions 33, 34, 35, 53, 59, 89, and 95, preferably SEQ ID NO: 1 amino acid positions 33, 35, 53, 59, 89, or 95; and (vii) 10 and 95, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions 33, 34, 35, 53, 59, 89, and 90, preferably SEQ ID NO: 1 amino acid positions 33, 35, 53, 89 or 90; and
(viii) 33 and 90, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions 10, 34, 35, 53, 59, 89, and 95, preferably SEQ ID NO: 1 amino acid positions 10, 35, 53, 59, or 95; and
(ix) 33 and 95, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions 10, 34, 35, 53, 59, 89, and 90, preferably SEQ ID NO: 1 amino acid positions 10, 35, 53, 59, or 90; and
(x) 53 and 90, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions 10, 33, 34, 35, 59, 89, and 95, preferably SEQ ID NO: 1 amino acid positions 10, 33, 35, or 95; and
(xi) 53 and 95, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions 10, 33, 34, 35, 59, 89, and 90, preferably SEQ ID NO: 1 amino acid positions 10, 33, 35, or 95; and
(xii) 89 and 90, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions 10, 33, 34, 35, 53, 59, and 95, preferably SEQ ID NO: 1 amino acid positions 10 or 95; and
(xiii) 89 and 95, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions 10, 33, 34, 35, 53, 59, and 90, preferably SEQ ID NO: 1 amino acid positions 10 or 90; and
(xiv) 90 and 95, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions 10, 33, 34, 35, 53, 59, and 89, preferably SEQ ID NO: 1 amino acid positions 10, 33, 35, 53, or 89.

In a 78th embodiment of the first aspect, which is also an embodiment of any one of the 63rd, 64th, 65th, 66th, 67th, 68th, 69th, 70th, 71st, 72nd, 73rd, 74th, 75th, 76th and 77th embodiment or of any one of other embodiments of the first aspect, the amino acid sequence of the polypeptide, preferably the glucose isomerase, comprises an amino acid substitution at two amino acid positions of SEQ ID NO: 1 selected from the group consisting of SEQ ID NO: 1 amino acid positions
(i) R10 and A33, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions L34, D35, F53, I59, A89, T90, and T95, preferably SEQ ID NO: 1 amino acid positions D35, F53, I59, T90 or T95; and
(ii) R10 and D35, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions A33, L34, F53, I59, A89, T90, and T95, preferably SEQ ID NO:1 amino acid positions A33, F53, I59, or T90; and
(iii) R10 and F53, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions A33, L34, D35, I59, A89, T90, and T95, preferably SEQ ID NO:1 amino acid positions A33, D35, T90 or T95; and
(iv) R10 and I59, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions A33, L34, D35, F53, A89, T90, and T95, preferably SEQ ID NO:1 amino acid positions A33, D35, or T90; and
(v) R10 and A89, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions A33, L34, D35, F53, I59, T90, and T95, preferably SEQ ID NO:1 amino acid positions T90 or T95; and
(vi) R10 and T90, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions A33, L34, D35, F53, I59, A89, and T95, preferably SEQ ID NO:1 amino acid positions A33, D35, F53, I59, A89, or T95; and
(vii) R10 and T95, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions A33, L34, D35, F53, I59, A89, and T90, preferably SEQ ID NO:1 amino acid positions A33, D35, F53, A89 or T90; and (viii) A33 and T90, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions R10, L34, D35, F53, I59, A89, and T95, preferably SEQ ID NO:1 amino acid positions R10, D35, F53, I59, or T95; and (ix) A33 and T95, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions R10, L34, D35, F53, I59, A89, and T90, preferably SEQ ID NO: 1 amino acid positions R10, D35, F53, I59, or T90; and (x) F53 and T90, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions R10, A33, L34, D35, I59, A89, and T95, preferably SEQ ID NO:1 amino acid positions R10, A33, D35, or T95; and (xi) F53 and T95, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions R10, A33, L34, D35, I59, A89, and T90, preferably SEQ ID NO:1 amino acid positions R10, A33, D35, or T95; and (xii) A89 and T90, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions R10, A33, L34, D35, F53, I59, and T95, preferably SEQ ID NO:1 amino acid positions R10 or T95; and (xiii) A89 and T95, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions R10, A33, L34, D35, F53, I59, and T90, preferably SEQ ID NO:1 amino acid positions R10 or T90; and (xiv) T90 and T95, wherein the amino acid sequence of the polypeptide, preferably the glucose isomerase, comprises an additional amino acid substitution at one or two or three further amino acid positions, wherein the one or two or three further amino acid positions are independently and individually selected from the group consisting of SEQ ID NO: 1 amino acid positions R10, A33, L34, D35, F53, I59, and A89, preferably SEQ ID NO:1 amino acid positions R10, A33, D35, F53, or A89.

In a preferred embodiment of the first aspect, which is also an embodiment of any one of the other embodiments of the first aspect, the amino acid sequence of the polypeptide, preferably the glucose isomerase, comprises an amino acid substitution at two or more amino acid positions of SEQ ID NO: 1, wherein the two amino acid positions are selected from the group consisting of SEQ ID NO: 1 amino acid positions 10 and 33, 10 and 35, 10 and 59, 10 and 89, 10 and 90, 10 and 95, 33 and 35, 33 and 59, 33 and 90, 33 and 95, 35 and 59, 35 and 90, 35 and 95, 59 and 90, 89 and 90, 89 and 95, and 90 and 95, preferably SEQ ID NO: 1 amino acid positions 10 and 33, 10 and 89, 10 and 90, 10 and 95, 33 and 90, 33 and 95, 89 and 90, 89 and 95, and 90 and 95.

In a preferred embodiment of the first aspect, which is also an embodiment of any one of the other embodiments of the first aspect, the amino acid sequence of the polypeptide, preferably the glucose isomerase, comprises an amino acid substitution at the two amino acid positions, wherein the two amino acid positions are selected from the group consisting of SEQ ID NO: 1 amino acid positions 10 and 33, 10 and 89, 10 and 90, 10 and 95, 33 and 90, 33 and 95, 89 and 90, 89 and 95, and 90 and 95.

In a preferred embodiment of the first aspect, which is also an embodiment of any one of the other embodiments of the first aspect, the two or more amino acid are selected from the group consisting of SEQ ID NO: 1 amino acid positions 10 and 33, 10 and 89, 10 and 90, 10 and 95, 33 and 90, 33 and 95, 89 and 90, 89 and 95, and 90 and 95, wherein the polypeptide, preferably the glucose isomerase, in addition comprises an amino acid substitution at SEQ ID NO: 1 amino acid position 53.

In yet another preferred embodiment of the first aspect, which is also an embodiment of any one of the other embodiments of the first aspect, the amino acid sequence of the polypeptide, preferably the glucose isomerase, comprises an amino acid substitution at the two amino acid positions selected from the group of SEQ ID NO: 1 amino acid positions 90 and 95, or 10 and 89, or 89 and 90, or 89 and 95.

In a preferred embodiment of the first aspect, which is also an embodiment of any one of the other embodiments of the first aspect, the amino acid sequence of the polypeptide, preferably the glucose isomerase, comprises an amino acid substitution at two amino acid positions of SEQ ID NO: 1 selected from the group consisting of SEQ ID NO: 1 amino acid positions R10 and A33, R10 and D35, R10 and I59, R10 and A89, R10 and T90, R10 and T95, A33 and D35, A33 and I59, A33 and T90, A33 and T95, D35 and I59, D35 and T90, D35 and T95, I59 and T90, A89 and T90, A89 and T95, and T90 and T95, preferably SEQ ID NO: 1 amino acid positions R10 and A33, R10 and A89, R10 and T90, R10 and T95, A33 and T90, A33 and T95, A89 and T90, A89 and T95, and T90 and T95.

In a preferred embodiment of the first aspect, which is also an embodiment of any one of the other embodiments of the first aspect, the amino acid sequence of the polypeptide, preferably the glucose isomerase, comprises an amino acid substitution at two amino acid positions of SEQ ID NO: 1 selected from the group consisting of SEQ ID NO: 1 amino acid positions 10 and 33, 10 and 35, 10 and 59, 10 and 89, 10 and 90, 10 and 95, 33 and 35, 33 and 59, 33 and 90, 33 and 95, 35 and 59, 35 and 90, 35 and 95, 59 and 90, 89 and 90, 89 and 95, and 90 and 95, preferably SEQ ID NO: 1 amino acid positions 10 and 33, 10 and 89, 10 and 90, 10 and 95, 33 and 90, 89 and 90, 89 and 95, and 90 and 95, and in addition comprises an amino acid substitution at one more additional amino acid position, wherein the one more additional amino acid position is SEQ ID NO: 1 amino acid position 53.

In a preferred embodiment of the first aspect, which is also an embodiment of any one of the other embodiments of the first aspect, the amino acid sequence of the polypeptide, preferably the glucose isomerase, comprises an amino acid substitution at two amino acid positions of SEQ ID NO: 1 selected from the group consisting of SEQ ID NO: 1 amino acid positions R10 and A33, R10 and D35, R10 and I59, R10 and A89, R10 and T90, R10 and T95, A33 and D35, A33 and I59, A33 and T90, A33 and T95, D35 and I59, D35 and T90, D35 and T95, I59 and T90, A89 and T90, A89 and T95, and T90 and T95, preferably SEQ ID NO: 1 amino acid positions R10 and A33, R10 and A89, R10 and T90, R10 and T95, A33 and T90, A89 and T90, A89 and T95, and T90 and T95, and in addition comprises an amino acid substitution at one more additional amino acid position, wherein the one more additional amino acid position is SEQ ID NO: 1 amino acid position F53.

In a 79$^{th}$ embodiment of the first aspect, which is also an embodiment of any one of the 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$ and 78$^{th}$ embodiment or of any one of the other embodiments of the first aspect, the amino acid sequence of the polypeptide, preferably the glucose isomerase, comprises an amino acid substitution at three amino acid positions of SEQ ID NO: 1 selected from the group consisting of SEQ ID NO:1 amino acid positions 10 and 33 and 35, 10 and 33 and 53, 10 and 33 and 59, 10 and 33 and 90, 10 and 33 and 95, 10 and 35 and 53, 10 and 35 and 59, 10 and 35 and 90, 10 and 35 and 95, 10 and 53 and 90, 10 and 53 and 95, 10 and 59 and 90, 10 and 89 and 90, 10 and 89 and 95, 10 and 90 and 95, 33 and 35 and 59, 33 and 35 and 90, 33 and 53 and 90, 33 and 53 and 95, 33 and 59 and 90, 33 and 90 and 95, 35 and 53 and 90, 35 and 53 and 95, 35 and 59 and 90, 53 and 90 and 95, and 89 and 90 and 95, preferably SEQ ID NO:1 amino acid positions 10 and 33 and 53, 10 and 33 and 90, 10 and 33 and 95, 10 and 53 and 90, 10 and 53 and 95, 10 and 89 and 90, 10 and 89 and 95, 10 and 90 and 95, 33 and 53 and 90, 33 and 53 and 95, 33 and 90 and 95, 53 and 90 and 95, and 89 and 90 and 95, more preferably SEQ ID NO:1 amino acid positions 10 and 53 and 90, 10 and 53 and 95, and 10 and 90 and 95.

In a preferred embodiment of the first aspect, which is also an embodiment of any one of the other embodiments of the first aspect, the polypeptide, preferably the glucose isomerase, comprises an amino acid substitution at three or more amino acid positions, wherein the three amino acid positions are selected from the group consisting of SEQ ID NO: 1 amino acid positions 10 and 33 and 35, 10 and 33 and 59, 10 and 33 and 90, 10 and 33 and 95, 10 and 35 and 59, 10 and 35 and 90, 10 and 35 and 95, 10 and 59 and 90, 10 and 89 and 90, 10 and 89 and 95, 10 and 90 and 95, 33 and 35 and 59, 33 and 35 and 90, 33 and 59 and 90, 33 and 90 and 95, 35 and 59 and 90, and 89 and 90 and 95.

Preferably, the three or more amino acid positions are the three amino acid positions SEQ ID NO: 1 amino acid positions 90, 95 and 10.

More preferably, the polypeptide, preferably the glucose isomerase, comprises in addition to the substitution at the one or more amino acid positions an additional amino acid substitution at SEQ ID NO: 1 amino acid position 53.

In an 80$^{th}$ embodiment of the first aspect, which is also an embodiment of any one of the 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$ and the 79$^{th}$ embodiment or of any one of the other embodiments of the first aspect, the amino acid sequence of the polypeptide, preferably the glucose isomerase, comprises an amino acid substitution at three amino acid positions of SEQ ID NO: 1 selected from the group consisting of SEQ ID NO:1 amino acid positions R10 and A33 and D35, R10 and A33 and F53, R10 and A33 and I59, R10 and A33 and T90, R10 and A33 and T95, R10 and D35 and F53, R10 and D35 and I59, R10 and D35 and T90, R10 and D35 and T95, R10 and F53 and T90, R10 and F53 and T95, R10 and I59 and T90, R10 and A89 and T90, R10 and A89 and T95, R10 and T90 and T95, A33 and D35 and I59, A33 and D35 and T90, A33 and F53 and T90, A33 and F53 and T95, A33 and I59 and T90, A33 and T90 and T95, D35 and F53 and T90, D35 and F53 and T95, D35 and I59 and T90, F53 and T90 and T95, and A89 and T90 and T95, preferably SEQ ID NO:1 amino acid positions R10 and A33 and F53, R10 and A33 and T90, R10 and A33 and T95, R10 and F53 and T90, R10 and F53 and T95, R10 and A89 and T90, R10 and A89 and T95, R10 and T90 and T95, A33 and F53 and T90, A33 and F53 and T95, A33 and T90 and T95, F53 and T90 and T95, and A89 and T90 and T95, more preferably SEQ ID NO:1 amino acid positions R10 and F53 and T90, R10 and F53 and T95, and R10 and T90 and T95.

In an 81$^{st}$ embodiment of the first aspect, which is also an embodiment of any one of the 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$ and the 80$^{th}$ embodiment or of any one of the other embodiments of the first aspect, the amino acid sequence of the polypeptide, preferably the glucose isomerase, comprises SEQ ID: 13 and/or SEQ ID NO: 16.

In an 82$^{nd}$ embodiment of the first aspect, which is also an embodiment of the 79$^{th}$ or 81$^{st}$ embodiment of the first aspect, one or two additional amino acid positions are independently and individually selected from the group consisting of SEQ ID NO 1 amino acid positions 10, 33, 34, 35, 53, 59, 89, 90, and 95.

In an 83$^{rd}$ embodiment of the first aspect, which is also an embodiment of the 82$^{nd}$ embodiment of the first aspect, the one or two additional amino acid positions are independently and individually selected from the group consisting of SEQ ID NO: 1 amino acid positions R10, A33, L34, D35, F53, I59, A89, T90, and T95.

In an 84$^{th}$ embodiment of the first aspect, which is also an embodiment of any one of the 63$^{rd}$, 64$^{th}$, 71$^{st}$, 72$^{nd}$, 65$^{th}$, 66$^{th}$, 67$^{th}$, 68$^{th}$, 69$^{th}$, 70$^{th}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$ and 83$^{rd}$ embodiment or of any one of the other embodiments of the first aspect, the amino acid sequence of the polypeptide, preferably the glucose isomerase, comprises an amino acid substitution at three amino acid positions of SEQ ID NO: 1 selected from the group consisting of SEQ ID NO:1 amino acid positions (i) 10 and 33 and 35, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions 34, 53, 59, 89, 90, and 95, preferably of SEQ ID NO: 1 amino acid positions 59 and 90; and (ii) 10 and 33 and 53, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions 34, 35, 59, 89, 90, and 95, preferably of SEQ ID NO: 1 amino acid positions 90 and 95; and (iii) 10 and 33 and 59, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions 34, 35, 53, 89, 90, and 95, preferably of SEQ ID NO: 1 amino acid positions 35 and 90; and (iv) 10 and 33 and 90 wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions 34, 35, 53, 59, 89, and 95, preferably of SEQ ID NO: 1 amino acid positions 35, 53, and 95; and (v) 10 and 33 and 95 wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO:1 amino acid positions 34, 35, 53, 59, 89, and 90, preferably of SEQ ID NO: 1 amino acid positions 35, 53, and 90; and (vi) 10 and 35 and 53, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions 33, 34, 59, 89, 90, and 95, preferably of SEQ ID NO: 1 amino acid positions 90 or 95; and (vii) 10 and 35 and 59, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions 33, 34, 53, 89, 90, and 95, preferably of SEQ ID NO:1 amino acid positions 33 and 90; and (viii) 10 and 35 and 90, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO:1 amino acid positions 33, 34, 53, 59, 89, and 95, preferably of SEQ ID NO:1 amino acid positions 33, 53, 59 and 95; and (ix) 10 and 35 and 95, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO:1 amino acid positions 33, 34, 53, 59, 89, and 90, preferably of SEQ ID NO:1 amino acid positions 33, 53, 59 and 90; and (x) 10 and 53 and 90, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions 33, 34, 35, 59, 89, and 95, preferably of SEQ ID NO:1 amino acid positions 33, 35 and 95; and (xi) 10 and 53 and 95, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO:1 amino acid positions 33, 34, 35, 59, 89, and 90, preferably of SEQ ID NO:1 amino acid positions 33, 35 and 90; and (xii) 10 and 59 and 90, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO:1 amino acid positions of SEQ ID NO:1 33, 34, 35, 53, 89, and 95, preferably of SEQ ID NO:1 amino acid positions 33 and 35; and (xiii) 10 and 89 and 90, wherein the amino acid sequence of the polypeptide, preferably the glucose isomerase, comprises an additional amino acid substitution at one further SEQ ID NO:1 amino acid position 33, 34, 35, 53, 59, and 95, preferably at SEQ ID NO:1 amino acid position 95; and (xiv) 10 and 90 and 95, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO:1 amino acid positions 33, 34, 35, 53, 59, and 89, preferably of SEQ ID NO:1 amino acid positions 33, 35, 53 and 89; and (xv) 33 and 53 and 90, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO:1 amino acid positions 10, 34, 35, 59, 89, and 95, preferably of SEQ ID NO:1 amino acid positions 10 and 95; and (xvi) 33 and 53 and 95, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions 10, 34, 35, 59, 89, and 90, preferably of SEQ ID NO:1 amino acid positions 10 and 90; and (xvii) 33 and 90 and 95, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO:1 amino acid positions 10, 34, 35, 53, 59, and 89, preferably of SEQ ID NO:1 amino acid positions 10 and 53; and (xviii) 53 and 90 and 95, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO:1 amino acid positions of SEQ ID NO:1 10, 33, 34, 35, 59, and 89, preferably of SEQ ID NO:1 amino acid positions 10, 33 and 35; and (xix) 89 and 90 and 95, wherein the amino acid sequence of the polypeptide, preferably the glucose isomerase, comprises an additional amino acid substitution at one further SEQ ID NO:1 amino acid position selected from the group consisting of SEQ ID NO: 1 amino acid positions 10, 33, 34, 35, 53, and 59, preferably at SEQ ID NO: 1 amino acid position 10.

In a preferred embodiment of the first aspect, which is also a preferred embodiment of any one of the other embodiments of the first aspect, the amino acid sequence of the polypeptide, preferably the glucose isomerase, comprises an amino acid substitution at four or more amino acid positions, wherein three of said four or more amino acid positions are SEQ ID NO: 1 amino acid positions 90, 95 and 10, and the fourth amino acid position is selected from the group consisting of SEQ ID NO: 1 amino acid positions 89, 33, 34, 35, 59, and 53, preferably wherein the fourth amino acid position is selected from the group consisting of SEQ ID NO: 1 amino acid positions 89 and 53.

In a preferred embodiment, the fourth amino acid position is the SEQ ID NO: 1 amino acid position 89.

In another preferred embodiment, the fourth amino acid position is the SEQ ID NO: 1 amino acid position 53.

In an 85$^{th}$ embodiment of the first aspect, which is also an embodiment of any one of the 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$ and 84$^{th}$ embodiment or of any one of the other embodiments of the first aspect, the amino acid sequence of the polypeptide, preferably the glucose isomerase, comprises an amino acid substitution at three amino acid positions of SEQ ID NO: 1 selected from the group consisting of SEQ ID NO: 1 amino acid positions (i) R10 and A33 and D35, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions L34, F53, I59, A89, T90, and T95, preferably of SEQ ID NO:1 amino acid positions I59 and T90; and (ii) R10 and A33 and F53, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions L34, D35, I59, A89, T90, and T95, preferably of SEQ ID NO:1 amino acid positions T90 and T95; and (iii) R10 and A33 and I59, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions L34, D35, F53, A89, T90, and T95, preferably of SEQ ID NO: 1 amino acid positions D35 and T90; and (iv) R10 and A33 and T90 wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions L34, D35, F53, I59, A89, and T95, preferably of SEQ ID NO: 1 amino acid positions D35, F53, and T95; and (v) R10 and A33 and T95 wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions L34, D35, F53, I59, A89, and T90, preferably of SEQ ID NO: 1 amino acid positions D35, F53, and T90; and (vi) R10 and D35 and F53, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions A33, L34, I59, A89, T90, and T95, preferably of SEQ ID NO: 1 amino acid positions T90 or T95; and (vii) R10 and D35 and I59, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions A33, L34, F53, A89, T90, and T95, preferably of SEQ ID NO: 1 amino acid positions A33 and T90; and (viii) R10 and D35 and T90, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions of SEQ ID NO:1 A33, L34, F53, I59, A89, and T95, preferably of SEQ ID NO: 1 amino acid positions A33, F53, I59 and T95; and (ix) R10 and D35 and T95, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions A33, L34, F53, I59, A89, and T90, preferably of SEQ ID NO: 1 amino acid positions A33, F53, I59 and T90; and (x) R10 and F53 and T90, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions A33, L34, D35, I59, A89, and T95, preferably of SEQ ID NO: 1 amino acid positions A33, D35 and T95; and
(xi) R10 and F53 and T95, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions of A33, L34, D35, I59, A89, and T90, preferably of SEQ ID NO: 1 amino acid positions A33, D35 and T90; and
(xii) R10 and I59 and T90, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions A33, L34, D35, F53, A89, and T95, preferably of SEQ ID NO: 1 amino acid positions A33 and D35; and
(xiii) R10 and A89 and T90, wherein the amino acid sequence of the polypeptide, preferably the glucose isomerase, comprises an additional amino acid substitution at one further amino acid position selected from the group consisting of SEQ ID NO: 1 amino acid positions A33, L34, D35, F53, I59, and T95, preferably at SEQ ID NO: 1 amino acid positionT95; and
(xiv) R10 and T90 and T95, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions A33, L34, D35, F53, I59, and A89, preferably of SEQ ID NO: 1 amino acid positions A33, D35, F53 and A89; and
(xv) A33 and F53 and T90, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions R10, L34, D35, I59, A89, and T95, preferably of SEQ ID NO:1 amino acid positions R10 and T95; and
(xvi) A33 and F53 and T95, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions R10, L34, D35, I59, A89, and T90, preferably of SEQ ID NO:1 amino acid positions R10 and T90; and
(xvii) A33 and T90 and T95, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions R10, L34, D35, F53, I59, and A89, preferably of SEQ ID NO:1 amino acid positions R10 and F53; and
(xviii) F53 and T90 and T95, wherein the amino acid sequence of the polypeptide, preferably the glucose isomerase, comprises an additional amino acid substitution at one or two further amino acid positions, wherein the one or two further amino acid positions are independently and individually selected from the group consisting of SEQ ID NO: 1 amino acid positions R10, A33, L34, D35, I59, and A89, preferably of SEQ ID NO:1 amino acid positions R10, A33 and D35; and
(xix) A89 and T90 and T95, wherein the amino acid sequence of the polypeptide, preferably the glucose isomerase, comprises an additional amino acid substitution at one further amino acid position selected from the group consisting of SEQ ID NO: 1 amino acid positions R10, A33, L34, D35, F53, and I59, preferably at SEQ ID NO: 1 amino acid position R10.

In a preferred embodiment of the first aspect, which is also an embodiment of any one of the other embodiments of the first aspect, the amino acid sequence of the polypeptide, preferably the glucose isomerase, comprises an amino acid substitution at three amino acid positions of SEQ ID NO: 1 selected from the group consisting of SEQ ID NO: 1 amino acid positions 10 and 33 and 35, 10 and 33 and 59, 10 and 33 and 90, 10 and 33 and 95, 10 and 35 and 59, 10 and 35 and 90, 10 and 35 and 95, 10 and 59 and 90, 10 and 89 and 90, 10 and 89 and 95, 10 and 90 and 95, 33 and 35 and 59, 33 and 35 and 90, 33 and 59 and 90, 33 and 90 and 95, 35 and 59 and 90, and 89 and 90 and 95, preferably selected from the group of SEQ ID NO:1 amino acid positions 10 and 33 and 90, 10 and 33 and 95, 10 and 89 and 90, 10 and 89 and 95, 10 and 90 and 95, 33 and 90 and 95, and 89 and 90 and 95.

In a preferred embodiment of the first aspect, which is also an embodiment of any one of the other embodiments of the first aspect, the amino acid sequence of the polypeptide, preferably the glucose isomerase, comprises an amino acid substitution at three amino acid positions of SEQ ID NO: 1 selected from the group consisting of SEQ ID NO: 1 amino acid positions R10 and A33 and D35, R10 and A33 and I59, R10 and A33 and T90, R10 and A33 and T95, R10 and D35 and I59, R10 and D35 and T90, R10 and D35 and T95, R10 and I59 and T90, R10 and A89 and T90, R10 and A89 and T95, R10 and T90 and T95, A33 and D35 and I59, A33 and D35 and T90, A33 and I59 and T90, A33 and T90 and T95, D35 and I59 and T90, and A89 and T90 and T95, preferably selected from the group of SEQ ID NO:1 amino acid positions R10 and A33 and T90, R10 and A33 and T95, R10 and A89 and T90, R10 and A89 and T95, R10 and T90 and T95, A33 and T90 and T95, and A89 and T90 and T95.

In a preferred embodiment of the first aspect, which is also an embodiment of any one of the other embodiments of the first aspect, the amino acid sequence of the polypeptide, preferably the glucose isomerase, comprises an amino acid substitution at three amino acid positions of SEQ ID NO: 1 selected from the group consisting of SEQ ID NO: 1 amino acid positions 10 and 33 and 35, 10 and 33 and 59, 10 and 33 and 90, 10 and 33 and 95, 10 and 35 and 59, 10 and 35 and 90, 10 and 35 and 95, 10 and 59 and 90, 10 and 89 and 90, 10 and 89 and 95, 10 and 90 and 95, 33 and 35 and 59, 33 and 35 and 90, 33 and 59 and 90, 33 and 90 and 95, 35 and 59 and 90, and 89 and 90 and 95, preferably selected from the group of SEQ ID NO:1 amino acid positions 10 and 33 and 90, 10 and 33 and 95, 10 and 89 and 90, 10 and 89 and 95, 10 and 90 and 95, 33 and 90 and 95, and 89 and 90 and 95, and in addition comprises an amino acid substitution at one more additional amino acid position, wherein the one more additional amino acid position is SEQ ID NO: 1 amino acid position 53.

In a preferred embodiment of the first aspect, which is also an embodiment of any one of the other embodiments of the first aspect, the amino acid sequence of the polypeptide, preferably the glucose isomerase, comprises an amino acid substitution at three amino acid positions of SEQ ID NO: 1 selected from the group consisting of SEQ ID NO: 1 amino acid positions R10 and A33 and D35, R10 and A33 and I59, R10 and A33 and T90, R10 and A33 and T95, R10 and D35 and I59, R10 and D35 and T90, R10 and D35 and T95, R10 and I59 and T90, R10 and A89 and T90, R10 and A89 and T95, R10 and T90 and T95, A33 and D35 and I59, A33 and D35 and T90, A33 and I59 and T90, A33 and T90 and T95, D35 and I59 and T90, and A89 and T90 and T95, preferably selected from the group of SEQ ID NO:1 amino acid positions R10 and A33 and T90, R10 and A33 and T95, R10 and A89 and T90, R10 and A89 and T95, R10 and T90 and T95, A33 and T90 and T95, and A89 and T90 and T95, and in addition comprises an amino acid substitution at one more additional amino acid position, wherein the one more additional amino acid position is SEQ ID NO: 1 amino acid position F53.

In an 86$^{th}$ embodiment of the first aspect, which is also an embodiment of any one of the 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$ and 85$^{th}$ embodiment or of any one of the other embodiments of the first aspect, the amino acid sequence of the polypeptide, preferably the glucose isomerase, comprises an amino acid substitution at SEQ ID NO: 1 amino acid positions selected from the group consisting of 10 and 33 and 35 and 59;
10 and 33 and 35 and 90;
10 and 33 and 35 and 95;
10 and 33 and 53 and 90;
10 and 33 and 53 and 95;
10 and 33 and 59 and 90;
10 and 33 and 90 and 95;
10 and 35 and 53 and 90;
10 and 35 and 53 and 95;
10 and 35 and 59 and 90;
10 and 35 and 90 and 95,
10 and 53 and 90 and 95,
10 and 59 and 90 and 95,
10 and 89 and 90 and 95,
33 and 53 and 90 and 95,
33 and 89 and 90 and 95,
34 and 89 and 90 and 95,
35 and 53 and 90 and 95,
35 and 89 and 90 and 95,
53 and 89 and 90 and 95,
59 and 89 and 90 and 95,
10 and 33 and 35 and 53 and 90,
10 and 33 and 35 and 53 and 95,
10 and 33 and 35 and 59 and 90;
10 and 33 and 35 and 59 and 95,
10 and 33 and 35 and 90 and 95,
10 and 33 and 53 and 90 and 95,
10 and 33 and 59 and 90 and 95,
10 and 33 and 89 and 90 and 95,
10 and 34 and 89 and 90 and 95,
10 and 35 and 53 and 59 and 90,
10 and 35 and 53 and 59 and 95,
10 and 35 and 53 and 90 and 95,
10 and 35 and 59 and 90 and 95,
10 and 35 and 89 and 90 and 95,
10 and 53 and 59 and 90 and 95,
10 and 53 and 89 and 90 and 95,
10 and 59 and 89 and 90 and 95,
33 and 34 and 89 and 90 and 95,
33 and 35 and 53 and 90 and 95,
33 and 35 and 89 and 90 and 95,
33 and 53 and 89 and 90 and 95,
33 and 59 and 89 and 90 and 95,
34 and 35 and 89 and 90 and 95,
34 and 53 and 89 and 90 and 95,
34 and 59 and 89 and 90 and 95,
35 and 53 and 89 and 90 and 95,
35 and 59 and 89 and 90 and 95,
53 and 59 and 89 and 90 and 95,
10 and 33 and 35 and 53 and 59 and 90,
10 and 33 and 35 and 53 and 59 and 95,
10 and 33 and 35 and 53 and 90 and 95
10 and 33 and 35 and 59 and 90 and 95,
10 and 33 and 35 and 89 and 90 and 95,
10 and 33 and 53 and 89 and 90 and 95,
10 and 33 and 59 and 89 and 90 and 95,
10 and 34 and 35 and 89 and 90 and 95,
10 and 34 and 53 and 89 and 90 and 95,
10 and 34 and 59 and 89 and 90 and 95,
10 and 35 and 53 and 59 and 90 and 95,
10 and 35 and 53 and 89 and 90 and 95,
10 and 35 and 59 and 89 and 90 and 95,
10 and 53 and 59 and 89 and 90 and 95,
33 and 34 and 35 and 89 and 90 and 95,
33 and 34 and 53 and 89 and 90 and 95,
33 and 34 and 59 and 89 and 90 and 95,
33 and 35 and 53 and 89 and 90 and 95,
33 and 35 and 59 and 89 and 90 and 95,
33 and 53 and 59 and 89 and 90 and 95,
34 and 35 and 53 and 89 and 90 and 95,
34 and 35 and 59 and 89 and 90 and 95,
34 and 53 and 59 and 89 and 90 and 95,
35 and 53 and 59 and 89 and 90 and 95,
10 and 33 and 35 and 53 and 59 and 90 and 95,
10 and 33 and 35 and 53 and 89 and 90 and 95,
10 and 33 and 35 and 59 and 89 and 90 and 95,
10 and 35 and 53 and 59 and 89 and 90 and 95,
33 and 34 and 35 and 53 and 89 and 90 and 95,
33 and 34 and 35 and 59 and 89 and 90 and 95,
33 and 34 and 53 and 59 and 89 and 90 and 95,
33 and 35 and 53 and 59 and 89 and 90 and 95,
34 and 35 and 53 and 59 and 89 and 90 and 95,
10 and 33 and 35 and 53 and 59 and 89 and 90 and 95, and
33 and 34 and 35 and 53 and 59 and 89 and 90 and 95.

In an 87$^{th}$ embodiment of the first aspect, which is also an embodiment of the 86$^{th}$ embodiment of the first aspect, the amino acid sequence of the polypeptide, preferably the glucose isomerase, comprises an amino acid substitution at SEQ ID NO: 1 amino acid positions selected from the group consisting of R10 and A33 and D35 and I59,
R10 and A33 and D35 and T90,
R10 and A33 and D35 and T95,
R10 and A33 and F53 and T90,
R10 and A33 and F53 and T95,
R10 and A33 and I59 and T90,
R10 and A33 and T90 and T95,
R10 and D35 and F53 and T90,
R10 and D35 and F53 and T95,
R10 and D35 and I59 and T90,
R10 and D35 and T90 and T95,
R10 and F53 and T90 and T95,
R10 and I59 and T90 and T95, R10 and A89 and T90 and T95,
A33 and F53 and T90 and T95,
A33 and A89 and T90 and T95,
L34 and A89 and T90 and T95,
D35 and F53 and T90 and T95,
D35 and A89 and T90 and T95,
F53 and A89 and T90 and T95,
I59 and A89 and T90 and T95,
R10 and A33 and D35 and F53 and T90,
R10 and A33 and D35 and F53 and T95,
R10 and A33 and D35 and I59 and T90,
R10 and A33 and D35 and I59 and T95,
R10 and A33 and D35 and T90 and T95,
R10 and A33 and F53 and T90 and T95,
R10 and A33 and I59 and T90 and T95,
R10 and A33 and A89 and T90 and T95,
R10 and L34 and A89 and T90 and T95,
R10 and D35 and F53 and I59 and T90,
R10 and D35 and F53 and I59 and T95,
R10 and D35 and F53 and T90 and T95,
R10 and D35 and I59 and T90 and T95,
R10 and D35 and A89 and T90 and T95,
R10 and F53 and I59 and T90 and T95,
R10 and F53 and A89 and T90 and T95,
R10 and I59 and A89 and T90 and T95,
A33 and L34 and A89 and T90 and T95,
A33 and D35 and F53 and T90 and T95,
A33 and D35 and A89 and T90 and T95,
A33 and F53 and A89 and T90 and T95,
A33 and I59 and A89 and T90 and T95,
L34 and D35 and A89 and T90 and T95,
L34 and F53 and A89 and T90 and T95,
L34 and I59 and A89 and T90 and T95,
D35 and F53 and A89 and T90 and T95,
D35 and I59 and A89 and T90 and T95,
F53 and I59 and A89 and T90 and T95,
R10 and A33 and D35 and F53 and I59 and T90,
R10 and A33 and D35 and F53 and I59 and T95,
R10 and A33 and D35 and F53 and T90 and T95
R10 and A33 and D35 and I59 and T90 and T95,
R10 and A33 and D35 and A89 and T90 and T95,
R10 and A33 and F53 and A89 and T90 and T95,
R10 and A33 and I59 and A89 and T90 and T95,
R10 and L34 and D35 and A89 and T90 and T95,
R10 and L34 and F53 and A89 and T90 and T95,
R10 and L34 and I59 and A89 and T90 and T95,
R10 and D35 and F53 and I59 and T90 and T95,
R10 and D35 and F53 and A89 and T90 and T95,
R10 and D35 and I59 and A89 and T90 and T95,
R10 and F53 and I59 and A89 and T90 and T95,
A33 and L34 and D35 and A89 and T90 and T95,
A33 and L34 and F53 and A89 and T90 and T95,
A33 and L34 and I59 and A89 and T90 and T95,
A33 and D35 and F53 and A89 and T90 and T95,
A33 and D35 and I59 and A89 and T90 and T95,
A33 and F53 and I59 and A89 and T90 and T95,
L34 and D35 and F53 and A89 and T90 and T95,
L34 and D35 and I59 and A89 and T90 and T95,
L34 and F53 and I59 and A89 and T90 and T95,
D35 and F53 and I59 and A89 and T90 and T95,
R10 and A33 and D35 and F53 and I59 and T90 and T95,
R10 and A33 and D35 and F53 and A89 and T90 and T95,
R10 and A33 and D35 and I59 and A89 and T90 and T95,
R10 and D35 and F53 and I59 and A89 and T90 and T95,
A33 and L34 and D35 and F53 and A89 and T90 and T95,
A33 and L34 and D35 and I59 and A89 and T90 and T95,
A33 and L34 and F53 and I59 and A89 and T90 and T95,
A33 and D35 and F53 and I59 and A89 and T90 and T95,
L34 and D35 and F53 and I59 and A89 and T90 and T95,
R10 and A33 and D35 and F53 and I59 and A89 and T90 and T95,
A33 and L34 and D35 and F53 and I59 and A89 and T90 and T95.

In an 88$^{th}$ embodiment of the first aspect, which is also an embodiment of any one of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 78$^{th}$, 77$^{th}$, 79$^{th}$, 80$^{th}$, 81$^{st}$, 82$^{nd}$, 83$^{rd}$, 84$^{th}$, 85$^{th}$, 86$^{th}$ and 87$^{th}$ embodiment or of any one of the other embodiments of the first aspect, preferably of any one of the eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$80$^{th}$, 81$^{st}$, 82$^{nd}$, 83$^{rd}$, 84$^{th}$, 85$^{th}$, 86$^{th}$, and 87$^{th}$ embodiment of the first aspect, preferably of any one of the 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$ 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$ and 87$^{th}$ embodiment of the first aspect, preferably of any one of the 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56th, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$. 78$^{th}$, 79$^{th}$, 80$^{th}$, 81$^{st}$, 82$^{nd}$, 83$^{rd}$, 84$^{th}$, 85$^{th}$, 86$^{th}$ and 87$^{th}$ embodiment of the first aspect, preferably of any one of the 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$ and 87$^{th}$ embodiment of the first aspect, more preferably of any one of the 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$ and 87$^{th}$ embodiment of the first aspect, even more preferable of any one of the 79$^{th}$, 80$^{th}$, 81$^{st}$, 82$^{nd}$, 83$^{rd}$, 84$^{th}$, 85$^{th}$, 86$^{th}$ and 87$^{th}$ embodiment of the first aspect, most preferably of any one of the 84$^{th}$, 85$^{th}$, 86$^{th}$ and 87$^{th}$ embodiment of the first aspect, the amino acid sequence of the polypeptide, preferably the glucose isomerase, comprises an amino acid substitution at one or more, preferably at all of the following positions (i) SEQ ID NO: 1 amino acid positions 10, 89, 90 and 95;
(ii) SEQ ID NO: 1 amino acid positions 10, 33, 53, 90 and 95; or
(iii) SEQ ID NO: 1 amino acid positions 10, 90 and 95.

In a preferred embodiment of the first aspect, which is also an embodiment of any one of the other embodiments of the first aspect, the amino acid sequence of the polypeptide, preferably the glucose isomerase, comprises an amino acid substitution at one or more, preferably at all of the following positions (i) SEQ ID NO: 1 amino acid positions 10, 89, 90 and 95;
(ii) SEQ ID NO: 1 amino acid positions 10, 33, 90 and 95; or
(iii) SEQ ID NO: 1 amino acid positions 10, 90 and 95;
preferably wherein the polypeptide, preferably the glucose isomerase, in addition comprises an amino acid substitution at one more additional amino acid position, wherein the one more additional amino acid position is SEQ ID NO: 1 amino acid position 53.

In an 89$^{th}$ embodiment of the first aspect, which is also an embodiment of any one of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$ 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 78$^{th}$, 77$^{th}$, 79$^{th}$, 80$^{th}$, 81$^{st}$, 82$^{nd}$, 83$^{rd}$, 84$^{th}$, 85$^{th}$, 86$^{th}$ and 87$^{th}$ embodiment or of any one of the other embodiments of the first aspect, preferably of any one of the eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38th39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$. 81$^{st}$, 82$^{nd}$, 83$^{rd}$, 84$^{th}$, 85$^{th}$, 86$^{th}$, and 87$^{th}$ embodiment of the first aspect, preferably of any one of the 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$ 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$ and 87$^{th}$ embodiment of the first aspect, preferably of any one of the 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$ and 87$^{th}$ embodiment of the first aspect, preferably of any one of the 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$ and 87$^{th}$ embodiment of the first aspect, more preferably of any one of the 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$ and 87$^{th}$ embodiment of the first aspect, even more preferable of any one of the 79$^{th}$, 80$^{th}$, 81$^{st}$, 82$^{nd}$, 83$^{rd}$, 84$^{th}$, 85$^{th}$, 86$^{th}$ and 87$^{th}$ embodiment of the first aspect, most preferably of any one of the 84$^{th}$, 85$^{th}$, 86$^{th}$ and 87$^{th}$ embodiment of the first aspect, the amino acid sequence of the polypeptide, preferably the glucose isomerase, comprises an amino acid substitution at one or more, preferably at all of the following positions (i) SEQ ID NO: 1 amino acid positions R10, A89, T90 and T95;

(ii) SEQ ID NO: 1 amino acid positions R10, A33, F53, T90 and T95; or (iii) SEQ ID NO: 1 amino acid positions R10, T90 and T95.

In a preferred embodiment of the first aspect, which is also an embodiment of any one of the other embodiments of the first aspect, the amino acid sequence of the polypeptide, preferably the glucose isomerase, comprises an amino acid substitution at one or more, preferably at all of the following positions, (i) SEQ ID NO: 1 amino acid positions R10, A89, T90 and T95;

(ii) SEQ ID NO: 1 amino acid positions R10, A33, T90 and T95; or (iii) SEQ ID NO: 1 amino acid positions R10, T90 and T95;

preferably wherein the polypeptide, preferably the glucose isomerase, in addition comprises an amino acid substitution at one more additional amino acid position, wherein the one more additional amino acid position is SEQ ID NO: 1 amino acid position F53.

In a 90$^{th}$ embodiment of the first aspect, which is also an embodiment of any one of the 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$ and 89$^{th}$ embodiment or of any one of the other embodiments of the first aspect, the amino acid sequence of the polypeptide, preferably the glucose isomerase, comprises an amino acid substitution at SEQ ID NO: 1 amino acid positions selected from the group consisting of SEQ ID NO: 1 amino acid positions (i) R10 and A33 and D35 and I59 and T90;

(ii) R10 and A33 and F53 and T90 and T95;

(iii) R10 and A33 and I59 and T90;

(iv) R10 and D35 and F53 and T90 and T95;

(v) R10 and F53 and T90;

(vi) R10 and F53 and T90 and T95;

(vii) R10 and F53 and T95; and (viii) R10 and A89 and T90 and T95.

In a preferred embodiment of the first aspect, which is also an embodiment of any one of the other embodiments of the first aspect, the amino acid sequence of the polypeptide, preferably the glucose isomerase, comprises an amino acid substitution at SEQ ID NO: 1 amino acid positions selected from the group consisting of SEQ ID NO: 1 amino acid positions (i) R10 and A33 and D35 and I59 and T90;

(ii) R10 and A33 and T90 and T95;

(iii) R10 and A33 and I59 and T90;

(iv) R10 and D35 and T90 and T95;

(v) R10 and T90;

(vi) R10 and T90 and T95;

(vii) R10 and T95; and (viii) R10 and A89 and T90 and T95, preferably wherein the polypeptide, preferably the glucose isomerase, in addition comprises an amino acid substitution at one more additional amino acid position, wherein the one more additional amino acid position is SEQ ID NO: 1 amino acid position F53.

In a 91$^{st}$ embodiment of the first aspect, which is also an embodiment of the 90$^{th}$ embodiment of the first aspect, the amino acid sequence of the polypeptide, preferably the glucose isomerase, comprises an amino acid substitution at SEQ ID NO: 1 amino acid positions selected from the group consisting of SEQ ID NO: 1 amino acid positions (i) R10 and A33 and D35 and I59 and T90;

(ii) R10 and A33 and F53 and T90 and T95;

(iii) R10 and A33 and I59 and T90;

(iv) R10 and D35 and F53 and T90 and T95;

(v) R10 and F53 and T90 and T95; and (vi) R10 and A89 and T90 and T95.

In a preferred embodiment of the first aspect, which is also an embodiment of any one of the other embodiments of the first aspect, the amino acid sequence of the polypeptide, preferably the glucose isomerase, comprises an amino acid substitution at SEQ ID NO: 1 amino acid positions selected from the group consisting of SEQ ID NO: 1 amino acid positions (i) R10 and A33 and D35 and I59 and T90;

(ii) R10 and A33 and T90 and T95;

(iii) R10 and A33 and I59 and T90;

(iv) R10 and D35 and T90 and T95;

(v) R10 and T90 and T95; and (vi) R10 and A89 and T90 and T95, preferably wherein the polypeptide, preferably the glucose isomerase, in addition comprises an amino acid substitution at one more additional amino acid position, wherein the one more additional amino acid position is SEQ ID NO: 1 amino acid position F53.

In a 92$^{nd}$ embodiment of the first aspect, which is also an embodiment of any one of the 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$ and 91$^{st}$ embodiment or of any one of the other embodiments of the first aspect, the amino acid sequence of the polypeptide, preferably the glucose isomerase, comprises an amino acid substitution at SEQ ID NO: 1 amino acid positions selected from the group consisting of SEQ ID NO: 1 amino acid positions
  (i) R10 and A33 and D35 and I59 and T90;
  (ii) R10 and A33 and F53 and T90 and T95;
  (iii) R10 and D35 and F53 and T90 and T95;
  (iv) R10 and F53 and T90 and T95; and
  (v) R10 and A89 and T90 and T95.

In a preferred embodiment of the first aspect, which is also an embodiment of any one of the other embodiments of the first aspect, the amino acid sequence of the polypeptide, preferably the glucose isomerase, comprises an amino acid substitution at SEQ ID NO: 1 amino acid positions selected from the group consisting of SEQ ID NO: 1 amino acid positions
  (i) R10 and A33 and D35 and I59 and T90;
  (ii) R10 and A33 and T90 and T95;
  (iii) R10 and D35 and T90 and T95;
  (iv) R10 and T90 and T95; and
  (v) R10 and A89 and T90 and T95;
preferably wherein the polypeptide, preferably the glucose isomerase, in addition comprises an amino acid substitution at one more additional amino acid position, wherein the one more additional amino acid position is SEQ ID NO: 1 amino acid position F53.

In a 93$^{rd}$ embodiment of the first aspect, which is also an embodiment of any one of the 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$ and 92$^{nd}$ embodiment or of any one of the other embodiments of the first aspect, the amino acid sequence of the polypeptide, preferably the glucose isomerase, solely carries amino acid substitutions at SEQ ID NO: 1 amino acid positions selected from the group consisting of SEQ ID NO: 1 amino acid positions
  (i) R10 and A33 and D35 and I59 and T90;
  (ii) R10 and A33 and F53 and T90 and T95;
  (iii) R10 and D35 and F53 and T90 and T95;
  (iv) R10 and F53 and T90 and T95; and
  (v) R10 and A89 and T90 and T95.

In a preferred embodiment of the first aspect, which is also an embodiment of any one of the other embodiments of the first aspect, the amino acid sequence of the polypeptide, preferably the glucose isomerase, solely carries amino acid substitutions at SEQ ID NO: 1 amino acid positions selected from the group consisting of SEQ ID NO: 1 amino acid positions
  (i) R10 and A33 and D35 and I59 and T90;
  (ii) R10 and A33 and T90 and T95;
  (iii) R10 and D35 and T90 and T95;
  (iv) R10 and T90 and T95; and
  (v) R10 and A89 and T90 and T95,
preferably wherein the polypeptide, preferably the glucose isomerase, in addition comprises an amino acid substitution at one more additional amino acid position, wherein the one more additional amino acid position is SEQ ID NO: 1 amino acid position F53.

In a 94$^{th}$ embodiment of the first aspect, which is also an embodiment of any one of the 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$, 92$^{nd}$ and 93$^{rd}$ embodiment or of any one of the other embodiments of the first aspect, the amino acid sequence of the polypeptide, preferably the glucose isomerase, comprises an amino acid substitution at SEQ ID NO: 1 amino acid positions selected from the group consisting of SEQ ID NO: 1 amino acid positions
  (i) R10 and A33 and D35 and I59 and T90; and
  (ii) R10 and A89 and T90 and T95.

In a 95$^{th}$ embodiment of the first aspect, which is also an embodiment of any one of the 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$ and 94$^{th}$ embodiment or of any one of the other embodiments of the first aspect, the amino acid sequence of the polypeptide, preferably the glucose isomerase, solely carries amino acid substitutions at SEQ ID NO: 1 amino acid positions selected from the group consisting of SEQ ID NO: 1 amino acid positions R10 and A33 and D35 and I59;
R10 and A33 and D35 and T90;
R10 and A33 and D35 and T95;
R10 and A33 and F53 and T90;
R10 and A33 and F53 and T95;
R10 and A33 and I59 and T90;
R10 and A33 and T90 and T95;
R10 and D35 and F53 and T90;
R10 and D35 and F53 and T95;
R10 and D35 and I59 and T90;
R10 and D35 and T90 and T95;
R10 and F53 and T90 and T95;
R10 and I59 and T90 and T95;
R10 and A89 and T90 and T95;
A33 and F53 and T90 and T95;
A33 and A89 and T90 and T95;
L34 and A89 and T90 and T95;
D35 and F53 and T90 and T95;
D35 and A89 and T90 and T95;
F53 and A89 and T90 and T95;
I59 and A89 and T90 and T95;
R10 and A33 and D35 and F53 and T90;
R10 and A33 and D35 and F53 and T95;
R10 and A33 and D35 and I59 and T90;
R10 and A33 and D35 and I59 and T95;
R10 and A33 and D35 and T90 and T95;
R10 and A33 and F53 and T90 and T95;
R10 and A33 and I59 and T90 and T95;
R10 and A33 and A89 and T90 and T95;
R10 and L34 and A89 and T90 and T95;
R10 and D35 and F53 and I59 and T90;
R10 and D35 and F53 and I59 and T95;
R10 and D35 and F53 and T90 and T95;
R10 and D35 and I59 and T90 and T95;
R10 and D35 and A89 and T90 and T95;
R10 and F53 and I59 and T90 and T95;
R10 and F53 and A89 and T90 and T95;
R10 and I59 and A89 and T90 and T95;
A33 and L34 and A89 and T90 and T95;
A33 and D35 and F53 and T90 and T95;
A33 and D35 and A89 and T90 and T95;
A33 and F53 and A89 and T90 and T95;

A33 and I59 and A89 and T90 and T95;
L34 and D35 and A89 and T90 and T95;
L34 and F53 and A89 and T90 and T95;
L34 and I59 and A89 and T90 and T95;
D35 and F53 and A89 and T90 and T95;
D35 and I59 and A89 and T90 and T95;
F53 and I59 and A89 and T90 and T95;
R10 and A33 and D35 and F53 and I59 and T90;
R10 and A33 and D35 and F53 and I59 and T95;
R10 and A33 and D35 and F53 and T90 and T95;
R10 and A33 and D35 and I59 and T90 and T95;
R10 and A33 and D35 and A89 and T90 and T95;
R10 and A33 and F53 and A89 and T90 and T95;
R10 and A33 and I59 and A89 and T90 and T95;
R10 and L34 and D35 and A89 and T90 and T95;
R10 and L34 and F53 and A89 and T90 and T95;
R10 and L34 and I59 and A89 and T90 and T95;
R10 and D35 and F53 and I59 and T90 and T95;
R10 and D35 and F53 and A89 and T90 and T95;
R10 and D35 and I59 and A89 and T90 and T95;
R10 and F53 and I59 and A89 and T90 and T95;
A33 and L34 and D35 and A89 and T90 and T95;
A33 and L34 and F53 and A89 and T90 and T95;
A33 and L34 and I59 and A89 and T90 and T95;
A33 and D35 and F53 and A89 and T90 and T95;
A33 and D35 and I59 and A89 and T90 and T95;
A33 and F53 and I59 and A89 and T90 and T95;
L34 and D35 and F53 and A89 and T90 and T95;
L34 and D35 and I59 and A89 and T90 and T95;
L34 and F53 and I59 and A89 and T90 and T95;
D35 and F53 and I59 and A89 and T90 and T95;
R10 and A33 and D35 and F53 and I59 and T90 and T95;
R10 and A33 and D35 and F53 and A89 and T90 and T95;
R10 and A33 and D35 and I59 and A89 and T90 and T95;
R10 and D35 and F53 and I59 and A89 and T90 and T95;
A33 and L34 and D35 and F53 and A89 and T90 and T95;
A33 and L34 and D35 and I59 and A89 and T90 and T95;
A33 and L34 and F53 and I59 and A89 and T90 and T95;
A33 and D35 and F53 and I59 and A89 and T90 and T95;
L34 and D35 and F53 and I59 and A89 and T90 and T95;
R10 and A33 and D35 and F53 and I59 and A89 and T90 and T95; and
A33 and L34 and D35 and F53 and I59 and A89 and T90 and T95.

In a preferred embodiment of the first aspect, which is also an embodiment of any one of the other embodiments of the first aspect, the amino acid sequence of the polypeptide, preferably the glucose isomerase, solely carries amino acid substitutions at SEQ ID NO: 1 amino acid positions selected from the group consisting of SEQ ID NO: 1 amino acid positions R10 and A33 and T90;
R10 and A33 and T95;
R10 and D35 and T90;
R10 and D35 and T95;
R10 and T90 and T95;
A33 and T90 and T95;
D35 and T90 and T95;
A89 and T90 and T95;
R10 and A33 and D35 and T90;
R10 and A33 and D35 and T95;
R10 and A33 and T90 and T95;
R10 and D35 and I59 and T90;
R10 and D35 and I59 and T95;
R10 and D35 and T90 and T95;
R10 and I59 and T90 and T95;
R10 and A89 and T90 and T95;
A33 and D35 and T90 and T95;
A33 and A89 and T90 and T95;
L34 and A89 and T90 and T95;
D35 and A89 and T90 and T95;
I59 and A89 and T90 and T95;
R10 and A33 and D35 and I59 and T90;
R10 and A33 and D35 and I59 and T95;
R10 and A33 and D35 and T90 and T95;
R10 and A33 and A89 and T90 and T95;
R10 and L34 and A89 and T90 and T95;
R10 and D35 and I59 and T90 and T95;
R10 and D35 and A89 and T90 and T95;
R10 and I59 and A89 and T90 and T95;
A33 and L34 and A89 and T90 and T95;
A33 and D35 and A89 and T90 and T95;
A33 and I59 and A89 and T90 and T95;
L34 and D35 and A89 and T90 and T95;
L34 and I59 and A89 and T90 and T95;
D35 and I59 and A89 and T90 and T95;
R10 and A33 and D35 and I59 and T90 and T95;
R10 and A33 and D35 and A89 and T90 and T95;
R10 and D35 and I59 and A89 and T90 and T95;
A33 and L34 and D35 and A89 and T90 and T95;
A33 and L34 and I59 and A89 and T90 and T95;
A33 and D35 and I59 and A89 and T90 and T95;
L34 and D35 and I59 and A89 and T90 and T95;
R10 and A33 and D35 and I59 and A89 and T90 and T95;
A33 and L34 and D35 and I59 and A89 and T90 and T95,
preferably wherein the polypeptide, preferably the glucose isomerase, in addition comprises an amino acid substitution at one more additional amino acid position, wherein the one more additional amino acid position is SEQ ID NO: 1 amino acid position F53.

In a 96$^{th}$ embodiment of the first aspect, which is also an embodiment of any one of the 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 83$^{th}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$, 94$^{th}$ and 95$^{th}$ embodiment or of any one of the other embodiments of the first aspect, the amino acid sequence of the polypeptide, preferably the glucose isomerase, comprises an amino acid sequence of SEQ ID NO: 13, 14, 15, 16, 17, 18, 19, 20, 21, 22, or 23.

In a 97$^{th}$ embodiment of the first aspect, which is also an embodiment of any one of the 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 83$^{th}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$, 94$^{th}$, 95$^{th}$ and 96$^{th}$ embodiment or of any one of the other embodiments of the first aspect, the amino acid sequence of the polypeptide, preferably the glucose isomerase, consists of an amino acid sequence of SEQ ID NO: 13, 14, 15, 16, 17, 18, 19, 20, 21, 22, or 23.

In a 98$^{th}$ embodiment of the first aspect, which is also an embodiment of any one of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{th}$, 34$^{th}$, 35$^{th}$, 36$^{th}$, 37$^{th}$, 38$^{th}$ 39$^{th}$, 40$^{th}$, 41$^{st}$, 42$^{th}$, 43$^{th}$, 44$^{th}$, 45$^{th}$, 46$^{th}$, 47$^{th}$, 48$^{th}$, 49$^{th}$, 50$^{th}$, 51$^{st}$, 52$^{th}$, 53$^{th}$, 54$^{th}$, 55$^{th}$, 56$^{th}$, 57$^{th}$, 58$^{th}$ 59$^{th}$, 60$^{th}$, 61$^{st}$, 62$^{th}$, 63$^{th}$, 64$^{th}$, 65$^{th}$, 66$^{th}$, 67$^{th}$, 68$^{th}$, 69$^{th}$, 70$^{th}$, 71$^{st}$, 72$^{th}$, 73$^{th}$, 74$^{th}$, 75$^{th}$, 76$^{th}$, 78$^{th}$, 77$^{th}$, 79$^{th}$, 80$^{th}$, 81$^{st}$, 82$^{th}$, 83$^{th}$, 84$^{th}$, 85$^{th}$, 86$^{th}$, 87$^{th}$, 88$^{th}$, 89$^{th}$, 90$^{th}$, 91$^{st}$, 92$^{th}$, 93$^{rd}$, 94$^{th}$, 95$^{th}$, 96$^{th}$ and 97$^{th}$ embodiment or of any one of the other embodiments of the first aspect, the substitution at any of the amino acid positions is individually and independently selected from the group of amino acids consisting of A, R, N, D, C, Q, E, G, H, I, L, K, M, F, P, S, T, W, Y, and V.

In a 99th embodiment of the first aspect, which is also an embodiment of the 98th embodiment of the first aspect, the substitution is at any of SEQ ID NO: 1 amino acid positions 10, 33, 34, 35, 53, 59, 89, 90, and 95.

In a 100th embodiment of the first aspect, which is also an embodiment of the 99th embodiment of the first aspect, the substitution is at any of SEQ ID NO: 1 amino acid positions R10, A33, L34, D35, F53, I59, A89, T90, and T95.

In a 101st embodiment of the first aspect, which is also an embodiment of any one of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 24th, 25th, 26th, 27th, 28th, 29th, 30th, 31st, 32nd, 33rd, 34th, 34th, 35th, 36th, 37th, 38th, 39th, 40th, 41st, 42nd, 43rd, 44th, 45th, 46th, 47th, 48th, 49th, 50th, 51st, 52nd, 53rd, 54th, 54th, 55th, 56th, 57th, 58th, 59th, 60th, 61st, 62nd, 63th, 64th, 65th, 66th, 67th, 68th, 69th, 70th, 71st, 72nd, 73th, 74th, 75th, 76th, 78th, 77th, 79th, 80th, 81st, 82nd, 83rd, 84th, 85th, 86th, 87th, 88th, 89th, 90th, 91st, 92nd, 93rd, 94th, 95th, 96th, 97th, 98th, 99th embodiment or of any one of the other embodiments of the first aspect, preferably any one of the 98th, 99th and 100th embodiment of the first aspect, the amino acid sequence of the polypeptide, preferably the glucose isomerase, comprises one or more substitutions, wherein the substitution is selected from the group consisting of an amino acid substitution at position R10 of SEQ ID NO: 1 with the substitution being R10H or R10K, preferably to R10K;

an amino acid substitution at position A33 of SEQ ID NO: 1 with the substitution being A33I, A33L, A33V, A33G, A33N, A33M, A33C, A33S, A33Q or A33T, preferably A33I or A33N, and most preferably A33I;

an amino acid substitution at position L34 of SEQ ID NO: 1 with the substitution being L34F, L34W, L34Y, or L34P, preferably L34F;

an amino acid substitution at position D35 of SEQ ID NO: 1 with the substitution being D35G, D35N, D35M, D35C, D35S, D35Q or D35T, preferably D35C or D35S, and more preferably D35S;

an amino acid substitution at position F53 of SEQ ID NO: 1 with the substitution being F53A, F53I, F53L, or F53V, preferably F53L;

an amino acid substitution at position I59 of SEQ ID NO: 1 with the substitution being I59F, I59W, I59Y or I59P, and preferably I59F;

an amino acid substitution at position A89 of SEQ ID NO: 1 with the substitution being A89I, A89L or A89V, and preferably A89V;

an amino acid substitution at position T90 of SEQ ID NO: 1 with the substitution being T90G, T90N, T90M, T90C, T90S or T90Q, and preferably T90S;

an amino acid substitution at position T95 of SEQ ID NO: 1 with the substitution being T95F, T95W, T95Y, T95P, T95R, T95H or T95K, preferably T95Y or T95R, and more preferably T95Y.

In a preferred embodiment of the first aspect, which is also a preferred embodiment of any one of the other embodiments of the first aspect, the amino acid sequence of the polypeptide, preferably the glucose isomerase, comprises an amino acid substitution at one or more amino acid positions, wherein the one or more amino acid positions is/are each and independently selected from the group consisting of SEQ ID NO: 1 amino acid positions A89V, A89I, A89L, T90S, T90G, T90N, T90M, T90C, T90Q, T95Y, T95F, T95W, T95P, T95R, T95H, T95K, R10K, R10H, A33N, A33I, L34F, L34W, L34Y, L34P, D35C, D35S, I59F, I59W, I59Y, and I59P.

In a preferred embodiment of the first aspect, which is also a preferred embodiment of any one of the other embodiments of the first aspect, the amino acid sequence of the polypeptide, preferably the glucose isomerase, comprises an amino acid substitution at one or more amino acid positions, wherein the one or more amino acid positions is/are each and independently selected from the group consisting of SEQ ID NO: 1 amino acid positions A89V, T90S, T95Y, T95R, R10K, A33N, A33I, L34F, D35C, D35S, and I59F.

In a preferred embodiment of the first aspect, which is also a preferred embodiment of any one of the other embodiments of the first aspect, the amino acid sequence of the polypeptide, preferably the glucose isomerase, comprises an amino acid substitution at one or more amino acid positions, wherein the one or more amino acid positions is/are each and independently selected from the group consisting of SEQ ID NO: 1 amino acid positions A89V, T90S, T95Y, R10K, A33N, and A33I.

In a preferred embodiment of the first aspect, which is also a preferred embodiment of any one of the other embodiments of the first aspect, the amino acid sequence of the polypeptide, preferably the glucose isomerase, comprises in addition to the substitution at the one or more amino acid positions an additional amino acid substitution at SEQ ID NO: 1 amino acid position F53L.

In a preferred embodiment of the first aspect, which is also a preferred embodiment of any one of the other embodiments of the first aspect, the amino acid sequence of the polypeptide, preferably the glucose isomerase, comprises an amino acid substitution at one or more amino acid positions, wherein the one or more amino acid positions is/are each and independently selected from the group consisting of SEQ ID NO: 1 amino acid positions A89V, T90S, T95Y, R10K, A33N, and A33I, wherein the amino acid sequence of the polypeptide, preferably the glucose isomerase, in addition comprises one more amino acid substitution at SEQ ID NO: 1 amino acid position F53L.

In a preferred embodiment of the first aspect, which is also a preferred embodiment of any one of the other embodiments of the first aspect, the amino acid sequence of the polypeptide, preferably the glucose isomerase, comprises an amino acid substitution at one amino acid position, wherein the one amino acid positions is independently selected from the group consisting of SEQ ID NO: 1 amino acid positions A89V, T90S, T95Y, R10K, A33N, and A33I, and in addition comprises one more amino acid substitution at SEQ ID NO: 1 amino acid position F53L.

In a preferred embodiment of the first aspect, which is also an embodiment of any of the previously described embodiments, the amino acid sequence of the polypeptide, preferably the glucose isomerase, comprises one substitution at SEQ ID NO: 1 amino acid position 59, preferably at position I59, wherein the substituted amino acid is selected from the group of amino acids consisting of A, R, N, D, C, Q, E, G, H, I, L, K, M, F, P, S, T, W, and Y, but is not V, preferably is not I59V.

In a preferred embodiment of the first aspect, which is also an embodiment of any of the previously described embodiments, the amino acid sequence of the polypeptide, preferably the glucose isomerase, comprises one substitution at SEQ ID NO: 1 amino acid position 95, preferably at position T95, wherein the substituted amino acid is selected from the group of amino acids consisting of V, R, N, D, C, Q, E, G, H, I, L, K, M, F, P, S, T, W, and Y, but is not A, preferably is not T95A.

In a preferred embodiment of the first aspect, which is also an embodiment of any of the previously described embodiments, the amino acid sequence of the polypeptide, preferably the glucose isomerase, comprises one substitution at SEQ ID NO: 1 amino acid position 53, preferably at position F53, wherein the substituted amino acid is selected from the group of amino acids consisting of A, R, N, D, C, Q, E, G, H, I, K, M, F, P, S, T, W, V and Y, but is not L, preferably is not F53L.

In a preferred embodiment of the first aspect, which is also an embodiment of any of the previously described embodiments, the amino acid sequence of the polypeptide, preferably the glucose isomerase, does not comprise a substitution at SEQ ID NO: 1 amino acid position 53, preferably at SEQ ID NO: 1 amino acid position F53, wherein the substitution is preferably not F53L.

In a preferred embodiment of the first aspect, which is also an embodiment of any of the previously described embodiments, the amino acid sequence of the polypeptide, preferably the glucose isomerase, does not comprise one or more substitution(s) at SEQ ID NO: 1 amino acid positions 16, 17, 19, 63, 219 or 306, preferably does not comprise one or more substitution(s) at SEQ ID NO: 1 positions W16, H17, F19, A63, G219, or C306, more preferably does not comprise one or more substitution(s) selected from the group consisting of SEQ ID NO: 1 amino acid positions W16H, A63S, A103G, G219N, G219F, G219A and C306A.

In a $102^{nd}$ embodiment of the first aspect, which is also an embodiment of any one of the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $78^{th}$, $77^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$, $97^{th}$, $98^{th}$, $99^{th}$, $100^{th}$ and $101^{st}$ embodiment or of any one of the other embodiments of the first aspect, the identity of the amino acid sequence of the polypeptide, preferably the glucose isomerase, with the amino acid sequence of SEQ ID NO: 1 is at least 95.5%, more preferably at least 96%, or at least 96.5%, or at least 97%, or at least 97.5%, or at least 98%, or at least 98.5%, or at least 99%, most preferably of at least 99.1%, or at least 99.2%, or at least 99.3%, or at least 99.4%, or at least 99.5%, or at least 99.6%, or at least 99.7%, or at least 99.8%, and in particular at least 99.9%, or 100%.

In a preferred embodiment of the first aspect, which is also a preferred embodiment of any one of the other embodiments of the first aspect, the amino acid sequence of the polypeptide, preferably the glucose isomerase, is at least 96% identical to the amino acid sequence of SEQ ID NO: 1.

In a $103^{rd}$ embodiment of the first aspect, which is also an embodiment of any of the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$, $97^{th}$, $98^{th}$, $99^{th}$, $100^{th}$, $101^{st}$, and $102^{nd}$, embodiment or of any one of the other embodiments of the first, aspect, the amino acid sequence of the polypeptide, preferably the glucose isomerase, is least 95% identical to an amino acid sequence of SEQ ID NO: 2, 3, 4, 5, 6, 7, 8, 9, 10, 11, 12, 13, 14, 15, 16, 17, 18, 19, 20, 21, 22, or 23.

In another preferred embodiment of the first aspect, which is also an embodiment of any of the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$, $97^{th}$, $98^{th}$, $99^{th}$, $100^{th}$, $101^{st}$, $102^{nd}$, or any of the other embodiments of the first aspect, the amino acid sequence of the polypeptide, preferably the glucose isomerase, is at least 95% identical to an amino acid sequence of SEQ ID NO: 2, 4, 7, 8, 9, 10, 13, 14, 15, 16, 17, 18, 19, 20, 21, 22, or 23.

In a $104^{th}$ embodiment of the first aspect, which is also an embodiment of the $103^{rd}$ embodiment or of any one of the other embodiments of the first aspect, the amino acid sequence of the polypeptide, preferably the glucose isomerase, is at least 95% identical to an amino acid sequence of SEQ ID NO: 13, 14, 15, 16, 17, 18, 19, 20, 21, 22, or 23.

In a $105^{th}$ embodiment of the first aspect, which is also an embodiment of the $104^{th}$ embodiment of the first aspect, the amino acid sequence of the polypeptide, preferably the glucose isomerase, is at least 95% identical to
(i) an amino acid sequence of SEQ ID NO: 14, 15, 17, 18, or 19; and/or
(ii) an amino acid sequence of SEQ ID NO: 20, or 21.

In a $106^{th}$ embodiment of the first aspect, which is also an embodiment of the $105^{th}$ embodiment of the first aspect, the amino acid sequence of the polypeptide, preferably the glucose isomerase, is at least 95% identical to
(i) an amino acid sequence of SEQ ID NO: 14, 15, 17, 18, or 19; and/or
(ii) an amino acid sequence of SEQ ID NO: 21.

In a $107^{th}$ embodiment of the first aspect, which is also an embodiment of the $106^{th}$ embodiment of the first aspect, the amino acid sequence of the polypeptide, preferably the glucose isomerase, is at least 95% identical to
(i) an amino acid sequence of SEQ ID NO: 15, 17, or 18; preferably an amino acid sequence of SEQ ID NO: 17; and/or
(ii) an amino acid sequence of SEQ ID NO: 21.

In a $108^{th}$ embodiment of the first aspect, which is also an embodiment of any one of the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $78^{th}$, $77^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$, $97^{th}$, $98^{th}$, $99^{th}$, $100^{th}$, $101^{st}$, $102^{nd}$, $103^{rd}$, $104^{th}$, $105^{th}$, $106^{th}$ and $107^{th}$ embodiment or of any one of the other embodiments of the first aspect, the amino acid sequence of the polypeptide, preferably the glucose isomerase, is least 95% identical to two or more of the amino acid sequences of SEQ ID NO: 2, 3, 4, 5, 6, 7, 8, 9, 10, 11, 12, 13, 14, 15, 16, 17, 18, 19, 20, 21, 22, or 23.

In a 109$^{th}$ embodiment of the first aspect, which is also an embodiment of the 108$^{th}$ embodiment of the first aspect, the amino acid sequence of the polypeptide, preferably the glucose isomerase, is at least 95% identical to two or more of the amino acid sequences of SEQ ID NO: 13, 14, 15, 16, 17, 18, 19, 20, 21, 22, or 23.

In a 110$^{th}$ embodiment of the first aspect, which is also an embodiment of the 109$^{th}$ embodiment of the first aspect, the amino acid sequence of the polypeptide, preferably the glucose isomerase, is at least 95% identical to two or more
  (i) of the amino acid sequences of SEQ ID NO: 14, 15, 17, 18, or 19; and/or
  (ii) of the amino acid sequences of SEQ ID NO: 20, or 21.

In a 111$^{th}$ embodiment of the first aspect, which is also an embodiment of the 110$^{th}$ embodiment of the first aspect, the amino acid sequence of the polypeptide, preferably the glucose isomerase, is at least 95% identical to two or more
  (i) of the amino acid sequences of SEQ ID NO: 14, 15, 17, 18, or 19; and/or
  (ii) of the amino acid sequences of SEQ ID NO: 21.

In a 112$^{th}$ embodiment of the first aspect, which is also an embodiment of the 111$^{th}$ embodiment of the first aspect, the amino acid sequence of the polypeptide, preferably the glucose isomerase, is at least 95% identical to
  (i) two or more of the amino acid sequences of SEQ ID NO: 15, 17, or 18, preferably an amino acid sequence of SEQ ID NO: 17; and/or
  (ii) amino acid sequence of SEQ ID NO: 21.

In a 113$^{th}$ embodiment of the first aspect, which is also an embodiment of any one of the 98$^{th}$, 99$^{th}$, 101$^{st}$, 102$^{nd}$ and 103$^{rd}$ embodiment or of any one of the other embodiments of the first aspect, the identity of the amino acid sequence is at least 95.5%, more preferably at least 96%, or at least 96.5%, or at least 97%, or at least 97.5%, or at least 98%, or at least 98.5%, or at least 99%, most preferably of at least 99.1%, or at least 99.2%, or at least 99.3%, or at least 99.4%, or at least 99.5%, or at least 99.6%, or at least 99.7%, or at least 99.8%, and in particular at least 99.9%, or 100%.

In a 114$^{th}$ embodiment of the first aspect, which is also an embodiment of any one of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 78$^{th}$, 77$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$, 94$^{th}$, 95$^{th}$, 96$^{th}$, 97$^{th}$, 98$^{th}$, 99$^{th}$, 100$^{th}$, 101$^{st}$, 102$^{nd}$, 103$^{rd}$, 104$^{th}$, 105$^{th}$, 106$^{th}$, 107$^{th}$, 108$^{th}$, 109$^{th}$, 110$^{th}$, 111$^{th}$, 112$^{th}$ and 113$^{th}$ embodiment or of any one of the other embodiments of the first aspect, preferably any one of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$, 94$^{th}$, 95$^{th}$, 96$^{th}$, 97$^{th}$, 98$^{th}$, 99$^{th}$, 100$^{th}$, 101$^{st}$ and 102$^{nd}$ embodiment of the first aspect, and more preferably any one of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$, 92$^{nd}$, 94$^{th}$, 93$^{rd}$, 95$^{th}$, 96$^{th}$, 97$^{th}$, 98$^{th}$, 99$^{th}$ and 100$^{th}$ embodiment of the first aspect, the homology of the amino acid sequence of the polypeptide, preferably the glucose isomerase, with the amino acid sequence of SEQ ID NO: 1 is at least 95.5%, more preferably at least 96%, or at least 96.5%, or at least 97%, or at least 97.5%, or at least 98%, or at least 98.5%, or at least 99%, most preferably of at least 99.1%, or at least 99.2%, or at least 99.3%, or at least 99.4%, or at least 99.5%, or at least 99.6%, or at least 99.7%, or at least 99.8%, and in particular at least 99.9%, or 100%.

In a 115$^{th}$ embodiment of the first aspect, which is also an embodiment of any one of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 78$^{th}$, 77$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$, 94$^{th}$, 95$^{th}$, 96$^{th}$, 97$^{th}$, 98$^{th}$, 99$^{th}$, 100$^{th}$, 101$^{st}$, 102$^{nd}$, 103$^{rd}$, 104$^{th}$, 105$^{th}$, 106$^{th}$, 107$^{th}$, 108$^{th}$, 109$^{th}$, 110$^{th}$, 111$^{th}$, 112$^{th}$, 113$^{th}$ and 114$^{th}$ embodiment or of any one of the other embodiments of the first aspect, the amino acid sequence of the polypeptide, preferably the glucose isomerase, is at least 95% homologous to an amino acid sequence of SEQ ID NO: 2, 3, 4, 5, 6, 7, 8, 9, 10, 11, 12, 13, 14, 15, 16, 17, 18, 19, 20, 21, 22, or 23.

In a 116$^{th}$ embodiment of the first aspect, which is also an embodiment of the 115$^{th}$ embodiment of the first aspect, the amino acid sequence of the polypeptide, preferably the glucose isomerase, is at least 95% homologous to an amino acid sequence of SEQ ID NO: 13, 14, 15, 16, 17, 18, 19, 20, 21, 22, or 23.

In a 117$^{th}$ embodiment of the first aspect, which is also an embodiment of the 116$^{th}$ embodiment of the first aspect, the amino acid sequence of the polypeptide, preferably the glucose isomerase, is at least 95% homologous
  (i) to an amino acid sequence of SEQ ID NO: 14, 15, 17, 18, or 19; and/or
  (ii) to an amino acid sequence of SEQ ID NO: 20, or 21.

In a 118$^{th}$ embodiment of the first aspect, which is also an embodiment of the 117$^{th}$ embodiment of the first aspect, the amino acid sequence of the polypeptide, preferably the glucose isomerase, is at least 95% homologous
  (i) to an amino acid sequence of SEQ ID NO: 14, 15, 17, 18, or 19; and/or
  (ii) to an amino acid sequence of SEQ ID NO: 21.

In a 119$^{th}$ embodiment of the first aspect, which is also an embodiment of the 118$^{th}$ embodiment of the first aspect, the amino acid sequence of the polypeptide, preferably the glucose isomerase, is at least 95% homologous
  (i) to an amino acid sequence of SEQ ID NO: 15, 17, or 18, preferably an amino acid sequence of SEQ ID NO: 17; and/or
  (ii) to an amino acid sequence of SEQ ID NO: 21.

In a 120$^{th}$ embodiment of the first aspect, which is also an embodiment of any one of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46th, 47th, 48th, 49th, 50th, 51st, 52nd, 53rd, 54th, 55th, 56th, 57th, 58th, 59th, 60th, 61st, 62nd, 63rd, 64th, 65th, 66th, 67th, 68th, 69th, 70th, 71st, 72nd, 73rd, 74th, 75th, 76th, 78th, 77th, 79th, 80th, 81st, 82nd, 83rd, 84th, 85th, 86th, 87th, 88th, 89th, 90th, 91st, 92nd, 93rd, 94th, 95th, 96th, 97th, 98th, 99th, 100th, 101st, 102nd, 103rd, 104th, 105th, 106th, 107th, 108th, 109th, 110th, 111th, 112th, 113th, 114th, 115th, 116th, 117th, 118th and 119th embodiment or of any one of the other embodiments of the first aspect, the amino acid sequence of the polypeptide, preferably the glucose isomerase, is at least 95% homologous to two or more amino acid sequences of SEQ ID NO: 2, 3, 4, 5, 6, 7, 8, 9, 10, 11, 12, 13, 14, 15, 16, 17, 18, 19, 20, 21, 22, or 23.

In a 121st embodiment of the first aspect, which is also an embodiment of the 120th embodiment of the first aspect, the amino acid sequence of the polypeptide, preferably the glucose isomerase, is at least 95% homologous to two or more amino acid sequences of SEQ ID NO: 13, 14, 15, 16, 17, 18, 19, 20, 21, 22, or 23.

In a 122nd embodiment of the first aspect, which is also an embodiment of the 121st embodiment of the first aspect, the amino acid sequence of the polypeptide, preferably the glucose isomerase, is at least 95% homologous
  (i) to two or more amino acid sequences of SEQ ID NO: 14, 15, 17, 18, or 19; and/or
  (ii) to two or more amino acid sequences of SEQ ID NO: 20, or 21.

In a 123rd embodiment of the first aspect, which is also an embodiment of the 122nd embodiment of the first aspect, the amino acid sequence of the polypeptide, preferably the glucose isomerase, is at least 95% homologous
  (i) to two or more amino acid sequences of SEQ ID NO: 14, 15, 17, 18, or 19; and/or
  (ii) to amino acid sequence of SEQ ID NO: 21.

In a 124th embodiment of the first aspect, which is also an embodiment of the 123rd embodiment of the first aspect, the amino acid sequence of the polypeptide, preferably the glucose isomerase, is at least 95% homologous
  (i) to two or more amino acid sequences of SEQ ID NO: 15, 17, or 18, preferably an amino acid sequence of SEQ ID NO: 17; and/or
  (ii) to amino acid sequence of SEQ ID NO: 21.

In a 125th embodiment of the first aspect, which is also an embodiment of any one of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th, 29th, 30th, 31st, 32nd, 33rd, 34th, 35th, 36th, 37th, 38th, 39th, 40th, 41st, 42nd, 43rd, 44th, 45th, 46th, 47th, 48th, 49th, 50th, 51st, 52nd, 53rd, 54th, 55th, 56th, 57th, 58th, 59th, 60th, 61st, 62nd, 63rd, 64th, 65th, 66th, 67th, 68th, 69th, 70th, 71st, 72nd, 73rd, 74th, 75th, 76th, 78th, 77th, 79th, 80th, 81st, 82nd, 83rd, 84th, 85th, 86th, 87th, 88th, 89th, 90th, 91st, 92nd, 93rd, 94th, 95th, 96th, 97th, 98th, 99th, 100th, 101st, 102nd, 103rd, 104th, 105th, 106th, 107th, 108th, 109th, 110th, 111th, 112th, 113th, 114th, 115th, 116th, 117th, 118th, 119th, 120th, 121st, 122nd, 123rd and 124th embodiment or of any one of the other embodiments of the first aspect, the amino acid sequence of the polypeptide, preferably the glucose isomerase, is at least 95% identical to two or more amino acid sequences of SEQ ID NO: 2, 3, 4, 5, 6, 7, 8, 9, 10, 11, 12, 13, 14, 15, 16, 17, 18, 19, 20, 21, 22, or 23.

In a 126th embodiment of the first aspect, which is also an embodiment of the 125th embodiment of the first aspect, the amino acid sequence of the polypeptide, preferably the glucose isomerase, is at least 95% identical to two or more amino acid sequences of SEQ ID NO: 13, 14, 15, 16, 17, 18, 19, 20, 21, 22, or 23.

In a 127th embodiment of the first aspect, which is also an embodiment of the 126th embodiment of the first aspect, the amino acid sequence of the polypeptide, preferably the glucose isomerase, is at least 95% identical
  (i) to two or more amino acid sequences of SEQ ID NO: 14, 15, 17, 18, or 19; and/or
  (ii) to amino acid sequences of SEQ ID NO: 20 and 21.

In a 128th embodiment of the first aspect, which is also an embodiment of the 127th embodiment of the first aspect, the amino acid sequence of the polypeptide, preferably the glucose isomerase, is at least 95% identical
  (i) to two or more amino acid sequences of SEQ ID NO: 14, 15, 17, 18, or 19; and/or
  (ii) to amino acid sequence of SEQ ID NO: 21.

In a 129th embodiment of the first aspect, which is also an embodiment of the 128th embodiment of the first aspect, the amino acid sequence of the polypeptide, preferably the glucose isomerase, is at least 95% identical
  (i) to two or more amino acid sequences of SEQ ID NO: 15, 17, or 18, preferably to an amino acid sequence of SEQ ID NO: 17; and/or
  (ii) to amino acid sequence of SEQ ID NO: 21.

In a 130th embodiment of the first aspect, which is also an embodiment of any one of the 114th, 115th, 116th, 117th, 118th, 119th, 120th, 121st, 122nd, 123rd, 124th, 125th, 126th, 127th, 128th and 129th embodiment of the first aspect, the homology or the identity of the amino acid sequence is at least 95.5%, more preferably at least 96%, or at least 96.5%, or at least 97%, or at least 97.5%, or at least 98%, or at least 98.5%, or at least 99%, most preferably of at least 99.1%, or at least 99.2%, or at least 99.3%, or at least 99.4%, or at least 99.5%, or at least 99.6%, or at least 99.7%, or at least 99.8%, and in particular at least 99.9%, or 100%.

In a 131st embodiment of the first aspect, which is also an embodiment of any one of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 24th, 25th, 26th, 27th, 28th, 29th, 30th, 31st, 32nd, 33rd, 34th, 34th, 35th, 36th, 37th, 38th, 39th, 40th, 41st, 42nd, 43rd, 44th, 45th, 46th, 47th, 48th, 49th, 50th, 51st, 52nd, 53rd, 54th, 54th, 55th, 56th, 57th, 58th, 59th, 60th, 61st, 62nd, 63rd, 64th, 65th, 66th, 67th, 68th, 69th, 70th, 71st, 72nd, 73rd, 74th, 75th, 76th, 78th, 77th, 79th, 80th, 81st, 82nd, 83rd, 84th, 85th, 86th, 87th, 88th, 89th, 90th, 91st, 92nd, 93rd, 94th, 95th, 96th, 97th, 98th, 99th, 100th, 10V, 102nd, 103rd, 104th, 105th, 106th, 107th, 108th, 109th, 110th, 111th, 112th, 113th, 114th, 115th, 116th, 117th, 118th, 119th, 120th, 12V, 122nd, 123rd, 124th, 125th, 126th, 127th, 128th, 129th and 130th embodiment or of any one of the other embodiments of the first aspect, the polypeptide, preferably the glucose isomerase, comprises an amino acid sequence of SEQ ID NO: 2, 3, 4, 5, 6, 7, 8, 9, 10, 11, 12, 13, 14, 15, 16, 17, 18, 19, 20, 21, 22, or 23.

In a 132nd embodiment of the first aspect, which is also an embodiment of the 131st embodiment of the first aspect, the polypeptide, preferably the glucose isomerase, comprises an amino acid sequence of SEQ ID NO: 13, 14, 15, 16, 17, 18, 19, 20, 21, 22, or 23.

In a 133rd embodiment of the first aspect, which is also an embodiment of the 132nd embodiment of the first aspect, the polypeptide, preferably the glucose isomerase, comprises
  (i) an amino acid sequence of SEQ ID NO: 14, 15, 17, 18, or 19; and/or
  (ii) an amino acid sequence of SEQ ID NO: 20, or 21.

In a 134th embodiment of the first aspect, which is also an embodiment of the 133rd embodiment of the first aspect, the polypeptide, preferably the glucose isomerase, comprises

49

(i) an amino acid sequence of SEQ ID NO: 14, 15, 17, 18, or 19; and/or (ii) an amino acid sequence of SEQ ID NO: 21.

In a 135th embodiment of the first aspect, which is also an embodiment of the 134th embodiment of the first aspect, the polypeptide, preferably the glucose isomerase, comprises (i) an amino acid sequence of SEQ ID NO: 15, 17, or 18, preferably an amino acid sequence of SEQ ID NO: 17; and/or (ii) an amino acid sequence of SEQ ID NO: 21.

In a 136th embodiment of the first aspect, which is also an embodiment of any one of the 130th, 131st, 132nd, 133rd, 134th and 135th embodiment of the first aspect, the polypeptide, preferably the glucose isomerase, consists of an amino acids sequence of SEQ ID NO: 2, 3, 4, 5, 6, 7, 8, 9, 10, 11, 12, 13, 14, 15, 16, 17, 18, 19, 20, 21, 22, or 23.

In a 137th embodiment of the first aspect, which is also an embodiment of any one of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th, 29th, 30th, 31st, 32nd, 33rd, 34th, 35th, 36th, 37th, 38th, 39th, 40th, 41st, 42nd, 43rd, 44th, 45th, 46th, 47th, 48th, 49th, 50th, 51st, 52nd, 53rd, 54th, 55th, 56th, 57th, 58th, 59th, 60th, 61st, 62nd, 63rd, 64th, 65th, 66th, 67th, 68th, 69th, 70th, 71st, 72nd, 73rd, 74th, 75th, 76th, 78th, 77th, 79th, 80th, 81st, 82nd, 83rd, 84th, 85th, 86th, 87th, 88th, 89th, 90th, 91st, 92nd, 93rd, 94th, 95th, 96th, 97th, 98th, 99th, 100th, 101st, 102nd, 103rd, 104th, 105th, 106th, 107th, 108th, 109th, 110th, 111th, 112th, 113th, 114th, 115th, 116th, 117th, 118th, 119th, 120th, 121st, 122nd, 123rd, 124th, 125th, 126th, 127th, 128th, 129th, 130th, 131st, 132nd, 133rd, 134th, 135th and 136th embodiment or of any one of the other embodiments of the first aspect, the polypeptide, preferably the glucose isomerase, is capable of catalyzing the conversion of (i) of an aldose molecule to a ketose molecule, and/or (ii) of a ketose molecule to an aldose molecule.

In a 138th embodiment of the first aspect, which is also an embodiment of any one of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th, 29th, 30th, 31st, 32nd, 33rd, 34th, 35th, 36th, 37th, 38th, 39th, 40th, 41st, 42nd, 43rd, 44th, 45th, 46th, 47th, 48th, 49th, 50th, 51st, 52nd, 53rd, 54th, 55th, 56th, 57th, 58th, 59th, 60th, 61st, 62nd, 63rd, 64th, 65th, 66th, 67th, 68th, 69th, 70th, 71st, 72nd, 73rd, 74th, 75th, 76th, 78th, 77th, 79th, 80th, 81st, 82nd, 83rd, 84th, 85th, 86th, 87th, 88th, 89th, 90th, 91st, 92nd, 93rd, 94th, 95th, 96th, 97th, 98th, 99th, 100th, 101st, 102nd, 103rd, 104th, 105th, 106th, 107th, 108th, 109th, 110th, 111th, 112th, 113th, 114th, 115th, 116th, 117th, 118th, 119th, 120th, 121st, 122nd, 123rd, 124th, 125th, 126th, 127th, 128th, 129th, 130th, 131st, 132nd, 133rd, 134th, 135th, 136th and 137th embodiment or of any one of the other embodiments of the first aspect, the polypeptide, preferably the glucose isomerase, is capable of catalyzing the conversion of (i) of an aldotetrose molecule to a ketotetrose molecule, and/or (ii) of a ketotetrose molecule to an aldotetrose molecule, and/or (ii) of an aldopentose molecule to a ketopentose molecule, and/or (iv) of a ketopentose molecule to an aldopentose molecule, and/or (v) of an aldohexose molecule to a ketohexose molecule, and/or (vi) of a ketohexose molecule to an aldohexose molecule and/or

50

(vii) of an aldoheptose molecule to a ketoheptose molecule, and/or (viii) of a ketoheptose molecule to an aldoheptose molecule.

In a 139th embodiment of the first aspect, which is also an embodiment of any one of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th, 29th, 30th, 31st, 32nd, 33rd, 34th, 35th, 36th, 37th, 38th, 39th, 40th, 41st, 42nd, 43rd, 44th, 45th, 46th, 47th, 48th, 49th, 50th, 51st, 52nd, 53rd, 54th, 55th, 56th, 57th, 58th, 59th, 60th, 61st, 62nd, 63rd, 64th, 65th, 66th, 67th, 68th, 69th, 70th, 71st, 72nd, 72nd, 73rd, 74th, 75th, 76th, 77th, 78th, 79th, 80th, 81st, 82nd, 83rd, 84th, 85th, 86th, 87th, 88th, 89th, 90th, 91st, 92nd, 93rd, 94th, 95th, 96th, 97th, 98th, 99th, 100th, 101st, 102nd, 103rd, 104th, 105th, 106th, 107th, 108th, 109th, 110th, 111th, 112th, 113th, 114th, 115th, 116th, 117th, 118th, 119th, 120th, 121st, 122nd, 123rd, 124th, 125th, 126th, 127th, 128th, 129th, 130th, 131st, 132nd, 133rd, 134th, 135th, 136th, 137th and 138th embodiment or of any of the other embodiments of the first aspect, the polypeptide, preferably the glucose isomerase, is capable of catalyzing the conversion of (i) of an aldopentose molecule to a ketopentose molecule, and/or (ii) of a ketopentose molecule to an aldopentose molecule, and/or (iii of an aldohexose molecule to a ketohexose molecule, and/or (iv) of a ketohexose molecule to an aldohexose molecule.

In a 140th embodiment of the first aspect, which is also an embodiment of any one of the 137th, 138th and 139th embodiment of the first aspect, the polypeptide, preferably the glucose isomerase, is capable of catalyzing the conversion (i) of an aldose molecule, selected from the group consisting of D-glucose, D-xylose, D-arabinose, L-arabinose, L-ribose, D-ribose, D-lyxose, D-allose, L-rhamnose, and D-mannose; and/or (ii) of a ketose molecule, selected from the group consisting of D-fructose, D-xylulose, D-ribulose, L-ribulose, D-psicose, and L-rhamnulose.

In a 141st embodiment of the first aspect, which is also an embodiment of any one of the 137th, 138th 139th and 140th embodiment of the first aspect, (i) the aldose molecule is an aldose molecule derivative selected from the group consisting of deoxy-carbohydrates, thio-carbohydrates, azido-carbohydrates, methylated carbohydrates, halogenated carbohydrates, and/or benzylated carbohydrates (ii) the ketose molecule is a ketose molecule derivative selected from the group consisting of deoxy-carbohydrates, thio-carbohydrates, azido-carbohydrates, methylated carbohydrates, halogenated carbohydrates, and/or benzylated carbohydrates.

In a 142nd embodiment of the first aspect, which is also an embodiment of any one of the 137th, 138th, 139th, 140th and 141st embodiment of the first aspect or of any one of the other embodiments of the first aspect, the polypeptide, preferably the glucose isomerase, is capable of catalyzing the conversion of (i) fructose to glucose and/or (ii) glucose to fructose.

In a 143th embodiment of the first aspect, which is also an embodiment of any one of the 137th, 138th, 139th, 140th, 141st and 142nd embodiment of the first aspect, the conversion is a reversible conversion.

In a 144th embodiment of the first aspect, which is also an embodiment of any one of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th, 29th, 30th, 31st, 32nd, 33rd, 34th, 34th, 35th, 36th, 37th, 38th, 39th, 40th, 41st, 42nd, 43rd, 44th, 45th, 46th, 47th, 48th, 49th, 50th, 51st, 52nd, 53rd, 54th, 54th, 55th, 56th, 57th, 58th, 59th, 60th, 61st, 62nd, 63th, 64th, 65th, 66th, 67th, 68th, 69th, 70th, 71st, 72nd, 73th, 74th, 75th, 76th, 78th, 77th, 79th, 80th, 81st, 82nd, 83th, 84th, 85th, 86th, 87th, 88th, 89th, 90th, 91st, 92nd, 93rd. 94th, 95th, 96th, 97th, 98th, 99th, 100th, 101st, 102nd, 103th, 104th, 105th, 106th, 107th, 108th, 109th, 110th, 111th, 112th, 113th, 114th, 115th, 116th, 117th, 118th, 119th, 120th, 121st, 122nd, 123th, 124th, 125th, 126th, 127th, 128th, 129th, 130th, 131st, 132nd, 133rd, 134th, 135th, 136th, 137th, 138th, 139th, 140th, 141st, 142nd and 143rd embodiment or of any one of the other embodiments of the first aspect, the polypeptide, preferably the glucose isomerase, is a polypeptide, preferably the glucose isomerase, according to EC number EC 5.3.1.5.

The problem underlying the present invention is solved in a second aspect, which is also a first embodiment of the second aspect, by a polypeptide, preferably the glucose isomerase, of the first aspect, including any embodiment thereof, wherein the polypeptide, preferably the glucose isomerase, has at least one of the characteristics selected from the group consisting of (A), (B), (C), (D), (E), and (F), or any combination thereof, wherein characteristic (A) is an increased activity, preferably increased Activity, of the polypeptide, preferably of the glucose isomerase, for the conversion of fructose to glucose at a concentration of 50 mM fructose in comparison to the polypeptide, preferably the glucose isomerase, of SEQ ID NO: 1
  (i) of at least 1.1-fold up to 1.6-fold, preferably of at least 1.2-fold up to 1.6-fold, more preferably of at least 1.3-fold up to 1.6-fold, most preferably of at least 1.4-fold up to 1.6-fold, or
  (ii) of at least 1.1-fold up to 3.0-fold, preferably of at least 1.4-fold up to 3.0-fold, preferably of at least 1.5-fold up to 3.0-fold, more preferably of at least 1.6-fold up to 3.0-fold, preferably of at least 1.7-fold up to 3.0-fold, preferably of at least 1.8-fold up to 3.0-fold, preferably of at least 1.9-fold up to 3.0-fold, preferably of at least 2.0-fold up to 3.0-fold, more preferably of at least 1.4-fold up to 2.8-fold, more preferably of at least 1.5-fold up to 2.8-fold, more preferably of at least 1.6-fold up to 2.8-fold, more preferably of at least 1.7-fold up to 2.8-fold, more preferably of at least 1.8-fold up to 2.8-fold, more preferably of at least 1.9-fold up to 2.8-fold, more preferably of at least 2.0-fold up to 2.8-fold, even more preferably of at least 1.4-fold up to 2.6-fold, even more preferably of at least 1.5-fold up to 2.6-fold, more preferably of at least 1.6-fold up to 2.6-fold, more preferably of at least 1.7-fold up to 2.6-fold, more preferably of at least 1.8-fold up to 2.6-fold, more preferably of at least 1.9-fold up to 2.6-fold, more preferably of at least 2.0-fold up to 2.6-fold, and most preferably of at least 1.4-fold up to 2.4-fold, most preferably of at least 1.5-fold up to 2.4-fold, most preferably of at least 1.6-fold up to 2.4-fold, most preferably of at least 1.7-fold up to 2.4-fold, most preferably of at least 1.8-fold up to 2.4-fold, most preferably of at least 1.9-fold up to 2.4-fold, and most preferably of at least 2.0-fold up to 2.4-fold, and utmost preferable of at least 1.7-fold up to 2.4-fold;

(B) is an increased activity, preferably increased Activity, of the polypeptide, preferably of the glucose isomerase, for the conversion of fructose to glucose at a concentration of 200 mM fructose in comparison to the polypeptide, preferably the glucose isomerase, of SEQ ID NO: 1
  (i) of at least 1.2-fold up to 1.6-fold, more preferably of at least 1.3-fold up to 1.6-fold, most preferably of at least 1.4-fold up to 1.6-fold, and/or
  (ii) of at least 1.2-fold up to 3.0-fold, preferably of at least 1.3-fold up to 3.0-fold, preferably of at least 1.4-fold up to 3.0-fold preferably of at least 1.5-fold up to 3.0-fold, more preferably of at least 1.6-fold up to 3.0-fold, preferably of at least 1.7-fold up to 3.0-fold, preferably of at least 1.8-fold up to 3.0-fold, preferably of at least 1.9-fold up to 3.0-fold, preferably of at least 2.0-fold up to 3.0-fold, more preferably of at least 1.3-fold up to 2.5-fold, more preferably of at least 1.4-fold up to 2.5-fold, more preferably of at least 1.5-fold up to 2.5-fold, more preferably of at least 1.6-fold up to 2.5-fold, more preferably of at least 1.7-fold up to 2.5-fold, more preferably of at least 1.8-fold up to 2.5-fold, more preferably of at least 1.9-fold up to 2.5-fold, more preferably of at least 2.0-fold up to 2.5-fold, even more preferably of at least 1.3-fold up to 2.2-fold, even more preferably of at least 1.4-fold up to 2.2-fold, even more preferably of at least 1.5-fold up to 2.2-fold, more preferably of at least 1.6-fold up to 2.2-fold, more preferably of at least 1.7-fold up to 2.2-fold, more preferably of at least 1.8-fold up to 2.2-fold, more preferably of at least 1.9-fold up to 2.2-fold, more preferably of at least 2.0-fold up to 2.2-fold, and utmost preferably of at least 1.5-fold up to 2.2-fold;

(C) is thermal stability of the polypeptide, preferably of the glucose isomerase, expressed as Residual Activity after incubation of the polypeptide, preferably the glucose isomerase, at a temperature of 74° C. for 15 minutes, wherein such Residual Activity is
  (i) at least 30% up to 100%, at least 40% up to 100%, at least 50% up to 100%, at least 30% up to 75%, at least 40% up to 75%, at least 50% up to 75%, at least 30% up to 65%, at least 40% up to 65%, at least 50% up to 65%, at least 41% up to 64%, and/or
  (ii) at least 30% up to 100%, at least 31% up to 100%, at least 32% up to 100%, at least 33% up to 100%, at least 34% up to 100%, at least 35% up to 100%, at least 36% up to 100%, at least 37% up to 100%, at least 38% up to 100%, at least 39% up to 100%, at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, at least 60% up to 100%, at least 61% up to 100%, at least 62% up to 100%, at least 63% up to 100%, at least 64% up to 100%, at least 65% up to 100%, at least 66% up to 100%, at least 67% up to 100%, at least 68% up to 100%, at least 69% up to 100%, at least 70% up to 100%, at least 71% up to 100%, at least 72% up to 100%, at least 73% up to 100%, at least 74% up to 100%, at least 75% up to 100%, at least 76% up to 100%, at least 77% up to 100%, at least 78% up to 100%, at least 79% up to 100%, at least 80% up to 100%, at least 30% up to 75%, at least 31% up to 75%, at least 32% up to 75%, at least 33% up to 75%, at least 34% up to 75%, at least 35% up to 75%, at least 36% up to 75%, at least 37% up to 75%, at least 38% up to 75%, at least 39% up to 75%, at least 40% up to 75%, at least 41% up to 75%, at least 42% up to 75%, at least 43% up to 75%, at least 44% up to 75%, at least 45% up to 75%, at least 46% up to 75%, at least 47% up to 75%, at least 48% up to 75%, at least 49% up to 75%, at least 50% up to 75%, at least 51% up to 75%, at least 52% up to 75%, at least 53% up to 75%, at least 54% up to 75%, at least 55% up to 75%, at least 56% up to 75%, at least 57% up to 75%, at least 58% up to 75%, at least 59% up to 75%, at least 60% up to 75%, at least 61% up to 75%, at least 62% up to 75%, at least 30% up to 70%, at least 31% up to 70%, at least 32% up to 70%, at least 33% up to 70%, at least 34% up to 70%, at least 35% up to 70%, at least 36% up to 70%, at least 37% up to 70%, at least 38% up to 70%, at least 39% up to 70%, at least 40% up to 70%, at least 41% up to 70%, at least 42% up to 70%, at least 43% up to 70%, at least 44% up to 70%, at least 45% up to 70%, at least 46% up to 70%, at least 47% up to 70%, at least 48% up to 70%, at least 49% up to 70%, at least 50% up to 70%, at least 51% up to 70%, at least 52% up to 70%, at least 53% up to 70%, at least 54% up to 70%, at least 55% up to 70%, at least 56% up to 70%, at least 57% up to 70%, at least 58% up to 70%, at least 59% up to 70%, at least 60% up to 70%, at least 61% up to 70%, at least 62% up to 70%, at least 30% up to 65%, at least 31% up to 65%, at least 32% up to 65%, at least 33% up to 65%, at least 34% up to 65%, at least 35% up to 65%, at least 36% up to 65%, at least 37% up to 65%, at least 38% up to 65%, at least 39% up to 65%, at least 40% up to 65%, at least 41% up to 65%, at least 42% up to 65%, at least 43% up to 65%, at least 44% up to 65%, at least 45% up to 65%, at least 46% up to 65%, at least 47% up to 65%, at least 48% up to 65%, at least 49% up to 65%, at least 50% up to 65%, at least 51% up to 65%, at least 52% up to 65%, at least 53% up to 65%, at least 54% up to 65%, at least 55% up to 65%, at least 56% up to 65%, at least 57% up to 65%, at least 58% up to 65%, at least 59% up to 65%, at least 60% up to 65%, at least 61% up to 65%, at least 62% up to 65%, more preferably at least 30% up to 65%, at least 34% up to 65%, at least 35% up to 65%, at least 38% up to 65%, at least 40% up to 65%, at least 41% up to 65%, at least 42% up to 65%, at least 46% up to 65%, at least 47% up to 65%, at least 50% up to 65%, at least 55% up to 65%, at least 59% up to 65%, at least 60% up to 65%, at least 62% up to 65%, even more preferably at least at least 40% up to 65%, and even more preferably at least 60% up to 65%, and most preferably of 62%;

(D) is a $K_M$ value of the polypeptide, preferably of the glucose isomerase,
  (i) of between 100 mM and 190 mM, preferably between 130 mM and 190 mM, preferably between 160 mM and 190 mM, more preferably between 170 mM and 185 mM, and most preferably between 175 mM and 180 mM; and/or
  (ii) of between 50 mM and 190 mM, 50 mM and 189 mM, 50 mM and 188 mM, 50 mM and 187 mM, 50 mM and 186 mM, 50 mM and 185 mM, preferably between 50 mM and 184 mM, preferably between 50 mM and 183 mM, preferably between 50 mM and 182 mM, preferably between 50 mM and 181 mM, preferably between 50 mM and 180 mM, preferably between 50 mM and 179 mM, preferably between 50 mM and 178 mM, preferably between 50 mM and 177 mM, preferably between 50 mM and 176 mM, preferably between 50 mM and 175 mM, preferably between 50 mM and 174 mM, preferably between 50 mM and 173 mM, preferably between 50 mM and 172 mM, preferably between 50 mM and 171 mM, preferably between 50 mM and 170 mM, preferably between 50 mM and 169 mM, preferably between 50 mM and 168 mM, preferably between 50 mM and 167 mM, preferably between 50 mM and 166 mM, preferably between 50 mM and 165 mM, preferably between 50 mM and 160 mM, preferably between 50 mM and 159 mM, preferably between 50 mM and 158 mM, preferably between 50 mM and 157 mM, preferably between 50 mM and 156 mM, preferably between 50 mM and 155 mM, preferably between 50 mM and 154 mM, preferably between 50 mM and 153 mM, preferably between 50 mM and 152 mM, 75 mM and 190 mM, 75 mM and 189 mM, 75 mM and 188 mM, 75 mM and 187 mM, 75 mM and 186 mM, 75 mM and 185 mM, preferably between 75 mM and 184 mM, preferably between 75 mM and 183 mM, preferably between 75 mM and 182 mM, preferably between 75 mM and 181 mM, preferably between 75 mM and 180 mM, preferably between 75 mM and 179 mM, preferably between 75 mM and 178 mM, preferably between 75 mM and 177 mM, preferably between 75 mM and 176 mM, preferably between 75 mM and 175 mM, preferably between 75 mM and 174 mM, preferably between 75 mM and 173 mM, preferably between 75 mM and 172 mM, preferably between 75 mM and 171 mM, preferably between 75 mM and 170 mM, preferably between 75 mM and 169 mM, preferably between 75 mM and 168 mM, preferably between 75 mM and 167 mM, preferably between 75 mM and 166 mM, preferably between 75 mM and 165 mM, preferably between 75 mM and 160 mM, preferably between 75 mM and 159 mM, preferably between 75 mM and 158 mM, preferably between 75 mM and 157 mM, preferably between 75 mM and 156 mM, preferably between 75 mM and 155 mM, preferably between 75 mM and 154 mM, preferably between 75 mM and 153 mM, preferably between 75 mM and 152 mM, 100 mM and 190 mM, 100 mM and 189 mM, 100 mM and 188 mM, 100 mM and 187 mM, 100 mM and 186 mM, 100 mM and 185 mM, preferably between 100 mM and 184 mM, preferably between 100 mM and 183 mM, preferably between 100 mM and 182 mM, preferably between 100 mM and 181 mM, preferably between 100 mM and 180 mM, preferably between 100 mM and 179 mM, preferably between 100 mM and 178 mM, preferably between 100 mM and 177 mM, preferably between 100 mM and 176 mM, preferably between 100 mM and 1100 mM, preferably between 100 mM and 174 mM, preferably between 100 mM and 173 mM, preferably between 100 mM and 172 mM, preferably between 100 mM and 171 mM, preferably between 100 mM and 170 mM, preferably between 100 mM and 169 mM, preferably between 100 mM and 168 mM, preferably between 100 mM and 167 mM, preferably between 100 mM and 166 mM, preferably between 100 mM and 165 mM, preferably between 100 mM and 160 mM, preferably between 100 mM and 159 mM, preferably between 100 mM and 158 mM, preferably between 100 mM and 157 mM, preferably between 100 mM and 156 mM, preferably between 100 mM and 155 mM, preferably between 100 mM and 154 mM, preferably between 100 mM and 153 mM, preferably between 100 mM and 152 mM, 115 mM and 190 mM, 115 mM and 189 mM, 115 mM and 188 mM, 115 mM and 187 mM, 115 mM and 186 mM, 115 mM and 185 mM, preferably between 115 mM and 184 mM, preferably between 115 mM and 183 mM, preferably between 115 mM and 182 mM, preferably between 115 mM and 181 mM, preferably between 115 mM and 180 mM, preferably between 115 mM and 179 mM, preferably between 115 mM and 178 mM, preferably between 115 mM and 177 mM, preferably between 115 mM and 176 mM, preferably between 115 mM and 175 mM, preferably between 115 mM and 174 mM, preferably between 115 mM and 173 mM, preferably between 115 mM and 172 mM, preferably between 115 mM and 171 mM, preferably between 115 mM and 170 mM, preferably between 115 mM and 169 mM, preferably between 115 mM and 168 mM, preferably between 115 mM and 167 mM, preferably between 115 mM and 166 mM, preferably between 115 mM and 165 mM, preferably between 115 mM and 160 mM, preferably between 115 mM and 159 mM, preferably between 115 mM and 158 mM, preferably between 115 mM and 157 mM, preferably between 115 mM and 156 mM, preferably between 115 mM and 155 mM, preferably between 115 mM and 154 mM, preferably between 115 mM and 153 mM, preferably between 115 mM and 152 mM, 130 mM and 185 mM, preferably between 130 mM and 184 mM, preferably between 130 mM and 183 mM, preferably between 130 mM and 182 mM, preferably between 130 mM and 181 mM, preferably between 130 mM and 180 mM, preferably between 130 mM and 179 mM, preferably between 130 mM and 178 mM, preferably between 130 mM and 177 mM, preferably between 130 mM and 176 mM, preferably between 130 mM and 175 mM, preferably between 130 mM and 174 mM, preferably between 130 mM and 173 mM, preferably between 130 mM and 172 mM, preferably between 130 mM and 171 mM, preferably between 130 mM and 170 mM, preferably between 130 mM and 169 mM, preferably between 130 mM and 168 mM, preferably between 130 mM and 167 mM, preferably between 130 mM and 166 mM, preferably between 130 mM and 165 mM, preferably between 130 mM and 160 mM, preferably between 130 mM and 159 mM, preferably between 130 mM and 158 mM, preferably between 130 mM and 157 mM, preferably between 130 mM and 156 mM, preferably between 130 mM and 155 mM, preferably between 130 mM and 154 mM, preferably between 130 mM and 153 mM, preferably between 130 mM and 152 mM, more preferably between 135 mM and 185 mM, more preferably between 135 mM and 184 mM, more preferably between 135 mM and 183 mM, more preferably between 135 mM and 182 mM, more preferably between 135 mM and 181 mM, more preferably between 135 mM and 180 mM, more preferably between 135 mM and 179 mM, more preferably between 135 mM and 178 mM, more preferably between 135 mM and 177 mM, more preferably between 135 mM and 176 mM, more preferably between 135 mM and 175 mM, more preferably between 135 mM and 174 mM, more preferably between 135 mM and 173 mM, more preferably between 135 mM and 172 mM, more preferably between 135 mM and 171 mM, more preferably between 135 mM and 170 mM, more preferably between 135 mM and 169 mM, more preferably between 135 mM and 168 mM, more preferably between 135 mM and 167 mM, more preferably between 135 mM and 166 mM, more preferably between 135 mM and 165 mM, more preferably between 135 mM and 160 mM, more preferably between 135 mM and 159 mM, more preferably between 135 mM and 158 mM, more preferably between 135 mM and 157 mM, more preferably between 135 mM and 156 mM, more preferably between 135 mM and 155 mM, more preferably between 135 mM and 154 mM, more preferably between 135 mM and 153 mM, more preferably between 135 mM and 152 mM, most preferably between 140 mM and 185 mM, most preferably between 140 mM and 184 mM, most preferably between 140 mM and 183 mM, most preferably between 140 mM and 182 mM, most preferably between 140 mM and 181 mM, most preferably between 140 mM and 180 mM, most preferably between 140 mM and 179 mM, most preferably between 140 mM and 178 mM, most preferably between 140 mM and 177 mM, most preferably between 140 mM and 176 mM, most preferably between 140 mM and 175 mM, most preferably between 140 mM and 174 mM, most preferably between 140 mM and 173 mM, most preferably between 140 mM and 172 mM, most preferably between 140 mM and 171 mM, most preferably between 140 mM and 170 mM, most preferably between 140 mM and 169 mM, most preferably between 140 mM and 168 mM, most preferably between 140 mM and 167 mM, most preferably between 140 mM and 166 mM, most preferably between 140 mM and 165 mM, most preferably between 140 mM and 160 mM, most preferably between 140 mM and 159 mM, most preferably between 140 mM and 158 mM, most preferably between 140 mM and 157 mM, most preferably between 140 mM and 156 mM, most preferably between 140 mM and 155 mM, most preferably between 140 mM and 154 mM, most preferably between 140 mM and 153 mM, and utmost preferably between 140 mM and 152 mM; and/or (iii) of less than 190 mM, 189 mM, 188 mM, 187 mM, 186 mM, 185 mM, 184 mM, 183 mM, 182 mM, 181 mM, 180 mM, 179 mM, 178 mM, 177 mM, 176 mM, 175 mM, 174 mM, 173 mM, 172 mM, 171 mM, 170 mM, 169 mM, 168 mM, 167 mM, 166 mM, 165 mM, 160 mM, 159 mM, 158 mM, 157 mM, 156 mM, 155 mM, 154 mM, 153 mM, 152 mM, preferably of less than 185 mM, more preferably less than 170 mM, even more preferably less than 160 mM, and most preferably less than 155 mM, and utmost preferably of 152 mM and less than 152 mM; and (E) is a Soluble Expression Level of the polypeptide, preferably of the glucose isomerase, defined as the ratio of the soluble expression level of said polypeptide and the soluble expression level of the polypeptide, preferably the glucose isomerase, of SEQ ID NO: 1

(i) of at least 1.04 up to 1.38, preferably of at least 1.07 up to 1.38, preferably of at least 1.10 up to 1.38, preferably of at least 1.31 up to 1.38, preferably of at least 1.33 up to 1.38, preferably of at least 1.36 up to 1.38, more preferably of at least 1.04 up to 1.36, more preferably of at least 1.07 up to 1.36, more preferably of at least 1.10 up to 1.36, more preferably of at least 1.31 up to 1.36, more preferably of at least 1.33 up to 1.36, and most preferably of at 1.36; and/or (ii) of at least 1.04 up to 1.80, preferably of at least 1.07 up to 1.80, preferably of at least 1.10 up to 1.80, preferably of at least 1.31 up to 1.80, preferably of at least 1.33 up to 1.80, preferably of at least 1.36 up to 1.80, preferably of at least 1.38 up to 1.80, preferably of at least 1.43 up to 1.80, more preferably of at least 1.04 up to 1.75, more preferably of at least 1.07 up to 1.75, more preferably of at least 1.10 up to 1.75, more preferably of at least 1.31 up to 1.75, more preferably of at least 1.33 up to 1.75, more preferably of at least 1.36 up to 1.75, more preferably of at least 1.38 up to 1.75, more preferably of at least 1.43 up to 1.75, more preferably of at least 1.47 up to 1.75, more preferably of at least 1.62 up to 1.75, even more preferably of at least 1.04 up to 1.70, even more preferably of at least 1.07 up to 1.70, even more preferably of at least 1.10 up to 1.70, even more preferably of at least 1.31 up to 1.70, even more preferably of at least 1.33 up to 1.70, even more preferably of at least 1.36 up to 1.70, even more preferably of at least 1.38 up to 1.70, even more preferably of at least 1.43 up to 1.70, even more preferably of at least 1.47 up to 1.70, even more preferably of at least 1.62 up to 1.70, even more preferably of at least 1.04 up to 1.65, even more preferably of at least 1.07 up to 1.65, even more preferably of at least 1.10 up to 1.65, even more preferably of at least 1.31 up to 1.65, even more preferably of at least 1.33 up to 1.65, even more preferably of at least 1.36 up to 1.65, even more preferably of at least 1.38 up to 1.65, even more preferably of at least 1.43 up to 1.65, even more preferably of at least 1.47 up to 1.65, even more preferably of at least 1.62 up to 1.65 and utmost preferably of at least 1.10 to 1.63, of at least 1.38 to 1.63, of at least 1.43 to 1.63, and/or of 1.63;

(F) is an increased catalytic activity of the polypeptide, preferably of the glucose isomerase, in comparison to SEQ ID NO:1 in converting fructose into glucose, expressed as Glucose Formation
of at least 1.2-fold up to 5-fold, of at least 1.2-fold up to 4.5-fold, of at least 1.2-fold up to 4-fold, of at least 1.2-fold up to 3.5-fold, of at least 1.2-fold up to 3.4-fold, of at least 1.2-fold up to 3.3-fold, of at least 1.2-fold up to 3.2-fold, of at least 1.2-fold up to 3.1-fold, of at least 1.2-fold up to 3-fold, of at least 1.2-fold up to 2.9-fold, of at least 1.2-fold up to 2.8-fold, of at least 1.2-fold up to 2.7-fold, of at least 1.2-fold up to 2.6-fold, of at least 1.2-fold up to 2.5-fold, of at least 1.2-fold up to 2.4-fold, of at least 1.2-fold up to 2.3-fold, of at least 1.2-fold up to 2.2-fold, preferably of at least 1.5-fold up to 5-fold, of at least 1.5-fold up to 4.5-fold, of at least 1.5-fold up to 4-fold, of at least 1.5-fold up to 3.5-fold, of at least 1.5-fold up to 3.4-fold, of at least 1.5-fold up to 3.3-fold, of at least 1.5-fold up to 3.2-fold, of at least 1.5-fold up to 3.1-fold, of at least 1.5-fold up to 3-fold, of at least 1.5-fold up to 2.9-fold, of at least 1.5-fold up to 2.8-fold, of at least 1.5-fold up to 2.7-fold, of at least 1.5-fold up to 2.6-fold, of at least 1.5-fold up to 2.5-fold, of at least 1.5-fold up to 2.4-fold, of at least 1.5-fold up to 2.3-fold, of at least 1.5-fold up to 2.2-fold, and more preferably of at least 1.9-fold up to 5-fold, of at least 1.9-fold up to 4.5-fold, of at least 1.9-fold up to 4-fold, of at least 1.9-fold up to 3.5-fold, of at least 1.9-fold up to 3.4-fold, of at least 1.9-fold up to 3.3-fold, of at least 1.9-fold up to 3.2-fold, of at least 1.9-fold up to 3.1-fold, of at least 1.9-fold up to 3-fold, of at least 1.9-fold up to 2.9-fold, of at least 1.9-fold up to 2.8-fold, of at least 1.9-fold up to 2.7-fold, of at least 1.9-fold up to 2.6-fold, of at least 1.9-fold up to 2.5-fold, of at least 1.9-fold up to 2.4-fold, of at least 1.9-fold up to 2.3-fold, of at least 1.9-fold up to 2.2-fold, and yet more preferably of at least 2.0-fold up to 5-fold, of at least 2.0-fold up to 4.5-fold, of at least 2.0-fold up to 4-fold, of at least 2.0-fold up to 3.5-fold, of at least 2.0-fold up to 3.4-fold, of at least 2.0-fold up to 3.3-fold, of at least 2.0-fold up to 3.2-fold, of at least 2.0-fold up to 3.1-fold, of at least 2.0-fold up to 3-fold, of at least 2.0-fold up to 2.9-fold, of at least 2.0-fold up to 2.8-fold, of at least 2.0-fold up to 2.7-fold, of at least 2.0-fold up to 2.6-fold, of at least 2.0-fold up to 2.5-fold, of at least 2.0-fold up to 2.4-fold, of at least 2.0-fold up to 2.3-fold of at least 2.0-fold up to 2.2-fold, and most preferably of at least 2.2-fold up to 3.3-fold.

In a preferred embodiment of the second aspect, which is also a preferred embodiment of any one of embodiments of the first aspect, the polypeptide, preferably the glucose isomerase, has at least one of the characteristics selected from the group consisting of (A), (C), (E), (D), (B), and (F), wherein for characteristic (A) the increased activity of the polypeptide, preferably of the glucose isomerase, for the conversion of fructose to glucose at a concentration of 50 mM fructose in comparison to the polypeptide, preferably the glucose isomerase, of SEQ ID NO: 1 is detected by means of an enzymatic assay for glucose isomerase activity at 50 mM fructose; and/or for characteristic (B) the increased activity of the polypeptide, preferably of the glucose isomerase, for the conversion of fructose to glucose at a concentration of 200 mM fructose in comparison to the polypeptide, preferably the glucose isomerase, of SEQ ID NO: 1 is detected by means of an enzymatic assay for glucose isomerase activity at 200 mM fructose; and/or for characteristic (C) the Residual Activity after incubation of the polypeptide, preferably the glucose isomerase, in comparison to the polypeptide, preferably the glucose isomerase, of SEQ ID NO: 1 is measured at a temperature of 74° C. for 15 minutes by means of an enzymatic assay for glucose isomerase activity at 50 mM fructose; and/or for characteristic (E) the Glucose Isomerase Soluble Expression Level of the polypeptide, preferably the glucose isomerase in comparison to the polypeptide, preferably the glucose isomerase, of SEQ ID NO: 1 is determined by means of denaturing polyacrylamide gel electrophoresis (SDS-PAGE) of cell free extracts of either polypeptide, preferably glucose isomerase, and quantified as band intensity per unit of non-processed bacterial culture volume, and/or for characteristic (F) the increased Glucose Formation of the polypeptide, preferably the glucose isomerase in comparison to the polypeptide, preferably the glucose isomerase, of SEQ ID NO: 1 is detected as the increase in amounts of glucose that is produced after reacting the polypeptide, preferably the glucose isomerase, with fructose in a concentration of 50 mM at 40° C. for 40 min.

In a preferred embodiment of the second aspect, which is also an embodiment of any one of the embodiments of the first aspect, the polypeptide, preferably the glucose isomerase, has at least one of the characteristics selected from the group consisting of (A), (C), (E), (D), (B), and (F), wherein for characteristic (A) the increased activity of the polypeptide, preferably of the glucose isomerase, for the conversion of fructose to glucose at a concentration of 50 mM fructose in comparison to the polypeptide, preferably the glucose isomerase, of SEQ ID NO: 1 is 1.4-fold up to 3.0-fold higher; and/or for characteristic (B) the increased activity of the polypeptide, preferably of the glucose isomerase, for the conversion of fructose to glucose at a concentration of 200 mM fructose in comparison to the polypeptide, preferably the glucose isomerase, of SEQ ID NO: 1 is 1.3-fold up to 3.0-fold higher; and/or for characteristic (C) the $K_M$ value of the polypeptide, preferably of the glucose isomerase is between 140 mM and 160 mM; and/or for characteristic (F) the increased Glucose Formation of the polypeptide, preferably of the glucose isomerase in comparison to the polypeptide, preferably the glucose isomerase, of SEQ ID NO: 1 is 2.2-fold up to 3.3-fold higher.

In a preferred embodiment of the second aspect, which is also a preferred embodiment of any one the embodiments of the first aspect, the polypeptide, preferably the glucose isomerase, has the characteristics (A) and (D), wherein in (A) the increased activity of the polypeptide, preferably of the glucose isomerase, for the conversion of fructose to glucose at a concentration of 50 mM fructose in comparison to the polypeptide, preferably the glucose isomerase, of SEQ ID NO: 1 is 1.2-fold up to 3.0-fold higher, and wherein in (D) the $K_M$ value of the polypeptide, preferably of the glucose isomerase is less than 190 mM.

In a preferred embodiment of the second aspect, which is also a preferred embodiment of any one of the embodiments of the first aspect, the polypeptide, preferably the glucose isomerase, has the characteristics (A), (C), and (E), wherein in (A) the increased activity of the polypeptide, preferably of the glucose isomerase, for the conversion of fructose to glucose at a concentration of 50 mM fructose in comparison to the polypeptide, preferably the glucose isomerase, of SEQ ID NO: 1 is 1.2-fold up to 3.0-fold higher, wherein in (C) the thermal stability of the polypeptide, preferably of the glucose isomerase, expressed as Residual Activity after incubation of the polypeptide, preferably the glucose isomerase, at a temperature of 74° C. for 15 minutes, is at least 30% up to 64%, and wherein in (E) the increased Soluble Expression Level of the polypeptide, preferably of the glucose isomerase, defined as the ratio of the soluble expression level of said polypeptide and the soluble expression level of the polypeptide, preferably the glucose isomerase, of SEQ ID NO: 1 is at least 1.04 up to 1.80.

In a preferred embodiment of the second aspect, which is also an embodiment of any one of the embodiments of the first aspect, the amino acid sequence of the polypeptide, preferably the glucose isomerase, is at least 95% identical to an amino acid sequence of SEQ ID NO: 1, wherein the polypeptide, preferably the glucose isomerase, has at least one of the characteristics selected from the group consisting of (A), (C), (E), (D), (B), and (F), preferably (A), (C), (D), and (E), or any combination thereof, more preferably a combination of characteristics (A), (C), and (E), or (A) and (D), wherein characteristics (A) is an increased activity for the conversion of fructose to glucose at a concentration of 50 mM fructose in comparison to the polypeptide, preferably the glucose isomerase, of SEQ ID NO: 1 of at least 1.1-fold up to 3.0-fold;

(B) is an increased activity for the conversion of fructose to glucose at a concentration of 200 mM fructose in comparison to the polypeptide, preferably the glucose isomerase, of SEQ ID NO: 1 of at least 1.2-fold up to 3.0-fold;

(C) is thermal stability of the polypeptide, preferably the glucose isomerase, expressed as Residual Activity after incubation of the polypeptide, preferably the glucose isomerase at a temperature of 74° C. for 15 minutes, wherein such Residual Activity is at least 30% up to 100%;

(D) is a $K_M$-value of the polypeptide, preferably the glucose isomerase, of SEQ ID NO: 1 of less than 190 mM;

(E) is Soluble Expression Level of the polypeptide, preferably the glucose isomerase, defined as the ratio of the soluble expression level of said polypeptide and the soluble expression level of the polypeptide, preferably the glucose isomerase, of SEQ ID NO: 1 of at least 1.04 up to 1.80; and (F) is an increased Glucose Formation, preferably of at least 1.2-fold up to 5-fold, or of at least 1.5-fold up to 5-fold, or of at least 1.9-fold up to 5-fold, or 1.9-fold up to 3.5-fold, or 2.2-fold up to 3.3-fold.

In a second embodiment of the second aspect, which is also an embodiment of the first embodiment of the second aspect or of any one of the embodiments of the first aspect, the polypeptide, preferably the glucose isomerase, has an increased activity, preferably increased Activity, for the conversion of fructose to glucose at a concentration of 50 mM fructose in comparison to the polypeptide, preferably the glucose isomerase, of SEQ ID NO: 1 of at least 1.1-fold up to 1.6-fold, preferably of at least 1.2-fold up to 1.6-fold, more preferably of at least 1.3-fold up to 1.6-fold, most preferably of at least 1.4-fold up to 1.6-fold, or of at least 1.1-fold up to 3.0-fold, preferably of at least 1.4-fold up to 3.0-fold, preferably of at least 1.5-fold up to 3.0-fold, more preferably of at least 1.6-fold up to 3.0-fold, preferably of at least 1.7-fold up to 3.0-fold, preferably of at least 1.8-fold up to 3.0-fold, preferably of at least 1.9-fold up to 3.0-fold, preferably of at least 2.0-fold up to 3.0-fold, more preferably of at least 1.4-fold up to 2.8-fold, more preferably of at least 1.5-fold up to 2.8-fold, more preferably of at least 1.6-fold up to 2.8-fold, more preferably of at least 1.7-fold up to 2.8-fold, more preferably of at least 1.8-fold up to 2.8-fold, more preferably of at least 1.9-fold up to 2.8-fold, more preferably of at least 2.0-fold up to 2.8-fold, even more preferably of at least 1.4-fold up to 2.6-fold, even more preferably of at least 1.5-fold up to 2.6-fold, more preferably of at least 1.6-fold up to 2.6-fold, more preferably of at least 1.7-fold up to 2.6-fold, more preferably of at least 1.8-fold up to 2.6-fold, more preferably of at least 1.9-fold up to 2.6-fold, more preferably of at least 2.0-fold up to 2.6-fold, and most preferably of at least 1.4-fold up to 2.4-fold, most preferably of at least 1.5-fold up to 2.4-fold, most preferably of at least 1.6-fold up to 2.4-fold, most preferably of at least 1.7-fold up to 2.4-fold, most preferably of at least 1.8-fold up to 2.4-fold, most preferably of at least 1.9-fold up to 2.4-fold, and most preferably of at least 2.0-fold up to 2.4-fold, and utmost preferable of at least 1.7-fold up to 2.4-fold.

In a third embodiment of the second aspect, which is also an embodiment of any one of the first and second embodiment of the second aspect or of any one of the embodiments of the first aspect, the polypeptide, preferably the glucose isomerase, has an increased activity, preferably increased Activity, for the conversion of fructose to glucose at a concentration of 200 mM fructose in comparison to the polypeptide, preferably the glucose isomerase, of SEQ ID NO: 1 of at least 1.2-fold up to 1.6-fold, more preferably of at least 1.3-fold up to 1.6-fold, most preferably of at least 1.4-fold up to 1.6-fold, and/or of at least 1.2-fold up to 3.0-fold, preferably of at least 1.3-fold up to 3.0-fold, preferably of at least 1.4-fold up to 3.0-fold preferably of at least 1.5-fold up to 3.0-fold, more preferably of at least 1.6-fold up to 3.0-fold, preferably of at least 1.7-fold up to 3.0-fold, preferably of at least 1.8-fold up to 3.0-fold, preferably of at least 1.9-fold up to 3.0-fold, preferably of at least 2.0-fold up to 3.0-fold, more preferably of at least 1.3-fold up to 2.5-fold, more preferably of at least 1.4-fold up to 2.5-fold, more preferably of at least 1.5-fold up to 2.5-fold, more preferably of at least 1.6-fold up to 2.5-fold, more preferably of at least 1.7-fold up to 2.5-fold, more preferably of at least 1.8-fold up to 2.5-fold, more preferably of at least 1.9-fold up to 2.5-fold, more preferably of at least 2.0-fold up to 2.5-fold, even more preferably of at least 1.3-fold up to 2.2-fold, even more preferably of at least 1.4-fold up to 2.2-fold, even more preferably of at least 1.5-fold up to 2.2-fold, more preferably of at least 1.6-fold up to 2.2-fold, more preferably of at least 1.7-fold up to 2.2-fold, more preferably of at least 1.8-fold up to 2.2-fold, more preferably of at least 1.9-fold up to 2.2-fold, more preferably of at least 2.0-fold up to 2.2-fold, and utmost preferably of at least 1.5-fold up to 2.2-fold.

In a fourth embodiment of the second aspect, which is also an embodiment of any one of the first, second and third embodiment of the second aspect or of any one of the embodiments of the first aspect, the polypeptide, preferably the glucose isomerase, has a thermal stability expressed as Residual Activity after incubation of the polypeptide, preferably the glucose isomerase, at a temperature of 74° C. for 15 minutes, wherein such Residual Activity is at least 30% up to 100%, at least 40% up to 100%, at least 50% up to 100%, at least 30% up to 75%, at least 40% up to 75%, at least 50% up to 75%, at least 30% up to 65%, at least 40% up to 65%, at least 50% up to 65%, at least 41% up to 64%, and/or at least 30% up to 100%, at least 31% up to 100%, at least 32% up to 100%, at least 33% up to 100%, at least 34% up to 100%, at least 35% up to 100%, at least 36% up to 100%, at least 37% up to 100%, at least 38% up to 100%, at least 39% up to 100%, at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, at least 60% up to 100%, at least 61% up to 100%, at least 62% up to 100%, at least 63% up to 100%, at least 64% up to 100%, at least 65% up to 100%, at least 66% up to 100%, at least 67% up to 100%, at least 68% up to 100%, at least 69% up to 100%, at least 70% up to 100%, at least 71% up to 100%, at least 72% up to 100%, at least 73% up to 100%, at least 74% up to 100%, at least 75% up to 100%, at least 76% up to 100%, at least 77% up to 100%, at least 78% up to 100%, at least 79% up to 100%, at least 80% up to 100%, at least 30% up to 75%, at least 31% up to 75%, at least 32% up to 75%, at least 33% up to 75%, at least 34% up to 75%, at least 35% up to 75%, at least 36% up to 75%, at least 37% up to 75%, at least 38% up to 75%, at least 39% up to 75%, at least 40% up to 75%, at least 41% up to 75%, at least 42% up to 75%, at least 43% up to 75%, at least 44% up to 75%, at least 45% up to 75%, at least 46% up to 75%, at least 47% up to 75%, at least 48% up to 75%, at least 49% up to 75%, at least 50% up to 75%, at least 51% up to 75%, at least 52% up to 75%, at least 53% up to 75%, at least 54% up to 75%, at least 55% up to 75%, at least 56% up to 75%, at least 57% up to 75%, at least 58% up to 75%, at least 59% up to 75%, at least 60% up to 75%, at least 61% up to 75%, at least 62% up to 75%, at least 30% up to 70%, at least 31% up to 70%, at least 32% up to 70%, at least 33% up to 70%, at least 34% up to 70%, at least 35% up to 70%, at least 36% up to 70%, at least 37% up to 70%, at least 38% up to 70%, at least 39% up to 70%, at least 40% up to 70%, at least 41% up to 70%, at least 42% up to 70%, at least 43% up to 70%, at least 44% up to 70%, at least 45% up to 70%, at least 46% up to 70%, at least 47% up to 70%, at least 48% up to 70%, at least 49% up to 70%, at least 50% up to 70%, at least 51% up to 70%, at least 52% up to 70%, at least 53% up to 70%, at least 54% up to 70%, at least 55% up to 70%, at least 56% up to 70%, at least 57% up to 70%, at least 58% up to 70%, at least 59% up to 70%, at least 60% up to 70%, at least 61% up to 70%, at least 62% up to 70%, at least 30% up to 65%, at least 31% up to 65%, at least 32% up to 65%, at least 33% up to 65%, at least 34% up to 65%, at least 35% up to 65%, at least 36% up to 65%, at least 37% up to 65%, at least 38% up to 65%, at least 39% up to 65%, at least 40% up to 65%, at least 41% up to 65%, at least 42% up to 65%, at least 43% up to 65%, at least 44% up to 65%, at least 45% up to 65%, at least 46% up to 65%, at least 47% up to 65%, at least 48% up to 65%, at least 49% up to 65%, at least 50% up to 65%, at least 51% up to 65%, at least 52% up to 65%, at least 53% up to 65%, at least 54% up to 65%, at least 55% up to 65%, at least 56% up to 65%, at least 57% up to 65%, at least 58% up to 65%, at least 59% up to 65%, at least 60% up to 65%, at least 61% up to 65%, at least 62% up to 65%, more preferably at least 30% up to 65%, at least 34% up to 65%, at least 35% up to 65%, at least 38% up to 65%, at least 40% up to 65%, at least 41% up to 65%, at least 42% up to 65%, at least 46% up to 65%, at least 47% up to 65%, at least 50% up to 65%, at least 55% up to 65%, at least 59% up to 65%, at least 60% up to 65%, at least 62% up to 65%, even more preferably at least at least 40% up to 65%, and even more preferably at least 60% up to 65%, and most preferably of 62%.

In a fifth embodiment of the second aspect, which is also an embodiment of any one of the first, second, third, and fourth embodiment of the second aspect or of any one of the embodiments of the first aspect, the polypeptide, preferably the glucose isomerase, has a Km value of between 100 mM and 190 mM, preferably between 130 mM and 190 mM, preferably between 160 mM and 190 mM, more preferably between 170 mM and 185 mM, and most preferably between 175 mM and 180 mM; and/or of between 50 mM and 190 mM, 50 mM and 189 mM, 50 mM and 188 mM, 50 mM and 187 mM, 50 mM and 186 mM, 50 mM and 185 mM, preferably between 50 mM and 184 mM, preferably between 50 mM and 183 mM, preferably between 50 mM and 182 mM, preferably between 50 mM and 181 mM, preferably between 50 mM and 180 mM, preferably between 50 mM and 179 mM, preferably between 50 mM and 178 mM, preferably between 50 mM and 177 mM, preferably between 50 mM and 176 mM, preferably between 50 mM and 175 mM, preferably between 50 mM and 174 mM, preferably between 50 mM and 173 mM, preferably between 50 mM and 172 mM, preferably between 50 mM and 171 mM, preferably between 50 mM and 170 mM, preferably between 50 mM and 169 mM, preferably between 50 mM and 168 mM, preferably between 50 mM and 167 mM, preferably between 50 mM and 166 mM, preferably between 50 mM and 165 mM, preferably between 50 mM and 160 mM, preferably between 50 mM and 159 mM, preferably between 50 mM and 158 mM, preferably between 50 mM and 157 mM, preferably between 50 mM and 156 mM, preferably between 50 mM and 155 mM, preferably between 50 mM and 154 mM, preferably between 50 mM and 153 mM, preferably between 50 mM and 152 mM, 75 mM and 190 mM, 75 mM and 189 mM, 75 mM and 188 mM, 75 mM and 187 mM, 75 mM and 186 mM, 75 mM and 185 mM, preferably between 75 mM and 184 mM, preferably between 75 mM and 183 mM, preferably between 75 mM and 182 mM, preferably between 75 mM and 181 mM, preferably between 75 mM and 180 mM, preferably between 75 mM and 179 mM, preferably between 75 mM and 178 mM, preferably between 75 mM and 177 mM, preferably between 75 mM and 176 mM, preferably between 75 mM and 175 mM, preferably between 75 mM and 174 mM, preferably between 75 mM and 173 mM, preferably between 75 mM and 172 mM, preferably between 75 mM and 171 mM, preferably between 75 mM and 170 mM, preferably between 75 mM and 169 mM, preferably between 75 mM and 168 mM, preferably between 75 mM and 167 mM, preferably between 75 mM and 166 mM, preferably between 75 mM and 165 mM, preferably between 75 mM and 160 mM, preferably between 75 mM and 159 mM, preferably between 75 mM and 158 mM, preferably between 75 mM and 157 mM, preferably between 75 mM and 156 mM, preferably between 75 mM and 155 mM, preferably between 75 mM and 154 mM, preferably between 75 mM and 153 mM, preferably between 75 mM and 152 mM, 100 mM and 190 mM, 100 mM and 189 mM, 100 mM and 188 mM, 100 mM and 187 mM, 100 mM and 186 mM, 100 mM and 185 mM, preferably between 100 mM and 184 mM, preferably between 100 mM and 183 mM, preferably between 100 mM and 182 mM, preferably between 100 mM and 181 mM, preferably between 100 mM and 180 mM, preferably between 100 mM and 179 mM, preferably between 100 mM and 178 mM, preferably between 100 mM and 177 mM, preferably between 100 mM and 176 mM, preferably between 100 mM and 1100 mM, preferably between 100 mM and 174 mM, preferably between 100 mM and 173 mM, preferably between 100 mM and 172 mM, preferably between 100 mM and 171 mM, preferably between 100 mM and 170 mM, preferably between 100 mM and 169 mM, preferably between 100 mM and 168 mM, preferably between 100 mM and 167 mM, preferably between 100 mM and 166 mM, preferably between 100 mM and 165 mM, preferably between 100 mM and 160 mM, preferably between 100 mM and 159 mM, preferably between 100 mM and 158 mM, preferably between 100 mM and 157 mM, preferably between 100 mM and 156 mM, preferably between 100 mM and 155 mM, preferably between 100 mM and 154 mM, preferably between 100 mM and 153 mM, preferably between 100 mM and 152 mM, 115 mM and 190 mM, 115 mM and 189 mM, 115 mM and 188 mM, 115 mM and 187 mM, 115 mM and 186 mM, 115 mM and 185 mM, preferably between 115 mM and 184 mM, preferably between 115 mM and 183 mM, preferably between 115 mM and 182 mM, preferably between 115 mM and 181 mM, preferably between 115 mM and 180 mM, preferably between 115 mM and 179 mM, preferably between 115 mM and 178 mM, preferably between 115 mM and 177 mM, preferably between 115 mM and 176 mM, preferably between 115 mM and 175 mM, preferably between 115 mM and 174 mM, preferably between 115 mM and 173 mM, preferably between 115 mM and 172 mM, preferably between 115 mM and 171 mM, preferably between 115 mM and 170 mM, preferably between 115 mM and 169 mM, preferably between 115 mM and 168 mM, preferably between 115 mM and 167 mM, preferably between 115 mM and 166 mM, preferably between 115 mM and 165 mM, preferably between 115 mM and 160 mM, preferably between 115 mM and 159 mM, preferably between 115 mM and 158 mM, preferably between 115 mM and 157 mM, preferably between 115 mM and 156 mM, preferably between 115 mM and 155 mM, preferably between 115 mM and 154 mM, preferably between 115 mM and 153 mM, preferably between 115 mM and 152 mM, 130 mM and 185 mM, preferably between 130 mM and 184 mM, preferably between 130 mM and 183 mM, preferably between 130 mM and 182 mM, preferably between 130 mM and 181 mM, preferably between 130 mM and 180 mM, preferably between 130 mM and 179 mM, preferably between 130 mM and 178 mM, preferably between 130 mM and 177 mM, preferably between 130 mM and 176 mM, preferably between 130 mM and 175 mM, preferably between 130 mM and 174 mM, preferably between 130 mM and 173 mM, preferably between 130 mM and 172 mM, preferably between 130 mM and 171 mM, preferably between 130 mM and 170 mM, preferably between 130 mM and 169 mM, preferably between 130 mM and 168 mM, preferably between 130 mM and 167 mM, preferably between 130 mM and 166 mM, preferably between 130 mM and 165 mM, preferably between 130 mM and 160 mM, preferably between 130 mM and 159 mM, preferably between 130 mM and 158 mM, preferably between 130 mM and 157 mM, preferably between 130 mM and 156 mM, preferably between 130 mM and 155 mM, preferably between 130 mM and 154 mM, preferably between 130 mM and 153 mM, preferably between 130 mM and 152 mM, more preferably between 135 mM and 185 mM, more preferably between 135 mM and 184 mM, more preferably between 135 mM and 183 mM, more preferably between 135 mM and 182 mM, more preferably between 135 mM and 181 mM, more preferably between 135 mM and 180 mM, more preferably between 135 mM and 179 mM, more preferably between 135 mM and 178 mM, more preferably between 135 mM and 177 mM, more preferably between 135 mM and 176 mM, more preferably between 135 mM and 175 mM, more preferably between 135 mM and 174 mM, more preferably between 135 mM and 173 mM, more preferably between 135 mM and 172 mM, more preferably between 135 mM and 171 mM, more preferably between 135 mM and 170 mM, more preferably between 135 mM and 169 mM, more preferably between 135 mM and 168 mM, more preferably between 135 mM and 167 mM, more preferably between 135 mM and 166 mM, more preferably between 135 mM and 165 mM, more preferably between 135 mM and 160 mM, more preferably between 135 mM and 159 mM, more preferably between 135 mM and 158 mM, more preferably between 135 mM and 157 mM, more preferably between 135 mM and 156 mM, more preferably between 135 mM and 155 mM, more preferably between 135 mM and 154 mM, more preferably between 135 mM and 153 mM, more preferably between 135 mM and 152 mM, most preferably between 140 mM and 185 mM, most preferably between 140 mM and 184 mM, most preferably between 140 mM and 183 mM, most preferably between 140 mM and 182 mM, most preferably between 140 mM and 181 mM, most preferably between 140 mM and 180 mM, most preferably between 140 mM and 179 mM, most preferably between 140 mM and 178 mM, most preferably between 140 mM and 177 mM, most preferably between 140 mM and 176 mM, most preferably between 140 mM and 175 mM, most preferably between 140 mM and 174 mM, most preferably between 140 mM and 173 mM, most preferably between 140 mM and 172 mM, most preferably between 140 mM and 171 mM, most preferably between 140 mM and 170 mM, most preferably between 140 mM and 169 mM, most preferably between 140 mM and 168 mM, most preferably between 140 mM and 167 mM, most preferably between 140 mM and 166 mM, most preferably between 140 mM and 165 mM, most preferably between 140 mM and 160 mM, most preferably between 140 mM and 159 mM, most preferably between 140 mM and 158 mM, most preferably between 140 mM and 157 mM, most preferably between 140 mM and 156 mM, most preferably between 140 mM and 155 mM, most preferably between 140 mM and 154 mM, most preferably between 140 mM and 153 mM, and utmost preferably between 140 mM and 152 mM; and/or of less than 190 mM, 189 mM, 188 mM, 187 mM, 186 mM, 185 mM, 184 mM, 183 mM, 182 mM, 181 mM, 180 mM, 179 mM, 178 mM, 177 mM, 176 mM, 175 mM, 174 mM, 173 mM, 172 mM, 171 mM, 170 mM, 169 mM, 168 mM, 167 mM, 166 mM, 165 mM, 160 mM, 159 mM, 158 mM, 157 mM, 156 mM, 155 mM, 154 mM, 153 mM, 152 mM, preferably of less than 185 mM, more preferably less than 170 mM, even more preferably less than 160 mM, and most preferably less than 155 mM, and utmost preferably of 152 mM and less than 152 mM.

In a sixth embodiment of the second aspect, which is also an embodiment of any one of the first, second, third, fourth and fifth embodiment of the second aspect or of any one of the embodiments of the first aspect, the polypeptide, preferably the glucose isomerase, has a Soluble Expression Level defined as the ratio of the soluble expression level of said polypeptide and the soluble expression level of the polypeptide, preferably the glucose isomerase, of SEQ ID NO: 1, of at least 1.04 up to 1.38, preferably of at least 1.07 up to 1.38, preferably of at least 1.10 up to 1.38, preferably of at least 1.31 up to 1.38, preferably of at least 1.33 up to 1.38, preferably of at least 1.36 up to 1.38, more preferably of at least 1.04 up to 1.36, more preferably of at least 1.07 up to 1.36, more preferably of at least 1.10 up to 1.36, more preferably of at least 1.31 up to 1.36, more preferably of at least 1.33 up to 1.36, and most preferably of at 1.36; and or of at least 1.04 up to 1.80, preferably of at least 1.07 up to 1.80, preferably of at least 1.10 up to 1.80, preferably of at least 1.31 up to 1.80, preferably of at least 1.33 up to 1.80, preferably of at least 1.36 up to 1.80, preferably of at least 1.38 up to 1.80, preferably of at least 1.43 up to 1.80, preferably of at least 1.04 up to 1.75, more preferably of at least 1.07 up to 1.75, more preferably of at least 1.10 up to 1.75, more preferably of at least 1.31 up to 1.75, more preferably of at least 1.33 up to 1.75, more preferably of at least 1.36 up to 1.75, more preferably of at least 1.38 up to 1.75, more preferably of at least 1.43 up to 1.75, more preferably of at least 1.47 up to 1.75, more preferably of at least 1.62 up to 1.75, even more preferably of at least 1.04 up to 1.70, even more preferably of at least 1.07 up to 1.70, even more preferably of at least 1.10 up to 1.70, even more preferably of at least 1.31 up to 1.70, even more preferably of at least 1.33 up to 1.70, even more preferably of at least 1.36 up to 1.70, even more preferably of at least 1.38 up to 1.70, even more preferably of at least 1.43 up to 1.70, even more preferably of at least 1.47 up to 1.70, even more preferably of at least 1.62 up to 1.70, even more preferably of at least 1.04 up to 1.65, even more preferably of at least 1.07 up to 1.65, even more preferably of at least 1.10 up to 1.65, even more preferably of at least 1.31 up to 1.65, even more preferably of at least 1.33 up to 1.65, even more preferably of at least 1.36 up to 1.65, even more preferably of at least 1.38 up to 1.65, even more preferably of at least 1.43 up to 1.65, even more preferably of at least 1.47 up to 1.65, even more preferably of at least 1.62 up to 1.65 and utmost preferably of at least 1.10 to 1.63, of at least 1.38 to 1.63, of at least 1.43 to 1.63, and/or of 1.63.

In another embodiment of the second aspect, which is also an embodiment of any one of the first, second, third, fourth and fifth embodiment of the second aspect or of any one of the embodiments of the first aspect, the polypeptide, preferably the glucose isomerase, has an increased catalytic activity of the polypeptide, preferably of the glucose isomerase, in comparison to SEQ ID NO: 1 in converting fructose into glucose, expressed as Glucose Formation of at least 1.2-fold up to 5-fold, of at least 1.2-fold up to 4.5-fold, of at least 1.2-fold up to 4-fold, of at least 1.2-fold up to 3.5-fold, of at least 1.2-fold up to 3.4-fold, of at least 1.2-fold up to 3.3-fold, of at least 1.2-fold up to 3.2-fold, of at least 1.2-fold up to 3.1-fold, of at least 1.2-fold up to 3-fold, of at least 1.2-fold up to 2.9-fold, of at least 1.2-fold up to 2.8-fold, of at least 1.2-fold up to 2.7-fold, of at least 1.2-fold up to 2.6-fold, of at least 1.2-fold up to 2.5-fold, of at least 1.2-fold up to 2.4-fold, of at least 1.2-fold up to 2.3-fold, of at least 1.2-fold up to 2.2-fold, preferably of at least 1.5-fold up to 5-fold, of at least 1.5-fold up to 4.5-fold, of at least 1.5-fold up to 4-fold, of at least 1.5-fold up to 3.5-fold, of at least 1.5-fold up to 3.4-fold, of at least 1.5-fold up to 3.3-fold, of at least 1.5-fold up to 3.2-fold, of at least 1.5-fold up to 3.1-fold, of at least 1.5-fold up to 3-fold, of at least 1.5-fold up to 2.9-fold, of at least 1.5-fold up to 2.8-fold, of at least 1.5-fold up to 2.7-fold, of at least 1.5-fold up to 2.6-fold, of at least 1.5-fold up to 2.5-fold, of at least 1.5-fold up to 2.4-fold, of at least 1.5-fold up to 2.3-fold, of at least 1.5-fold up to 2.2-fold, and more preferably of at least 1.9-fold up to 5-fold, of at least 1.9-fold up to 4.5-fold, of at least 1.9-fold up to 4-fold, of at least 1.9-fold up to 3.5-fold, of at least 1.9-fold up to 3.4-fold, of at least 1.9-fold up to 3.3-fold, of at least 1.9-fold up to 3.2-fold, of at least 1.9-fold up to 3.1-fold, of at least 1.9-fold up to 3-fold, of at least 1.9-fold up to 2.9-fold, of at least 1.9-fold up to 2.8-fold, of at least 1.9-fold up to 2.7-fold, of at least 1.9-fold up to 2.6-fold, of at least 1.9-fold up to 2.5-fold, of at least 1.9-fold up to 2.4-fold, of at least 1.9-fold up to 2.3-fold, of at least 1.9-fold up to 2.2-fold, and yet more preferably of at least 2.0-fold up to 5-fold, of at least 2.0-fold up to 4.5-fold, of at least 2.0-fold up to 4-fold, of at least 2.0-fold up to 3.5-fold, of at least 2.0-fold up to 3.4-fold, of at least 2.0-fold up to 3.3-fold, of at least 2.0-fold up to 3.2-fold, of at least 2.0-fold up to 3.1-fold, of at least 2.0-fold up to 3-fold, of at least 2.0-fold up to 2.9-fold, of at least 2.0-fold up to 2.8-fold, of at least 2.0-fold up to 2.7-fold, of at least 2.0-fold up to 2.6-fold, of at least 2.0-fold up to 2.5-fold, of at least 2.0-fold up to 2.4-fold, of at least 2.0-fold up to 2.3-fold of at least 2.0-fold up to 2.2-fold, and most preferably of at least 2.2-fold up to 3.3-fold.

In a seventh embodiment of the second aspect, which is also an embodiment of any one of the first, second, third, fourth, fifth and sixth embodiment or any other embodiment of the second aspect or of any one of the embodiments of the first aspect, the polypeptide, preferably the glucose isomerase, is a polypeptide, preferably a glucose isomerase, of any one of the first, second, third, fourth, fifth, sixth, seventh, eighth, ninth and tenth embodiment of the first aspect, preferably a polypeptide, preferably a glucose isomerase, of any one of the third, fourth, fifth, sixth, seventh, eighth, ninth and tenth embodiment of the first aspect, more preferably a polypeptide, preferably a glucose isomerase, of any one of the fifth, sixth, seventh, eighth, ninth and tenth embodiment of the first aspect, even more preferably a polypeptide, preferably a glucose isomerase, of any one of the seventh, eighth, ninth and tenth embodiment of the first aspect, and most preferably a polypeptide, preferably a glucose isomerase, of any one of the ninth and tenth embodiment of the first aspect, and a polypeptide, preferably a glucose isomerase, of any one of the $103^{rd}$, $108^{th}$, $113^{th}$, $114^{th}$, $115^{th}$, $120^{th}$, $125^{th}$, $130^{th}$ and $131^{st}$ embodiment of the first aspect, and/or a polypeptide, preferably a glucose isomerase, of any one of the eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, 86th$87^{th}$, $88^{th}$, $89^{th}$, $90^{th}$, $91^{st}$, $92^{nd}$, $93^{rd}$, $94^{th}$, $95^{th}$, $96^{th}$ and $97^{th}$ embodiment or of any one of the other embodiments of the first aspect, preferably a polypeptide, preferably a glucose isomerase, of any one of the $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$ and $97^{th}$, embodiment of the first aspect, more preferably a polypeptide, preferably a glucose isomerase, of any one of the $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$ and $97^{th}$, embodiment of the first aspect, even more preferably a polypeptide, preferably a glucose isomerase, of any one of the $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$ and $97^{th}$, embodiment of the first aspect, most preferably a polypeptide, preferably a glucose isomerase, of any one of the $63^{rd}$, and $97^{th}$, embodiment of the first aspect, and a polypeptide, preferably a glucose isomerase, of any one of the $104^{th}$, $105^{th}$, $106^{th}$, $107^{th}$, $109^{th}$, $110^{th}$, $111^{th}$, $112^{th}$, $113^{th}$, $114^{th}$, $116^{th}$, $117^{th}$, $118^{th}$, $119^{th}$, $121^{st}$, $122^{nd}$, $123^{rd}$, $124^{th}$, $126^{th}$, $127^{th}$, $128^{th}$, $129^{th}$, $130^{th}$, $132^{nd}$, $133^{rd}$, $134^{th}$ and $135^{th}$, embodiment of the first aspect.

In an eighth embodiment of the second aspect, which is also an embodiment of any one of the first, second, third, fourth, fifth, sixth and seventh embodiment of the second aspect or of any one of the embodiments of the first aspect, and which preferably is also an embodiment of the first embodiment of the second aspect, the polypeptide, preferably the glucose isomerase, has an increased activity, preferably increased Activity, for the conversion of fructose to glucose at a concentration of 50 mM fructose in comparison to the polypeptide, preferably the glucose isomerase, of SEQ ID NO: 1 of at least 1.1-fold up to 3.0-fold, preferably of at least 1.4-fold up to 3.0-fold, preferably of at least 1.5-fold up to 3.0-fold, more preferably of at least 1.6-fold up to 3.0-fold, preferably of at least 1.7-fold up to 3.0-fold, preferably of at least 1.8-fold up to 3.0-fold, preferably of at least 1.9-fold up to 3.0-fold, preferably of at least 2.0-fold up to 3.0-fold, more preferably of at least 1.4-fold up to 2.8-fold, more preferably of at least 1.5-fold up to 2.8-fold, more preferably of at least 1.6-fold up to 2.8-fold, more preferably of at least 1.7-fold up to 2.8-fold, more preferably of at least 1.8-fold up to 2.8-fold, more preferably of at least 1.9-fold up to 2.8-fold, more preferably of at least 2.0-fold up to 2.8-fold, even more preferably of at least 1.4-fold up to 2.6-fold, even more preferably of at least 1.5-fold up to 2.6-fold, more preferably of at least 1.6-fold up to 2.6-fold, more preferably of at least 1.7-fold up to 2.6-fold, more preferably of at least 1.8-fold up to 2.6-fold, more preferably of at least 1.9-fold up to 2.6-fold, more preferably of at least 2.0-fold up to 2.6-fold, and most preferably of at least 1.4-fold up to 2.4-fold, most preferably of at least 1.5-fold up to 2.4-fold, most preferably of at least 1.6-fold up to 2.4-fold, most preferably of at least 1.7-fold up to 2.4-fold, most preferably of at least 1.8-fold up to 2.4-fold, most preferably of at least 1.9-fold up to 2.4-fold, and most preferably of at least 2.0-fold up to 2.4-fold, and utmost preferable of at least 1.7-fold up to 2.4-fold.

In a ninth embodiment of the second aspect, which is also an embodiment of any one of the first, second, third, fourth, fifth, sixth, seventh and eighth embodiment of the second aspect or of any one of the embodiments of the first aspect, the polypeptide, preferably the glucose isomerase, has an increased activity, preferably increased Activity, for the conversion of fructose to glucose at a concentration of 200 mM fructose in comparison to the polypeptide, preferably the glucose isomerase, of SEQ ID NO: 1 of at least 1.2-fold up to 3.0-fold, preferably of at least 1.3-fold up to 3.0-fold, preferably of at least 1.4-fold up to 3.0-fold preferably of at least 1.5-fold up to 3.0-fold, more preferably of at least 1.6-fold up to 3.0-fold, preferably of at least 1.7-fold up to 3.0-fold, preferably of at least 1.8-fold up to 3.0-fold, preferably of at least 1.9-fold up to 3.0-fold, preferably of at least 2.0-fold up to 3.0-fold, more preferably of at least 1.3-fold up to 2.5-fold, more preferably of at least 1.4-fold up to 2.5-fold, more preferably of at least 1.5-fold up to 2.5-fold, more preferably of at least 1.6-fold up to 2.5-fold, more preferably of at least 1.7-fold up to 2.5-fold, more preferably of at least 1.8-fold up to 2.5-fold, more preferably of at least 1.9-fold up to 2.5-fold, more preferably of at least 2.0-fold up to 2.5-fold, even more preferably of at least 1.3-fold up to 2.2-fold, even more preferably of at least 1.4-fold up to 2.2-fold, even more preferably of at least 1.5-fold up to 2.2-fold, more preferably of at least 1.6-fold up to 2.2-fold, more preferably of at least 1.7-fold up to 2.2-fold, more preferably of at least 1.8-fold up to 2.2-fold, more preferably of at least 1.9-fold up to 2.2-fold, more preferably of at least 2.0-fold up to 2.2-fold, and utmost preferably of at least 1.5-fold up to 2.2-fold.

In a tenth embodiment of the second aspect, which is also an embodiment of any one of the first, second, third, fourth, fifth, sixth, seventh, eighth and ninth embodiment of the second aspect or of any one of the embodiments of the first aspect, the polypeptide, preferably the glucose isomerase, has a thermal stability, expressed as Residual Activity after incubation of the polypeptide, preferably the glucose isomerase at a temperature of 74° C. for 15 minutes, wherein such Residual Activity is at least 30% up to 100%, at least 31% up to 100%, at least 32% up to 100%, at least 33% up to 100%, at least 34% up to 100%, at least 35% up to 100%, at least 36% up to 100%, at least 37% up to 100%, at least 38% up to 100%, at least 39% up to 100%, at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, at least 60% up to 100%, at least 61% up to 100%, at least 62% up to 100%, at least 63% up to 100%, at least 64% up to 100%, at least 65% up to 100%, at least 66% up to 100%, at least 67% up to 100%, at least 68% up to 100%, at least 69% up to 100%, at least 70% up to 100%, at least 71% up to 100%, at least 72% up to 100%, at least 73% up to 100%, at least 74% up to 100%, at least 75% up to 100%, at least 76% up to 100%, at least 77% up to 100%, at least 78% up to 100%, at least 79% up to 100%, at least 80% up to 100%, at least 30% up to 75%, at least 31% up to 75%, at least 32% up to 75%, at least 33% up to 75%, at least 34% up to 75%, at least 35% up to 75%, at least 36% up to 75%, at least 37% up to 75%, at least 38% up to 75%, at least 39% up to 75%, at least 40% up to 75%, at least 41% up to 75%, at least 42% up to 75%, at least 43% up to 75%, at least 44% up to 75%, at least 45% up to 75%, at least 46% up to 75%, at least 47% up to 75%, at least 48% up to 75%, at least 49% up to 75%, at least 50% up to 75%, at least 51% up to 75%, at least 52% up to 75%, at least 53% up to 75%, at least 54% up to 75%, at least 55% up to 75%, at least 56% up to 75%, at least 57% up to 75%, at least 58% up to 75%, at least 59% up to 75%, at least 60% up to 75%, at least 61% up to 75%, at least 62% up to 75%, at least 30% up to 70%, at least 31% up to 70%, at least 32% up to 70%, at least 33% up to 70%, at least 34% up to 70%, at least 35% up to 70%, at least 36% up to 70%, at least 37% up to 70%, at least 38% up to 70%, at least 39% up to 70%, at least 40% up to 70%, at least 41% up to 70%, at least 42% up to 70%, at least 43% up to 70%, at least 44% up to 70%, at least 45% up to 70%, at least 46% up to 70%, at least 47% up to 70%, at least 48% up to 70%, at least 49% up to 70%, at least 50% up to 70%, at least 51% up to 70%, at least 52% up to 70%, at least 53% up to 70%, at least 54% up to 70%, at least 55% up to 70%, at least 56% up to 70%, at least 57% up to 70%, at least 58% up to 70%, at least 59% up to 70%, at least 60% up to 70%, at least 61% up to 70%, at least 62% up to 70%, at least 30% up to 65%, at least 31% up to 65%, at least 32% up to 65%, at least 33% up to 65%, at least 34% up to 65%, at least 35% up to 65%, at least 36% up to 65%, at least 37% up to 65%, at least 38% up to 65%, at least 39% up to 65%, at least 40% up to 65%, at least 41% up to 65%, at least 42% up to 65%, at least 43% up to 65%, at least 44% up to 65%, at least 45% up to 65%, at least 46% up to 65%, at least 47% up to 65%, at least 48% up to 65%, at least 49% up to 65%, at least 50% up to 65%, at least 51% up to 65%, at least 52% up to 65%, at least 53% up to 65%, at least 54% up to 65%, at least 55% up to 65%, at least 56% up to 65%, at least 57% up to 65%, at least 58% up to 65%, at least 59% up to 65%, at least 60% up to 65%, at least 61% up to 65%, at least 62% up to 65%, more preferably at least 30% up to 65%, at least 34% up to 65%, at least 35% up to 65%, at least 38% up to 65%, at least 40% up to 65%, at least 41% up to 65%, at least 42% up to 65%, at least 46% up to 65%, at least 47% up to 65%, at least 50% up to 65%, at least 55% up to 65%, at least 59% up to 65%, at least 60% up to 65%, at least 62% up to 65%, even more preferably at least at least 40% up to 65%, and even more preferably at least 60% up to 65%, and most preferably of 62%.

In an eleventh embodiment of the second aspect, which is also an embodiment of any one of the first, second, third, fourth, fifth, sixth, seventh, eighth, ninth and tenth embodiment of the second aspect or of any one of the embodiments of the first aspect, the polypeptide, preferably the glucose isomerase, has a $K_M$ value of between 50 mM and 190 mM, 50 mM and 189 mM, 50 mM and 188 mM, 50 mM and 187 mM, 50 mM and 186 mM, 50 mM and 185 mM, preferably between 50 mM and 184 mM, preferably between 50 mM and 183 mM, preferably between 50 mM and 182 mM, preferably between 50 mM and 181 mM, preferably between 50 mM and 180 mM, preferably between 50 mM and 179 mM, preferably between 50 mM and 178 mM, preferably between 50 mM and 177 mM, preferably between 50 mM and 176 mM, preferably between 50 mM and 175 mM, preferably between 50 mM and 174 mM, preferably between 50 mM and 173 mM, preferably between 50 mM and 172 mM, preferably between 50 mM and 171 mM, preferably between 50 mM and 170 mM, preferably between 50 mM and 169 mM, preferably between 50 mM and 168 mM, preferably between 50 mM and 167 mM, preferably between 50 mM and 166 mM, preferably between 50 mM and 165 mM, preferably between 50 mM and 160 mM, preferably between 50 mM and 159 mM, preferably between 50 mM and 158 mM, preferably between 50 mM and 157 mM, preferably between 50 mM and 156 mM, preferably between 50 mM and 155 mM, preferably between 50 mM and 154 mM, preferably between 50 mM and 153 mM, preferably between 50 mM and 152 mM, 75 mM and 190 mM, 75 mM and 189 mM, 75 mM and 188 mM, 75 mM and 187 mM, 75 mM and 186 mM, 75 mM and 185 mM, preferably between 75 mM and 184 mM, preferably between 75 mM and 183 mM, preferably between 75 mM and 182 mM, preferably between 75 mM and 181 mM, preferably between 75 mM and 180 mM, preferably between 75 mM and 179 mM, preferably between 75 mM and 178 mM, preferably between 75 mM and 177 mM, preferably between 75 mM and 176 mM, preferably between 75 mM and 175 mM, preferably between 75 mM and 174 mM, preferably between 75 mM and 173 mM, preferably between 75 mM and 172 mM, preferably between 75 mM and 171 mM, preferably between 75 mM and 170 mM, preferably between 75 mM and 169 mM, preferably between 75 mM and 168 mM, preferably between 75 mM and 167 mM, preferably between 75 mM and 166 mM, preferably between 75 mM and 165 mM, preferably between 75 mM and 160 mM, preferably between 75 mM and 159 mM, preferably between 75 mM and 158 mM, preferably between 75 mM and 157 mM, preferably between 75 mM and 156 mM, preferably between 75 mM and 155 mM, preferably between 75 mM and 154 mM, preferably between 75 mM and 153 mM, preferably between 75 mM and 152 mM, 100 mM and 190 mM, 100 mM and 189 mM, 100 mM and 188 mM, 100 mM and 187 mM, 100 mM and 186 mM, 100 mM and 185 mM, preferably between 100 mM and 184 mM, preferably between 100 mM and 183 mM, preferably between 100 mM and 182 mM, preferably between 100 mM and 181 mM, preferably between 100 mM and 180 mM, preferably between 100 mM and 179 mM, preferably between 100 mM and 178 mM, preferably between 100 mM and 177 mM, preferably between 100 mM and 176 mM, preferably between 100 mM and 1100 mM, preferably between 100 mM and 174 mM, preferably between 100 mM and 173 mM, preferably between 100 mM and 172 mM, preferably between 100 mM and 171 mM, preferably between 100 mM and 170 mM, preferably between 100 mM and 169 mM, preferably between 100 mM and 168 mM, preferably between 100 mM and 167 mM, preferably between 100 mM and 166 mM, preferably between 100 mM and 165 mM, preferably between 100 mM and 160 mM, preferably between 100 mM and 159 mM, preferably between 100 mM and 158 mM, preferably between 100 mM and 157 mM, preferably between 100 mM and 156 mM, preferably between 100 mM and 155 mM, preferably between 100 mM and 154 mM, preferably between 100 mM and 153 mM, preferably between 100 mM and 152 mM, 115 mM and 190 mM, 115 mM and 189 mM, 115 mM and 188 mM, 115 mM and 187 mM, 115 mM and 186 mM, 115 mM and 185 mM, preferably between 115 mM and 184 mM, preferably between 115 mM and 183 mM, preferably between 115 mM and 182 mM, preferably between 115 mM and 181 mM, preferably between 115 mM and 180 mM, preferably between 115 mM and 179 mM, preferably between 115 mM and 178 mM, preferably between 115 mM and 177 mM, preferably between 115 mM and 176 mM, preferably between 115 mM and 175 mM, preferably between 115 mM and 174 mM, preferably between 115 mM and 173 mM, preferably between 115 mM and 172 mM, preferably between 115 mM and 171 mM, preferably between 115 mM and 170 mM, preferably between 115 mM and 169 mM, preferably between 115 mM and 168 mM, preferably between 115 mM and 167 mM, preferably between 115 mM and 166 mM, preferably between 115 mM and 165 mM, preferably between 115 mM and 160 mM, preferably between 115 mM and 159 mM, preferably between 115 mM and 158 mM, preferably between 115 mM and 157 mM, preferably between 115 mM and 156 mM, preferably between 115 mM and 155 mM, preferably between 115 mM and 154 mM, preferably between 115 mM and 153 mM, preferably between 115 mM and 152 mM, 130 mM and 185 mM, preferably between 130 mM and 184 mM, preferably between 130 mM and 183 mM, preferably between 130 mM and 182 mM, preferably between 130 mM and 181 mM, preferably between 130 mM and 180 mM, preferably between 130 mM and 179 mM, preferably between 130 mM and 178 mM, preferably between 130 mM and 177 mM, preferably between 130 mM and 176 mM, preferably between 130 mM and 175 mM, preferably between 130 mM and 174 mM, preferably between 130 mM and 173 mM, preferably between 130 mM and 172 mM, preferably between 130 mM and 171 mM, preferably between 130 mM and 170 mM, preferably between 130 mM and 169 mM, preferably between 130 mM and 168 mM, preferably between 130 mM and 167 mM, preferably between 130 mM and 166 mM, preferably between 130 mM and 165 mM, preferably between 130 mM and 160 mM, preferably between 130 mM and 159 mM, preferably between 130 mM and 158 mM, preferably between 130 mM and 157 mM, preferably between 130 mM and 156 mM, preferably between 130 mM and 155 mM, preferably between 130 mM and 154 mM, preferably between 130 mM and 153 mM, preferably between 130 mM and 152 mM, more preferably between 135 mM and 185 mM, more preferably between 135 mM and 184 mM, more preferably between 135 mM and 183 mM, more preferably between 135 mM and 182 mM, more preferably between 135 mM and 181 mM, more preferably between 135 mM and 180 mM, more preferably between 135 mM and 179 mM, more preferably between 135 mM and 178 mM, more preferably between 135 mM and 177 mM, more preferably between 135 mM and 176 mM, more preferably between 135 mM and 175 mM, more preferably between 135 mM and 174 mM, more preferably between 135 mM and 173 mM, more preferably between 135 mM and 172 mM, more preferably between 135 mM and 171 mM, more preferably between 135 mM and 170 mM, more preferably between 135 mM and 169 mM, more preferably between 135 mM and 168 mM, more preferably between 135 mM and 167 mM, more preferably between 135 mM and 166 mM, more preferably between 135 mM and 165 mM, more preferably between 135 mM and 160 mM, more preferably between 135 mM and 159 mM, more preferably between 135 mM and 158 mM, more preferably between 135 mM and 157 mM, more preferably between 135 mM and 156 mM, more preferably between 135 mM and 155 mM, more preferably between 135 mM and 154 mM, more preferably between 135 mM and 153 mM, more preferably between 135 mM and 152 mM, most preferably between 140 mM and 185 mM, most preferably between 140 mM and 184 mM, most preferably between 140 mM and 183 mM, most preferably between 140 mM and 182 mM, most preferably between 140 mM and 181 mM, most preferably between 140 mM and 180 mM, most preferably between 140 mM and 179 mM, most preferably between 140 mM and 178 mM, most preferably between 140 mM and 177 mM, most preferably between 140 mM and 176 mM, most preferably between 140 mM and 175 mM, most preferably between 140 mM and 174 mM, most preferably between 140 mM and 173 mM, most preferably between 140 mM and 172 mM, most preferably between 140 mM and 171 mM, most preferably between 140 mM and 170 mM, most preferably between 140 mM and 169 mM, most preferably between 140 mM and 168 mM, most preferably between 140 mM and 167 mM, most preferably between 140 mM and 166 mM, most preferably between 140 mM and 165 mM, most preferably between 140 mM and 160 mM, most preferably between 140 mM and 159 mM, most preferably between 140 mM and 158 mM, most preferably between 140 mM and 157 mM, most preferably between 140 mM and 156 mM, most preferably between 140 mM and 155 mM, most preferably between 140 mM and 154 mM, most preferably between 140 mM and 153 mM, and utmost preferably between 140 mM and 152 mM; and/or of less than 190 mM, 189 mM, 188 mM, 187 mM, 186 mM, 185 mM, 184 mM, 183 mM, 182 mM, 181 mM, 180 mM, 179 mM, 178 mM, 177 mM, 176 mM, 175 mM, 174 mM, 173 mM, 172 mM, 171 mM, 170 mM, 169 mM, 168 mM, 167 mM, 166 mM, 165 mM, 160 mM, 159 mM, 158 mM, 157 mM, 156 mM, 155 mM, 154 mM, 153 mM, 152 mM, preferably of less than 185 mM, more preferably less than 170 mM, even more preferably less than 160 mM, and most preferably less than 155 mM, and utmost preferably of 152 mM and less than 152 mM.

In a twelfth embodiment of the second aspect, which is also an embodiment of any one of the first, second, third, fourth, fifth, sixth, seventh, eighth, ninth, tenth and eleventh embodiment of the second aspect or of any one of the embodiments of the first aspect, the polypeptide, preferably the glucose isomerase, has Soluble Expression Level, defined as the ratio of the soluble expression level of said polypeptide and the soluble expression level of the polypeptide, preferably the glucose isomerase, of SEQ ID NO: 1 of at least 1.04 up to 1.80, preferably of at least 1.07 up to 1.80, preferably of at least 1.10 up to 1.80, preferably of at least 1.31 up to 1.80, preferably of at least 1.33 up to 1.80, preferably of at least 1.36 up to 1.80, preferably of at least 1.38 up to 1.80, preferably of at least 1.43 up to 1.80, more preferably of at least 1.04 up to 1.75, more preferably of at least 1.07 up to 1.75, more preferably of at least 1.10 up to 1.75, more preferably of at least 1.31 up to 1.75, more preferably of at least 1.33 up to 1.75, more preferably of at least 1.36 up to 1.75, more preferably of at least 1.38 up to 1.75, more preferably of at least 1.43 up to 1.75, more preferably of at least 1.47 up to 1.75, more preferably of at least 1.62 up to 1.75, even more preferably of at least 1.04 up to 1.70, even more preferably of at least 1.07 up to 1.70, even more preferably of at least 1.10 up to 1.70, even more preferably of at least 1.31 up to 1.70, even more preferably of at least 1.33 up to 1.70, even more preferably of at least 1.36 up to 1.70, even more preferably of at least 1.38 up to 1.70, even more preferably of at least 1.43 up to 1.70, even more preferably of at least 1.47 up to 1.70, even more preferably of at least 1.62 up to 1.70, even more preferably of at least 1.04 up to 1.65, even more preferably of at least 1.07 up to 1.65, even more preferably of at least 1.10 up to 1.65, even more preferably of at least 1.31 up to 1.65, even more preferably of at least 1.33 up to 1.65, even more preferably of at least 1.36 up to 1.65, even more preferably of at least 1.38 up to 1.65, even more preferably of at least 1.43 up to 1.65, even more preferably of at least 1.47 up to 1.65, even more preferably of at least 1.62 up to 1.65 and utmost preferably of at least 1.10 to 1.63, of at least 1.38 to 1.63, of at least 1.43 to 1.63, and/or of 1.63.

In another embodiment of the second aspect, which is also an embodiment of any one of the first, second, third, fourth, fifth, sixth, seventh, eighth, ninth, tenth and eleventh or any other embodiment of the second aspect or of any one of the embodiments of the first aspect, the polypeptide, preferably the glucose isomerase, has an increased catalytic activity of the polypeptide, preferably of the glucose isomerase, in comparison to SEQ ID NO: 1 in converting fructose into glucose, expressed as Glucose Formation of at least 1.2-fold up to 5-fold, of at least 1.2-fold up to 4.5-fold, of at least 1.2-fold up to 4-fold, of at least 1.2-fold up to 3.5-fold, of at least 1.2-fold up to 3.4-fold, of at least 1.2-fold up to 3.3-fold, of at least 1.2-fold up to 3.2-fold, of at least 1.2-fold up to 3.1-fold, of at least 1.2-fold up to 3-fold, of at least 1.2-fold up to 2.9-fold, of at least 1.2-fold up to 2.8-fold, of at least 1.2-fold up to 2.7-fold, of at least 1.2-fold up to 2.6-fold, of at least 1.2-fold up to 2.5-fold, of at least 1.2-fold up to 2.4-fold, of at least 1.2-fold up to 2.3-fold, of at least 1.2-fold up to 2.2-fold, preferably of at least 1.5-fold up to 5-fold, of at least 1.5-fold up to 4.5-fold, of at least 1.5-fold up to 4-fold, of at least 1.5-fold up to 3.5-fold, of at least 1.5-fold up to 3.4-fold, of at least 1.5-fold up to 3.3-fold, of at least 1.5-fold up to 3.2-fold, of at least 1.5-fold up to 3.1-fold, of at least 1.5-fold up to 3-fold, of at least 1.5-fold up to 2.9-fold, of at least 1.5-fold up to 2.8-fold, of at least 1.5-fold up to 2.7-fold, of at least 1.5-fold up to 2.6-fold, of at least 1.5-fold up to 2.5-fold, of at least 1.5-fold up to 2.4-fold, of at least 1.5-fold up to 2.3-fold, of at least 1.5-fold up to 2.2-fold, and more preferably of at least 1.9-fold up to 5-fold, of at least 1.9-fold up to 4.5-fold, of at least 1.9-fold up to 4-fold, of at least 1.9-fold up to 3.5-fold, of at least 1.9-fold up to 3.4-fold, of at least 1.9-fold up to 3.3-fold, of at least 1.9-fold up to 3.2-fold, of at least 1.9-fold up to 3.1-fold, of at least 1.9-fold up to 3-fold, of at least 1.9-fold up to 2.9-fold, of at least 1.9-fold up to 2.8-fold, of at least 1.9-fold up to 2.7-fold, of at least 1.9-fold up to 2.6-fold, of at least 1.9-fold up to 2.5-fold, of at least 1.9-fold up to 2.4-fold, of at least 1.9-fold up to 2.3-fold, of at least 1.9-fold up to 2.2-fold, and yet more preferably of at least 2.0-fold up to 5-fold, of at least 2.0-fold up to 4.5-fold, of at least 2.0-fold up to 4-fold, of at least 2.0-fold up to 3.5-fold, of at least 2.0-fold up to 3.4-fold, of at least 2.0-fold up to 3.3-fold, of at least 2.0-fold up to 3.2-fold, of at least 2.0-fold up to 3.1-fold, of at least 2.0-fold up to 3-fold, of at least 2.0-fold up to 2.9-fold, of at least 2.0-fold up to 2.8-fold, of at least 2.0-fold up to 2.7-fold, of at least 2.0-fold up to 2.6-fold, of at least 2.0-fold up to 2.5-fold, of at least 2.0-fold up to 2.4-fold, of at least 2.0-fold up to 2.3-fold of at least 2.0-fold up to 2.2-fold, and most preferably of at least 2.2-fold up to 3.3-fold.

In a $13^{th}$ embodiment of the second aspect, which is also an embodiment of any one of the eighth, ninth, tenth, eleventh and twelfth embodiment of the second aspect, the polypeptide, preferably the glucose isomerase, is any one of the eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$ and $97^{th}$ embodiment or of any one of the other embodiments of the first aspect, preferably the polypeptide, preferably the glucose isomerase, is any one of the $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, 94th, 95th, 96th and 97th embodiment of the first aspect, more preferably the polypeptide, preferably the glucose isomerase, is any one of the 28th, 29th, 30th, 31st, 32nd, 33rd, 34th, 35th, 36th, 37th, 38th, 39th, 40th, 41st, 42nd, 43rd, 44th, 45th, 46th, 47th, 48th, 49th, 50th, 51st, 52nd, 53rd, 54th, 55th, 56th, 57th, 58th, 59th, 60th, 61st, 62nd, 63rd, 64th, 65th, 66th, 67th, 68th, 69th, 70th, 71st, 72nd, 73rd, 74th, 75th, 76th, 77th, 78th, 79th, 80th, 81st, 82nd, 83rd, 84th, 85th, 86th, 87th, 88th, 89th, 90th, 91st, 92nd, 93rd, 94th, 95th, 96th and 97th embodiment of the first aspect, even more preferably the polypeptide, preferably the glucose isomerase, is any one of 39th, 40th, 41st, 42nd, 43rd, 44th, 45th, 46th, 47th, 48th, 49th, 50th, 51st, 52nd, 53rd, 54th, 55th, 56th, 57th, 58th, 59th, 60th, 61st, 62nd, 63rd, 64th, 65th, 66th, 67th, 68th, 69th, 70th, 71st, 72nd, 73rd, 74th, 75th, 76th, 77th, 78th, 79th80th, 81st, 82nd, 83rd, 84th, 85th, 86th, 87th, 88th, 89th, 90th, 91st, 92nd, 93rd, 94th, 95th, 96th and 97th embodiment of the first aspect, most preferably the polypeptide, preferably the glucose isomerase, is any one of the 63rd and 97th embodiment of the first aspect, or the polypeptide, preferably the glucose isomerase, is any one of the 104th, 105th, 106th, 107th, 109th, 110th, 111th, 112th, 113th, 114th, 116th, 117th, 118th, 119th, 121st, 122nd, 123rd, 124th, 126th, 127th, 128, 129th, 130th, 132nd133rd, 134th and 135th embodiment or of any one of the other embodiments of the first aspect.

The problem underlying the present invention is solved in a third aspect, which is also a first embodiment of the third aspect, by a polypeptide, preferably a glucose isomerase, of any one of the first, second, third, fourth, fifth, sixth, seventh, eighth, ninth, tenth, eleventh, twelfth, 13th, 14th, 15th, 36th, 37th, 38th, 39th, 40th, 41st, 42nd, 43rd, 44th, 45th, 46th, 47th, 48th, 49th, 50th, 51st, 52nd, 53rd, 54th, 55th, 56th, 57th, 58th, 59th, 60th, 61st, 62nd, 63rd, 64th, 65th, 66th, 67th, 68th, 69th, 70th, 71st, 72nd, 73rd, 74th, 75th, 76th, 77th, 78th, 79th, 80th, 81st, 82nd, 83rd, 84th, 85th, 86th, 87th, 88th, 89th, 90th, 91st, 92nd, 93rd, 94th, 95th, 96th, 97th, 98th, 99th, 100th, 101st, 102nd, 103rd, 104th, 105th, 106th, 107th, 108th, 109th, 110th, 111th, 112th, 113th, 114th, 115th, 116th, 117th, 118th, 119th, 120th, 121st, 122nd, 123rd, 124th, 125th, 126th, 127th, 128th, 129th, 130th, 131st, 132nd, 133rd, 134th, 135th, 136th, 137th, 138th, 139th, 140th, 141st, 142nd, 143rd and 144th embodiment or of any one of the other embodiments of the first aspect, and a polypeptide, preferably a glucose isomerase, of any one of the first, second, third, fourth, fifth, sixth, seventh, eighth, ninth, tenth, eleventh, twelfth, 13th embodiment of the second aspect, preferably a polypeptide, preferably a glucose isomerase, of any one of the eleventh, twelfth, 13th, 14th, 15th, 16th, 17th, 18th, 19th, 20th, 21st, 22nd, 23rd, 24th, 25th, 26th, 27th, 28th, 29th, 30th, 31st, 32nd, 33rd, 34th, 35th, 36th, 37th, 38th, 39th, 40th, 41st, 42nd, 43rd, 44th, 45th, 46th, 47th, 48th, 49th, 50th, 51st, 52nd, 53rd, 54th, 55th, 56th, 57th, 58th, 59th, 60th, 61st, 62nd, 63rd, 64th, 65th, 66th, 67th, 68th, 69th, 70th, 71st, 72nd, 73rd, 74th, 75th, 76th, 77th, 78th, 79th, 80th, 81st, 82nd, 83rd, 84th, 85th, 86th, 87th, 88th, 89th, 90th, 91st, 92nd, 93rd, 94th, 95th, 96th and 97th embodiment or of any one of the other embodiments of the first aspect, preferably a polypeptide, preferably a glucose isomerase, of any one of the 23rd, 24th, 25th, 26th, 27th, 28th, 29th, 30th, 31st, 32nd, 33rd, 34th, 35th, 36th, 37th, 38th, 39th, 40th, 41st, 42nd, 43rd, 44th, 45th, 46th, 47th, 48th, 49th, 50th, 51st, 52nd, 53rd, 54th, 55th, 56th, 57th, 58th, 59th, 60th, 61st, 62nd, 63rd, 64th, 65th, 66th, 67th, 68th, 69th, 70th, 71st, 72nd, 73rd, 74th, 75th, 76th, 77th, 78th, 79th, 80th, 81st, 82nd, 83rd, 84th, 85th, 86th, 87th, 88th, 89th, 90th, 91st, 92nd, 93rd, 94th, 95th, 96th and 97th embodiment of the first aspect, more preferably a polypeptide, preferably a glucose isomerase, of any one of the 28th, 29th, 30th, 31st, 32nd, 33rd, 34th, 35th, 36th, 37th, 38th, 39th, 40th, 41st, 42nd, 43rd, 44th, 45th, 46th, 47th, 48th, 49th, 50th, 51st, 52nd, 53rd, 54th, 55th, 56th, 57th, 58th, 59th, 60th, 61st, 62nd, 63rd, 64th, 65th, 66th, 67th, 68th, 69th, 70th, 71st, 72nd, 73rd, 74th, 75th, 76th, 77th, 78th, 79th, 80th, 81st, 82nd, 83rd, 84th, 85th, 86th, 87th, 88th, 89th, 90th, 91st, 92nd, 93rd, 94th, 95th, 96th and 97th embodiment of the first aspect, even more preferably a polypeptide, preferably a glucose isomerase, of any one of the 39th, 40th, 41st, 42nd, 43rd, 44th, 45th, 46th, 47th, 48th, 49th, 50th, 51st, 52nd, 53rd, 54th, 55th, 56th, 57th, 58th59th, 60th, 61st, 62nd, 63rd, 64th, 65th, 66th, 67th, 68th, 69th, 70th, 71st, 72nd, 73rd, 74th, 75th, 76th, 77th, 78th, 79th80th, 81st, 82nd, 83rd, 84th, 85th, 86th, 87th, 88th, 89th, 90th, 91st, 92nd, 93rd, 94th, 95th, 96th and 97th embodiment of the first aspect, and most preferably a polypeptide, preferably a glucose isomerase, of any one of the 63rd and 97th embodiment of the first aspect, or wherein the polypeptide, preferably the glucose isomerase, is any one of the 104th, 105th, 106th, 107th, 109th, 110th, 111th, 112th, 113th, 114th, 116th, 117th, 118th, 119th, 121st, 122nd, 123rd, 124th, 126th, 127th, 128th, 129th, 130th, 132nd133rd, 134th and 135th embodiment or of any one of the other embodiments of the first aspect, wherein the polypeptide, preferably the glucose isomerase, compared to a polypeptide, preferably the glucose isomerase, of SEQ ID NO:1, is characterized by an increased activity, preferably increased Activity, for the conversion of fructose to glucose at a concentration of 50 mM fructose of at least 1.1-fold up to 3.0-fold, preferably of at least 1.4-fold up to 3.0-fold, preferably of at least 1.5-fold up to 3.0-fold, more preferably of at least 1.6-fold up to 3.0-fold, preferably of at least 1.7-fold up to 3.0-fold, preferably of at least 1.8-fold up to 3.0-fold, preferably of at least 1.9-fold up to 3.0-fold, preferably of at least 2.0-fold up to 3.0-fold, more preferably of at least 1.4-fold up to 2.8-fold, more preferably of at least 1.5-fold up to 2.8-fold, more preferably of at least 1.6-fold up to 2.8-fold, more preferably of at least 1.7-fold up to 2.8-fold, more preferably of at least 1.8-fold up to 2.8-fold, more preferably of at least 1.9-fold up to 2.8-fold, more preferably of at least 2.0-fold up to 2.8-fold, even more preferably of at least 1.4-fold up to 2.6-fold, even more preferably of at least 1.5-fold up to 2.6-fold, more preferably of at least 1.6-fold up to 2.6-fold, more preferably of at least 1.7-fold up to 2.6-fold, more preferably of at least 1.8-fold up to 2.6-fold, more preferably of at least 1.9-fold up to 2.6-fold, more preferably of at least 2.0-fold up to 2.6-fold, and most preferably of at least 1.4-fold up to 2.4-fold, most preferably of at least 1.5-fold up to 2.4-fold, most preferably of at least 1.6-fold up to 2.4-fold, most preferably of at least 1.7-fold up to 2.4-fold, most preferably of at least 1.8-fold up to 2.4-fold, most preferably of at least 1.9-fold up to 2.4-fold, and most preferably of at least 2.0-fold up to 2.4-fold, and utmost preferable of at least 1.7-fold up to 2.4-fold; and/or an increased activity, preferably increased Activity, for the conversion of fructose to glucose at a concentration of 200 mM fructose of at least 1.2-fold up to 3.0-fold, preferably of at least 1.3-fold up to 3.0-fold, preferably of at least 1.4-fold up to 3.0-fold preferably of at least 1.5-fold up to 3.0-fold, more preferably of at least 1.6-fold up to 3.0-fold, preferably of at least 1.7-fold up to 3.0-fold, preferably of at least 1.8-fold up to 3.0-fold, preferably of at least 1.9-fold up to 3.0-fold, preferably of at least 2.0-fold up to 3.0-fold, more preferably of at least 1.3-fold up to 2.5-fold, more preferably of at least 1.4-fold up to 2.5-fold, more preferably of at least 1.5-fold up to 2.5-fold, more preferably of at least 1.6-fold up to 2.5-fold, more preferably of at least 1.7-fold up to 2.5-fold, more preferably of at least 1.8-fold up to 2.5-fold, more preferably of at least 1.9-fold up to 2.5-fold, more preferably of at least 2.0-fold up to 2.5-fold, even more preferably of at least 1.3-fold up to 2.2-fold, even more preferably of at least 1.4-fold up to 2.2-fold, even more preferably of at least 1.5-fold up to 2.2-fold, more preferably of at least 1.6-fold up to 2.2-fold, more preferably of at least 1.7-fold up to 2.2-fold, more preferably of at least 1.8-fold up to 2.2-fold, more preferably of at least 1.9-fold up to 2.2-fold, more preferably of at least 2.0-fold up to 2.2-fold, and utmost preferably of at least 1.5-fold up to 2.2-fold; and/or;

an increase in thermal stability expressed as Residual Activity after incubation of the polypeptide, preferably the glucose isomerase, at a temperature of 74° C. for 15 minutes, wherein such Residual Activity is at least 30% up to 100%, at least 31% up to 100%, at least 32% up to 100%, at least 33% up to 100%, at least 34% up to 100%, at least 35% up to 100%, at least 36% up to 100%, at least 37% up to 100%, at least 38% up to 100%, at least 39% up to 100%, at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, at least 60% up to 100%, at least 61% up to 100%, at least 62% up to 100%, at least 63% up to 100%, at least 64% up to 100%, at least 65% up to 100%, at least 66% up to 100%, at least 67% up to 100%, at least 68% up to 100%, at least 69% up to 100%, at least 70% up to 100%, at least 71% up to 100%, at least 72% up to 100%, at least 73% up to 100%, at least 74% up to 100%, at least 75% up to 100%, at least 76% up to 100%, at least 77% up to 100%, at least 78% up to 100%, at least 79% up to 100%, at least 80% up to 100%, at least 30% up to 75%, at least 31% up to 75%, at least 32% up to 75%, at least 33% up to 75%, at least 34% up to 75%, at least 35% up to 75%, at least 36% up to 75%, at least 37% up to 75%, at least 38% up to 75%, at least 39% up to 75%, at least 40% up to 75%, at least 41% up to 75%, at least 42% up to 75%, at least 43% up to 75%, at least 44% up to 75%, at least 45% up to 75%, at least 46% up to 75%, at least 47% up to 75%, at least 48% up to 75%, at least 49% up to 75%, at least 50% up to 75%, at least 51% up to 75%, at least 52% up to 75%, at least 53% up to 75%, at least 54% up to 75%, at least 55% up to 75%, at least 56% up to 75%, at least 57% up to 75%, at least 58% up to 75%, at least 59% up to 75%, at least 60% up to 75%, at least 61% up to 75%, at least 62% up to 75%, at least 30% up to 70%, at least 31% up to 70%, at least 32% up to 70%, at least 33% up to 70%, at least 34% up to 70%, at least 35% up to 70%, at least 36% up to 70%, at least 37% up to 70%, at least 38% up to 70%, at least 39% up to 70%, at least 40% up to 70%, at least 41% up to 70%, at least 42% up to 70%, at least 43% up to 70%, at least 44% up to 70%, at least 45% up to 70%, at least 46% up to 70%, at least 47% up to 70%, at least 48% up to 70%, at least 49% up to 70%, at least 50% up to 70%, at least 51% up to 70%, at least 52% up to 70%, at least 53% up to 70%, at least 54% up to 70%, at least 55% up to 70%, at least 56% up to 70%, at least 57% up to 70%, at least 58% up to 70%, at least 59% up to 70%, at least 60% up to 70%, at least 61% up to 70%, at least 62% up to 70%, at least 30% up to 65%, at least 31% up to 65%, at least 32% up to 65%, at least 33% up to 65%, at least 34% up to 65%, at least 35% up to 65%, at least 36% up to 65%, at least 37% up to 65%, at least 38% up to 65%, at least 39% up to 65%, at least 40% up to 65%, at least 41% up to 65%, at least 42% up to 65%, at least 43% up to 65%, at least 44% up to 65%, at least 45% up to 65%, at least 46% up to 65%, at least 47% up to 65%, at least 48% up to 65%, at least 49% up to 65%, at least 50% up to 65%, at least 51% up to 65%, at least 52% up to 65%, at least 53% up to 65%, at least 54% up to 65%, at least 55% up to 65%, at least 56% up to 65%, at least 57% up to 65%, at least 58% up to 65%, at least 59% up to 65%, at least 60% up to 65%, at least 61% up to 65%, at least 62% up to 65%, more preferably at least 30% up to 65%, at least 34% up to 65%, at least 35% up to 65%, at least 38% up to 65%, at least 40% up to 65%, at least 41% up to 65%, at least 42% up to 65%, at least 46% up to 65%, at least 47% up to 65%, at least 50% up to 65%, at least 55% up to 65%, at least 59% up to 65%, at least 60% up to 65%, at least 62% up to 65%, even more preferably at least at least 40% up to 65%, and even more preferably at least 60% up to 65%, and most preferably of 62%; and/or a $K_M$ value of between 50 mM and 190 mM, 50 mM and 189 mM, 50 mM and 188 mM, 50 mM and 187 mM, 50 mM and 186 mM, 50 mM and 185 mM, preferably between 50 mM and 184 mM, preferably between 50 mM and 183 mM, preferably between 50 mM and 182 mM, preferably between 50 mM and 181 mM, preferably between 50 mM and 180 mM, preferably between 50 mM and 179 mM, preferably between 50 mM and 178 mM, preferably between 50 mM and 177 mM, preferably between 50 mM and 176 mM, preferably between 50 mM and 175 mM, preferably between 50 mM and 174 mM, preferably between 50 mM and 173 mM, preferably between 50 mM and 172 mM, preferably between 50 mM and 171 mM, preferably between 50 mM and 170 mM, preferably between 50 mM and 169 mM, preferably between 50 mM and 168 mM, preferably between 50 mM and 167 mM, preferably between 50 mM and 166 mM, preferably between 50 mM and 165 mM, preferably between 50 mM and 160 mM, preferably between 50 mM and 159 mM, preferably between 50 mM and 158 mM, preferably between 50 mM and 157 mM, preferably between 50 mM and 156 mM, preferably between 50 mM and 155 mM, preferably between 50 mM and 154 mM, preferably between 50 mM and 153 mM, preferably between 50 mM and 152 mM, 75 mM and 190 mM, 75 mM and 189 mM, 75 mM and 188 mM, 75 mM and 187 mM, 75 mM and 186 mM, 75 mM and 185 mM, preferably between 75 mM and 184 mM, preferably between 75 mM and 183 mM, preferably between 75 mM and 182 mM, preferably between 75 mM and 181 mM, preferably between 75 mM and 180 mM, preferably between 75 mM and 179 mM, preferably between 75 mM and 178 mM, preferably between 75 mM and 177 mM, preferably between 75 mM and 176 mM, preferably between 75 mM and 175 mM, preferably between 75 mM and 174 mM, preferably between 75 mM and 173 mM, preferably between 75 mM and 172 mM, preferably between 75 mM and 171 mM, preferably between 75 mM and 170 mM, preferably between 75 mM and 169 mM, preferably between 75 mM and 168 mM, preferably between 75 mM and 167 mM, preferably between 75 mM and 166 mM, preferably between 75 mM and 165 mM, preferably between 75 mM and 160 mM, preferably between 75 mM and 159 mM, preferably between 75 mM and 158 mM, preferably between 75 mM and 157 mM, preferably between 75 mM and 156 mM, preferably between 75 mM and 155 mM, preferably between 75 mM and 154 mM, preferably between 75 mM and 153 mM, preferably between 75 mM and 152 mM, 100 mM and 190 mM, 100 mM and 189 mM, 100 mM and 188 mM, 100 mM and 187 mM, 100 mM and 186 mM, 100 mM and 185 mM, preferably between 100 mM and 184 mM, preferably between 100 mM and 183 mM, preferably between 100 mM and 182 mM, preferably between 100 mM and 181 mM, preferably between 100 mM and 180 mM, preferably between 100 mM and 179 mM, preferably between 100 mM and 178 mM, preferably between 100 mM and 177 mM, preferably between 100 mM and 176 mM, preferably between 100 mM and 1100 mM, preferably between 100 mM and 174 mM, preferably between 100 mM and 173 mM, preferably between 100 mM and 172 mM, preferably between 100 mM and 171 mM, preferably between 100 mM and 170 mM, preferably between 100 mM and 169 mM, preferably between 100 mM and 168 mM, preferably between 100 mM and 167 mM, preferably between 100 mM and 166 mM, preferably between 100 mM and 165 mM, preferably between 100 mM and 160 mM, preferably between 100 mM and 159 mM, preferably between 100 mM and 158 mM, preferably between 100 mM and 157 mM, preferably between 100 mM and 156 mM, preferably between 100 mM and 155 mM, preferably between 100 mM and 154 mM, preferably between 100 mM and 153 mM, preferably between 100 mM and 152 mM, 115 mM and 190 mM, 115 mM and 189 mM, 115 mM and 188 mM, 115 mM and 187 mM, 115 mM and 186 mM, 115 mM and 185 mM, preferably between 115 mM and 184 mM, preferably between 115 mM and 183 mM, preferably between 115 mM and 182 mM, preferably between 115 mM and 181 mM, preferably between 115 mM and 180 mM, preferably between 115 mM and 179 mM, preferably between 115 mM and 178 mM, preferably between 115 mM and 177 mM, preferably between 115 mM and 176 mM, preferably between 115 mM and 175 mM, preferably between 115 mM and 174 mM, preferably between 115 mM and 173 mM, preferably between 115 mM and 172 mM, preferably between 115 mM and 171 mM, preferably between 115 mM and 170 mM, preferably between 115 mM and 169 mM, preferably between 115 mM and 168 mM, preferably between 115 mM and 167 mM, preferably between 115 mM and 166 mM, preferably between 115 mM and 165 mM, preferably between 115 mM and 160 mM, preferably between 115 mM and 159 mM, preferably between 115 mM and 158 mM, preferably between 115 mM and 157 mM, preferably between 115 mM and 156 mM, preferably between 115 mM and 155 mM, preferably between 115 mM and 154 mM, preferably between 115 mM and 153 mM, preferably between 115 mM and 152 mM, 130 mM and 185 mM, preferably between 130 mM and 184 mM, preferably between 130 mM and 183 mM, preferably between 130 mM and 182 mM, preferably between 130 mM and 181 mM, preferably between 130 mM and 180 mM, preferably between 130 mM and 179 mM, preferably between 130 mM and 178 mM, preferably between 130 mM and 177 mM, preferably between 130 mM and 176 mM, preferably between 130 mM and 175 mM, preferably between 130 mM and 174 mM, preferably between 130 mM and 173 mM, preferably between 130 mM and 172 mM, preferably between 130 mM and 171 mM, preferably between 130 mM and 170 mM, preferably between 130 mM and 169 mM, preferably between 130 mM and 168 mM, preferably between 130 mM and 167 mM, preferably between 130 mM and 166 mM, preferably between 130 mM and 165 mM, preferably between 130 mM and 160 mM, preferably between 130 mM and 159 mM, preferably between 130 mM and 158 mM, preferably between 130 mM and 157 mM, preferably between 130 mM and 156 mM, preferably between 130 mM and 155 mM, preferably between 130 mM and 154 mM, preferably between 130 mM and 153 mM, preferably between 130 mM and 152 mM, more preferably between 135 mM and 185 mM, more preferably between 135 mM and 184 mM, more preferably between 135 mM and 183 mM, more preferably between 135 mM and 182 mM, more preferably between 135 mM and 181 mM, more preferably between 135 mM and 180 mM, more preferably between 135 mM and 179 mM, more preferably between 135 mM and 178 mM, more preferably between 135 mM and 177 mM, more preferably between 135 mM and 176 mM, more preferably between 135 mM and 175 mM, more preferably between 135 mM and 174 mM, more preferably between 135 mM and 173 mM, more preferably between 135 mM and 172 mM, more preferably between 135 mM and 171 mM, more preferably between 135 mM and 170 mM, more preferably between 135 mM and 169 mM, more preferably between 135 mM and 168 mM, more preferably between 135 mM and 167 mM, more preferably between 135 mM and 166 mM, more preferably between 135 mM and 165 mM, more preferably between 135 mM and 160 mM, more preferably between 135 mM and 159 mM, more preferably between 135 mM and 158 mM, more preferably between 135 mM and 157 mM, more preferably between 135 mM and 156 mM, more preferably between 135 mM and 155 mM, more preferably between 135 mM and 154 mM, more preferably between 135 mM and 153 mM, more preferably between 135 mM and 152 mM, most preferably between 140 mM and 185 mM, most preferably between 140 mM and 184 mM, most preferably between 140 mM and 183 mM, most preferably between 140 mM and 182 mM, most preferably between 140 mM and 181 mM, most preferably between 140 mM and 180 mM, most preferably between 140 mM and 179 mM, most preferably between 140 mM and 178 mM, most preferably between 140 mM and 177 mM, most preferably between 140 mM and 176 mM, most preferably between 140 mM and 175 mM, most preferably between 140 mM and 174 mM, most preferably between 140 mM and 173 mM, most preferably between 140 mM and 172 mM, most preferably between 140 mM and 171 mM, most preferably between 140 mM and 170 mM, most preferably between 140 mM and 169 mM, most preferably between 140 mM and 168 mM, most preferably between 140 mM and 167 mM, most preferably between 140 mM and 166 mM, most preferably between 140 mM and 165 mM, most preferably between 140 mM and 160 mM, most preferably between 140 mM and 159 mM, most preferably between 140 mM and 158 mM, most preferably between 140 mM and 157 mM, most preferably between 140 mM and 156 mM, most preferably between 140 mM and 155 mM, most preferably between 140 mM and 154 mM, most preferably between 140 mM and 153 mM, and utmost preferably between 140 mM and 152 mM; and/or of less than 190 mM, 189 mM, 188 mM, 187 mM, 186 mM, 185 mM, 184 mM, 183 mM, 182 mM, 181 mM, 180 mM, 179 mM, 178 mM, 177 mM, 176 mM, 175 mM, 174 mM, 173 mM, 172 mM, 171 mM, 170 mM, 169 mM, 168 mM, 167 mM, 166 mM, 165 mM, 160 mM, 159 mM, 158 mM, 157 mM, 156 mM, 155 mM, 154 mM, 153 mM, 152 mM, preferably of less than 185 mM, more preferably less than 170 mM, even more preferably less than 160 mM, and most preferably less than 155 mM, and utmost preferably of 152 mM and less than 152 mM; and/or a Soluble Expression Level of the polypeptide, preferably the glucose isomerase, defined as the ratio of the soluble expression level of said polypeptide and the soluble expression level of the polypeptide, preferably the glucose isomerase, of SEQ ID NO: 1, of at least 1.04 up to 1.80, preferably of at least 1.07 up to 1.80, preferably of at least 1.10 up to 1.80, preferably of at least 1.31 up to 1.80, preferably of at least 1.33 up to 1.80, preferably of at least 1.36 up to 1.80, preferably of at least 1.38 up to 1.80, preferably of at least 1.43 up to 1.80, more preferably of at least 1.04 up to 1.75, more preferably of at least 1.07 up to 1.75, more preferably of at least 1.10 up to 1.75, more preferably of at least 1.31 up to 1.75, more preferably of at least 1.33 up to 1.75, more preferably of at least 1.36 up to 1.75, more preferably of at least 1.38 up to 1.75, more preferably of at least 1.43 up to 1.75, more preferably of at least 1.47 up to 1.75, more preferably of at least 1.62 up to 1.75, even more preferably of at least 1.04 up to 1.70, even more preferably of at least 1.07 up to 1.70, even more preferably of at least 1.10 up to 1.70, even more preferably of at least 1.31 up to 1.70, even more preferably of at least 1.33 up to 1.70, even more preferably of at least 1.36 up to 1.70, even more preferably of at least 1.38 up to 1.70, even more preferably of at least 1.43 up to 1.70, even more preferably of at least 1.47 up to 1.70, even more preferably of at least 1.62 up to 1.70, even more preferably of at least 1.04 up to 1.65, even more preferably of at least 1.07 up to 1.65, even more preferably of at least 1.10 up to 1.65, even more preferably of at least 1.31 up to 1.65, even more preferably of at least 1.33 up to 1.65, even more preferably of at least 1.36 up to 1.65, even more preferably of at least 1.38 up to 1.65, even more preferably of at least 1.43 up to 1.65, even more preferably of at least 1.47 up to 1.65, even more preferably of at least 1.62 up to 1.65 and utmost preferably of at least 1.10 to 1.63, of at least 1.38 to 1.63, of at least 1.43 to 1.63, and/or of 1.63; and/or an increased catalytic activity of the polypeptide, preferably of the glucose isomerase, in comparison to SEQ ID NO:1 in converting fructose into glucose, expressed as Glucose Formation of at least 1.2-fold up to 5-fold, of at least 1.2-fold up to 4.5-fold, of at least 1.2-fold up to 4-fold, of at least 1.2-fold up to 3.5-fold, of at least 1.2-fold up to 3.4-fold, of at least 1.2-fold up to 3.3-fold, of at least 1.2-fold up to 3.2-fold, of at least 1.2-fold up to 3.1-fold, of at least 1.2-fold up to 3-fold, of at least 1.2-fold up to 2.9-fold, of at least 1.2-fold up to 2.8-fold, of at least 1.2-fold up to 2.7-fold, of at least 1.2-fold up to 2.6-fold, of at least 1.2-fold up to 2.5-fold, of at least 1.2-fold up to 2.4-fold, of at least 1.2-fold up to 2.3-fold, of at least 1.2-fold up to 2.2-fold, preferably of at least 1.5-fold up to 5-fold, of at least 1.5-fold up to 4.5-fold, of at least 1.5-fold up to 4-fold, of at least 1.5-fold up to 3.5-fold, of at least 1.5-fold up to 3.4-fold, of at least 1.5-fold up to 3.3-fold, of at least 1.5-fold up to 3.2-fold, of at least 1.5-fold up to 3.1-fold, of at least 1.5-fold up to 3-fold, of at least 1.5-fold up to 2.9-fold, of at least 1.5-fold up to 2.8-fold, of at least 1.5-fold up to 2.7-fold, of at least 1.5-fold up to 2.6-fold, of at least 1.5-fold up to 2.5-fold, of at least 1.5-fold up to 2.4-fold, of at least 1.5-fold up to 2.3-fold, of at least 1.5-fold up to 2.2-fold, and more preferably of at least 1.9-fold up to 5-fold, of at least 1.9-fold up to 4.5-fold, of at least 1.9-fold up to 4-fold, of at least 1.9-fold up to 3.5-fold, of at least 1.9-fold up to 3.4-fold, of at least 1.9-fold up to 3.3-fold, of at least 1.9-fold up to 3.2-fold, of at least 1.9-fold up to 3.1-fold, of at least 1.9-fold up to 3-fold, of at least 1.9-fold up to 2.9-fold, of at least 1.9-fold up to 2.8-fold, of at least 1.9-fold up to 2.7-fold, of at least 1.9-fold up to 2.6-fold, of at least 1.9-fold up to 2.5-fold, of at least 1.9-fold up to 2.4-fold, of at least 1.9-fold up to 2.3-fold, of at least 1.9-fold up to 2.2-fold, and yet more preferably of at least 2.0-fold up to 5-fold, of at least 2.0-fold up to 4.5-fold, of at least 2.0-fold up to 4-fold, of at least 2.0-fold up to 3.5-fold, of at least 2.0-fold up to 3.4-fold, of at least 2.0-fold up to 3.3-fold, of at least 2.0-fold up to 3.2-fold, of at least 2.0-fold up to 3.1-fold, of at least 2.0-fold up to 3-fold, of at least 2.0-fold up to 2.9-fold, of at least 2.0-fold up to 2.8-fold, of at least 2.0-fold up to 2.7-fold, of at least 2.0-fold up to 2.6-fold, of at least 2.0-fold up to 2.5-fold, of at least 2.0-fold up to 2.4-fold, of at least 2.0-fold up to 2.3-fold of at least 2.0-fold up to 2.2-fold, and most preferably of at least 2.2-fold up to 3.3-fold.

The problem underlying the present invention is solved in a fourth aspect, which is also a first embodiment of the fourth aspect or of any one of the embodiments of the first, second or third aspect, by a polypeptide, preferably the glucose isomerase, comprising an amino acid sequence, wherein the amino acid sequence of the polypeptide, preferably the glucose isomerase, is at least 95% identical to and/or at least 95% homologous to an amino acid sequence of SEQ ID NO: 1, wherein the polypeptide, preferably the glucose isomerase, has at least one of the characteristics selected from the group consisting of (A), (B), (C), (D), (E), and (F) or any combination thereof, wherein characteristic (A) is an increased activity, preferably increased Activity, for the conversion of fructose to glucose at a concentration of 50 mM fructose in comparison to the polypeptide, preferably the glucose isomerase, of SEQ ID NO: 1

(i) of at least 1.1-fold up to 1.6-fold, preferably of at least 1.2-fold up to 1.6-fold, more preferably of at least 1.3-fold up to 1.6-fold, most preferably of at least 1.4-fold up to 1.6-fold, or
(ii) of at least 1.1-fold up to 3.0-fold, preferably of at least 1.4-fold up to 3.0-fold, preferably of at least 1.5-fold up to 3.0-fold, more preferably of at least 1.6-fold up to 3.0-fold, preferably of at least 1.7-fold up to 3.0-fold, preferably of at least 1.8-fold up to 3.0-fold, preferably of at least 1.9-fold up to 3.0-fold, preferably of at least 2.0-fold up to 3.0-fold, more preferably of at least 1.4-fold up to 2.8-fold, more preferably of at least 1.5-fold up to 2.8-fold, more preferably of at least 1.6-fold up to 2.8-fold, more preferably of at least 1.7-fold up to 2.8-fold, more preferably of at least 1.8-fold up to 2.8-fold, more preferably of at least 1.9-fold up to 2.8-fold, more preferably of at least 2.0-fold up to 2.8-fold, even more preferably of at least 1.4-fold up to 2.6-fold, even more preferably of at least 1.5-fold up to 2.6-fold, more preferably of at least 1.6-fold up to 2.6-fold, more preferably of at least 1.7-fold up to 2.6-fold, more preferably of at least 1.8-fold up to 2.6-fold, more preferably of at least 1.9-fold up to 2.6-fold, more preferably of at least 2.0-fold up to 2.6-fold, and most preferably of at least 1.4-fold up to 2.4-fold, most preferably of at least 1.5-fold up to 2.4-fold, most preferably of at least 1.6-fold up to 2.4-fold, most preferably of at least 1.7-fold up to 2.4-fold, most preferably of at least 1.8-fold up to 2.4-fold, most preferably of at least 1.9-fold up to 2.4-fold, and most preferably of at least 2.0-fold up to 2.4-fold, and utmost preferable of at least 1.7-fold up to 2.4-fold;

(B) is an increased activity, preferably increased Activity, for the conversion of fructose to glucose at a concentration of 200 mM fructose in comparison to the polypeptide, preferably the glucose isomerase, of SEQ ID NO: 1

(i) of at least 1.2-fold up to 1.6-fold, more preferably of at least 1.3-fold up to 1.6-fold, most preferably of at least 1.4-fold up to 1.6-fold, and/or
(ii) of at least 1.2-fold up to 3.0-fold, preferably of at least 1.3-fold up to 3.0-fold, preferably of at least 1.4-fold up to 3.0-fold preferably of at least 1.5-fold up to 3.0-fold, more preferably of at least 1.6-fold up to 3.0-fold, preferably of at least 1.7-fold up to 3.0-fold, preferably of at least 1.8-fold up to 3.0-fold, preferably of at least 1.9-fold up to 3.0-fold, preferably of at least 2.0-fold up to 3.0-fold, more preferably of at least 1.3-fold up to 2.5-fold, more preferably of at least 1.4-fold up to 2.5-fold, more preferably of at least 1.5-fold up to 2.5-fold, more preferably of at least 1.6-fold up to 2.5-fold, more preferably of at least 1.7-fold up to 2.5-fold, more preferably of at least 1.8-fold up to 2.5-fold, more preferably of at least 1.9-fold up to 2.5-fold, more preferably of at least 2.0-fold up to 2.5-fold, even more preferably of at least 1.3-fold up to 2.2-fold, even more preferably of at least 1.4-fold up to 2.2-fold, even more preferably of at least 1.5-fold up to 2.2-fold, more preferably of at least 1.6-fold up to 2.2-fold, more preferably of at least 1.7-fold up to 2.2-fold, more preferably of at least 1.8-fold up to 2.2-fold, more preferably of at least 1.9-fold up to 2.2-fold, more preferably of at least 2.0-fold up to 2.2-fold, and utmost preferably of at least 1.5-fold up to 2.2-fold;

(C) is thermal stability of polypeptide, preferably the glucose isomerase, expressed as Residual Activity after incubation of the polypeptide, preferably the glucose isomerase at a temperature of 74° C. for 15 minutes, wherein such Residual Activity is (i) at least 30% up to 100%, at least 40% up to 100%, at least 50% up to 100%, at least 30% up to 75%, at least 40% up to 75%, at least 50% up to 75%, at least 30% up to 65%, at least 40% up to 65%, at least 50% up to 65%, at least 41% up to 64%, and/or
(ii) at least 30% up to 100%, at least 31% up to 100%, at least 32% up to 100%, at least 33% up to 100%, at least 34% up to 100%, at least 35% up to 100%, at least 36% up to 100%, at least 37% up to 100%, at least 38% up to 100%, at least 39% up to 100%, at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, at least 60% up to 100%, at least 61% up to 100%, at least 62% up to 100%, at least 63% up to 100%, at least 64% up to 100%, at least 65% up to 100%, at least 66% up to 100%, at least 67% up to 100%, at least 68% up to 100%, at least 69% up to 100%, at least 70% up to 100%, at least 71% up to 100%, at least 72% up to 100%, at least 73% up to 100%, at least 74% up to 100%, at least 75% up to 100%, at least 76% up to 100%, at least 77% up to 100%, at least 78% up to 100%, at least 79% up to 100%, at least 80% up to 100%, at least 30% up to 75%, at least 31% up to 75%, at least 32% up to 75%, at least 33% up to 75%, at least 34% up to 75%, at least 35% up to 75%, at least 36% up to 75%, at least 37% up to 75%, at least 38% up to 75%, at least 39% up to 75%, at least 40% up to 75%, at least 41% up to 75%, at least 42% up to 75%, at least 43% up to 75%, at least 44% up to 75%, at least 45% up to 75%, at least 46% up to 75%, at least 47% up to 75%, at least 48% up to 75%, at least 49% up to 75%, at least 50% up to 75%, at least 51% up to 75%, at least 52% up to 75%, at least 53% up to 75%, at least 54% up to 75%, at least 55% up to 75%, at least 56% up to 75%, at least 57% up to 75%, at least 58% up to 75%, at least 59% up to 75%, at least 60% up to 75%, at least 61% up to 75%, at least 62% up to 75%, at least 30% up to 70%, at least 31% up to 70%, at least 32% up to 70%, at least 33% up to 70%, at least 34% up to 70%, at least 35% up to 70%, at least 36% up to 70%, at least 37% up to 70%, at least 38% up to 70%, at least 39% up to 70%, at least 40% up to 70%, at least 41% up to 70%, at least 42% up to 70%, at least 43% up to 70%, at least 44% up to 70%, at least 45% up to 70%, at least 46% up to 70%, at least 47% up to 70%, at least 48% up to 70%, at least 49% up to 70%, at least 50% up to 70%, at least 51% up to 70%, at least 52% up to 70%, at least 53% up to 70%, at least 54% up to 70%, at least 55% up to 70%, at least 56% up to 70%, at least 57% up to 70%, at least 58% up to 70%, at least 59% up to 70%, at least 60% up to 70%, at least 61% up to 70%, at least 62% up to 70%, at least 30% up to 65%, at least 31% up to 65%, at least 32% up to 65%, at least 33% up to 65%, at least 34% up to 65%, at least 35% up to 65%, at least 36% up to 65%, at least 37% up to 65%, at least 38% up to 65%, at least 39% up to 65%, at least 40% up to 65%, at least 41% up to 65%, at least 42% up to 65%, at least 43% up to 65%, at least 44% up to 65%, at least 45% up to 65%, at least 46% up to 65%, at least 47% up to 65%, at least 48% up to 65%, at least 49% up to 65%, at least 50% up to 65%, at least 51% up to 65%, at least 52% up to 65%, at least 53% up to 65%, at least 54% up to 65%, at least 55% up to 65%, at least 56% up to 65%, at least 57% up to 65%, at least 58% up to 65%, at least 59% up to 65%, at least 60% up to 65%, at least 61% up to 65%, at least 62% up to 65%, more preferably at least 30% up to 65%, at least 34% up to 65%, at least 35% up to 65%, at least 38% up to 65%, at least 40% up to 65%, at least 41% up to 65%, at least 42% up to 65%, at least 46% up to 65%, at least 47% up to 65%, at least 50% up to 65%, at least 55% up to 65%, at least 59% up to 65%, at least 60% up to 65%, at least 62% up to 65%, even more preferably at least at least 40% up to 65%, and even more preferably at least 60% up to 65%, and most preferably of 62%;

(D) is a $K_M$ value
  (i) of between 100 mM and 190 mM, preferably between 130 mM and 190 mM, preferably between 160 mM and 190 mM, more preferably between 170 mM and 185 mM, and most preferably between 175 mM and 180 mM; and/or
  (ii) of between 50 mM and 190 mM, 50 mM and 189 mM, 50 mM and 188 mM, 50 mM and 187 mM, 50 mM and 186 mM, 50 mM and 185 mM, preferably between 50 mM and 184 mM, preferably between 50 mM and 183 mM, preferably between 50 mM and 182 mM, preferably between 50 mM and 181 mM, preferably between 50 mM and 180 mM, preferably between 50 mM and 179 mM, preferably between 50 mM and 178 mM, preferably between 50 mM and 177 mM, preferably between 50 mM and 176 mM, preferably between 50 mM and 175 mM, preferably between 50 mM and 174 mM, preferably between 50 mM and 173 mM, preferably between 50 mM and 172 mM, preferably between 50 mM and 171 mM, preferably between 50 mM and 170 mM, preferably between 50 mM and 169 mM, preferably between 50 mM and 168 mM, preferably between 50 mM and 167 mM, preferably between 50 mM and 166 mM, preferably between 50 mM and 165 mM, preferably between 50 mM and 160 mM, preferably between 50 mM and 159 mM, preferably between 50 mM and 158 mM, preferably between 50 mM and 157 mM, preferably between 50 mM and 156 mM, preferably between 50 mM and 155 mM, preferably between 50 mM and 154 mM, preferably between 50 mM and 153 mM, preferably between 50 mM and 152 mM, 75 mM and 190 mM, 75 mM and 189 mM, 75 mM and 188 mM, 75 mM and 187 mM, 75 mM and 186 mM, 75 mM and 185 mM, preferably between 75 mM and 184 mM, preferably between 75 mM and 183 mM, preferably between 75 mM and 182 mM, preferably between 75 mM and 181 mM, preferably between 75 mM and 180 mM, preferably between 75 mM and 179 mM, preferably between 75 mM and 178 mM, preferably between 75 mM and 177 mM, preferably between 75 mM and 176 mM, preferably between 75 mM and 175 mM, preferably between 75 mM and 174 mM, preferably between 75 mM and 173 mM, preferably between 75 mM and 172 mM, preferably between 75 mM and 171 mM, preferably between 75 mM and 170 mM, preferably between 75 mM and 169 mM, preferably between 75 mM and 168 mM, preferably between 75 mM and 167 mM, preferably between 75 mM and 166 mM, preferably between 75 mM and 165 mM, preferably between 75 mM and 160 mM, preferably between 75 mM and 159 mM, preferably between 75 mM and 158 mM, preferably between 75 mM and 157 mM, preferably between 75 mM and 156 mM, preferably between 75 mM and 155 mM, preferably between 75 mM and 154 mM, preferably between 75 mM and 153 mM, preferably between 75 mM and 152 mM, 100 mM and 190 mM, 100 mM and 189 mM, 100 mM and 188 mM, 100 mM and 187 mM, 100 mM and 186 mM, 100 mM and 185 mM, preferably between 100 mM and 184 mM, preferably between 100 mM and 183 mM, preferably between 100 mM and 182 mM, preferably between 100 mM and 181 mM, preferably between 100 mM and 180 mM, preferably between 100 mM and 179 mM, preferably between 100 mM and 178 mM, preferably between 100 mM and 177 mM, preferably between 100 mM and 176 mM, preferably between 100 mM and 1100 mM, preferably between 100 mM and 174 mM, preferably between 100 mM and 173 mM, preferably between 100 mM and 172 mM, preferably between 100 mM and 171 mM, preferably between 100 mM and 170 mM, preferably between 100 mM and 169 mM, preferably between 100 mM and 168 mM, preferably between 100 mM and 167 mM, preferably between 100 mM and 166 mM, preferably between 100 mM and 165 mM, preferably between 100 mM and 160 mM, preferably between 100 mM and 159 mM, preferably between 100 mM and 158 mM, preferably between 100 mM and 157 mM, preferably between 100 mM and 156 mM, preferably between 100 mM and 155 mM, preferably between 100 mM and 154 mM, preferably between 100 mM and 153 mM, preferably between 100 mM and 152 mM, 115 mM and 190 mM, 115 mM and 189 mM, 115 mM and 188 mM, 115 mM and 187 mM, 115 mM and 186 mM, 115 mM and 185 mM, preferably between 115 mM and 184 mM, preferably between 115 mM and 183 mM, preferably between 115 mM and 182 mM, preferably between 115 mM and 181 mM, preferably between 115 mM and 180 mM, preferably between 115 mM and 179 mM, preferably between 115 mM and 178 mM, preferably between 115 mM and 177 mM, preferably between 115 mM and 176 mM, preferably between 115 mM and 175 mM, preferably between 115 mM and 174 mM, preferably between 115 mM and 173 mM, preferably between 115 mM and 172 mM, preferably between 115 mM and 171 mM, preferably between 115 mM and 170 mM, preferably between 115 mM and 169 mM, preferably between 115 mM and 168 mM, preferably between 115 mM and 167 mM, preferably between 115 mM and 166 mM, preferably between 115 mM and 165 mM, preferably between 115 mM and 160 mM, preferably between 115 mM and 159 mM, preferably between 115 mM and 158 mM, preferably between 115 mM and 157 mM, preferably between 115 mM and 156 mM, preferably between 115 mM and 155 mM, preferably between 115 mM and 154 mM, preferably between 115 mM and 153 mM, preferably between 115 mM and 152 mM, 130 mM and 185 mM, preferably between 130 mM and 184 mM, preferably between 130 mM and 183 mM, preferably between 130 mM and 182 mM, preferably between 130 mM and 181 mM, preferably between 130 mM and 180 mM, preferably between 130 mM and 179 mM, preferably between 130 mM and 178 mM, preferably between 130 mM and 177 mM, preferably between 130 mM and 176 mM, preferably between 130 mM and 175 mM, preferably between 130 mM and 174 mM, preferably between 130 mM and 173 mM, preferably between 130 mM and 172 mM, preferably between 130 mM and 171 mM, preferably between 130 mM and 170 mM, preferably between 130 mM and 169 mM, preferably between 130 mM and 168 mM, preferably between 130 mM and 167 mM, preferably between 130 mM and 166 mM, preferably between 130 mM and 165 mM, preferably between 130 mM and 160 mM, preferably between 130 mM and 159 mM, preferably between 130 mM and 158 mM, preferably between 130 mM and 157 mM, preferably between 130 mM and 156 mM, preferably between 130 mM and 155 mM, preferably between 130 mM and 154 mM, preferably between 130 mM and 153 mM, preferably between 130 mM and 152 mM, more preferably between 135 mM and 185 mM, more preferably between 135 mM and 184 mM, more preferably between 135 mM and 183 mM, more preferably between 135 mM and 182 mM, more preferably between 135 mM and 181 mM, more preferably between 135 mM and 180 mM, more preferably between 135 mM and 179 mM, more preferably between 135 mM and 178 mM, more preferably between 135 mM and 177 mM, more preferably between 135 mM and 176 mM, more preferably between 135 mM and 175 mM, more preferably between 135 mM and 174 mM, more preferably between 135 mM and 173 mM, more preferably between 135 mM and 172 mM, more preferably between 135 mM and 171 mM, more preferably between 135 mM and 170 mM, more preferably between 135 mM and 169 mM, more preferably between 135 mM and 168 mM, more preferably between 135 mM and 167 mM, more preferably between 135 mM and 166 mM, more preferably between 135 mM and 165 mM, more preferably between 135 mM and 160 mM, more preferably between 135 mM and 159 mM, more preferably between 135 mM and 158 mM, more preferably between 135 mM and 157 mM, more preferably between 135 mM and 156 mM, more preferably between 135 mM and 155 mM, more preferably between 135 mM and 154 mM, more preferably between 135 mM and 153 mM, more preferably between 135 mM and 152 mM, most preferably between 140 mM and 185 mM, most preferably between 140 mM and 184 mM, most preferably between 140 mM and 183 mM, most preferably between 140 mM and 182 mM, most preferably between 140 mM and 181 mM, most preferably between 140 mM and 180 mM, most preferably between 140 mM and 179 mM, most preferably between 140 mM and 178 mM, most preferably between 140 mM and 177 mM, most preferably between 140 mM and 176 mM, most preferably between 140 mM and 175 mM, most preferably between 140 mM and 174 mM, most preferably between 140 mM and 173 mM, most preferably between 140 mM and 172 mM, most preferably between 140 mM and 171 mM, most preferably between 140 mM and 170 mM, most preferably between 140 mM and 169 mM, most preferably between 140 mM and 168 mM, most preferably between 140 mM and 167 mM, most preferably between 140 mM and 166 mM, most preferably between 140 mM and 165 mM, most preferably between 140 mM and 160 mM, most preferably between 140 mM and 159 mM, most preferably between 140 mM and 158 mM, most preferably between 140 mM and 157 mM, most preferably between 140 mM and 156 mM, most preferably between 140 mM and 155 mM, most preferably between 140 mM and 154 mM, most preferably between 140 mM and 153 mM, and utmost preferably between 140 mM and 152 mM; and/or (iii) of less than 190 mM, 189 mM, 188 mM, 187 mM, 186 mM, 185 mM, 184 mM, 183 mM, 182 mM, 181 mM, 180 mM, 179 mM, 178 mM, 177 mM, 176 mM, 175 mM, 174 mM, 173 mM, 172 mM, 171 mM, 170 mM, 169 mM, 168 mM, 167 mM, 166 mM, 165 mM, 160 mM, 159 mM, 158 mM, 157 mM, 156 mM, 155 mM, 154 mM, 153 mM, 152 mM, preferably of less than 185 mM, more preferably less than 170 mM, even more preferably less than 160 mM, and most preferably less than 155 mM, and utmost preferably of 152 mM and less than 152 mM;

(E) is Soluble Expression Level of the polypeptide, preferably the glucose isomerase, defined as the ratio of the soluble expression level of said polypeptide and the soluble expression level of the polypeptide, preferably the glucose isomerase, of SEQ ID NO: 1

(i) of at least 1.04 up to 1.38, preferably of at least 1.07 up to 1.38, preferably of at least 1.10 up to 1.38, preferably of at least 1.31 up to 1.38, preferably of at least 1.33 up to 1.38, preferably of at least 1.36 up to 1.38, more preferably of at least 1.04 up to 1.36, more preferably of at least 1.07 up to 1.36, more preferably of at least 1.10 up to 1.36, more preferably of at least 1.31 up to 1.36, more preferably of at least 1.33 up to 1.36, and most preferably of at 1.36; and or (ii) of at least 1.04 up to 1.80, preferably of at least 1.07 up to 1.80, preferably of at least 1.10 up to 1.80, preferably of at least 1.31 up to 1.80, preferably of at least 1.33 up to 1.80, preferably of at least 1.36 up to 1.80, preferably of at least 1.38 up to 1.80, preferably of at least 1.43 up to 1.80, more preferably of at least 1.04 up to 1.75, more preferably of at least 1.07 up to 1.75, more preferably of at least 1.10 up to 1.75, more preferably of at least 1.31 up to 1.75, more preferably of at least 1.33 up to 1.75, more preferably of at least 1.36 up to 1.75, more preferably of at least 1.38 up to 1.75, more preferably of at least 1.43 up to 1.75, more preferably of at least 1.47 up to 1.75, more preferably of at least 1.62 up to 1.75, even more preferably of at least 1.04 up to 1.70, even more preferably of at least 1.07 up to 1.70, even more preferably of at least 1.10 up to 1.70, even more preferably of at least 1.31 up to 1.70, even more preferably of at least 1.33 up to 1.70, even more preferably of at least 1.36 up to 1.70, even more preferably of at least 1.38 up to 1.70, even more preferably of at least 1.43 up to 1.70, even more preferably of at least 1.47 up to 1.70, even more preferably of at least 1.62 up to 1.70, even more preferably of at least 1.04 up to 1.65, even more preferably of at least 1.07 up to 1.65, even more preferably of at least 1.10 up to 1.65, even more preferably of at least 1.31 up to 1.65, even more preferably of at least 1.33 up to 1.65, even more preferably of at least 1.36 up to 1.65, even more preferably of at least 1.38 up to 1.65, even more preferably of at least 1.43 up to 1.65, even more preferably of at least 1.47 up to 1.65, even more preferably of at least 1.62 up to 1.65 and utmost preferably of at least 1.10 to 1.63, of at least 1.38 to 1.63, of at least 1.43 to 1.63, and/or of 1.63; and
(F) is an increased catalytic activity of the polypeptide, preferably of the glucose isomerase, in comparison to SEQ ID NO:1 in converting fructose into glucose, expressed as Glucose Formation
of at least 1.2-fold up to 5-fold, of at least 1.2-fold up to 4.5-fold, of at least 1.2-fold up to 4-fold, of at least 1.2-fold up to 3.5-fold, of at least 1.2-fold up to 3.4-fold, of at least 1.2-fold up to 3.3-fold, of at least 1.2-fold up to 3.2-fold, of at least 1.2-fold up to 3.1-fold, of at least 1.2-fold up to 3-fold, of at least 1.2-fold up to 2.9-fold, of at least 1.2-fold up to 2.8-fold, of at least 1.2-fold up to 2.7-fold, of at least 1.2-fold up to 2.6-fold, of at least 1.2-fold up to 2.5-fold, of at least 1.2-fold up to 2.4-fold, of at least 1.2-fold up to 2.3-fold, of at least 1.2-fold up to 2.2-fold, preferably of at least 1.5-fold up to 5-fold, of at least 1.5-fold up to 4.5-fold, of at least 1.5-fold up to 4-fold, of at least 1.5-fold up to 3.5-fold, of at least 1.5-fold up to 3.4-fold, of at least 1.5-fold up to 3.3-fold, of at least 1.5-fold up to 3.2-fold, of at least 1.5-fold up to 3.1-fold, of at least 1.5-fold up to 3-fold, of at least 1.5-fold up to 2.9-fold, of at least 1.5-fold up to 2.8-fold, of at least 1.5-fold up to 2.7-fold, of at least 1.5-fold up to 2.6-fold, of at least 1.5-fold up to 2.5-fold, of at least 1.5-fold up to 2.4-fold, of at least 1.5-fold up to 2.3-fold, of at least 1.5-fold up to 2.2-fold, and more preferably of at least 1.9-fold up to 5-fold, of at least 1.9-fold up to 4.5-fold, of at least 1.9-fold up to 4-fold, of at least 1.9-fold up to 3.5-fold, of at least 1.9-fold up to 3.4-fold, of at least 1.9-fold up to 3.3-fold, of at least 1.9-fold up to 3.2-fold, of at least 1.9-fold up to 3.1-fold, of at least 1.9-fold up to 3-fold, of at least 1.9-fold up to 2.9-fold, of at least 1.9-fold up to 2.8-fold, of at least 1.9-fold up to 2.7-fold, of at least 1.9-fold up to 2.6-fold, of at least 1.9-fold up to 2.5-fold, of at least 1.9-fold up to 2.4-fold, of at least 1.9-fold up to 2.3-fold, of at least 1.9-fold up to 2.2-fold, and yet more preferably of at least 2.0-fold up to 5-fold, of at least 2.0-fold up to 4.5-fold, of at least 2.0-fold up to 4-fold, of at least 2.0-fold up to 3.5-fold, of at least 2.0-fold up to 3.4-fold, of at least 2.0-fold up to 3.3-fold, of at least 2.0-fold up to 3.2-fold, of at least 2.0-fold up to 3.1-fold, of at least 2.0-fold up to 3-fold, of at least 2.0-fold up to 2.9-fold, of at least 2.0-fold up to 2.8-fold, of at least 2.0-fold up to 2.7-fold, of at least 2.0-fold up to 2.6-fold, of at least 2.0-fold up to 2.5-fold, of at least 2.0-fold up to 2.4-fold, of at least 2.0-fold up to 2.3-fold of at least 2.0-fold up to 2.2-fold, and most preferably of at least 2.2-fold up to 3.3-fold.

In a second embodiment of the fourth aspect, which is also an embodiment of the first embodiment of the fourth aspect, the polypeptide, preferably the glucose isomerase, has an increased activity, preferably increased Activity, for the conversion of fructose to glucose at a concentration of 50 mM fructose in comparison to the polypeptide, preferably the glucose isomerase, of SEQ ID NO: 1 of at least 1.1-fold up to 1.6-fold, preferably of at least 1.2-fold up to 1.6-fold, more preferably of at least 1.3-fold up to 1.6-fold, most preferably of at least 1.4-fold up to 1.6-fold, or of at least 1.1-fold up to 3.0-fold, preferably of at least 1.4-fold up to 3.0-fold, preferably of at least 1.5-fold up to 3.0-fold, more preferably of at least 1.6-fold up to 3.0-fold, preferably of at least 1.7-fold up to 3.0-fold, preferably of at least 1.8-fold up to 3.0-fold, preferably of at least 1.9-fold up to 3.0-fold, preferably of at least 2.0-fold up to 3.0-fold, more preferably of at least 1.4-fold up to 2.8-fold, more preferably of at least 1.5-fold up to 2.8-fold, more preferably of at least 1.6-fold up to 2.8-fold, more preferably of at least 1.7-fold up to 2.8-fold, more preferably of at least 1.8-fold up to 2.8-fold, more preferably of at least 1.9-fold up to 2.8-fold, more preferably of at least 2.0-fold up to 2.8-fold, even more preferably of at least 1.4-fold up to 2.6-fold, even more preferably of at least 1.5-fold up to 2.6-fold, more preferably of at least 1.6-fold up to 2.6-fold, more preferably of at least 1.7-fold up to 2.6-fold, more preferably of at least 1.8-fold up to 2.6-fold, more preferably of at least 1.9-fold up to 2.6-fold, more preferably of at least 2.0-fold up to 2.6-fold, and most preferably of at least 1.4-fold up to 2.4-fold, most preferably of at least 1.5-fold up to 2.4-fold, most preferably of at least 1.6-fold up to 2.4-fold, most preferably of at least 1.7-fold up to 2.4-fold, most preferably of at least 1.8-fold up to 2.4-fold, most preferably of at least 1.9-fold up to 2.4-fold, and most preferably of at least 2.0-fold up to 2.4-fold, and utmost preferable of at least 1.7-fold up to 2.4-fold.

In a third embodiment of the fourth aspect, which is also an embodiment of the first and second embodiment of the fourth aspect, the polypeptide, preferably the glucose isomerase, has an increased activity, preferably increased Activity, for the conversion of fructose to glucose at a concentration of 200 mM fructose in comparison to the polypeptide, preferably the glucose isomerase, of SEQ ID NO: 1
of at least 1.2-fold up to 1.6-fold, more preferably of at least 1.3-fold up to 1.6-fold, most preferably of at least 1.4-fold up to 1.6-fold, and/or
of at least 1.2-fold up to 3.0-fold, preferably of at least 1.3-fold up to 3.0-fold, preferably of at least 1.4-fold up to 3.0-fold preferably of at least 1.5-fold up to 3.0-fold, more preferably of at least 1.6-fold up to 3.0-fold, preferably of at least 1.7-fold up to 3.0-fold, preferably of at least 1.8-fold up to 3.0-fold, preferably of at least 1.9-fold up to 3.0-fold, preferably of at least 2.0-fold up to 3.0-fold, more preferably of at least 1.3-fold up to 2.5-fold, more preferably of at least 1.4-fold up to 2.5-fold, more preferably of at least 1.5-fold up to 2.5-fold, more preferably of at least 1.6-fold up to 2.5-fold, more preferably of at least 1.7-fold up to 2.5-fold, more preferably of at least 1.8-fold up to 2.5-fold, more preferably of at least 1.9-fold up to 2.5-fold, more preferably of at least 2.0-fold up to 2.5-fold, even more preferably of at least 1.3-fold up to 2.2-fold, even more preferably of at least 1.4-fold up to 2.2-fold, even more preferably of at least 1.5-fold up to 2.2-fold, more preferably of at least 1.6-fold up to 2.2-fold, more preferably of at least 1.7-fold up to 2.2-fold, more preferably of at least 1.8-fold up to 2.2-fold, more preferably of at least 1.9-fold up to 2.2-fold, more preferably of at least 2.0-fold up to 2.2-fold, and utmost preferably of at least 1.5-fold up to 2.2-fold.

In a fourth embodiment of the fourth aspect, which is also an embodiment of the first, second and third embodiment of the fourth aspect, the polypeptide, preferably the glucose isomerase, has a thermal stability expressed as Residual Activity after incubation of the polypeptide, preferably the glucose isomerase at a temperature of 74° C. for 15 minutes, wherein the polypeptide, preferably the glucose isomerase, has a Residual Activity of
at least 30% up to 100%, at least 40% up to 100%, at least 50% up to 100%, at least 30% up to 75%, at least 40% up to 75%, at least 50% up to 75%, at least 30% up to 65%, at least 40% up to 65%, at least 50% up to 65%, at least 41% up to 64%, and/or at least 30% up to 100%, at least 31% up to 100%, at least 32% up to 100%, at least 33% up to 100%, at least 34% up to 100%, at least 35% up to 100%, at least 36% up to 100%, at least 37% up to 100%, at least 38% up to 100%, at least 39% up to 100%, at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, at least 60% up to 100%, at least 61% up to 100%, at least 62% up to 100%, at least 63% up to 100%, at least 64% up to 100%, at least 65% up to 100%, at least 66% up to 100%, at least 67% up to 100%, at least 68% up to 100%, at least 69% up to 100%, at least 70% up to 100%, at least 71% up to 100%, at least 72% up to 100%, at least 73% up to 100%, at least 74% up to 100%, at least 75% up to 100%, at least 76% up to 100%, at least 77% up to 100%, at least 78% up to 100%, at least 79% up to 100%, at least 80% up to 100%, at least 30% up to 75%, at least 31% up to 75%, at least 32% up to 75%, at least 33% up to 75%, at least 34% up to 75%, at least 35% up to 75%, at least 36% up to 75%, at least 37% up to 75%, at least 38% up to 75%, at least 39% up to 75%, at least 40% up to 75%, at least 41% up to 75%, at least 42% up to 75%, at least 43% up to 75%, at least 44% up to 75%, at least 45% up to 75%, at least 46% up to 75%, at least 47% up to 75%, at least 48% up to 75%, at least 49% up to 75%, at least 50% up to 75%, at least 51% up to 75%, at least 52% up to 75%, at least 53% up to 75%, at least 54% up to 75%, at least 55% up to 75%, at least 56% up to 75%, at least 57% up to 75%, at least 58% up to 75%, at least 59% up to 75%, at least 60% up to 75%, at least 61% up to 75%, at least 62% up to 75%, at least 30% up to 70%, at least 31% up to 70%, at least 32% up to 70%, at least 33% up to 70%, at least 34% up to 70%, at least 35% up to 70%, at least 36% up to 70%, at least 37% up to 70%, at least 38% up to 70%, at least 39% up to 70%, at least 40% up to 70%, at least 41% up to 70%, at least 42% up to 70%, at least 43% up to 70%, at least 44% up to 70%, at least 45% up to 70%, at least 46% up to 70%, at least 47% up to 70%, at least 48% up to 70%, at least 49% up to 70%, at least 50% up to 70%, at least 51% up to 70%, at least 52% up to 70%, at least 53% up to 70%, at least 54% up to 70%, at least 55% up to 70%, at least 56% up to 70%, at least 57% up to 70%, at least 58% up to 70%, at least 59% up to 70%, at least 60% up to 70%, at least 61% up to 70%, at least 62% up to 70%, at least 30% up to 65%, at least 31% up to 65%, at least 32% up to 65%, at least 33% up to 65%, at least 34% up to 65%, at least 35% up to 65%, at least 36% up to 65%, at least 37% up to 65%, at least 38% up to 65%, at least 39% up to 65%, at least 40% up to 65%, at least 41% up to 65%, at least 42% up to 65%, at least 43% up to 65%, at least 44% up to 65%, at least 45% up to 65%, at least 46% up to 65%, at least 47% up to 65%, at least 48% up to 65%, at least 49% up to 65%, at least 50% up to 65%, at least 51% up to 65%, at least 52% up to 65%, at least 53% up to 65%, at least 54% up to 65%, at least 55% up to 65%, at least 56% up to 65%, at least 57% up to 65%, at least 58% up to 65%, at least 59% up to 65%, at least 60% up to 65%, at least 61% up to 65%, at least 62% up to 65%, more preferably at least 30% up to 65%, at least 34% up to 65%, at least 35% up to 65%, at least 38% up to 65%, at least 40% up to 65%, at least 41% up to 65%, at least 42% up to 65%, at least 46% up to 65%, at least 47% up to 65%, at least 50% up to 65%, at least 55% up to 65%, at least 59% up to 65%, at least 60% up to 65%, at least 62% up to 65%, even more preferably at least at least 40% up to 65%, and even more preferably at least 60% up to 65%, and most preferably of 62%.

In a fifth embodiment of the fourth aspect, which is also an embodiment of the first, second, third and fourth embodiment of the fourth aspect, the polypeptide, preferably the glucose isomerase, has a Km value of between 100 mM and 190 mM, preferably between 130 mM and 190 mM, preferably between 160 mM and 190 mM, more preferably between 170 mM and 185 mM, and most preferably between 175 mM and 180 mM; and/or of between 50 mM and 190 mM, 50 mM and 189 mM, 50 mM and 188 mM, 50 mM and 187 mM, 50 mM and 186 mM, 50 mM and 185 mM, preferably between 50 mM and 184 mM, preferably between 50 mM and 183 mM, preferably between 50 mM and 182 mM, preferably between 50 mM and 181 mM, preferably between 50 mM and 180 mM, preferably between 50 mM and 179 mM, preferably between 50 mM and 178 mM, preferably between 50 mM and 177 mM, preferably between 50 mM and 176 mM, preferably between 50 mM and 175 mM, preferably between 50 mM and 174 mM, preferably between 50 mM and 173 mM, preferably between 50 mM and 172 mM, preferably between 50 mM and 171 mM, preferably between 50 mM and 170 mM, preferably between 50 mM and 169 mM, preferably between 50 mM and 168 mM, preferably between 50 mM and 167 mM, preferably between 50 mM and 166 mM, preferably between 50 mM and 165 mM, preferably between 50 mM and 160 mM, preferably between 50 mM and 159 mM, preferably between 50 mM and 158 mM, preferably between 50 mM and 157 mM, preferably between 50 mM and 156 mM, preferably between 50 mM and 155 mM, preferably between 50 mM and 154 mM, preferably between 50 mM and 153 mM, preferably between 50 mM and 152 mM, 75 mM and 190 mM, 75 mM and 189 mM, 75 mM and 188 mM, 75 mM and 187 mM, 75 mM and 186 mM, 75 mM and 185 mM, preferably between 75 mM and 184 mM, preferably between 75 mM and 183 mM, preferably between 75 mM and 182 mM, preferably between 75 mM and 181 mM, preferably between 75 mM and 180 mM, preferably between 75 mM and 179 mM, preferably between 75 mM and 178 mM, preferably between 75 mM and 177 mM, preferably between 75 mM and 176 mM, preferably between 75 mM and 175 mM, preferably between 75 mM and 174 mM, preferably between 75 mM and 173 mM, preferably between 75 mM and 172 mM, preferably between 75 mM and 171 mM, preferably between 75 mM and 170 mM, preferably between 75 mM and 169 mM, preferably between 75 mM and 168 mM, preferably between 75 mM and 167 mM, preferably between 75 mM and 166 mM, preferably between 75 mM and 165 mM, preferably between 75 mM and 160 mM, preferably between 75 mM and 159 mM, preferably between 75 mM and 158 mM, preferably between 75 mM and 157 mM, preferably between 75 mM and 156 mM, preferably between 75 mM and 155 mM, preferably between 75 mM and 154 mM, preferably between 75 mM and 153 mM, preferably between 75 mM and 152 mM, 100 mM and 190 mM, 100 mM and 189 mM, 100 mM and 188 mM, 100 mM and 187 mM, 100 mM and 186 mM, 100 mM and 185 mM, preferably between 100 mM and 184 mM, preferably between 100 mM and 183 mM, preferably between 100 mM and 182 mM, preferably between 100 mM and 181 mM, preferably between 100 mM and 180 mM, preferably between 100 mM and 179 mM, preferably between 100 mM and 178 mM, preferably between 100 mM and 177 mM, preferably between 100 mM and 176 mM, preferably between 100 mM and 1100 mM, preferably between 100 mM and 174 mM, preferably between 100 mM and 173 mM, preferably between 100 mM and 172 mM, preferably between 100 mM and 171 mM, preferably between 100 mM and 170 mM, preferably between 100 mM and 169 mM, preferably between 100 mM and 168 mM, preferably between 100 mM and 167 mM, preferably between 100 mM and 166 mM, preferably between 100 mM and 165 mM, preferably between 100 mM and 160 mM, preferably between 100 mM and 159 mM, preferably between 100 mM and 158 mM, preferably between 100 mM and 157 mM, preferably between 100 mM and 156 mM, preferably between 100 mM and 155 mM, preferably between 100 mM and 154 mM, preferably between 100 mM and 153 mM, preferably between 100 mM and 152 mM, 115 mM and 190 mM, 115 mM and 189 mM, 115 mM and 188 mM, 115 mM and 187 mM, 115 mM and 186 mM, 115 mM and 185 mM, preferably between 115 mM and 184 mM, preferably between 115 mM and 183 mM, preferably between 115 mM and 182 mM, preferably between 115 mM and 181 mM, preferably between 115 mM and 180 mM, preferably between 115 mM and 179 mM, preferably between 115 mM and 178 mM, preferably between 115 mM and 177 mM, preferably between 115 mM and 176 mM, preferably between 115 mM and 175 mM, preferably between 115 mM and 174 mM, preferably between 115 mM and 173 mM, preferably between 115 mM and 172 mM, preferably between 115 mM and 171 mM, preferably between 115 mM and 170 mM, preferably between 115 mM and 169 mM, preferably between 115 mM and 168 mM, preferably between 115 mM and 167 mM, preferably between 115 mM and 166 mM, preferably between 115 mM and 165 mM, preferably between 115 mM and 160 mM, preferably between 115 mM and 159 mM, preferably between 115 mM and 158 mM, preferably between 115 mM and 157 mM, preferably between 115 mM and 156 mM, preferably between 115 mM and 155 mM, preferably between 115 mM and 154 mM, preferably between 115 mM and 153 mM, preferably between 115 mM and 152 mM, 130 mM and 185 mM, preferably between 130 mM and 184 mM, preferably between 130 mM and 183 mM, preferably between 130 mM and 182 mM, preferably between 130 mM and 181 mM, preferably between 130 mM and 180 mM, preferably between 130 mM and 179 mM, preferably between 130 mM and 178 mM, preferably between 130 mM and 177 mM, preferably between 130 mM and 176 mM, preferably between 130 mM and 175 mM, preferably between 130 mM and 174 mM, preferably between 130 mM and 173 mM, preferably between 130 mM and 172 mM, preferably between 130 mM and 171 mM, preferably between 130 mM and 170 mM, preferably between 130 mM and 169 mM, preferably between 130 mM and 168 mM, preferably between 130 mM and 167 mM, preferably between 130 mM and 166 mM, preferably between 130 mM and 165 mM, preferably between 130 mM and 160 mM, preferably between 130 mM and 159 mM, preferably between 130 mM and 158 mM, preferably between 130 mM and 157 mM, preferably between 130 mM and 156 mM, preferably between 130 mM and 155 mM, preferably between 130 mM and 154 mM, preferably between 130 mM and 153 mM, preferably between 130 mM and 152 mM, more preferably between 135 mM and 185 mM, more preferably between 135 mM and 184 mM, more preferably between 135 mM and 183 mM, more preferably between 135 mM and 182 mM, more preferably between 135 mM and 181 mM, more preferably between 135 mM and 180 mM, more preferably between 135 mM and 179 mM, more preferably between 135 mM and 178 mM, more preferably between 135 mM and 177 mM, more preferably between 135 mM and 176 mM, more preferably between 135 mM and 175 mM, more preferably between 135 mM and 174 mM, more preferably between 135 mM and 173 mM, more preferably between 135 mM and 172 mM, more preferably between 135 mM and 171 mM, more preferably between 135 mM and 170 mM, more preferably between 135 mM and 169 mM, more preferably between 135 mM and 168 mM, more preferably between 135 mM and 167 mM, more preferably between 135 mM and 166 mM, more preferably between 135 mM and 165 mM, more preferably between 135 mM and 160 mM, more preferably between 135 mM and 159 mM, more preferably between 135 mM and 158 mM, more preferably between 135 mM and 157 mM, more preferably between 135 mM and 156 mM, more preferably between 135 mM and 155 mM, more preferably between 135 mM and 154 mM, more preferably between 135 mM and 153 mM, more preferably between 135 mM and 152 mM, most preferably between 140 mM and 185 mM, most preferably between 140 mM and 184 mM, most preferably between 140 mM and 183 mM, most preferably between 140 mM and 182 mM, most preferably between 140 mM and 181 mM, most preferably between 140 mM and 180 mM, most preferably between 140 mM and 179 mM, most preferably between 140 mM and 178 mM, most preferably between 140 mM and 177 mM, most preferably between 140 mM and 176 mM, most preferably between 140 mM and 175 mM, most preferably between 140 mM and 174 mM, most preferably between 140 mM and 173 mM, most preferably between 140 mM and 172 mM, most preferably between 140 mM and 171 mM, most preferably between 140 mM and 170 mM, most preferably between 140 mM and 169 mM, most preferably between 140 mM and 168 mM, most preferably between 140 mM and 167 mM, most preferably between 140 mM and 166 mM, most preferably between 140 mM and 165 mM, most preferably between 140 mM and 160 mM, most preferably between 140 mM and 159 mM, most preferably between 140 mM and 158 mM, most preferably between 140 mM and 157 mM, most preferably between 140 mM and 156 mM, most preferably between 140 mM and 155 mM, most preferably between 140 mM and 154 mM, most preferably between 140 mM and 153 mM, and utmost preferably between 140 mM and 152 mM; and/or of less than 190 mM, 189 mM, 188 mM, 187 mM, 186 mM, 185 mM, 184 mM, 183 mM, 182 mM, 181 mM, 180 mM, 179 mM, 178 mM, 177 mM, 176 mM, 175 mM, 174 mM, 173 mM, 172 mM, 171 mM, 170 mM, 169 mM, 168 mM, 167 mM, 166 mM, 165 mM, 160 mM, 159 mM, 158 mM, 157 mM, 156 mM, 155 mM, 154 mM, 153 mM, 152 mM, preferably of less than 185 mM, more preferably less than 170 mM, even more preferably less than 160 mM, and most preferably less than 155 mM, and utmost preferably of 152 mM and less than 152 mM.

In a sixth embodiment of the fourth aspect, which is also an embodiment of the first, second, third, fourth and fifth embodiment of the fourth aspect, the polypeptide, preferably the glucose isomerase, has a Soluble Expression Level, defined as the ratio of the soluble expression level of said polypeptide and the soluble expression level of the polypeptide, preferably the glucose isomerase, of SEQ ID NO: 1 of at least 1.04 up to 1.38, preferably of at least 1.07 up to 1.38, preferably of at least 1.10 up to 1.38, preferably of at least 1.31 up to 1.38, preferably of at least 1.33 up to 1.38, preferably of at least 1.36 up to 1.38, more preferably of at least 1.04 up to 1.36, more preferably of at least 1.07 up to 1.36, more preferably of at least 1.10 up to 1.36, more preferably of at least 1.31 up to 1.36, more preferably of at least 1.33 up to 1.36, and most preferably of at 1.36; and or of at least 1.04 up to 1.80, preferably of at least 1.07 up to 1.80, preferably of at least 1.10 up to 1.80, preferably of at least 1.31 up to 1.80, preferably of at least 1.33 up to 1.80, preferably of at least 1.36 up to 1.80, preferably of at least 1.38 up to 1.80, preferably of at least 1.43 up to 1.80, more preferably of at least 1.04 up to 1.75, more preferably of at least 1.07 up to 1.75, more preferably of at least 1.10 up to 1.75, more preferably of at least 1.31 up to 1.75, more preferably of at least 1.33 up to 1.75, more preferably of at least 1.36 up to 1.75, more preferably of at least 1.38 up to 1.75, more preferably of at least 1.43 up to 1.75, more preferably of at least 1.47 up to 1.75, more preferably of at least 1.62 up to 1.75, even more preferably of at least 1.04 up to 1.70, even more preferably of at least 1.07 up to 1.70, even more preferably of at least 1.10 up to 1.70, even more preferably of at least 1.31 up to 1.70, even more preferably of at least 1.33 up to 1.70, even more preferably of at least 1.36 up to 1.70, even more preferably of at least 1.38 up to 1.70, even more preferably of at least 1.43 up to 1.70, even more preferably of at least 1.47 up to 1.70, even more preferably of at least 1.62 up to 1.70, even more preferably of at least 1.04 up to 1.65, even more preferably of at least 1.07 up to 1.65, even more preferably of at least 1.10 up to 1.65, even more preferably of at least 1.31 up to 1.65, even more preferably of at least 1.33 up to 1.65, even more preferably of at least 1.36 up to 1.65, even more preferably of at least 1.38 up to 1.65, even more preferably of at least 1.43 up to 1.65, even more preferably of at least 1.47 up to 1.65, even more preferably of at least 1.62 up to 1.65 and utmost preferably of at least 1.10 to 1.63, of at least 1.38 to 1.63, of at least 1.43 to 1.63, and/or of 1.63.

In a preferred embodiment of the fourth aspect, which is also an embodiment of the first, second, third, fourth and fifth embodiment or any other embodiment of the fourth aspect, the polypeptide, preferably the glucose isomerase, has an increased catalytic activity of the polypeptide, preferably of the glucose isomerase, in comparison to SEQ ID NO:1 in converting fructose into glucose, expressed as Glucose Formation of at least 1.2-fold up to 5-fold, of at least 1.2-fold up to 4.5-fold, of at least 1.2-fold up to 4-fold, of at least 1.2-fold up to 3.5-fold, of at least 1.2-fold up to 3.4-fold, of at least 1.2-fold up to 3.3-fold, of at least 1.2-fold up to 3.2-fold, of at least 1.2-fold up to 3.1-fold, of at least 1.2-fold up to 3-fold, of at least 1.2-fold up to 2.9-fold, of at least 1.2-fold up to 2.8-fold, of at least 1.2-fold up to 2.7-fold, of at least 1.2-fold up to 2.6-fold, of at least 1.2-fold up to 2.5-fold, of at least 1.2-fold up to 2.4-fold, of at least 1.2-fold up to 2.3-fold, of at least 1.2-fold up to 2.2-fold, preferably of at least 1.5-fold up to 5-fold, of at least 1.5-fold up to 4.5-fold, of at least 1.5-fold up to 4-fold, of at least 1.5-fold up to 3.5-fold, of at least 1.5-fold up to 3.4-fold, of at least 1.5-fold up to 3.3-fold, of at least 1.5-fold up to 3.2-fold, of at least 1.5-fold up to 3.1-fold, of at least 1.5-fold up to 3-fold, of at least 1.5-fold up to 2.9-fold, of at least 1.5-fold up to 2.8-fold, of at least 1.5-fold up to 2.7-fold, of at least 1.5-fold up to 2.6-fold, of at least 1.5-fold up to 2.5-fold, of at least 1.5-fold up to 2.4-fold, of at least 1.5-fold up to 2.3-fold, of at least 1.5-fold up to 2.2-fold, and more preferably of at least 1.9-fold up to 5-fold, of at least 1.9-fold up to 4.5-fold, of at least 1.9-fold up to 4-fold, of at least 1.9-fold up to 3.5-fold, of at least 1.9-fold up to 3.4-fold, of at least 1.9-fold up to 3.3-fold, of at least 1.9-fold up to 3.2-fold, of at least 1.9-fold up to 3.1-fold, of at least 1.9-fold up to 3-fold, of at least 1.9-fold up to 2.9-fold, of at least 1.9-fold up to 2.8-fold, of at least 1.9-fold up to 2.7-fold, of at least 1.9-fold up to 2.6-fold, of at least 1.9-fold up to 2.5-fold, of at least 1.9-fold up to 2.4-fold, of at least 1.9-fold up to 2.3-fold, of at least 1.9-fold up to 2.2-fold, and yet more preferably of at least 2.0-fold up to 5-fold, of at least 2.0-fold up to 4.5-fold, of at least 2.0-fold up to 4-fold, of at least 2.0-fold up to 3.5-fold, of at least 2.0-fold up to 3.4-fold, of at least 2.0-fold up to 3.3-fold, of at least 2.0-fold up to 3.2-fold, of at least 2.0-fold up to 3.1-fold, of at least 2.0-fold up to 3-fold, of at least 2.0-fold up to 2.9-fold, of at least 2.0-fold up to 2.8-fold, of at least 2.0-fold up to 2.7-fold, of at least 2.0-fold up to 2.6-fold, of at least 2.0-fold up to 2.5-fold, of at least 2.0-fold up to 2.4-fold, of at least 2.0-fold up to 2.3-fold of at least 2.0-fold up to 2.2-fold, and most preferably of at least 2.2-fold up to 3.3-fold.

In a seventh embodiment of the fourth aspect, which is also an embodiment of the first, second, third, fourth, fifth and sixth embodiment of the fourth aspect, the polypeptide, preferably the glucose isomerase, is one of any one of the first, second, third, fourth, fifth, sixth, seventh, eighth, ninth and tenth embodiment of the first aspect, preferably the polypeptide, preferably the glucose isomerase, is one of any one of the third, fourth, fifth, sixth, seventh, eighth, ninth and tenth embodiment of the first aspect, more preferably the polypeptide, preferably the glucose isomerase, is one of any one of the fifth, sixth, seventh, eighth, ninth and tenth embodiment of the first aspect, even more preferably the polypeptide, preferably the glucose isomerase, is one of any one of the seventh, eighth, ninth and tenth embodiment of the first aspect, and most preferably the polypeptide, preferably the glucose isomerase, is one of any one of the ninth and tenth embodiment of the first aspect, and/or the polypeptide, preferably the glucose isomerase, is one of any one of the eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, and $95^{th}$ embodiment or of any one of the other embodiments of the first aspect, preferably the polypeptide, preferably the glucose isomerase, is one of any one of the $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{rd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87\text{th}88^{th}$, $89^{th}$, $90^{th}$, $91^{st}$, $92^{nd}$, $93^{rd}$, $94^{th}$ and $95^{th}$ embodiment of the first aspect, more preferably the polypeptide, preferably the glucose isomerase, is one of any one of the $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$ and $95^{th}$ embodiment of the first aspect, even more preferably the polypeptide, preferably the glucose isomerase, is one of any one of the $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$ and $95^{th}$ embodiment of the first aspect, and most preferably the polypeptide, preferably the glucose isomerase, is one of any one of the $63^{rd}$ and $95^{th}$ embodiment of the first aspect, and any one of the $102^{nd}$, $103^{rd}$, $104^{th}$, $105^{th}$, $107^{th}$, $108^{th}$, $109^{th}$, $110^{th}$, $111^{th}$, $112^{th}$, $114^{th}$, $115^{th}$, $116^{th}$, $117^{th}$, $119^{th}$, $120^{th}$, $121^{st}$, $122^{nd}$, $124^{th}$, $125^{th}$, $126^{th}$, $127^{th}$, $128^{th}$, $130^{th}$, $131^{st}$, $132^{nd}$ and $133^{rd}$ embodiment or of any one of the other embodiments of the first aspect.

In an eighth embodiment of the fourth aspect, which is also an embodiment of the first embodiment of the fourth aspect, the polypeptide, preferably the glucose isomerase, has an increased activity, preferably increased Activity, for the conversion of fructose to glucose at a concentration of 50 mM fructose in comparison to the polypeptide, preferably the glucose isomerase, of SEQ ID NO: 1
of at least 1.1-fold up to 3.0-fold, preferably of at least 1.4-fold up to 3.0-fold, preferably of at least 1.5-fold up to 3.0-fold, more preferably of at least 1.6-fold up to 3.0-fold, preferably of at least 1.7-fold up to 3.0-fold, preferably of at least 1.8-fold up to 3.0-fold, preferably of at least 1.9-fold up to 3.0-fold, preferably of at least 2.0-fold up to 3.0-fold, more preferably of at least 1.4-fold up to 2.8-fold, more preferably of at least 1.5-fold up to 2.8-fold, more preferably of at least 1.6-fold up to 2.8-fold, more preferably of at least 1.7-fold up to 2.8-fold, more preferably of at least 1.8-fold up to 2.8-fold, more preferably of at least 1.9-fold up to 2.8-fold, more preferably of at least 2.0-fold up to 2.8-fold, even more preferably of at least 1.4-fold up to 2.6-fold, even more preferably of at least 1.5-fold up to 2.6-fold, more preferably of at least 1.6-fold up to 2.6-fold, more preferably of at least 1.7-fold up to 2.6-fold, more preferably of at least 1.8-fold up to 2.6-fold, more preferably of at least 1.9-fold up to 2.6-fold, more preferably of at least 2.0-fold up to 2.6-fold, and most preferably of at least 1.4-fold up to 2.4-fold, most preferably of at least 1.5-fold up to 2.4-fold, most preferably of at least 1.6-fold up to 2.4-fold, most preferably of at least 1.7-fold up to 2.4-fold, most preferably of at least 1.8-fold up to 2.4-fold, most preferably of at least 1.9-fold up to 2.4-fold, and most preferably of at least 2.0-fold up to 2.4-fold, and utmost preferable of at least 1.7-fold up to 2.4-fold, and wherein the polypeptide, preferably the glucose isomerase, is any one of the eleventh, twelfth $13^{th}$, $14^{th}$, $15^{th}$, $16^{th}$, $17^{th}$, $18^{th}$, $19^{th}$, $20^{th}$, $21^{st}22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66\text{th}67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$ and $97^{th}$ embodiment or of any one of the other embodiments of the first aspect, preferably the polypeptide, preferably the glucose isomerase, is any one of the $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $84^{th}$, $85^{th}$, $86^{th}$, $87^{th}$, $88^{th}$, $89^{th}$, $90^{th}$, $91^{st}$, $92^{nd}$, $74^{th}$, $75^{th}$, $76^{th}$, $77^{th}$, $78^{th}$, $79^{th}$, $80^{th}$, $81^{st}$, $82^{nd}$, $83^{rd}$, $93^{rd}$, $94^{th}$, $95^{th}$, $96^{th}$ and $97^{th}$ embodiment of the first aspect, more preferably the polypeptide, preferably the glucose isomerase, is any one of $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$ and $97^{th}$ embodiment of the first aspect, even more preferably the polypeptide, preferably the glucose isomerase, is any one of the $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$ and $97^{th}$ embodiment of the first aspect, most preferably the polypeptide, preferably the glucose isomerase, is any one of the $63^{rd}$ and $97^{th}$ embodiment of the first aspect, any one of the polypeptide, preferably the glucose isomerase, of any one of the $104^{th}$, $105^{th}$, $106^{th}$, $107^{th}$, $109^{th}$, $110^{th}$, $111^{th}$, $112^{th}$, $113^{th}$, $114^{th}$, $116^{th}$, $117^{th}$, $118^{th}$, $119^{th}$, $121^{st}$, $122^{nd}$, $123^{rd}$, $124^{th}$, $126^{th}$, $127^{th}$, $128^{th}$, $129^{th}$, $130^{th}$, $132^{nd}$, $133^{rd}$ $134^{th}$ and $135^{th}$ embodiment or of any one of the other embodiments of the first aspect.

In a ninth embodiment of the fourth aspect, which is also an embodiment of any one of the first, second, third, fourth, fifth, sixth, seventh and eighth embodiment of the fourth aspect, the polypeptide, preferably the glucose isomerase, has an increased activity, preferably increased Activity, for the conversion of fructose to glucose at a concentration of 200 mM fructose in comparison to the polypeptide, preferably the glucose isomerase, of SEQ ID NO: 1
of at least 1.2-fold up to 3.0-fold, preferably of at least 1.3-fold up to 3.0-fold, preferably of at least 1.4-fold up to 3.0-fold preferably of at least 1.5-fold up to 3.0-fold, more preferably of at least 1.6-fold up to 3.0-fold, preferably of at least 1.7-fold up to 3.0-fold, preferably of at least 1.8-fold up to 3.0-fold, preferably of at least 1.9-fold up to 3.0-fold, preferably of at least 2.0-fold up to 3.0-fold, more preferably of at least 1.3-fold up to 2.5-fold, more preferably of at least 1.4-fold up to 2.5-fold, more preferably of at least 1.5-fold up to 2.5-fold, more preferably of at least 1.6-fold up to 2.5-fold, more preferably of at least 1.7-fold up to 2.5-fold, more preferably of at least 1.8-fold up to 2.5-fold, more preferably of at least 1.9-fold up to 2.5-fold, more preferably of at least 2.0-fold up to 2.5-fold, even more preferably of at least 1.3-fold up to 2.2-fold, even more preferably of at least 1.4-fold up to 2.2-fold, even more preferably of at least 1.5-fold up to 2.2-fold, more preferably of at least 1.6-fold up to 2.2-fold, more preferably of at least 1.7-fold up to 2.2-fold, more preferably of at least 1.8-fold up to 2.2-fold, more preferably of at least 1.9-fold up to 2.2-fold, more preferably of at least 2.0-fold up to 2.2-fold, and utmost preferably of at least 1.5-fold up to 2.2-fold,
and wherein the polypeptide, preferably the glucose isomerase, is any one of the eleventh, twelfth $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$ and $97^{th}$ embodiment or of any one of the other embodiments of the first aspect, preferably any one of the $23^{th}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$ and $97^{th}$ embodiment of the first aspect, more preferably any one of the $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$ and $97^{th}$ embodiment of the first aspect, even more preferably any one of the $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$$91^{st}$, $92^{nd}$, $93^{rd}$, $94^{th}$, $95^{th}$, $96^{th}$ and $97^{th}$ embodiment of the first aspect, and most preferably any one of the $63^{rd}$ and $97^{th}$ embodiment of the first aspect, and most preferably any one of the $104^{th}$, $105^{th}$, $106^{th}$ and $107^{th}$, $109^{th}$, $110^{th}$, $111^{th}$ and $112^{th}$, $113^{th}$ and $114^{th}$, $116^{th}$, $117^{th}$, $118^{th}$, $119^{th}$, $121^{st}$, $122^{nd}$, $123^{rd}$, $124^{th}$, $126^{th}$, $127^{th}$, $128^{th}$, $129^{th}$, $130^{th}$, $132^{nd}$, $133^{rd}$, $134^{th}$ and $135^{th}$ embodiment or of any one of the other embodiments of the first aspect.

In a tenth embodiment of the fourth aspect, which is also an embodiment of any one of the first, second, third, fourth, fifth, sixth, seventh, eighth and ninth embodiment of the fourth aspect, the polypeptide, preferably the glucose isomerase, has a thermal stability expressed as Residual Activity after incubation of the polypeptide, preferably the glucose isomerase at a temperature of 74° C. for 15 minutes, wherein the polypeptide, preferably the glucose isomerase, has a Residual Activity of
at least 30% up to 100%, at least 31% up to 100%, at least 32% up to 100%, at least 33% up to 100%, at least 34% up to 100%, at least 35% up to 100%, at least 36% up to 100%, at least 37% up to 100%, at least 38% up to 100%, at least 39% up to 100%, at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, at least 60% up to 100%, at least 61% up to 100%, at least 62% up to 100%, at least 63% up to 100%, at least 64% up to 100%, at least 65% up to 100%, at least 66% up to 100%, at least 67% up to 100%, at least 68% up to 100%, at least 69% up to 100%, at least 70% up to 100%, at least 71% up to 100%, at least 72% up to 100%, at least 73% up to 100%, at least 74% up to 100%, at least 75% up to 100%, at least 76% up to 100%, at least 77% up to 100%, at least 78% up to 100%, at least 79% up to 100%, at least 80% up to 100%, at least 30% up to 75%, at least 31% up to 75%, at least 32% up to 75%, at least 33% up to 75%, at least 34% up to 75%, at least 35% up to 75%, at least 36% up to 75%, at least 37% up to 75%, at least 38% up to 75%, at least 39% up to 75%, at least 40% up to 75%, at least 41% up to 75%, at least 42% up to 75%, at least 43% up to 75%, at least 44% up to 75%, at least 45% up to 75%, at least 46% up to 75%, at least 47% up to 75%, at least 48% up to 75%, at least 49% up to 75%, at least 50% up to 75%, at least 51% up to 75%, at least 52% up to 75%, at least 53% up to 75%, at least 54% up to 75%, at least 55% up to 75%, at least 56% up to 75%, at least 57% up to 75%, at least 58% up to 75%, at least 59% up to 75%, at least 60% up to 75%, at least 61% up to 75%, at least 62% up to 75%, at least 30% up to 70%, at least 31% up to 70%, at least 32% up to 70%, at least 33% up to 70%, at least 34% up to 70%, at least 35% up to 70%, at least 36% up to 70%, at least 37% up to 70%, at least 38% up to 70%, at least 39% up to 70%, at least 40% up to 70%, at least 41% up to 70%, at least 42% up to 70%, at least 43% up to 70%, at least 44% up to 70%, at least 45% up to 70%, at least 46% up to 70%, at least 47% up to 70%, at least 48% up to 70%, at least 49% up to 70%, at least 50% up to 70%, at least 51% up to 70%, at least 52% up to 70%, at least 53% up to 70%, at least 54% up to 70%, at least 55% up to 70%, at least 56% up to 70%, at least 57% up to 70%, at least 58% up to 70%, at least 59% up to 70%, at least 60% up to 70%, at least 61% up to 70%, at least 62% up to 70%, at least 30% up to 65%, at least 31% up to 65%, at least 32% up to 65%, at least 33% up to 65%, at least 34% up to 65%, at least 35% up to 65%, at least 36% up to 65%, at least 37% up to 65%, at least 38% up to 65%, at least 39% up to 65%, at least 40% up to 65%, at least 41% up to 65%, at least 42% up to 65%, at least 43% up to 65%, at least 44% up to 65%, at least 45% up to 65%, at least 46% up to 65%, at least 47% up to 65%, at least 48% up to 65%, at least 49% up to 65%, at least 50% up to 65%, at least 51% up to 65%, at least 52% up to 65%, at least 53% up to 65%, at least 54% up to 65%, at least 55% up to 65%, at least 56% up to 65%, at least 57% up to 65%, at least 58% up to 65%, at least 59% up to 65%, at least 60% up to 65%, at least 61% up to 65%, at least 62% up to 65%, more preferably at least 30% up to 65%, at least 34% up to 65%, at least 35% up to 65%, at least 38% up to 65%, at least 40% up to 65%, at least 41% up to 65%, at least 42% up to 65%, at least 46% up to 65%, at least 47% up to 65%, at least 50% up to 65%, at least 55% up to 65%, at least 59% up to 65%, at least 60% up to 65%, at least 62% up to 65%, even more preferably at least at least 40% up to 65%, and even more preferably at least 60% up to 65%, and most preferably of 62%, and wherein the polypeptide, preferably the glucose isomerase, is any one of the eleventh, twelfth 13$^{th}$, 14$^{th}$, 15$^{th}$, 16$^{th}$, 17$^{th}$, 18$^{th}$, 19$^{th}$, 20$^{th}$, 21$^{st}$22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47th48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66th67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$, 94$^{th}$, 95$^{th}$, 96$^{th}$ and 97$^{th}$ embodiment or of any one of the other embodiments of the first aspect, preferably the polypeptide, preferably the glucose isomerase, is any one of the 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$, 94$^{th}$, 95$^{th}$, 96$^{th}$ and 97$^{th}$ embodiment of the first aspect, more preferably the polypeptide, preferably the glucose isomerase, is any one of 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$, 94$^{th}$, 95$^{th}$, 96$^{th}$ and 97$^{th}$ embodiment of the first aspect, even more preferably the polypeptide, preferably the glucose isomerase, is any one of the 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65th66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$, 94$^{th}$, 95$^{th}$, 96$^{th}$ and 97$^{th}$ embodiment of the first aspect, most preferably the polypeptide, preferably the glucose isomerase, is any one of the 63$^{rd}$ and 97$^{th}$ embodiment of the first aspect, any one of the polypeptide, preferably the glucose isomerase, of any one of the 104$^{th}$, 105$^{th}$, 106$^{th}$, 107$^{th}$, 109$^{th}$, 110$^{th}$, 111$^{th}$, 112$^{th}$, 113$^{th}$, 114$^{th}$, 116$^{th}$, 117$^{th}$, 118$^{th}$, 119$^{th}$, 121$^{st}$, 122$^{nd}$, 123$^{rd}$, 124$^{th}$, 126$^{th}$, 127$^{th}$, 128$^{th}$, 129$^{th}$, 130$^{th}$, 132$^{nd}$133$^{rd}$ 134$^{th}$ and 135$^{th}$ embodiment or of any one of the other embodiments of the first aspect.

In an eleventh embodiment of the fourth aspect, which is also an embodiment of any one of the first, second, third, fourth, fifth, sixth, seventh, eighth, ninth and tenth embodiment of the fourth aspect, the polypeptide, preferably the glucose isomerase, has a $K_M$ value of between 50 mM and 190 mM, 50 mM and 189 mM, 50 mM and 188 mM, 50 mM and 187 mM, 50 mM and 186 mM, 50 mM and 185 mM, preferably between 50 mM and 184 mM, preferably between 50 mM and 183 mM, preferably between 50 mM and 182 mM, preferably between 50 mM and 181 mM, preferably between 50 mM and 180 mM, preferably between 50 mM and 179 mM, preferably between 50 mM and 178 mM, preferably between 50 mM and 177 mM, preferably between 50 mM and 176 mM, preferably between 50 mM and 175 mM, preferably between 50 mM and 174 mM, preferably between 50 mM and 173 mM, preferably between 50 mM and 172 mM, preferably between 50 mM and 171 mM, preferably between 50 mM and 170 mM, preferably between 50 mM and 169 mM, preferably between 50 mM and 168 mM, preferably between 50 mM and 167 mM, preferably between 50 mM and 166 mM, preferably between 50 mM and 165 mM, preferably between 50 mM and 160 mM, preferably between 50 mM and 159 mM, preferably between 50 mM and 158 mM, preferably between 50 mM and 157 mM, preferably between 50 mM and 156 mM, preferably between 50 mM and 155 mM, preferably between 50 mM and 154 mM, preferably between 50 mM and 153 mM, preferably between 50 mM and 152 mM, 75 mM and 190 mM, 75 mM and 189 mM, 75 mM and 188 mM, 75 mM and 187 mM, 75 mM and 186 mM, 75 mM and 185 mM, preferably between 75 mM and 184 mM, preferably between 75 mM and 183 mM, preferably between 75 mM and 182 mM, preferably between 75 mM and 181 mM, preferably between 75 mM and 180 mM, preferably between 75 mM and 179 mM, preferably between 75 mM and 178 mM, preferably between 75 mM and 177 mM, preferably between 75 mM and 176 mM, preferably between 75 mM and 175 mM, preferably between 75 mM and 174 mM, preferably between 75 mM and 173 mM, preferably between 75 mM and 172 mM, preferably between 75 mM and 171 mM, preferably between 75 mM and 170 mM, preferably between 75 mM and 169 mM, preferably between 75 mM and 168 mM, preferably between 75 mM and 167 mM, preferably between 75 mM and 166 mM, preferably between 75 mM and 165 mM, preferably between 75 mM and 160 mM, preferably between 75 mM and 159 mM, preferably between 75 mM and 158 mM, preferably between 75 mM and 157 mM, preferably between 75 mM and 156 mM, preferably between 75 mM and 155 mM, preferably between 75 mM and 154 mM, preferably between 75 mM and 153 mM, preferably between 75 mM and 152 mM, 100 mM and 190 mM, 100 mM and 189 mM, 100 mM and 188 mM, 100 mM and 187 mM, 100 mM and 186 mM, 100 mM and 185 mM, preferably between 100 mM and 184 mM, preferably between 100 mM and 183 mM, preferably between 100 mM and 182 mM, preferably between 100 mM and 181 mM, preferably between 100 mM and 180 mM, preferably between 100 mM and 179 mM, preferably between 100 mM and 178 mM, preferably between 100 mM and 177 mM, preferably between 100 mM and 176 mM, preferably between 100 mM and 1100 mM, preferably between 100 mM and 174 mM, preferably between 100 mM and 173 mM, preferably between 100 mM and 172 mM, preferably between 100 mM and 171 mM, preferably between 100 mM and 170 mM, preferably between 100 mM and 169 mM, preferably between 100 mM and 168 mM, preferably between 100 mM and 167 mM, preferably between 100 mM and 166 mM, preferably between 100 mM and 165 mM, preferably between 100 mM and 160 mM, preferably between 100 mM and 159 mM, preferably between 100 mM and 158 mM, preferably between 100 mM and 157 mM, preferably between 100 mM and 156 mM, preferably between 100 mM and 155 mM, preferably between 100 mM and 154 mM, preferably between 100 mM and 153 mM, preferably between 100 mM and 152 mM, 115 mM and 190 mM, 115 mM and 189 mM, 115 mM and 188 mM, 115 mM and 187 mM, 115 mM and 186 mM, 115 mM and 185 mM, preferably between 115 mM and 184 mM, preferably between 115 mM and 183 mM, preferably between 115 mM and 182 mM, preferably between 115 mM and 181 mM, preferably between 115 mM and 180 mM, preferably between 115 mM and 179 mM, preferably between 115 mM and 178 mM, preferably between 115 mM and 177 mM, preferably between 115 mM and 176 mM, preferably between 115 mM and 175 mM, preferably between 115 mM and 174 mM, preferably between 115 mM and 173 mM, preferably between 115 mM and 172 mM, preferably between 115 mM and 171 mM, preferably between 115 mM and 170 mM, preferably between 115 mM and 169 mM, preferably between 115 mM and 168 mM, preferably between 115 mM and 167 mM, preferably between 115 mM and 166 mM, preferably between 115 mM and 165 mM, preferably between 115 mM and 160 mM, preferably between 115 mM and 159 mM, preferably between 115 mM and 158 mM, preferably between 115 mM and 157 mM, preferably between 115 mM and 156 mM, preferably between 115 mM and 155 mM, preferably between 115 mM and 154 mM, preferably between 115 mM and 153 mM, preferably between 115 mM and 152 mM, 130 mM and 185 mM, preferably between 130 mM and 184 mM, preferably between 130 mM and 183 mM, preferably between 130 mM and 182 mM, preferably between 130 mM and 181 mM, preferably between 130 mM and 180 mM, preferably between 130 mM and 179 mM, preferably between 130 mM and 178 mM, preferably between 130 mM and 177 mM, preferably between 130 mM and 176 mM, preferably between 130 mM and 175 mM, preferably between 130 mM and 174 mM, preferably between 130 mM and 173 mM, preferably between 130 mM and 172 mM, preferably between 130 mM and 171 mM, preferably between 130 mM and 170 mM, preferably between 130 mM and 169 mM, preferably between 130 mM and 168 mM, preferably between 130 mM and 167 mM, preferably between 130 mM and 166 mM, preferably between 130 mM and 165 mM, preferably between 130 mM and 160 mM, preferably between 130 mM and 159 mM, preferably between 130 mM and 158 mM, preferably between 130 mM and 157 mM, preferably between 130 mM and 156 mM, preferably between 130 mM and 155 mM, preferably between 130 mM and 154 mM, preferably between 130 mM and 153 mM, preferably between 130 mM and 152 mM, more preferably between 135 mM and 185 mM, more preferably between 135 mM and 184 mM, more preferably between 135 mM and 183 mM, more preferably between 135 mM and 182 mM, more preferably between 135 mM and 181 mM, more preferably between 135 mM and 180 mM, more preferably between 135 mM and 179 mM, more preferably between 135 mM and 178 mM, more preferably between 135 mM and 177 mM, more preferably between 135 mM and 176 mM, more preferably between 135 mM and 175 mM, more preferably between 135 mM and 174 mM, more preferably between 135 mM and 173 mM, more preferably between 135 mM and 172 mM, more preferably between 135 mM and 171 mM, more preferably between 135 mM and 170 mM, more preferably between 135 mM and 169 mM, more preferably between 135 mM and 168 mM, more preferably between 135 mM and 167 mM, more preferably between 135 mM and 166 mM, more preferably between 135 mM and 165 mM, more preferably between 135 mM and 160 mM, more preferably between 135 mM and 159 mM, more preferably between 135 mM and 158 mM, more preferably between 135 mM and 157 mM, more preferably between 135 mM and 156 mM, more preferably between 135 mM and 155 mM, more preferably between 135 mM and 154 mM, more preferably between 135 mM and 153 mM, more preferably between 135 mM and 152 mM, most preferably between 140 mM and 185 mM, most preferably between 140 mM and 184 mM, most preferably between 140 mM and 183 mM, most preferably between 140 mM and 182 mM, most preferably between 140 mM and 181 mM, most preferably between 140 mM and 180 mM, most preferably between 140 mM and 179 mM, most preferably between 140 mM and 178 mM, most preferably between 140 mM and 177 mM, most preferably between 140 mM and 176 mM, most preferably between 140 mM and 175 mM, most preferably between 140 mM and 174 mM, most preferably between 140 mM and 173 mM, most preferably between 140 mM and 172 mM, most preferably between 140 mM and 171 mM, most preferably between 140 mM and 170 mM, most preferably between 140 mM and 169 mM, most preferably between 140 mM and 168 mM, most preferably between 140 mM and 167 mM, most preferably between 140 mM and 166 mM, most preferably between 140 mM and 165 mM, most preferably between 140 mM and 160 mM, most preferably between 140 mM and 159 mM, most preferably between 140 mM and 158 mM, most preferably between 140 mM and 157 mM, most preferably between 140 mM and 156 mM, most preferably between 140 mM and 155 mM, most preferably between 140 mM and 154 mM, most preferably between 140 mM and 153 mM, and utmost preferably between 140 mM and 152 mM; and/or of less than 190 mM, 189 mM, 188 mM, 187 mM, 186 mM, 185 mM, 184 mM, 183 mM, 182 mM, 181 mM, 180 mM, 179 mM, 178 mM, 177 mM, 176 mM, 175 mM, 174 mM, 173 mM, 172 mM, 171 mM, 170 mM, 169 mM, 168 mM, 167 mM, 166 mM, 165 mM, 160 mM, 159 mM, 158 mM, 157 mM, 156 mM, 155 mM, 154 mM, 153 mM, 152 mM, preferably of less than 185 mM, more preferably less than 170 mM, even more preferably less than 160 mM, and most preferably less than 155 mM, and utmost preferably of 152 mM and less than 152 mM, and wherein the polypeptide, preferably the glucose isomerase, is any one of the eleventh, twelfth $13^{th}$, $14^{th}$, 15th16th$17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, 47th$48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, 66th$67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$ and $97^{th}$ embodiment or of any one of the other embodiments of the first aspect, preferably the polypeptide, preferably the glucose isomerase, is any one of the $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$ and $97^{th}$ embodiment of the first aspect, more preferably the polypeptide, preferably the glucose isomerase, is any one of $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, 54th$55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$ and $97^{th}$ embodiment of the first aspect, even more preferably the polypeptide, preferably the glucose isomerase, is any one of the $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, 65th$66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$ and $97^{th}$ embodiment of the first aspect, most preferably the polypeptide, preferably the glucose isomerase, is any one of the $63^{rd}$ and $97^{th}$ embodiment of the first aspect, any one of the polypeptide, preferably the glucose isomerase, of any one of the $104^{th}$, $105^{th}$, $106^{th}$, $107^{th}$, $109^{th}$, $110^{th}$, $111^{th}$, $112^{th}$, $113^{th}$, $114^{th}$, $116^{th}$, $117^{th}$, $118^{th}$, $119^{th}$, $121^{st}$, $122^{nd}$, $123^{rd}$, $124^{th}$, $126^{th}$, $127^{th}$, $128^{th}$, $129^{th}$, $130^{th}$, $132^{nd}$$133^{rd}$ $134^{th}$ and $135^{th}$ embodiment or of any one of the other embodiments of the first aspect.

In a twelfth embodiment of the fourth aspect, which is also an embodiment of any one of the first, second, third, fourth, fifth, sixth, seventh, eighth, ninth, tenth and eleventh embodiment of the fourth aspect, the polypeptide, preferably the glucose isomerase, has a Soluble Expression Level, defined as the ratio of the soluble expression level of said polypeptide and the soluble expression level of the polypeptide, preferably the glucose isomerase, of SEQ ID NO: 1 of at least 1.04 up to 1.80, preferably of at least 1.07 up to 1.80, preferably of at least 1.10 up to 1.80, preferably of at least 1.31 up to 1.80, preferably of at least 1.33 up to 1.80, preferably of at least 1.36 up to 1.80, preferably of at least 1.38 up to 1.80, preferably of at least 1.43 up to 1.80, more preferably of at least 1.04 up to 1.75, more preferably of at least 1.07 up to 1.75, more preferably of at least 1.10 up to 1.75, more preferably of at least 1.31 up to 1.75, more preferably of at least 1.33 up to 1.75, more preferably of at least 1.36 up to 1.75, more preferably of at least 1.38 up to 1.75, more preferably of at least 1.43 up to 1.75, more preferably of at least 1.47 up to 1.75, more preferably of at least 1.62 up to 1.75, even more preferably of at least 1.04 up to 1.70, even more preferably of at least 1.07 up to 1.70, even more preferably of at least 1.10 up to 1.70, even more preferably of at least 1.31 up to 1.70, even more preferably of at least 1.33 up to 1.70, even more preferably of at least 1.36 up to 1.70, even more preferably of at least 1.38 up to 1.70, even more preferably of at least 1.43 up to 1.70, even more preferably of at least 1.47 up to 1.70, even more preferably of at least 1.62 up to 1.70, even more preferably of at least 1.04 up to 1.65, even more preferably of at least 1.07 up to 1.65, even more preferably of at least 1.10 up to 1.65, even more preferably of at least 1.31 up to 1.65, even more preferably of at least 1.33 up to 1.65, even more preferably of at least 1.36 up to 1.65, even more preferably of at least 1.38 up to 1.65, even more preferably of at least 1.43 up to 1.65, even more preferably of at least 1.47 up to 1.65, even more preferably of at least 1.62 up to 1.65 and utmost preferably of at least 1.10 to 1.63, of at least 1.38 to 1.63, of at least 1.43 to 1.63, and/or of 1.63;

and wherein the polypeptide, preferably the glucose isomerase, is any one of the eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$$23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$ and $97^{th}$ embodiment or of any one of the other embodiments of the first aspect, preferably the polypeptide, preferably the glucose isomerase, is any one of the $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $84^{th}$, $85^{th}$, $86^{th}$, $87^{th}$, $88^{th}$, $89^{th}$, $90^{th}$, $91^{st}$, $92^{nd}$, $74^{th}$, $75^{th}$, $76^{th}$, $77^{th}$, $78^{th}$, $79^{th}$, $80^{th}$, $81^{st}$, $82^{nd}$, $83^{rd}$, $93^{rd}$, $94^{th}$, $95^{th}$, $96^{th}$ and $97^{th}$ embodiment of the first aspect, more preferably the polypeptide, preferably the glucose isomerase, is any one of $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$ and $97^{th}$ embodiment of the first aspect, even more preferably the polypeptide, preferably the glucose isomerase, is any one of the $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$, 94$^{th}$, 95$^{th}$, 96$^{th}$ and 97$^{th}$ embodiment of the first aspect, most preferably the polypeptide, preferably the glucose isomerase, is any one of the 63$^{rd}$ and 97$^{th}$ embodiment of the first aspect, any one of the polypeptide, preferably the glucose isomerase, of any one of the 104$^{th}$, 105$^{th}$, 106$^{th}$, 107$^{th}$, 109$^{th}$, 110$^{th}$, 111$^{th}$, 112$^{th}$, 113$^{th}$, 114$^{th}$, 116$^{th}$, 117$^{th}$, 118$^{th}$, 119$^{th}$, 121$^{st}$, 122$^{nd}$, 123$^{rd}$, 124$^{th}$, 126$^{th}$, 127$^{th}$, 128$^{th}$, 129$^{th}$, 130$^{th}$, 132$^{nd}$, 133$^{rd}$ 134$^{th}$ and 135$^{th}$ embodiment or of any one of the other embodiments of the first aspect.

In a preferred embodiment of the fourth aspect, which is also an embodiment of any one of the first, second, third, fourth, fifth, sixth, seventh, eighth, ninth, tenth, eleventh and twelfth embodiment of the fourth aspect, the polypeptide, preferably the glucose isomerase, has an increased catalytic activity of the polypeptide, preferably of the glucose isomerase, in comparison to SEQ ID NO:1 in converting fructose into glucose, expressed as Glucose Formation
of at least 1.2-fold up to 5-fold, of at least 1.2-fold up to 4.5-fold, of at least 1.2-fold up to 4-fold, of at least 1.2-fold up to 3.5-fold, of at least 1.2-fold up to 3.4-fold, of at least 1.2-fold up to 3.3-fold, of at least 1.2-fold up to 3.2-fold, of at least 1.2-fold up to 3.1-fold, of at least 1.2-fold up to 3-fold, of at least 1.2-fold up to 2.9-fold, of at least 1.2-fold up to 2.8-fold, of at least 1.2-fold up to 2.7-fold, of at least 1.2-fold up to 2.6-fold, of at least 1.2-fold up to 2.5-fold, of at least 1.2-fold up to 2.4-fold, of at least 1.2-fold up to 2.3-fold, of at least 1.2-fold up to 2.2-fold, preferably of at least 1.5-fold up to 5-fold, of at least 1.5-fold up to 4.5-fold, of at least 1.5-fold up to 4-fold, of at least 1.5-fold up to 3.5-fold, of at least 1.5-fold up to 3.4-fold, of at least 1.5-fold up to 3.3-fold, of at least 1.5-fold up to 3.2-fold, of at least 1.5-fold up to 3.1-fold, of at least 1.5-fold up to 3-fold, of at least 1.5-fold up to 2.9-fold, of at least 1.5-fold up to 2.8-fold, of at least 1.5-fold up to 2.7-fold, of at least 1.5-fold up to 2.6-fold, of at least 1.5-fold up to 2.5-fold, of at least 1.5-fold up to 2.4-fold, of at least 1.5-fold up to 2.3-fold, of at least 1.5-fold up to 2.2-fold, and more preferably of at least 1.9-fold up to 5-fold, of at least 1.9-fold up to 4.5-fold, of at least 1.9-fold up to 4-fold, of at least 1.9-fold up to 3.5-fold, of at least 1.9-fold up to 3.4-fold, of at least 1.9-fold up to 3.3-fold, of at least 1.9-fold up to 3.2-fold, of at least 1.9-fold up to 3.1-fold, of at least 1.9-fold up to 3-fold, of at least 1.9-fold up to 2.9-fold, of at least 1.9-fold up to 2.8-fold, of at least 1.9-fold up to 2.7-fold, of at least 1.9-fold up to 2.6-fold, of at least 1.9-fold up to 2.5-fold, of at least 1.9-fold up to 2.4-fold, of at least 1.9-fold up to 2.3-fold, of at least 1.9-fold up to 2.2-fold, and yet more preferably of at least 2.0-fold up to 5-fold, of at least 2.0-fold up to 4.5-fold, of at least 2.0-fold up to 4-fold, of at least 2.0-fold up to 3.5-fold, of at least 2.0-fold up to 3.4-fold, of at least 2.0-fold up to 3.3-fold, of at least 2.0-fold up to 3.2-fold, of at least 2.0-fold up to 3.1-fold, of at least 2.0-fold up to 3-fold, of at least 2.0-fold up to 2.9-fold, of at least 2.0-fold up to 2.8-fold, of at least 2.0-fold up to 2.7-fold, of at least 2.0-fold up to 2.6-fold, of at least 2.0-fold up to 2.5-fold, of at least 2.0-fold up to 2.4-fold, of at least 2.0-fold up to 2.3-fold of at least 2.0-fold up to 2.2-fold, and most preferably of at least 2.2-fold up to 3.3-fold, and wherein the polypeptide, preferably the glucose isomerase, is any one of the ninth, tenth, eleventh, twelfth 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64th65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$, 94$^{th}$, 95$^{th}$, 96$^{th}$ and 97$^{th}$ embodiment or of any of the other embodiments of the first aspect, preferably the polypeptide, preferably the glucose isomerase, is any one of the 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$, 94$^{th}$, 95$^{th}$, 96$^{th}$ and 97$^{th}$ embodiment of the first aspect, more preferably the polypeptide, preferably the glucose isomerase, is any one of 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54th55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$, 94$^{th}$, 95$^{th}$, 96$^{th}$ and 97$^{th}$ embodiment of the first aspect, even more preferably the polypeptide, preferably the glucose isomerase, is any one of the 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65th66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$, 94$^{th}$, 95$^{th}$, 96$^{th}$ and 97$^{th}$ embodiment of the first aspect, most preferably the polypeptide, preferably the glucose isomerase, is any one of the 63$^{rd}$ and 97$^{th}$ embodiment of the first aspect, any one of the polypeptide, preferably the glucose isomerase, of any one of the 104$^{th}$, 105$^{th}$, 106$^{th}$, 107$^{th}$, 109$^{th}$, 110$^{th}$, 111$^{th}$, 112$^{th}$, 113$^{th}$, 114$^{th}$, 116$^{th}$, 117$^{th}$, 118$^{th}$, 119$^{th}$, 121$^{st}$, 122$^{nd}$, 123$^{rd}$, 124$^{th}$, 126$^{th}$, 127$^{th}$, 128$^{th}$, 129$^{th}$, 130$^{th}$, 132$^{nd}$133$^{rd}$ 134$^{th}$ and 135$^{th}$ embodiment or of any one of the other embodiments of the first aspect.

In a 13$^{th}$ embodiment of the fourth aspect, which is also an embodiment of any one of the first, second, third, fourth, fifth, sixth, seventh, eighth, ninth, tenth, eleventh and 12$^{th}$ embodiment of the fourth aspect, the polypeptide, preferably the glucose isomerase, is a polypeptide, preferably a glucose isomerase, of any one of the eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$, 94$^{th}$, 95$^{th}$, 96$^{th}$, 97$^{th}$, 98$^{th}$, 99$^{th}$, 100$^{th}$, 101$^{st}$, 102$^{nd}$, 103$^{rd}$, 104$^{th}$, 105$^{th}$, 106$^{th}$, 107$^{th}$, 108$^{th}$, 109$^{th}$, 110$^{th}$, 111$^{th}$, 112$^{th}$, 113$^{th}$, 114$^{th}$, 115$^{th}$, 116$^{th}$, 117$^{th}$, 118$^{th}$, 119$^{th}$, 120$^{th}$, 121$^{st}$, 122$^{nd}$, 123$^{rd}$, 124$^{th}$, 125$^{th}$, 126$^{th}$, 127$^{th}$, 128$^{th}$, 129$^{th}$, 130$^{th}$, 131$^{st}$, 132$^{nd}$, 133$^{rd}$, 134$^{th}$, and 135$^{th}$ embodiment or of any of the other embodiments of the first aspect, preferably of any one of the eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56th, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87th88$^{th}$, 89$^{th}$, 90$^{th}$, 91$^{st}$, 92$^{nd}$, 93$^{rd}$, 94$^{th}$, 95$^{th}$, 96$^{th}$ and 97$^{th}$ embodiment of the first aspect, preferably of any of the 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$, 94$^{th}$, 95$^{th}$, 96$^{th}$ and 97$^{th}$ embodiment of the first aspect, more preferably of any one of the 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$, 94$^{th}$, 95$^{th}$, 96$^{th}$ and 97$^{th}$ embodiment of the first aspect, even more preferably of any one of the 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$, 94$^{th}$, 95$^{th}$, 96$^{th}$ and 97$^{th}$ embodiment of the first aspect, most preferably of any one of the 63$^{rd}$ and 97$^{th}$ embodiment of the first aspect, or wherein the polypeptide, preferably the glucose isomerase, is any one of the 104$^{th}$, 105$^{th}$, 106$^{th}$, 107$^{th}$, 109$^{th}$, 110$^{th}$, 111$^{th}$, 112$^{th}$, 113$^{th}$, 114$^{th}$, 116$^{th}$, 117$^{th}$, 118$^{th}$, 119$^{th}$, 121$^{st}$, 122$^{nd}$, 123$^{rd}$, 124$^{th}$, 126$^{th}$, 127$^{th}$, 128$^{th}$, 129$^{th}$, 130$^{th}$, 132$^{nd}$, 133$^{rd}$, 134$^{th}$ and 135$^{th}$ embodiment or of any of the other embodiments of the first aspect.

In a 14$^{th}$ embodiment of the fourth aspect, which is also an embodiment of any one of the first, second, third, fourth, fifth, sixth, seventh, eighth, ninth, tenth, eleventh, 12$^{th}$ and 13$^{th}$ embodiment of the fourth aspect, the polypeptide, preferably the glucose isomerase, is capable of catalyzing the conversion of
(i) of an aldose molecule to a ketose molecule, and/or
(ii) of a ketose molecule to an aldose molecule.

In a 15$^{th}$ embodiment of the fourth aspect, which is also an embodiment of any one of the first, second, third, fourth, fifth, sixth, seventh, eighth, ninth, tenth, eleventh, 12$^{th}$, 13$^{th}$ and 14$^{th}$ embodiment of the fourth aspect, the polypeptide, preferably the glucose isomerase, is capable of catalyzing the conversion of
(i) of an aldotetrose molecule to a ketotetrose molecule, and/or
(ii) of a ketotetrose molecule to an aldotetrose molecule, and/or
(ii) of an aldopentose molecule to a ketopentose molecule, and/or
(iv) of a ketopentose molecule to an aldopentose molecule, and/or
(v) of an aldohexose molecule to a ketohexose molecule, and/or
(vi) of a ketohexose molecule to an aldohexose molecule and/or
(vii) of an aldoheptose molecule to a ketoheptose molecule, and/or
(viii) of a ketoheptose molecule to an aldoheptose molecule.

In a 16$^{th}$ embodiment of the fourth aspect, which is also an embodiment of any one of the first, second, third, fourth, fifth, sixth, seventh, eighth, ninth, tenth, eleventh, 12$^{th}$, 13$^{th}$, 14$^{th}$ and 15$^{th}$ embodiment of the fourth aspect, the polypeptide, preferably the glucose isomerase, is capable of catalyzing the conversion of
(i) of an aldopentose molecule to a ketopentose molecule, and/or
(ii) of a ketopentose molecule to an aldopentose molecule, and/or
(iii of an aldohexose molecule to a ketohexose molecule, and/or
(iv) of a ketohexose molecule to an aldohexose molecule.

In a 17$^{th}$ embodiment of the fourth aspect, which is also an embodiment of any one of the first, second, third, fourth, fifth, sixth, seventh, eighth, ninth, tenth, eleventh, 12$^{th}$, 13$^{th}$, 14$^{th}$, 15$^{th}$ and 16$^{th}$ embodiment of the fourth aspect, the polypeptide, preferably the glucose isomerase, is capable of catalyzing the conversion
(i) of an aldose molecule, selected from the group consisting of D-glucose, D-xylose, D-arabinose, L-arabinose, L-ribose, D-ribose, D-lyxose, D-allose, L-rhamnose and D-mannose; and/or
(ii) of a ketose molecule, selected from the group consisting of fructose, D-xylulose, D-ribulose, L-ribulose, D-psicose and L-rhamnulose.

In an 18$^{th}$ embodiment of the fourth aspect, which is also an embodiment of any one of the first, second, third, fourth, fifth, sixth, seventh, eighth, ninth, tenth, eleventh, 12$^{th}$, 13$^{th}$, 14$^{th}$, 15$^{th}$, 16$^{th}$ and 17$^{th}$ embodiment of the fourth aspect,
(i) the aldose molecule is an aldose molecule derivative selected from the group consisting of deoxy-carbohydrates, thio-carbohydrates, azido-carbohydrates, methylated carbohydrates, halogenated carbohydrates, and benzylated carbohydrates; and
(ii) the ketose molecule is a ketose molecule derivative selected from the group consisting of deoxy-carbohydrates, thio-carbohydrates, azido-carbohydrates, methylated carbohydrates, halogenated carbohydrates, and benzylated carbohydrates.

In a 19$^{th}$ embodiment of the fourth aspect, which is also an embodiment of any one of the first, second, third, fourth, fifth, sixth, seventh, eighth, ninth, tenth, eleventh, 12$^{th}$, 13$^{th}$, 14$^{th}$, 15$^{th}$, 16$^{th}$, 17$^{th}$ and 18$^{th}$ embodiment of the fourth aspect, the polypeptide, preferably the glucose isomerase, is capable of catalyzing the conversion of
(i) fructose to glucose and/or
(ii) glucose to fructose.

In a 20$^{th}$ embodiment of the fourth aspect, which is also an embodiment of any one of the first, second, third, fourth, fifth, sixth, seventh, eighth, ninth, tenth, eleventh, 12$^{th}$, 13$^{th}$, 14$^{th}$, 15$^{th}$, 16$^{th}$, 17$^{th}$, 18$^{th}$ and 19$^{th}$ embodiment of the fourth aspect, the conversion is a reversible conversion.

In a 21$^{st}$ embodiment of the fourth aspect, which is also an embodiment of any one of the first, second, third, fourth, fifth, sixth, seventh, eighth, ninth, tenth, eleventh, 12$^{th}$, 13$^{th}$, 14$^{th}$, 15$^{th}$, 16$^{th}$, 17$^{th}$, 18$^{th}$, 19$^{th}$ and 20$^{th}$ embodiment of the fourth aspect, the polypeptide, preferably the glucose isomerase, is a polypeptide preferably a glucose isomerase according to EC number EC 5.3.1.5.

The problem underlying the present invention is solved in a fifth aspect, which is also a first embodiment of the fifth aspect, by a glucose isomerase variant with an increased activity, preferably increased Activity, in converting fructose into glucose, wherein the variant has a $K_M$ value of less than 190 mM, preferably less than 170 mM, more preferably less than 160 mM and utmost preferably of 152 mM and less.

In a second embodiment of the fifth aspect, which is also an embodiment of the first embodiment of the fifth aspect, the variant has an increased activity, preferably increased Activity, for the conversion of fructose to glucose at a concentration of 50 mM fructose in comparison to the polypeptide, preferably the glucose isomerase, of SEQ ID NO: 1 of at least 1.1-fold up to 3.0-fold, preferably of at least 1.4-fold up to 3.0-fold, more preferably of at least 1.6-fold up to 3.0-fold, even more preferably of at least 1.7-fold up to 3.0-fold and utmost preferably of at least 1.7-fold up to 2.4 fold.

In a third embodiment of the fifth aspect, which is also an embodiment of the first and second embodiment of the fifth aspect, the variant has an increased activity, preferably increased Activity, for the conversion of fructose to glucose at a concentration of 200 mM fructose in comparison to the polypeptide, preferably the glucose isomerase, of SEQ ID NO: 1 of at least 1.2-fold up to 3.0-fold, preferably of at least 1.3-fold up to 3.0-fold, preferably of at least 1.4-fold up to 3.0-fold, more preferably of at least 1.5-fold up to 3.0-fold, and utmost preferably of at least 1.5-fold up to 2.2-fold.

In a fourth embodiment of the fifth aspect, which is also an embodiment of the first, second and third embodiment of the fifth aspect, the variant has thermal stability expressed as Residual Activity after incubation of the variant at a temperature of 74° C. for 15 minutes, wherein the variant has a Residual Activity of at least 30%, preferably has a Residual Activity of at least 40%, and more preferably has a Residual Activity of at least 60% and utmost preferably has a Residual Activity of 62%.

In a fifth embodiment of the fifth aspect, which is also an embodiment of the first, second, third and fourth embodiment of the fifth aspect, the variant has an increased Soluble Expression Level defined as the ratio of the soluble expression level of said polypeptide and the soluble expression level of the polypeptide, preferably the glucose isomerase, of SEQ ID NO: 1, wherein the Soluble Expression Level is at least 1.1, preferably the Soluble Expression Level is at least 1.3, and more preferably the Soluble Expression Level is at least 1.4, and most preferably the Soluble Expression Level is at least 1.6.

In a preferred embodiment of the fifth aspect, which is also an embodiment of the first, second, third, fourth and fifth or any other embodiment of the fifth aspect, the variant has increased catalytic activity of the polypeptide, preferably of the glucose isomerase, in comparison to SEQ ID NO:1 in converting fructose into glucose, expressed as Glucose Formation of at least 1.2-fold up to 5-fold, preferably of at least 1.5-fold up to 5-fold, more preferably of at least 1.9-fold up to 5-fold, yet more preferably of at least 1.9-fold up to 3.5-fold and utmost preferred of at least 2.2-fold up to 3.3-fold.

The problem underlying the present invention is solved in a sixth aspect, which is also a first embodiment of the sixth aspect, by a glucose isomerase variant of *Streptomyces* sp. SK with an increased activity, preferably increased Activity, in converting fructose into glucose, wherein the variant has a Km value of less than 190 mM, preferably less than 170 mM, more preferably less than 160 mM and utmost preferably of 152 mM and less.

The problem underlying the present invention is solved in a seventh aspect, which is also a first embodiment of the seventh aspect, by a glucose isomerase variant of the glucose isomerase comprising the amino acid sequence of SEQ ID NO: 1, wherein the variant has an increased activity, preferably increased Activity, in converting fructose into glucose, wherein the variant has a $K_M$ value of less than 190 mM, preferably less than 170 mM, more preferably less than 160 mM and utmost preferably of 152 mM and less.

In a second embodiment of the sixth aspect, which is also an embodiment of the first embodiment of the sixth aspect, and in a second aspect of the seventh aspect, which is also an embodiment of the first embodiment of the seventh aspect, (i) the variant in comparison to the polypeptide of SEQ ID NO: 1 has an increased activity, preferably increased Activity, for the conversion of fructose to glucose at a concentration of 50 mM fructose compared to the activity of a polypeptide, preferably a glucose isomerase, of SEQ ID NO: 1 for the conversion of fructose to glucose at a concentration of 50 mM fructose of at least 1.1-fold up to 3.0-fold, preferably of at least 1.4-fold up to 3.0-fold, more preferably of at least 1.6-fold up to 3.0-fold, even more preferably of at least 1.7-fold up to 3.0-fold and utmost preferably of at least 1.7-fold up to 2.4 fold; and/or (ii) the variant in comparison to the polypeptide of SEQ ID NO: 1 has an increased activity, preferably increased Activity, for the conversion of fructose to glucose at a concentration of 200 mM fructose in comparison to the polypeptide of SEQ ID NO: 1 of at least 1.2-fold up to 3.0-fold, preferably of at least 1.3-fold up to 3.0-fold, preferably of at least 1.4-fold up to 3.0-fold, more preferably of at least 1.5-fold up to 3.0-fold, and utmost preferably of at least 1.5-fold up to 2.2-fold; and/or (iii) wherein the variant has thermal stability expressed as Residual Activity after incubation of the variant at a temperature of 74° C. for 15 minutes of at least 30%, preferably has a Residual Activity of at least 40%, and more preferably has a Residual Activity of at least 60% and utmost preferably has a Residual Activity of 62%; and/or (iv) the variant in comparison to the polypeptide of SEQ ID NO: 1 has an increased Soluble Expression Level, defined as the ratio of the soluble expression level of said variant and the soluble expression level of the polypeptide, preferably the glucose isomerase, of SEQ ID NO: 1, wherein the Soluble Expression Level is at least 1.1, preferably the Soluble Expression Level is at least 1.3, and more preferably the Soluble Expression Level is at least 1.4, and most preferably the Soluble Expression Level is at least 1.6; and/or (v) the variant in comparison to the polypeptide of SEQ ID NO: 1 has an increased catalytic activity in converting fructose into glucose, expressed as Glucose Formation of at least 1.2-fold up to 5-fold, preferably of at least 1.5-fold up to 5-fold, more preferably of at least 1.9-fold up to 5-fold, yet more preferably of at least 1.9-fold up to 3.5-fold and utmost preferred of at least 2.2-fold up to 3.3-fold.

The problem underlying the present invention is solved in an eighth aspect, which is also a first embodiment of the eight aspect, by a glucose isomerase variant with an increased activity, preferably increased Activity, in converting fructose into glucose, wherein the variant has an increased activity, preferably increased Activity, in converting fructose into glucose at a concentration of 50 mM fructose in comparison to the polypeptide, preferably the glucose isomerase, of SEQ ID NO: 1, of at least 1.1-fold up to 3.0-fold, preferably of at least 1.4-fold up to 3.0-fold, more preferably of at least 1.6-fold up to 3.0-fold, even more preferably of at least 1.7-fold up to 3.0-fold and utmost preferably of at least 1.7-fold up to 2.4 fold.

In a second embodiment of the eighth aspect, which is also an embodiment of the first embodiment of the eighth aspect, the variant has thermal stability expressed as Residual Activity after incubation of the variant at a temperature of 74° C. for 15 minutes, wherein the variant has a Residual Activity of at least 30%, preferably has a Residual Activity of at least 40%, and more preferably has a Residual Activity of at least 60% and utmost preferably has a Residual Activity of 62%.

In a third embodiment of the eighth aspect, which is also an embodiment of the first and second embodiment of the eighth aspect, the variant has an increased Soluble Expression Level defined as the ratio of the soluble expression level of said variant and the soluble expression level of the polypeptide, preferably the glucose isomerase, of SEQ ID NO: 1, wherein the Soluble Expression Level is at least 1.1, preferably the Soluble Expression Level is at least 1.3, and more preferably the Soluble Expression Level is at least 1.4, and most preferably the Soluble Expression Level is at least 1.6.

In a fourth embodiment of the eighth aspect, which is also an embodiment of the first, second and third embodiment of the eighth aspect, the variant has a $K_M$ value of less than 190 mM, preferably less than 170 mM, more preferably less than 160 mM and utmost preferably of 152 mM and less.

In a fifth embodiment of the eighth aspect, which is also an embodiment of the first, second, third and fourth embodiment of the eighth aspect, the variant has an increased activity, preferably increased Activity, for the conversion of fructose to glucose at a concentration of 200 mM fructose in comparison to the polypeptide, preferably the glucose isomerase, of SEQ ID NO: 1, of at least 1.2-fold up to 3.0-fold, preferably of at least 1.3-fold up to 3.0-fold, preferably of at least 1.4-fold up to 3.0-fold, more preferably of at least 1.5-fold up to 3.0-fold, and utmost preferably of at least 1.5-fold up to 2.2-fold.

In a preferred embodiment of the eighth aspect, which is also an embodiment of the first, second, third, fourth and fifth embodiment of the eighth aspect, the variant has increased catalytic activity of the polypeptide, preferably of the glucose isomerase, in comparison to SEQ ID NO:1 in converting fructose into glucose, expressed as Glucose Formation of at least 1.2-fold up to 5-fold, preferably of at least 1.5-fold up to 5-fold, more preferably of at least 1.9-fold up to 5-fold, yet more preferably of at least 1.9-fold up to 3.5-fold and utmost preferred of at least 2.2-fold up to 3.3-fold.

The problem underlying the present invention is solved in a ninth aspect, which is also a first embodiment of the ninth aspect, by a glucose isomerase variant of *Streptomyces* sp. SK with an increased activity, preferably increased Activity, in converting fructose into glucose, wherein the variant has an increased activity, preferably increased Activity, in converting fructose into glucose at a concentration of 50 mM fructose in comparison to the polypeptide, preferably the glucose isomerase, of SEQ ID NO: 1, of at least 1.1-fold up to 3.0-fold, preferably of at least 1.4-fold up to 3.0-fold, more preferably of at least 1.6-fold up to 3.0-fold, even more preferably of at least 1.7-fold up to 3.0-fold and utmost preferably of at least 1.7-fold up to 2.4 fold.

The problem underlying the present invention is solved in a tenth aspect, which is also a first embodiment of the tenth aspect, by a glucose isomerase variant of the glucose isomerase comprising the amino acid sequence of SEQ ID NO: 1, wherein the variant has an increased activity, preferably increased Activity, in converting fructose into glucose at a concentration of 50 mM fructose in comparison to the polypeptide, preferably the glucose isomerase, of SEQ ID NO: 1, of at least 1.1-fold up to 3.0-fold, preferably of at least 1.4-fold up to 3.0-fold, more preferably of at least 1.6-fold up to 3.0-fold, even more preferably of at least 1.7-fold up to 3.0-fold and utmost preferably of at least 1.7-fold up to 2.4 fold.

In a second embodiment of the ninth aspect, which is also an embodiment of the first embodiment of the ninth aspect, and in a second embodiment of the tenth aspect, which is also an embodiment of the first embodiment of the tenth aspect, variant
  (i) has thermal stability expressed as Residual Activity after incubation of the variant at a temperature of 74° C. for 15 minutes, wherein the variant has a Residual Activity of at least 30%, preferably has a Residual Activity of at least 40%, and more preferably has a Residual Activity of at least 60% and utmost preferably has a Residual Activity of 62%; and/or
  (ii) has an increased Soluble Expression Level defined as the ratio of the soluble expression level of said variant and the soluble expression level of the polypeptide, preferably the glucose isomerase, of SEQ ID NO: 1, wherein the Soluble Expression Level is at least 1.1, preferably the Soluble Expression Level is at least 1.3, and more preferably the Soluble Expression Level is at least 1.4, and most preferably the Soluble Expression Level is at least 1.6; and/or
  (iii) has a $K_M$ value of less than 190 mM, preferably less than 170 mM, more preferably less than 160 mM and utmost preferably of 152 mM and less; and/or
  (iv) has an increased activity, preferably increased Activity, for the conversion of fructose to glucose at a concentration of 200 mM fructose in comparison to the polypeptide, preferably the glucose isomerase, of SEQ ID NO: 1, of at least 1.2-fold up to 3.0-fold, preferably of at least 1.3-fold up to 3.0-fold, preferably of at least 1.4-fold up to 3.0-fold, more preferably of at least 1.5-fold up to 3.0-fold, and utmost preferably of at least 1.5-fold up to 2.2-fold
  (v) the variant in comparison to the polypeptide of SEQ ID NO: 1 has an increased catalytic activity in converting fructose into glucose, expressed as Glucose Formation of at least 1.2-fold up to 5-fold, preferably of at least 1.5-fold up to 5-fold, more preferably of at least 1.9-fold up to 5-fold, yet more preferably of at least 1.9-fold up to 3.5-fold and utmost preferred of at least 2.2-fold up to 3.3-fold.

The problem underlying the present invention is solved in an eleventh aspect, which is also a first embodiment of the eleventh aspect, by a glucose isomerase variant with an increased Soluble Expression Level defined as the ratio of the soluble expression level of said variant and the soluble expression level of the polypeptide, preferably the glucose isomerase, of SEQ ID NO: 1, wherein the Soluble Expression Level is at least 1.1, preferably the Soluble Expression Level is at least 1.3, and more preferably the Soluble Expression Level is at least 1.4, and most preferably the Soluble Expression Level is at least 1.6.

In a second embodiment of the eleventh aspect, which is also an embodiment of the first embodiment of the eleventh aspect, the variant has an increased activity, preferably increased Activity, in converting fructose into glucose, wherein the variant has an increased activity, preferably increased Activity, in converting fructose into glucose at a concentration of 50 mM fructose in comparison to the polypeptide, preferably the glucose isomerase, of SEQ ID NO: 1, of at least 1.1-fold up to 3.0-fold, preferably of at least 1.4-fold up to 3.0-fold, more preferably of at least 1.6-fold up to 3.0-fold, even more preferably of at least 1.7-fold up to 3.0-fold and utmost preferably of at least 1.7-fold up to 2.4 fold.

In a third embodiment of the eleventh aspect, which is also an embodiment of the first and second embodiment of the eleventh aspect, the variant has a $K_M$ value of less than 190 mM, preferably less than 170 mM, more preferably less than 160 mM and utmost preferably of 152 mM and less.

In a fourth embodiment of the eleventh aspect, which is also an embodiment of the first, second and third embodiment of the eleventh aspect, the variant has thermal stability expressed as Residual Activity after incubation of the variant at a temperature of 74° C. for 15 minutes, wherein the variant has a Residual Activity of at least 30%, preferably has a Residual Activity of at least 40%, and more preferably has a Residual Activity of at least 60% and utmost preferably has a Residual Activity of 62%.

In a fifth embodiment of the eleventh aspect, which is also an embodiment of the first, second, third and fourth embodiment of the eleventh aspect, the variant has an increased activity, preferably increased Activity, for the conversion of fructose to glucose at a concentration of 200 mM fructose in comparison to the polypeptide, preferably the glucose isomerase, of SEQ ID NO: 1, of at least 1.2-fold up to 3.0-fold, preferably of at least 1.3-fold up to 3.0-fold, preferably of at least 1.4-fold up to 3.0-fold, more preferably of at least 1.5-fold up to 3.0-fold, and utmost preferably of at least 1.5-fold up to 2.2-fold.

In a preferred embodiment of the eleventh aspect, which is also an embodiment of the first, second, third, fourth and fifth embodiment of the eleventh aspect, the variant has increased catalytic activity of the polypeptide, preferably of the glucose isomerase, in comparison to SEQ ID NO:1 in converting fructose into glucose, expressed as Glucose Formation, of at least 1.2-fold up to 5-fold, preferably of at least 1.5-fold up to 5-fold, more preferably of at least 1.9-fold up to 5-fold, yet more preferably of at least 1.9-fold up to 3.5-fold and utmost preferred of at least 2.2-fold up to 3.3-fold.

The problem underlying the present invention is solved in a twelfth aspect, which is also a first embodiment of the twelfth aspect, by a glucose isomerase variant of *Streptomyces* sp. SK with an increased Soluble Expression Level defined as the ratio of the soluble expression level of said variant and the soluble expression level of the polypeptide, preferably the glucose isomerase, of SEQ ID NO: 1, wherein the Soluble Expression Level is at least 1.1, preferably the Soluble Expression Level is at least 1.3, and more preferably the Soluble Expression Level is at least 1.4, and most preferably the Soluble Expression Level is at least 1.6.

The problem underlying the present invention is solved in a $13^{th}$ aspect, which is also a first embodiment of the $13^{th}$ aspect, by a glucose isomerase variant of the glucose isomerase comprising the amino acid sequence of SEQ ID NO: 1, wherein the variant has increased Soluble Expression Level defined as the ratio of the soluble expression level of said variant and the soluble expression level of the polypeptide, preferably the glucose isomerase, of SEQ ID NO: 1, wherein the Soluble Expression Level is at least 1.1, preferably the Soluble Expression Level is at least 1.3, and more preferably the Soluble Expression Level is at least 1.4, and most preferably the Soluble Expression Level is at least 1.6.

In a second embodiment of the twelfth aspect, which is also an embodiment of the first embodiment of the twelfth aspect, and a second embodiment of the $13^{th}$ aspect, which is also an embodiment of the first embodiment of the $13^{th}$ aspect, the variant
  (i) has an increased activity, preferably increased Activity, in converting fructose into glucose at a concentration of 50 mM fructose in comparison to the polypeptide, preferably the glucose isomerase, of SEQ ID NO: 1, of at least 1.1-fold up to 3.0-fold, preferably of at least 1.4-fold up to 3.0-fold, more preferably of at least 1.6-fold up to 3.0-fold, even more preferably of at least 1.7-fold up to 3.0-fold and utmost preferably of at least 1.7-fold up to 2.4 fold;
  (ii) has a $K_M$ value of less than 190 mM, preferably less than 170 mM, more preferably less than 160 mM and utmost preferably of 152 mM and less; and/or
  (iii) has thermal stability expressed as Residual Activity after incubation of the variant at a temperature of 74° C. for 15 minutes, wherein the variant has a Residual Activity of at least 30%, preferably has a Residual Activity of at least 40%, and more preferably has a Residual Activity of at least 60% and utmost preferably has a Residual Activity of 62%; and/or
  (iv) has an increased activity, preferably increased Activity, for the conversion of fructose to glucose at a concentration of 200 mM fructose in comparison to the polypeptide, preferably the glucose isomerase, of SEQ ID NO: 1, of at least 1.2-fold up to 3.0-fold, preferably of at least 1.3-fold up to 3.0-fold, more preferably of at least 1.4-fold up to 3.0-fold, more preferably of at least 1.5-fold up to 3.0-fold, and utmost preferably of at least 1.5-fold up to 2.2-fold; and/or
  (v) in comparison to the polypeptide of SEQ ID NO: 1 has an increased catalytic activity in converting fructose into glucose, expressed as Glucose Formation of at least 1.2-fold up to 5-fold, preferably of at least 1.5-fold up to 5-fold, more preferably of at least 1.9-fold up to 5-fold, yet more preferably of at least 1.9-fold up to 3.5-fold and utmost preferred of at least 2.2-fold up to 3.3-fold.

In a $22^{nd}$ embodiment of the fourth aspect which is also an embodiment of any one of the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$ and $21^{st}$ embodiment of the fourth aspect, the polypeptide, preferably the glucose isomerase comprises an amino acid sequence as defined in any embodiment of the first aspect, including any one of the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}94^{th}$, $95^{th}$, $96^{th}$, $97^{th}$, $98^{th}$, $99^{th}$, $100^{th}$, $101^{st}$, $102^{nd}$, $103^{rd}$, $104^{th}$, $105^{th}$, $106^{th}$, $107^{th}$, $108^{th}$, $109^{th}$, $110^{th}$, $111^{th}$, $112^{th}$, $113^{th}$, $114^{th}$, $115^{th}$, $116^{th}$, $117^{th}$, $118^{th}$, $119^{th}$, $120^{th}$, $121^{st}$, $122^{nd}$, $123^{rd}$, $124^{th}$, $125^{th}$, $126^{th}$, $127^{th}$, $128^{th}$, $129^{th}$, $130^{th}$, $131^{st}$, $132^{nd}$, $133^{rd}$, $134^{th}$, $135^{th}$, $136^{th}$, $137^{th}$, $138^{th}$, $139^{th}$, $140^{th}$, $141^{st}$, $142^{nd}$, $143^{rd}$ and $144^{th}$ embodiment or of any one of the other embodiments of the first aspect, as defined in any embodiment of the second aspect, including any one of the first, second, third, fourth, fifth, sixth, seventh, eighth, ninth, tenth, eleventh, twelfth and $13^{th}$ embodiment of the second aspect, preferably as defined in any embodiment of the third aspect, preferably as defined in any one of the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $78^{th}$, $77^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$, $97^{th}$, $98^{th}$, $99^{th}$, $100^{th}$, $101^{st}$, $102^{nd}$, $103^{rd}$, $104^{th}$, $105^{th}$, $106^{th}$, $107^{th}$, $108^{th}$, $109^{th}$, $110^{th}$, $111^{th}$, $112^{th}$, $113^{th}$, $114^{th}$, $115^{th}$, $116^{th}$, $117^{th}$, $118^{th}$, $119^{th}$, $120^{th}$, $121^{st}$, $122^{nd}$, $123^{rd}$, $124^{th}$, $125^{th}$, $126^{th}$, $127^{th}$, $128^{th}$, $129^{th}$, $130^{th}$, $131^{st}$, $132^{nd}$, $133^{rd}$, $134^{th}$ and $135^{th}$ embodiment of the third aspect.

In a sixth embodiment of the fifth aspect which is also an embodiment of any one of the first, second, third, fourth and fifth embodiment of the fifth aspect, in a third embodiment of the sixth aspect which is also an embodiment of any one of the first and the second embodiment of the sixth aspect, in a third embodiment of the seventh aspect which is also an embodiment of any one of the first and second embodiment of the seventh aspect, in a sixth embodiment of the eighth aspect which is also an embodiment of any one of the first, second, third, fourth and fifth embodiment of the eighth aspect, in a third embodiment of the ninth aspect which is also an embodiment of any one of the first and second embodiment of the ninth aspect, in a third aspect of the tenth aspect which is also an embodiment of the first and second embodiment of the tenth aspect, in a sixth embodiment of the eleventh aspect which is also an embodiment of any one of the first, second, third, fourth and fifth embodiment of the eleventh aspect, in a third embodiment of the twelfth aspect which is also an embodiment of any one of the first and second embodiment of the twelfth aspect, in a third embodiment of the $13^{th}$ aspect which is also an embodiment of any one of the first and second embodiment of the $13^{th}$ aspect, the variant comprises an amino acid sequence as defined in any embodiment of the first aspect, including any one of the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$ $24^{th}$, $25^{th}$, $26^{th}$, $27^{th}$, $28^{th}$, $29^{th}$, $30^{th}$, $31^{st}$ $32^{nd}$, $33^{rd}$, $34^{th}$, $35^{th}$, $36^{th}$, $37^{th}$, $38^{th}$, $39^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $58^{th}$, $59^{th}$, $60^{th}$, $61^{st}$, $62^{nd}$, $63^{rd}$ $64^{th}$, $65^{th}$, $66^{th}$, $67^{th}$, $68^{th}$, $69^{th}$, $70^{th}$, $71^{st}$, $72^{nd}$, $84^{th}$, $85^{th}$, $86^{th}$, $87^{th}$, $88^{th}$, $89^{th}$, $90^{th}$, $91^{st}$, $92^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $93^{rd}$, $94^{th}$, $95^{th}$, $96^{th}$, $97^{th}$, $98^{th}$, $99^{th}$, $100^{th}$, $101^{st}$, $102^{nd}$, $103^{rd}$, $104^{th}$, $105^{th}$, $106^{th}$, $107^{th}$, $108^{th}$, $109^{th}$, $110^{th}$, $111^{th}$, $112^{th}$, $113^{th}$, $114^{th}$, $115^{th}$, $116^{th}$, $117^{th}$, $118^{th}$, $119^{th}$, $120^{th}$, $121^{st}$, $122^{nd}$, $123^{rd}$, $124^{th}$, $125^{th}$, $126^{th}$, $127^{th}$, $128^{th}$, $129^{th}$, $130^{th}$, $131^{st}$, $132^{nd}$, $133^{rd}$, $134^{th}$, $135^{th}$, $136^{th}$, $137^{th}$, $138^{th}$, $139^{th}$, $140^{th}$, $141^{st}$, $142^{nd}$, $143^{rd}$ and $144^{th}$ embodiment or any one of the other embodiments of the first aspect, as defined in any embodiment of the second aspect, including any one of the first, second, third, fourth, fifth, sixth, seventh, eighth, ninth, tenth, eleventh, twelfth, $13^{th}$ embodiment of the second aspect, as defined in any embodiment of the third aspect, preferably as defined in any one of the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$ $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $39^{th}$, $38^{th}$, $40^{th}$, $41^{st}$, $42^{nd}$, $43^{rd}$, $44^{th}$, $45^{th}$, $46^{th}$, $47^{th}$, $48^{th}$, $49^{th}$, $50^{th}$, $51^{st}$, $52^{nd}$, $53^{rd}$, $54^{th}$, $55^{th}$, $56^{th}$, $57^{th}$, $59^{th}$, $58^{th}$, $59^{th}$, $60^{th}$, $61^{st}$, $62^{nd}$, $63^{rd}$, $64^{th}$, $65^{th}$, $66^{th}$, $67^{th}$, $68^{th}$, $69^{th}$, $70^{th}$, $71^{st}$, $72^{nd}$, $73^{rd}$, $74^{th}$, $75^{th}$, $76^{th}$, $77^{th}$, $78^{th}$, $79^{th}$, $80^{th}$, $81^{st}$, $82^{nd}$, $83^{rd}$, $84^{th}$, $85^{th}$, $86^{th}$, $87^{th}$, $88^{th}$, $89^{th}$, $90^{th}$, $91^{st}$, $92^{nd}$, $93^{rd}$, $94^{th}$, $95^{th}$, $96^{th}$, $97^{th}$, $98^{th}$, $99^{th}$, $100^{th}$, $101^{st}$, $102^{nd}$, $103^{rd}$, $104^{th}$, $105^{th}$, $106^{th}$, $107^{th}$, $108^{th}$, $109^{th}$, $110^{th}$, $111^{th}$, $112^{th}$, $113^{th}$, $114^{th}$, $115^{th}$, $116^{th}$, $117^{th}$, $118^{th}$, $119^{th}$, $120^{th}$, $121^{st}$, $122^{nd}$, $123^{rd}$, $124^{th}$, $125^{th}$, $126^{th}$, $127^{th}$, $128^{th}$, $129^{th}$, $130^{th}$, $131^{st}$, $132^{nd}$, $133^{rd}$, $134^{th}$ and $135^{th}$ embodiment or in any one of other embodiments of the first aspect.

The problem underlying the present invention is solved in a $14^{th}$ aspect, which is also a first embodiment of the $14^{th}$ aspect, by a method for converting of a ketose molecule to an aldose molecule, wherein the method comprises reacting the ketose molecule with a glucose isomerase as defined in any embodiment of the first aspect, including any one of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th, 29th, 30th, 31st, 32nd, 33rd, 34th, 35th, 36th, 37th, 38th, 39th, 40th, 41st, 42nd, 43rd, 44th, 45th, 46th, 47th, 48th, 49th, 50th, 51st, 52nd, 53rd, 54th, 55th, 56th, 57th, 58th, 59th, 60th, 61st, 62nd, 63rd, 64th, 65th, 66th, 67th, 68th, 69th, 70th, 71st, 72nd, 73rd, 74th, 75th, 76th, 77th, 78th, 79th, 80th, 81st, 82nd, 83rd, 84th, 85th, 86th, 87th, 88th, 89th, 90th, 91st, 92nd, 93rd, 94th, 95th, 96th, 97th, 98th, 99th, 100th, 101st, 102nd, 103rd, 104th, 105th, 106th, 107th, 108th, 109th, 110th, 111th, 112th, 113th, 114th, 115th, 116th, 117th, 118th, 119th, 120th, 121st, 122nd, 123rd, 124th, 125th, 126th, 127th, 128th, 129th, 130th, 131st, 132nd, 133rd, 134th, 135th, 136th, 137th, 138th, 139th, 140th, 141st, 142nd, 143rd, 144th embodiment or in any one of the other embodiments of the first aspect, as defined in any embodiment of the second aspect, including any one of the first, second, third, fourth, fifth, sixth, seventh, eighth, ninth, tenth, eleventh, twelfth and 13th, embodiment of the second aspect, and as defined in any embodiment of the third aspect, or as defined in any embodiment of the fourth aspect, including any one of the first, second, third, fourth, fifth, sixth, seventh, eighth, ninth, tenth, eleventh, twelfth, 13th, 14th, 15th, 16th, 17th, 18th, 19th, 20th, $21^{st}$ and 22nd embodiment of the fourth aspect, as defined in any embodiment of the fifth aspect, including any one of the first, second, third, fourth, fifth and sixth embodiment of the fifth aspect, as defined in any embodiment of the sixth aspect, including any one of the first, second and third embodiment of the sixth aspect, as defined in any embodiment of the seventh aspect, including any one of the first, second and third embodiment of the seventh aspect, as defined in any embodiment of the eighth aspect, including any one of the first, second, third, fourth, fifth and sixth embodiment of the eighth aspect, as defined in any embodiment of the ninth aspect, including any one of the first, second and third embodiment of the ninth aspect, as defined in any embodiment of the tenth aspect, including any one of the first, second and third embodiment of the tenth aspect, as defined in any embodiment of the eleventh aspect, including any one of the first, second, third, fourth, fifth and sixth embodiment of the eleventh aspect, as defined in any one of the twelfth aspect, including any one of the first, second and third embodiment of the twelfth aspect, as defined in any one of the 13th, aspect, including any one of the first, second and third embodiment of the 13th, aspect.

The problem underlying the present invention is solved in a $15^{th}$ aspect, which is also a first embodiment of the $15^{th}$ aspect, by a method for converting fructose to glucose, wherein the method comprises reacting fructose with a glucose isomerase as defined in any embodiment of the first aspect, including any one of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70$^{th}$, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 84$^{th}$, 85$^{th}$, 86$^{th}$, 87$^{th}$, 88$^{th}$, 89$^{th}$, 90$^{th}$, 91$^{st}$, 92$^{nd}$, 93$^{rd}$, 94$^{th}$, 95$^{th}$, 96$^{th}$, 97$^{th}$, 98$^{th}$, 99$^{th}$, 100$^{th}$, 101$^{st}$, 102$^{nd}$, 103$^{rd}$, 104$^{th}$, 105$^{th}$, 106$^{th}$, 107$^{th}$, 108$^{th}$, 109$^{th}$, 110$^{th}$, 111$^{th}$, 112$^{th}$, 113$^{th}$, 114$^{th}$, 115$^{th}$, 116$^{th}$, 117$^{th}$, 118$^{th}$, 119$^{th}$, 120$^{th}$, 121$^{st}$, 122$^{nd}$, 123$^{rd}$, 124$^{th}$, 125$^{th}$ 126$^{th}$, 127$^{th}$, 128$^{th}$, 129$^{th}$, 130$^{th}$, 131$^{st}$, 132$^{nd}$, 133$^{rd}$, 134$^{th}$, 135$^{th}$, 136$^{th}$, 137$^{th}$, 138$^{th}$, 139$^{th}$, 140$^{th}$, 141$^{st}$, 142$^{nd}$, 143$^{rd}$ and 144$^{th}$ embodiment or any of the other embodiments of the first aspect, as defined in any embodiment of the second aspect, including any one of the first, second, third, fourth, fifth, sixth, seventh, eighth, ninth, tenth, eleventh, twelfth and 13$^{th}$ embodiment of the second aspect, and as defined in any embodiment of the third aspect, or as defined in any embodiment of the fourth aspect, including any one of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$ and 22$^{nd}$ embodiment of the fourth aspect, as defined in any embodiment of the fifth aspect, including any one of the first, second, third, fourth, fifth and sixth embodiment of the fifth aspect, as defined in any embodiment of the sixth aspect, including any one of the first, second and third embodiment of the sixth aspect, as defined in any embodiment of the seventh aspect, including any one of the first, second and third embodiment of the seventh aspect, as defined in any embodiment of the eighth aspect, including any one of the first, second, third, fourth, fifth and sixth embodiment of the eighth aspect, as defined in any embodiment of the ninth aspect, including any one of the first, second and third embodiment of the ninth aspect, as defined in any embodiment of the tenth aspect, including any one of the first, second and third embodiment of the tenth aspect, as defined in any embodiment of the eleventh aspect, including any one of the first, second, third, fourth, fifth and sixth embodiment of the eleventh aspect, as defined in any one of the twelfth aspect, including any one of the first, second and third embodiment of the twelfth aspect, as defined in any one of the 13$^{th}$ aspect, including any one of the first, second and third embodiment of the 13$^{th}$ aspect.

In a second embodiment of the 14$^{th}$ aspect, which is also an embodiment of the first embodiment of the 14$^{th}$ aspect, and in a second embodiment of the 15$^{th}$ aspect, which is also an embodiment of the first embodiment of the 15$^{th}$ aspect, the reaction is reversible.

The problem underlying the present invention is solved in a 16$^{th}$ aspect, which is also a first embodiment of the 16$^{th}$ aspect, by a method for preparing glucose comprising reacting fructose in the presence of a glucose isomerase, wherein the glucose isomerase (i) has a K$_M$ value of less than 190 mM, preferably less than 170 mM, more preferably less than 160 mM and utmost preferably of 152 mM and less, and/or (ii) an increased activity, preferably increased Activity, for the conversion of fructose to glucose at a concentration of 50 mM fructose in comparison to the polypeptide, preferably the glucose isomerase, of SEQ ID NO: 1, of at least 1.1-fold up to 3.0-fold, preferably of at least 1.4-fold up to 3.0-fold, more preferably of at least 1.6-fold up to 3.0-fold, even more preferably of at least 1.7-fold up to 3.0-fold and utmost preferably of at least 1.7-fold up to 2.4 fold; and/or (iii) has thermal stability expressed as Residual Activity after incubation of the glucose isomerase at a temperature of 74° C. for 15 minutes, wherein the variant has a Residual Activity of at least 30%, preferably has a Residual Activity of at least 40%, and more preferably has a Residual Activity of at least 60% and utmost preferably has a Residual Activity of 62%; and/or (iv) has an increased Soluble Expression Level, defined as the ratio of the soluble expression level of the glucose isomerase and the expression level of the polypeptide, preferably of the glucose isomerase of SEQ ID No:1, wherein the Soluble Expression Level is at least 1.1, preferably the Soluble Expression Level is at least 1.3, and more preferably the Soluble Expression Level is at least 1.4, and most preferably the Soluble Expression Level is at least 1.6; and/or (v) in comparison to the polypeptide of SEQ ID NO: 1 has an increased catalytic activity in converting fructose into glucose, expressed as Glucose Formation of at least 1.2-fold up to 5-fold, preferably of at least 1.5-fold up to 5-fold, more preferably of at least 1.9-fold up to 5-fold, yet more preferably of at least 1.9-fold up to 3.5-fold and utmost preferred of at least 2.2-fold up to 3.3-fold.

In a second embodiment of the 16$^{th}$ aspect, which is also an embodiment of the first embodiment of the 16$^{th}$, aspect, the glucose isomerase is a mutant glucose phosphorylase.

In a third embodiment of the 16$^{th}$ aspect, which is also an embodiment of the first and second embodiment of the 16$^{th}$ aspect, the glucose isomerase is a recombinant glucose isomerase.

In a third embodiment of the 14$^{th}$ aspect which is an embodiment of the first and second embodiment of the 14$^{th}$ aspect, in a third embodiment of the 15$^{th}$ aspect which is an embodiment of the first and second embodiment of the 15$^{th}$ aspect, and in a fourth embodiment of the 16$^{th}$ aspect which is an embodiment of the first, second and third embodiment of the 16$^{th}$ aspect, the glucose isomerase is present in non-immobilized form.

In a fourth embodiment of the 14$^{th}$ aspect which is an embodiment of the first and second embodiment of the 14$^{th}$ aspect, in a fourth embodiment of the 15$^{th}$ aspect which is an embodiment of the first and second embodiment of the 15$^{th}$ aspect, and in a fifth embodiment of the 16$^{th}$ aspect which is an embodiment of the first, second and third embodiment of the 16$^{th}$ aspect, the glucose isomerase is present in an immobilized form.

In a fifth embodiment of the 14$^{th}$ aspect which is an embodiment of the first, second, third and fourth embodiment of the 14$^{th}$ aspect, in a fifth embodiment of the 15$^{th}$ aspect which is an embodiment of the first, second, third and fourth embodiment of the 15$^{th}$ aspect, and in a sixth embodiment of the 16$^{th}$ aspect which is an embodiment of the first, second, third, fourth and fifth embodiment of the 16$^{th}$ aspect, the glucose isomerase is a glucose isomerase as defined in any embodiment of the first aspect, including any one of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$, 38$^{th}$, 39$^{th}$, 40$^{th}$, 41$^{st}$, 42$^{nd}$, 43$^{rd}$, 44$^{th}$, 45$^{th}$, 46$^{th}$, 47$^{th}$, 48$^{th}$, 49$^{th}$, 50$^{th}$, 51$^{st}$, 52$^{nd}$, 53$^{rd}$, 54$^{th}$, 55$^{th}$, 56$^{th}$, 57$^{th}$, 58$^{th}$, 59$^{th}$, 60$^{th}$, 61$^{st}$, 62$^{nd}$, 63$^{rd}$, 64$^{th}$, 65$^{th}$, 66$^{th}$, 67$^{th}$, 68$^{th}$, 69$^{th}$, 70th, 71$^{st}$, 72$^{nd}$, 73$^{rd}$, 74$^{th}$, 75$^{th}$, 76$^{th}$, 77$^{th}$, 78$^{th}$, 79$^{th}$, 80$^{th}$, 81$^{st}$, 82$^{nd}$, 83$^{rd}$, 84$^{th}$, 85$^{th}$, 86$^{th}$, 87$^{th}$, 88$^{th}$, 89$^{th}$, 90th, 91$^{st}$, 92$^{nd}$, 93$^{rd}$, 94$^{th}$, 95$^{th}$, 96$^{th}$, 97$^{th}$, 98$^{th}$, 99$^{th}$, 100$^{th}$, 101$^{st}$, 102$^{nd}$, 103$^{rd}$, 104$^{th}$, 105$^{th}$, 106$^{th}$, 107$^{th}$, 108$^{th}$, 109$^{th}$, 110$^{th}$, 111$^{th}$, 112$^{th}$, 113$^{th}$, 114$^{th}$, 115$^{th}$, 116th, 117th, 118th, 119th, 120th, 121st, 122nd, 123rd, 124th, 125th, 126th, 127th, 128th, 129th, 130th, 131st, 132nd, 133rd, 134th, 135th, 136th, 137th, 138th, 139th, 140th, 141st, 142nd, 143rd, 144th embodiment or any of the other embodiments of the first aspect, as defined in any embodiment of the second aspect, including any one of the first, second, third, fourth, fifth, sixth, seventh, eighth, ninth, tenth, eleventh, twelfth and 13th embodiment of the second aspect, and as defined in any embodiment of the third aspect, or as defined in any embodiment of the fourth aspect, including any one of the first, second, third, fourth, fifth, sixth, seventh, eighth, ninth, tenth, eleventh, twelfth, 13th, 14th, 15th, 16th, 17th, 18th, 19th, 20th, 21st and 22nd embodiment of the fourth aspect, as defined in any embodiment of the fifth aspect, including any one of the first, second, third, fourth, fifth and sixth embodiment of the fifth aspect, as defined in any embodiment of the sixth aspect, including any one of the first, second and third embodiment of the sixth aspect, as defined in any embodiment of the seventh aspect, including any one of the first, second and third embodiment of the seventh aspect, as defined in any embodiment of the eighth aspect, including any one of the first, second, third, fourth, fifth and sixth embodiment of the eighth aspect, as defined in any embodiment of the ninth aspect, including any one of the first, second and third embodiment of the ninth aspect, as defined in any embodiment of the tenth aspect, including any one of the first, second and third embodiment of the tenth aspect, as defined in any embodiment of the eleventh aspect, including any one of the first, second, third, fourth, fifth and sixth embodiment of the eleventh aspect, as defined in any one of the twelfth aspect, including any one of the first, second and third embodiment of the twelfth aspect, as defined in any one of the 13th aspect, including any one of the first, second and third embodiment of the 13th aspect.

The problem underlying the present invention is solved in a 17th aspect, which is also a first embodiment of the 17th aspect, by the use of a glucose isomerase for producing glucose, wherein the glucose isomerase is defined as in any embodiment of the first aspect, including any one of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th, 29th, 30th, 31st, 32nd, 33rd, 34th, 35th, 36th, 37th, 38th, 39th, 40th, 41st, 42nd, 43rd, 44th, 45th, 46th, 47th, 48th, 49th, 50th, 51st, 52nd, 53rd, 54th, 54th, 55th, 56th, 57th, 58th, 59th, 60th, 61st, 62nd, 63rd, 64th, 64th, 65th, 66th, 67th, 68th, 69th, 70th, 71st, 72nd, 73rd, 74th, 74th, 75th, 76th, 77th, 78th, 79th, 80th, 81st, 82nd, 83rd, 84th, 84th, 85th, 86th, 87th, 88th, 89th, 90th, 91st, 92nd, 93rd, 94th, 94th, 95th, 96th, 97th, 98th, 99th, 100th, 101st, 102nd, 103rd, 104th, 105th, 106th, 107th, 108th, 109th, 110th, 111th, 112th, 113th, 114th, 115th, 116th, 117th, 118th, 119th, 120th, 121st, 122nd, 123th, 124th, 125th, 126th, 127th, 128th, 129th, 130th, 131st, 132nd, 133th, 134th, 135th, 136th, 137th, 138th, 139th, 140th, 141st, 142nd, 143th, 144th embodiment or any of the other embodiments of the first aspect, as defined in any embodiment of the second aspect, including any one of the first, second, third, fourth, fifth, sixth, seventh, eighth, ninth, tenth, eleventh, twelfth and 13th embodiment of the second aspect, and as defined in any embodiment of the third aspect, or is defined as in any embodiment of the fourth aspect, including any one of the first, second, third, fourth, fifth, sixth, seventh, eighth, ninth, tenth, eleventh, twelfth, 13th, 14th, 15th, 16th, 17th, 18th, 19th, 20th, 21st and 22nd embodiment of the fourth aspect, as defined in any embodiment of the fifth aspect, including any one of the first, second, third, fourth, fifth and sixth embodiment of the fifth aspect, as defined in any embodiment of the sixth aspect, including any one of the first, second and third embodiment of the sixth aspect, as defined in any embodiment of the seventh aspect, including any one of the first, second and third embodiment of the seventh aspect, as defined in any embodiment of the eighth aspect, including any one of the first, second, third, fourth, fifth and sixth embodiment of the eighth aspect, as defined in any embodiment of the ninth aspect, including any one of the first, second and third embodiment of the ninth aspect, as defined in any embodiment of the tenth aspect, including any one of the first, second and third embodiment of the tenth aspect, as defined in any embodiment of the eleventh aspect, including any one of the first, second, third, fourth, fifth and sixth embodiment of the eleventh aspect, as defined in any one of the twelfth aspect, including any one of the first, second, third and fourth embodiment of the twelfth aspect, as defined in any one of the 13th aspect, including any one of the first, second and third embodiment of the 13th aspect.

The problem underlying the present invention is solved in a 18th aspect, which is also a first embodiment of the 18th aspect, by a method for increasing the activity of a polypeptide, preferably a glucose isomerase, for the conversion of fructose to glucose at a concentration of 50 mM fructose, wherein the method comprises:
  aligning an amino acid sequence of a first glucose isomerase with an amino acid sequence of a second glucose isomerase,
  identifying one or more amino acid positions of the amino acid sequence of the second glucose isomerase which correspond to one or more amino acid positions of the amino acid sequence of the first glucose isomerase, wherein substitution of an amino acid residue at the one or more amino acid position of the amino acid sequence of the first glucose isomerase increases activity of the first glucose isomerase,
  substituting an amino acid residue at the one or more amino acid positions of the second glucose isomerase corresponding to the one or more amino acid positions of the amino acid sequence of the first glucose isomerase, wherein substitution of an amino acid residue at the one or more amino acid position of the amino acid sequence of the first glucose isomerase increases the activity for the conversion of fructose to glucose at a concentration of 50 mM fructose of the first glucose isomerase;
  wherein the first glucose isomerase is a glucose isomerase comprising an amino acid sequence according to SEQ ID NO: 1.

In a second embodiment of the 18th aspect, which is also an embodiment of the first embodiment of the 18th aspect, the method comprises
  testing whether the substituted amino acid residue at the one or more amino acid positions of the second glucose isomerase corresponding to the one or more amino acid positions of the amino acid sequence of the first glucose isomerase, results in increased activity, preferably increased Activity, for the conversion of fructose to glucose at a concentration of 50 mM fructose of the second glucose isomerase compared to the activity for the conversion of fructose to glucose at a concentration of 50 mM fructose of the first glucose isomerase.

In a third embodiment of the 18th aspect, which is also an embodiment of the first and second embodiment of the 18th aspect, the amino acid residue at the one or more amino acid positions of the second glucose isomerase corresponding to the one or more amino acid positions of the amino acid sequence of the first glucose isomerase, is substituted such that the substituted amino acid residue results in increased activity, preferably increased Activity, for the conversion of fructose to glucose at a concentration of 50 mM fructose of the second glucose isomerase.

The problem underlying the present invention is solved in a 19$^{th}$ aspect, which is also a first embodiment of the 19$^{th}$ aspect, by a method for increasing the activity of a polypeptide, preferably a glucose isomerase, for the conversion of fructose to glucose at a concentration of 200 mM fructose, wherein the method comprises:
  aligning an amino acid sequence of a first glucose isomerase with an amino acid sequence of a second glucose isomerase,
  identifying one or more amino acid positions of the amino acid sequence of the second glucose isomerase which correspond to one or more amino acid positions of the amino acid sequence of the first glucose isomerase, wherein substitution of an amino acid residue at the one or more amino acid position of the amino acid sequence of the first glucose isomerase increases activity of the first glucose isomerase,
  substituting an amino acid residue at the one or more amino acid positions of the second glucose isomerase corresponding to the one or more amino acid positions of the amino acid sequence of the first glucose isomerase, wherein substitution of an amino acid residue at the one or more amino acid position of the amino acid sequence of the first glucose isomerase increases the activity for the conversion of fructose to glucose at a concentration of 200 mM fructose of the first glucose isomerase;
  wherein the first glucose isomerase is a glucose isomerase comprising an amino acid sequence according to SEQ ID NO: 1.

In a second embodiment of the 19$^{th}$ aspect, which is also an embodiment of the first embodiment of the 19$^{th}$ aspect, the method comprises
  testing whether the substituted amino acid residue at the one or more amino acid positions of the second glucose isomerase corresponding to the one or more amino acid positions of the amino acid sequence of the first glucose isomerase, results in increased activity, preferably increased Activity, for the conversion of fructose to glucose at a concentration of 200 mM fructose of the second glucose isomerase compared to the activity for the conversion of fructose to glucose at a concentration of 200 mM fructose of the first glucose isomerase.

In a third embodiment of the 19$^{th}$ aspect, which is also an embodiment of the first and second embodiment of the 19$^{th}$ aspect, the amino acid residue at the one or more amino acid positions of the second glucose isomerase corresponding to the one or more amino acid positions of the amino acid sequence of the first glucose isomerase, is substituted such that the substituted amino acid residue results in increased activity, preferably increased Activity, for the conversion of fructose to glucose at a concentration of 200 mM fructose of the second glucose isomerase.

The problem underlying the present invention is solved in a 20$^{th}$ aspect, which is also a first embodiment of the 20$^{th}$ aspect, by a method for reducing the K$_M$ value for fructose of a polypeptide, preferably a glucose isomerase, wherein the method comprises:
  aligning an amino acid sequence of a first glucose isomerase with an amino acid sequence of a second glucose isomerase,
  identifying one or more amino acid positions of the amino acid sequence of the second glucose isomerase which correspond to one or more amino acid positions of the amino acid sequence of the first glucose isomerase, wherein substitution of an amino acid residue at the one or more amino acid position of the amino acid sequence of the first glucose isomerase reduces the K$_M$ value for fructose of the first glucose isomerase,
  substituting an amino acid residue at the one or more amino acid positions of the second glucose isomerase corresponding to the one or more amino acid positions of the amino acid sequence of the first glucose isomerase, wherein substitution of an amino acid residue at the one or more amino acid position of the amino acid sequence of the first glucose isomerase reduces the Km value of the first glucose isomerase;
  wherein the first glucose isomerase is a glucose isomerase comprising an amino acid sequence according to SEQ ID NO: 1.

In a second embodiment of the 20$^{th}$ aspect, which is also an embodiment of the first embodiment of the 20$^{th}$ aspect, the method comprises
  testing whether the substituted amino acid residue at the one or more amino acid positions of the second glucose isomerase corresponding to the one or more amino acid positions of the amino acid sequence of the first glucose isomerase, results in reduced K$_M$ value compared to the K$_M$ value of the first glucose isomerase.

In a third embodiment of the 20$^{th}$ aspect, which is also an embodiment of the first and second embodiment of the 20$^{th}$ aspect, the amino acid residue at the one or more amino acid positions of the second glucose isomerase corresponding to the one or more amino acid positions of the amino acid sequence of the first glucose isomerase, is substituted such that the substituted amino acid residue results in a reduced K$_M$ value of the second glucose isomerase.

The problem underlying the present invention is solved in a 21$^{st}$ aspect, which is also a first embodiment of the 21$^{st}$ aspect, by a method for increasing the soluble expression of a polypeptide, preferably a glucose isomerase, wherein the method comprises:
  aligning an amino acid sequence of a first glucose isomerase with an amino acid sequence of a second glucose isomerase,
  identifying one or more amino acid positions of the amino acid sequence of the second glucose isomerase which correspond to one or more amino acid positions of the amino acid sequence of the first glucose isomerase, wherein substitution of an amino acid residue at the one or more amino acid position of the amino acid sequence of the first glucose isomerase increases the soluble expression of the first glucose isomerase,
  substituting an amino acid residue at the one or more amino acid positions of the second glucose isomerase corresponding to the one or more amino acid positions of the amino acid sequence of the first glucose isomerase, wherein substitution of an amino acid residue at the one or more amino acid position of the amino acid sequence of the first glucose isomerase increases soluble expression of the first glucose isomerase;
  wherein the first glucose isomerase is a glucose isomerase comprising an amino acid sequence according to SEQ ID NO: 1.

In a second embodiment of the 21$^{st}$ aspect, which is also an embodiment of the first embodiment of the 21$^{st}$ aspect, wherein the method comprises
  testing whether the substituted amino acid residue at the one or more amino acid positions of the second glucose isomerase corresponding to the one or more amino acid positions of the amino acid sequence of the first glucose isomerase, results in increased soluble expression compared to the soluble expression of the first glucose isomerase.

In a third embodiment of the 21$^{st}$ aspect, which is also an embodiment of the first and second embodiment of the 21$^{st}$ aspect, the amino acid residue at the one or more amino acid positions of the second glucose isomerase corresponding to the one or more amino acid positions of the amino acid sequence of the first glucose isomerase, is substituted such that the substituted amino acid residue results in increased soluble expression of the second glucose isomerase.

In a fourth embodiment of the 18$^{th}$ aspect, which is also an embodiment of any one of the first, second and third embodiment of the 18$^{th}$ aspect, in a fourth embodiment of the 19$^{th}$ aspect, which is also an embodiment of any one of the first, second and third embodiment of the 19$^{th}$ aspect, in a fourth embodiment of the 20$^{th}$ aspect, which is also an embodiment of any one of the first, second and third embodiment of the 20$^{th}$ aspect, and in a fourth embodiment of the 21$^{st}$ aspect, which is also an embodiment of any one of the first, second and third embodiment of the 21$^{st}$ aspect, the homology between the amino acid sequence of the first glucose isomerase and the amino acid sequence of the second glucose isomerase is at least 50%.

In a fifth embodiment of the 18$^{th}$ aspect, which is also an embodiment of the fourth embodiment of the 18$^{th}$ aspect, in a fifth embodiment of the 19$^{th}$ aspect, which is also an embodiment of the fourth embodiment of the 19$^{th}$ aspect, in a fifth embodiment of the 20$^{th}$ aspect, which is also an embodiment of the fourth embodiment of the 20$^{th}$ aspect, and in a fifth embodiment of the 21$^{st}$ aspect, which is also an embodiment of the fourth embodiment of the 21$^{st}$ aspect, the homology is at least 55%, 56%, 57%, 58%, 59%, 60%, 61%, 62%, 63%, 64%, 65%, 66%, 67%, 68%, 69%, 70,%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%, preferably the homology is at least 55%, 75%, 90%, 95%, 98% or 99%.

In a sixth embodiment of the 18$^{th}$ aspect, which is also an embodiment of any one of the first, second and third embodiment of the 18$^{th}$ aspect, in a sixth embodiment of the 19$^{th}$ aspect, which is also an embodiment of any one of the first, second and third embodiment of the 19$^{th}$ aspect, in a sixth embodiment of the 20$^{th}$ aspect, which is also an embodiment of any one of the first, second and third embodiment of the 20$^{th}$ aspect, and in a sixth embodiment of the 21$^{st}$ aspect, which is also an embodiment of any one of the first, second and third embodiment of the 21$^{st}$ aspect, the identity between the amino acid sequence of the first glucose isomerase and the amino acid sequence of the second glucose isomerase is at least 50%.

In a seventh embodiment of the 18$^{th}$ aspect, which is also an embodiment of the sixth embodiment of the 18$^{th}$ aspect, in a seventh embodiment of the 19$^{th}$ aspect, which is also an embodiment of the sixth embodiment of the 19$^{th}$ aspect, in a seventh embodiment of the 20$^{th}$ aspect, which is also an embodiment of the sixth embodiment of the 20$^{th}$ aspect, and in a seventh embodiment of the 21$^{st}$ aspect, which is also an embodiment of the sixth embodiment of the 21$^{st}$ aspect, the identity is at least 55%, 56%, 57%, 58%, 59%, 60%, 61%, 62%, 63%, 64%, 65%, 66%, 67%, 68%, 69%, 70,%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%, preferably, the identity is at least 55%, 75%, 90%, 95%, 98% or 99%.

In an eighth embodiment of the 18$^{th}$ aspect, which is also an embodiment of any one of the first, second, third, fourth, fifth, sixth and seventh embodiment of the 18$^{th}$ aspect, in an eighth embodiment of the 19$^{th}$ aspect, which is also an embodiment of any one of first, second, third, fourth, fifth, sixth and seventh embodiment of the 19$^{th}$ aspect, in an eighth embodiment of the 20$^{th}$ aspect, which is also an embodiment of any one of the first, second, third, fourth, fifth, sixth and seventh embodiment of the 20$^{th}$ aspect, and in an eighth embodiment of the 21$^{st}$ aspect, which is also an embodiment of any one of the first, second, third, fourth, fifth, sixth and seventh embodiment of the 21$^{st}$ aspect, the one or more amino acid positions of the amino acid sequence of the first glucose isomerase is each and individually selected from the group consisting of SEQ ID NO: 1 amino acid positions 10, 33, 34, 35, 53, 59, 89, 90, and 95, and preferably selected from the group consisting of SEQ ID NO: 1 amino acid positions 10, 33, 34, 35, 59, 89, 90, and 95.

In a ninth embodiment of the 18$^{th}$ aspect, which is also an embodiment of the eighth embodiment of the 18$^{th}$ aspect, in an ninth embodiment of the 19$^{th}$ aspect, which is also an embodiment of the eighth embodiment of the 19$^{th}$ aspect, in a ninth embodiment of the 20$^{th}$ aspect, which is also an embodiment of the eighth embodiment of the 20$^{th}$ aspect, and in a ninth embodiment of the 21$^{st}$ aspect, which is also an embodiment of the eighth embodiment of the 21$^{st}$ aspect, the one or more amino acid positions of the amino acid sequence of the first glucose isomerase is independently and individually selected from the group consisting of SEQ ID NO: 1 amino acid positions R10, A33, L34, D35, F53, I59, A89, T90, and T95, and preferably selected from the group consisting of SEQ ID NO: 1 amino acid positions R10, A33, L34, D35, I59, A89, T90, and T95.

In a tenth embodiment of the 18$^{th}$ aspect, which is also an embodiment of any one of the first, second, third, fourth, fifth, sixth, seventh, eighth and ninth embodiment of the 18$^{th}$ aspect, in a tenth embodiment of the 19$^{th}$ aspect, which is also an embodiment of any one of first, second, third, fourth, fifth, sixth, seventh, eighth and ninth embodiment of the 19$^{th}$ aspect, in a tenth embodiment of the 20$^{th}$ aspect, which is also an embodiment of any one of the first, second, third, fourth, fifth, sixth, seventh, eighth and ninth embodiment of the 20$^{th}$ aspect, and in a tenth embodiment of the 21$^{st}$ aspect, which is also an embodiment of any one of the first, second, third, fourth, fifth, sixth, seventh, eighth and ninth embodiment of the 21$^{st}$ aspect, the substituted amino acid residue is H or K, preferably K for the amino acid position of the second glucose isomerase corresponding to amino acid position 10 of SEQ ID NO: 1 of the first glucose isomerase;

I, L, V, G, N, M, C, S, Q or T, preferably to I and N, and most preferably I for the amino acid position of the second glucose isomerase corresponding to amino acid position 33 of SEQ ID NO: 1 of the first glucose isomerase;

F, W, Y, or P, preferably F for the amino acid position of the second glucose isomerase corresponding to amino acid position 34 of SEQ ID NO: 1 of the first glucose isomerase;

G, N, M, C, S, Q or T, preferably C or S, and most preferably S for the amino acid position of the second glucose isomerase corresponding to amino acid position 35 of SEQ ID NO: 1 of the first glucose isomerase;

A, I, L, or V, preferably L for the amino acid position of the second glucose isomerase corresponding to amino acid position 53 of SEQ ID NO: 1 of the first glucose isomerase;

F, W, Y or P, and preferably F for the amino acid position of the second glucose isomerase corresponding to amino acid position 59 of SEQ ID NO: 1 of the first glucose isomerase;

I, L or V, and preferably V for the amino acid position of the second glucose isomerase corresponding to amino acid position 89 of SEQ ID NO: 1 of the first glucose isomerase;

G, N, M, C, S or Q, and preferably S for the amino acid position of the second glucose isomerase corresponding to amino acid position 90 of SEQ ID NO: 1 of the first glucose isomerase;

F, W, Y, P, R, H or K, preferably Y or R, and most preferably Y for the amino acid position of the second glucose isomerase corresponding to amino acid position 95 of SEQ ID NO: 1 of the first glucose isomerase.

In an eleventh embodiment of the 18$^{th}$ aspect, which is also an embodiment of any one of the first, second, third, fourth, fifth, sixth, seventh, eighth, ninth and tenth embodiment of the 18$^{th}$ aspect, in an eleventh embodiment of the 19$^{th}$ aspect, which is also an embodiment of any one of first, second, third, fourth, fifth, sixth, seventh, eighth, ninth and tenth embodiment of the 19$^{th}$ aspect, in an eleventh embodiment of the 20$^{th}$ aspect, which is also an embodiment of any one of the first, second, third, fourth, fifth, sixth, seventh, eighth, ninth and tenth embodiment of the 20$^{th}$ aspect, and in an eleventh embodiment of the 21$^{st}$ aspect, which is also an embodiment of any one of the first, second, third, fourth, fifth, sixth, seventh, eighth, ninth and tenth embodiment of the 21$^{st}$ aspect, if the amino acid residue of the second glucose isomerase corresponding to one or more amino acid positions of the amino acid sequence of the first glucose isomerase, is the same as the substituted amino acid residue of the first glucose isomerase, the amino acid residue of the second glucose isomerase is not substituted.

In an twelfth embodiment of the 18$^{th}$ aspect, which is also an embodiment of any one of the first, second, third, fourth, fifth, sixth, seventh, eighth, ninth, tenth and eleventh embodiment of the 18$^{th}$ aspect, in a twelfth embodiment of the 19$^{th}$ aspect, which is also an embodiment of any one of first, second, third, fourth, fifth, sixth, seventh, eighth, ninth, tenth and eleventh embodiment of the 19$^{th}$ aspect, in a twelfth embodiment of the 20$^{th}$ aspect, which is also an embodiment of any one of the first, second, third, fourth, fifth, sixth, seventh, eighth, ninth, tenth and eleventh embodiment of the 20$^{th}$ aspect, and in a twelfth embodiment of the 21$^{st}$ aspect, which is also an embodiment of any one of the first, second, third, fourth, fifth, sixth, seventh, eighth, ninth, tenth and eleventh embodiment of the 21$^{st}$ aspect, the increased activity, preferably increased Activity, of the glucose isomerase for the conversion of fructose to glucose at a concentration of 50 mM fructose is expressed as a Normalized Activity value as defined in the description.

In an 13$^{th}$ embodiment of the 18$^{th}$ aspect, which is also an embodiment of any one of the first, second, third, fourth, fifth, sixth, seventh, eighth, ninth, tenth, eleventh and twelfth embodiment of the 18$^{th}$ aspect, in a 13$^{th}$ embodiment of the 19$^{th}$ aspect, which is also an embodiment of any one of first, second, third, fourth, fifth, sixth, seventh, eighth, ninth, tenth, eleventh and twelfth embodiment of the 19$^{th}$ aspect, in a 13$^{th}$ embodiment of the 20$^{th}$ aspect, which is also an embodiment of any one of the first, second, third, fourth, fifth, sixth, seventh, eighth, ninth, tenth, eleventh and twelfth embodiment of the 20$^{th}$ aspect, and in a 13$^{th}$ embodiment of the 21$^{st}$ aspect, which is also an embodiment of any one of the first, second, third, fourth, fifth, sixth, seventh, eighth, ninth, tenth, eleventh and twelfth embodiment of the 21$^{st}$ aspect, the increased activity, preferably increased Activity, ratio for the conversion of fructose to glucose at 200 mM fructose of a polypeptide is expressed as a Normalized Activity value as defined in the description.

In an 14$^{th}$ embodiment of the 18$^{th}$ aspect, which is also an embodiment of any one of the first, second, third, fourth, fifth, sixth, seventh, eighth, ninth, tenth, eleventh, twelfth and 13$^{th}$ embodiment of the 18$^{th}$ aspect, in a 14$^{th}$ embodiment of the 19$^{th}$ aspect, which is also an embodiment of any one of first, second, third, fourth, fifth, sixth, seventh, eighth, ninth, tenth, eleventh, twelfth and 13$^{th}$ embodiment of the 19$^{th}$ aspect, in a 14$^{th}$ embodiment of the 20$^{th}$ aspect, which is also an embodiment of any one of the first, second, third, fourth, fifth, sixth, seventh, eighth, ninth, tenth, eleventh, twelfth and 13$^{th}$ embodiment of the 20$^{th}$ aspect, and in a 14$^{th}$ embodiment of the 21$^{st}$ aspect, which is also an embodiment of any one of the first, second, third, fourth, fifth, sixth, seventh, eighth, ninth, tenth, eleventh, twelfth and 13$^{th}$ embodiment of the 21$^{st}$ aspect, the increased soluble expression of the glucose isomerase is expressed as a Soluble Expression Level value as defined in the description.

The glucose isomerase described herein in its various aspects and embodiments may also be referred to as the glucose isomerase of the present invention. The glucose isomerase of the invention is a mutant of wild type glucose isomerase, which is obtained by enzyme engineering and which in comparison to the wild type glucose isomerase is distinguished by an improved activity, preferably the Activity, and/or decreased $K_M$ value for fructose, both resulting in an improved conversion rate of fructose to glucose at low fructose concentrations and/or an increased soluble expression and/or—increased—thermal stability.

Specifically, the glucose isomerase of the invention relates to glucose isomerase variants of a wild type glucose isomerase from *Streptomyces* sp. SK which in comparison to the wild type glucose isomerase shows improved activity, preferably the Activity, in terms of converting fructose into glucose and/or decreased $K_M$ value for fructose. In preferred embodiments, the glucose isomerase of the invention also shows improved soluble expression in a recombinant expression system such as the one described herein, and/or also shows no or only minor reduction of its thermal stability in comparison to the wild type glucose isomerase, and/or shows an increased catalytic activity in converting fructose into glucose, expressed as Glucose Formation.

The wild type glucose isomerase from *Streptomyces* sp. SK has an amino acid sequence according to SEQ ID NO: 1 and was taken from GenBank database. The enzyme sequence was elucidated by Borgi et al (Biochimie, 86, 561-568, 2004) and deposited in the GenBank sequence database (NCBI Accession number: CAA75672.2, first deposited 14.11. 1997).

The present invention is based on the surprising finding that a wild type glucose isomerase enzyme according to SEQ ID NO: 1 of EC number EC 5.3.1.5 from *Streptomyces* sp. SK can be improved by enzyme engineering in such a way to provide high activities at a low substrate concentration for converting fructose to glucose at moderate temperatures, preferably temperatures such as about 30° C. to about 50° C.

The present inventors have surprisingly found that replacing an amino acid residue at one or several of the following amino acid positions of the amino acid sequence of SEQ ID NO: 1 is suitable for improving the reaction characteristics of the glucose isomerase of SEQ ID NO: 1: 10, 33, 34, 35, 53, 59, 89, 90, and 95. Among these amino acid positions of SEQ ID NO: 1 amino acid positions 10, 33, 34, 35, 59, 89, 90, and 95, and/or amino acid positions 10, 33, 34, 35, and 59, and/or amino acid positions 10, 33, and 35, each of SEQ ID NO: 1, are particularly suitable, and whereby amino acid positions 10, 33, 53, 90, and 95, and/or amino acid positions 10, 89, 90, and 95, and/or amino acid positions 10, 90, and 95, each of SEQ ID NO: 1, being even more suitable.

It is within the present invention that the glucose isomerase of the invention comprises one amino acid mutation at a given amino acid residue position, preferably at one given amino acid residue position of SEQ ID NO: 1. In an embodiment of the invention where the glucose isomerase of the invention comprises one single mutation only, the mutant amino acid residue position of SEQ ID NO: 1 is different from amino acid position 53 of SEQ ID NO: 1, i.e. the mutant amino acid residue of the glucose isomerase of the invention is different from amino acid position 53 of the amino acid sequence of SEQ ID NO: 1. In a further embodiment of the invention where the glucose isomerase of the invention comprises one single mutation only, the mutant amino acid residue position of SEQ ID NO: 1 is amino acid position 53 of SEQ ID NO: 1, whereby the mutant amino acid is different from leucine. In an embodiment of the invention where the glucose isomerase of the invention comprises one single mutation only, the mutant amino acid residue position of SEQ ID NO: 1 is different from amino acid position 90 of SEQ ID NO: 1, i.e. the mutant amino acid residue of the glucose isomerase of the invention is different from amino acid position 90 of the amino acid sequence of SEQ ID NO: 1. In a further embodiment of the invention where the glucose isomerase of the invention comprises one single mutation only, the mutant amino acid residue position of SEQ ID NO: 1 is amino acid position 90 of SEQ ID NO: 1, whereby the mutant amino acid is different from serine. In an embodiment of the invention where the glucose isomerase of the invention comprises one single mutation only, the mutant amino acid residue position of SEQ ID NO: 1 is different from amino acid position 89 of SEQ ID NO: 1, i.e. the mutant amino acid residue of the glucose isomerase of the invention is different from amino acid position 89 of the amino acid sequence of SEQ ID NO: 1. In a further embodiment of the invention where the glucose isomerase of the invention comprises one single mutation only, the mutant amino acid residue position of SEQ ID NO: 1 is amino acid position 89 of SEQ ID NO: 1, whereby the mutant amino acid is different from valine.

It is within the present invention that the glucose isomerase of the invention comprises an amino acid mutation at two or more amino acid residue positions, preferably at two or more amino acid residue positions of SEQ ID NO: 1. As in case of the glucose isomerase of the invention comprising one amino acid mutation at a given amino acid residue position only, the glucose isomerase of the invention comprising an amino acid mutation at two or more amino acid residue positions shows surprising and unexpected effects. Such surprising and unexpected effects may be even more pronounced in those embodiments of the glucose isomerase of the invention where the glucose isomerase comprises a mutation at three or four or five amino acid residue positions.

In an embodiment of the various aspects of the present invention where the glucose isomerase of the invention comprises an amino acid mutation at two or more amino acid residue positions, preferably at two or more amino acid residue positions of SEQ ID NO: 1, the glucose isomerase of the invention is different from a glucose isomerase comprising a mutation at amino acid position 53 of SEQ ID NO: 1, preferably the glucose isomerase of the invention is different from a glucose isomerase comprising a mutation at amino acid position 53 of SEQ ID NO: 1, whereby the mutant amino acid is different from leucine. In an embodiment of the various aspects of the present invention where the glucose isomerase of the invention comprises an amino acid mutation at two or more amino acid residue positions, preferably at two or more amino acid residue positions of SEQ ID NO: 1, the glucose isomerase of the invention is different from a glucose isomerase comprising a mutation at amino acid position 90 of SEQ ID NO: 1, preferably the glucose isomerase of the invention is different from a glucose isomerase comprising a mutation at amino acid position 90 of SEQ ID NO: 1, whereby the mutant amino acid is different from serine. In an embodiment of the various aspects of the present invention where the glucose isomerase of the invention comprises an amino acid mutation at two or more amino acid residue positions, preferably at two or more amino acid residue positions of SEQ ID NO: 1, the glucose isomerase of the invention is different from a glucose isomerase comprising a mutation at amino acid position 89 of SEQ ID NO: 1, preferably the glucose isomerase of the invention is different from a glucose isomerase comprising a mutation at amino acid position 89 of SEQ ID NO: 1, whereby the mutant amino acid is different from valine.

The performance of a glucose isomerase can be evaluated by several characteristics, such as, e.g., activity, preferably the Activity, for the conversion of fructose to glucose at a fructose concentration of 50 mM; activity, preferably the Activity, for the conversion of fructose to glucose at a fructose concentration of 200 mM; thermal stability expressed as Residual Activity after incubation, preferably at 74° C. for 15 minutes, $K_M$ value; Soluble Expression Level; and Glucose Formation.

Throughout the context of the present invention, the performance of a glucose isomerase is meant to be improved when one or more of these characteristics is/are realized as, e.g., activity, preferably when the Activity, for the conversion of fructose to glucose at a fructose concentration of 50 mM is increased; activity, preferably when the Activity, for the conversion of fructose to glucose at a fructose concentration of 200 mM is increased; when the thermal stability expressed as Residual Activity after incubation, preferably at 74° C. for 15 minutes is above 40%, preferably of above 60%; when the $K_M$ value is decreased to less than 190 mM; when the Soluble Expression Level is increased; and/or when the Glucose Formation is increased. A preferred combination of features used in the assessment of glucose isomerases, including those of the invention, is activity, preferably the Activity, for the conversion of fructose to glucose at a fructose concentration of 50 mM, thermal stability expressed as Residual Activity after incubation, and improved Soluble Expression Level. Another preferred combination is the activity, preferably the Activity, for the conversion of fructose to glucose at a fructose concentration of 50 mM, improved Soluble Expression Level, and $K_M$ value. Yet another preferred combination is activity, preferably the Activity, for the conversion of fructose to glucose at a fructose concentration of 50 mM, $K_M$ value, and thermal stability expressed as Residual Activity after incubation. Another preferred combination is activity, preferably the Activity, for the conversion of fructose to glucose at a fructose concentration of 50 mM, and the $K_M$ value.

In an embodiment, if not indicated to the contrary, any activity, enzymatic activity displayed or to be displayed by the polypeptide and, preferably any glucose isomerase, of the present invention is defined and, respectively, determined by the methods and assays, respectively, disclosed herein. Accordingly, the assays used for determining these characteristics are preferably the ones disclosed herein and described in the following. In connection therewith it is to be acknowledged that the following definitions refer to glucose isomerase; it is, however, within the present invention that the very same definitions equally apply to a polypeptide and preferably to a polypeptide of the invention. It is also to be acknowledged that the terms glucose isomerase and GI are used herein interchangeably.

Glucose isomerase Activity (herein also referred to as Activity): As glucose isomerases catalyze the reversible isomerisation of glucose to fructose, activity, preferably the Activity, can be determined either in the direction of glucose to fructose isomerisation, or fructose to glucose isomerisation. For the purpose of this invention, glucose isomerase Activity is defined as the activity in the fructose to glucose isomerisation at the conditions of either Assay I or Assay II as described below. It is within the present invention that any activity and any activity of the glucose isomerase, preferably the Activity, is in an embodiment a catalytic activity. 1 unit of glucose isomerase activity is defined as the amount of enzyme that catalyzes the conversion of 1 µmole of fructose to glucose in 1 min at specified conditions, whereby such specific conditions are 50 mM potassium phosphate buffer pH 7.0, 10 mM $Mg^{2+}$, and 40° C.

Assay I: Glucose isomerase Activity is assayed by monitoring the formation of glucose from fructose at 40° C. using the following conditions: 50 mM potassium phosphate buffer pH 7, 10 mM $Mg^{2+}$ (as $MgCl_2$ or $MgSO_4$) and 50 or 200 mM fructose concentrations as given. The glucose produced from fructose by the action of glucose isomerase was determined using a discontinuous coupled assay in which the glucose is converted to glucose-6-phosphate by hexokinase. Glucose-6-phosphate and NADP is converted to 6-phospho-gluconate and NADPH by glucose 6-phosphate dehydrogenase. The detection is based on measuring the absorbance of NADPH at 340 nm. The D-GLUCOSE—HK kit (HK/G6P-DH Format) was employed in the microplate format (product no. K-GLUHK-110A or K-GLUHK-220A available from Megazyme International Ireland, Wicklow, Ireland). The assay is performed according to the manufacturer recommendations and the amount of glucose in the sample is quantified using external standards. In principle, the glucose produced by the glucose isomerase could also be quantified by any other suitable method known in the art.

Assay II: The reaction for measuring glucose isomerase Activity is conducted by monitoring the formation of glucose from fructose at following conditions: 50 mM potassium phosphate buffer pH 7, 10 mM $MgSO_4$, 50-1000 mM fructose concentrations, and 40° C. The reaction is quenched by adding 0.1 mL 0.25 M HCl per mL reaction. The glucose produced from fructose by the action of glucose isomerase is determined using a discontinuous coupled assay in which glucose is converted to gluconolactone by glucose oxidase. Hydrogen peroxide, a by-product of this reaction, is used by horseradish peroxidase to oxidize 2,2'-azino-bis(3-ethylbenzothiazoline-6-sulphonic acid (ABTS), yielding a coloured product, which shows absorbance at 405 nm. A 10 µL aliquot of acid-quenched reaction is mixed with 90 µL of an assay mix containing 50 mM potassium phosphate buffer pH 6, 1 mM ABTS, 5 U/mL glucose oxidase and 1 U/mL horseradish peroxidase. After 60-70 min incubation at 30° C., the absorbance at 405 nm is measured (endpoint measurement). The amount of glucose in the sample is quantified using external standards. In principle, the glucose produced by the glucose isomerase could also be quantified by any other method known in the art.

Glucose Isomerase Volumetric Activity: Glucose Isomerase Volumetric Activity is defined as glucose isomerase Activity per volume. For the purpose of this invention the Volumetric Activity is expressed as the amount of glucose isomerase units obtained from one milliliter (1 mL) of culture volume, e.g. bacterial culture volume.

Glucose Isomerase Normalized Activity: Glucose Isomerase Normalized Activity shall mean the Glucose Isomerase Volumetric Activity of a specific glucose isomerase variant, which is normalized to its expression level by dividing the Glucose Isomerase Volumetric Activity of that specific variant by the Glucose Isomerase Soluble Expression Level.

Glucose Formation: Glucose Formation is an indicative measure for the catalytic activity of the polypeptide, preferably the glucose isomerase, in conversion of fructose into glucose, and is defined as the amount of glucose that is produced after reacting the polypeptide, preferably the glucose isomerase, with fructose at a concentration of 50 mM fructose at 40° C. for 40 min in solution (50 mM potassium phosphate buffer pH 7). Glucose amounts are quantified by use of commercially available test assays such as, for example, the D-GLUCOSE—HK kit (HK/G6P-DH Format) (product no. K-GLUHK-110A or K-GLUHK-220A, available from Megazyme International Ireland, Wicklow, Ireland). The Glucose Formation can be quantified as the glucose concentration achieved in an individual reaction (e.g. in mM glucose), or as a relative Glucose Formation being the ratio of the glucose amount produced by a variant polypeptide, preferably glucose isomerase, to the glucose amount produced by the glucose isomerase of SEQ ID NO: 1.

Glucose Isomerase Soluble Expression Level: The Glucose Isomerase Soluble Expression Level of glucose isomerase variants is defined as the ratio of the soluble expression level of a glucose isomerase variant and the soluble expression level of the wild type glucose isomerase having the amino acid sequence of SEQ ID No: 1. The soluble expression level of a glucose isomerase variant is determined by means of SDS-PAGE of cell free extracts of glucose isomerase variants and quantification of the glucose isomerase band intensity per unit of non-processed bacterial culture volume. The person skilled in the art is aware of how to select experimental conditions for SDS-PAGE in order to assure proper separation of proteins and allow correct quantification.

Thermal stability: Thermal stability is the ability of an enzyme to resist irreversible inactivation after exposure to a specified elevated temperature over a given period of time. There are many ways of measuring and describing thermal stability. For the purpose of this invention thermal stability was determined by measuring and describing one or more of the following characteristics of any of a wild type glucose isomerase and/or any variant of a or the wild type glucose isomerase, including and in particular any variant or mutant glucose isomerase of the invention:

Residual Activity is the ratio of the glucose isomerase Activity of a glucose isomerase enzyme after incubation of the enzyme at the elevated temperature for a certain time divided by the initial glucose isomerase Activity of the same enzyme, expressed as a percentage. The initial activity, preferably the Activity, of an enzyme is the activity, preferably the Activity, of the respective enzyme without temperature treatment, i.e. with incubation at room temperature, such as at 20-25° C., and explicitly at any temperature at which the enzyme remains fully active within the incubation period. In measuring the Residual Activity of a glucose isomerase, the respective glucose isomerase activity can be determined in principle by using any activity assay, at any elevated temperature, and for any incubation time. For the purpose of this invention Assay I as described herein was used with 50 mM fructose, and enzymes were incubated for 15 minutes at 74° C. as specified in the examples.

Tm50-value is the temperature at which the enzyme possesses 50% of its initial activity, i.e. 50% Residual Activity, after incubation of the enzyme at this temperature for a certain time as a percentage of the initial glucose isomerase Activity of the same enzyme. The initial activity, preferably the Activity, of an enzyme is the activity of the respective enzyme without temperature treatment, i.e. with incubation at room temperature such as at 20-25° C., and explicitly at any temperature at which the enzyme remains fully active within the incubation period.

In measuring the thermal stability of a glucose isomerase, the respective glucose isomerase activity can be determined in principle by using any activity assay, at any elevated temperature, and for any incubation time. For the purpose of this invention Assay I as described herein was used with 200 mM fructose, and enzymes were incubated for 15 minutes at temperatures ranging from 65-85° C. as specified in the examples.

In accordance therewith, the present invention equally relates in a first aspect to a polypeptide, preferably a glucose isomerase, comprising an amino acid sequence, wherein the amino acid sequence of the glucose isomerase is at least 95% identical to and/or at least 95% homologous to an amino acid sequence of SEQ ID NO:1, wherein the amino acid sequence of the polypeptide, preferably the glucose isomerase, comprises an amino acid substitution at one or more amino acid positions, wherein the one or more amino acid positions is/are each and independently selected from the group consisting of SEQ ID NO: 1 amino acid positions 10, 33, 34, 35, 53, 59, 89, 90, and 95. In an embodiment of the glucose isomerase of the present invention wherein the glucose isomerase comprises an amino acid substitution at one or more amino acid positions, the glucose isomerase comprises an amino acid substitution at amino acid position 10, an amino acid substitution at amino acid position 90, or an amino acid substitution at amino acid position 95, each of SEQ ID NO: 1.

In an embodiment, the polypeptide of the first aspect is a glucose isomerase, preferably a glucose isomerase having one or several of the characteristics disclosed herein. In accordance therewith, the disclosure of the glucose isomerase of the instant invention and in particular according to each and any aspect equally applies to the polypeptide of the instant invention, and vice versa. Furthermore, in an embodiment the polypeptide of the present invention is a polypeptide having glucose isomerase activity, preferably the Activity. Preferably, glucose isomerase activity, preferably the Activity, is one which is defined herein.

The wording that a glucose isomerase comprises an amino acid sequence, wherein the amino acid sequence of the glucose isomerase is at least 95% identical to and/or at least 95% homologous to an amino acid sequence of SEQ ID NO:1, wherein the amino acid sequence of the glucose isomerase comprises an amino acid substitution at one or more amino acid positions, wherein the one or more amino acid positions is/are selected from the group consisting of SEQ ID NO: 1 amino acid positions 10, 33, 34, 35, 53, 59, 89, 90, and 95, has, in an embodiment, the same meaning as the wording that a glucose isomerase has at least 95% homology to SEQ ID NO: 1, wherein the glucose isomerase comprises a substitution at one or more amino acid positions selected from 10, 33, 34, 35, 53, 59, 89, 90, and 95, where each amino acid position corresponds to a position of the amino acid sequence of SEQ ID NO: 1.

The term "SEQ ID NO: 1 amino acid positions" is intended to refer to the amino acid positions of SEQ ID NO: 1. Insofar, the glucose isomerase of the present invention, preferably including any aspect of the present invention, is a mutant glucose isomerase and more specifically a mutant glucose isomerase of a glucose isomerase having an amino acid sequence of SEQ ID NO: 1. In an embodiment, the glucose isomerase of the present invention is a glucose isomerase having an amino acid sequence different from the amino acid sequence of SEQ ID NO: 1. In a further embodiment, the glucose isomerase of the present invention is a glucose isomerase which is different from a glucose isomerase consisting of an amino acid sequence of SEQ ID NO: 1.

Preferably, a mutant glucose isomerase is a glucose isomerase which has one or more amino acid residue changes such as replacements/substitutions or deletions compared to the non-mutant glucose isomerase. The non-mutant glucose isomerase is preferably a glucose isomerase having an amino acid sequence from which the amino acid sequence of the mutant glucose isomerase differs only at the one or more changed amino acid residues. In other words, the mutant glucose isomerase and the underlying glucose isomerase share the same amino acid backbone, but differ at said one or more changed amino acid residues. In a preferred embodiment, the underlying glucose isomerase is a wild type glucose isomerase.

In accordance with the first aspect of the present invention the glucose isomerase of the present invention comprises at least one amino acid substitution at at least one amino acid position of SEQ ID NO: 1. In accordance therewith, in an embodiment of the glucose isomerase of the present invention the amino acid substitution is made at one of the specific, indicated amino acid positions of SEQ ID NO: 1, whereby, optionally, the very amino acid residue present at such position of SEQ ID NO: 1 does not have any bearing on the kind of substituted amino acid residue present in the glucose isomerase of the present invention; alternatively, and again optionally, the very amino acid residue present at such position of SEQ ID NO:1 has a bearing on the kind of substituted amino acid residue present in the glucose isomerase of the present invention. The substitution may be non-conservative or conservative. For the purposes of the present invention, conservative means an exchange of the amino acid G to A; A to G, S; V to I, L, A, T or S; I to V, L, or M; L to I, M, or V; M to L, I, or V; P to A, S, or N; F to Y, W, or H; Y to F, W, or H; W to Y, F, or H; R to K, E, or D; K to R, E, or D; H to Q, N, or S; D to N, E, K, R, or Q; E to Q, D, K, R, or N; S to T, or A; T to S, V, or A; C to S, T, or A; N to D, Q, H, or S; Q to E, N, H, K, or R.

Also in accordance therewith, in an embodiment of the glucose isomerase of the present invention the amino acid substitution is one where the very amino acid residue of any of the indicated amino acid positions of SEQ ID NO: 1 is substituted, whereby, optionally, the amino acid position of the substituted amino acid residue is not exactly the one as indicated by reference to SEQ ID NO: 1; rather, in an embodiment, the amino acid position of the substituted amino acid residue differs from the corresponding position of SEQ ID NO: 1, preferably by one to five, preferably two to five, more preferably three to five, even more preferably four to five amino acid position, and most preferably at four amino acid positions.

To the extent the glucose isomerase of the present invention is characterized as comprising an amino acid substitution at one or more specified amino acid positions it will be understood that, in one embodiment, the glucose isomerase of the present invention is one which has a single amino acid substitution at one of the indicated amino acid positions. In another embodiment of the glucose isomerase of the present invention being characterized as comprising an amino acid substitution at one or more specified amino acid positions, the glucose isomerase of the present invention is one which has an amino acid substitution at two or more, such as two, three, four, five etc. of the indicated amino acid positions. In the latter case, the number of amino acid residues which is substituted is any integer between one and the number of amino acid residues indicated and defined as being substituted. In accordance therewith, the glucose isomerase of the present invention is any glucose isomerase which has or realizes one amino acid substitution or any combination, including each and any permutation, of the amino acid residues indicated and defined as being substituted.

In accordance therewith, the glucose isomerase may comprise an amino acid substitution at one or any combination and, respectively, permutation of amino acid positions 10, 33, 34, 35, 53, 59, 89, 90, and 95. Accordingly, in an embodiment the glucose isomerase of the present invention comprises at least an amino acid substitution at one of said amino acid positions of SEQ ID NO: 1, at least one amino acid substitution at at least two of said amino acid positions of SEQ ID NO: 1, at least one amino acid substitution at at least three of said amino acid positions of SEQ ID NO: 1, at least one amino acid at at least four of said amino acid positions of SEQ ID NO: 1, and at least one amino acid substitution at at least five of said amino acid positions of SEQ ID NO: 1. Among those embodiments, the glucose isomerase of the invention comprising an amino acid substitution at four amino acid positions of SEQ ID NO: 1 is particularly preferred. Alternatively, among those embodiments, the glucose isomerase of the invention comprising an amino acid substitution at four to five amino acid positions, or at five amino acid positions of SEQ ID NO: 1 is particularly preferred.

It is, however, also within the present invention that the glucose isomerase of the present invention comprises even more than the above indicated substitutions at the indicated amino acid positions of SEQ ID NO: 1, preferably under the provision that the amino acid sequence of the glucose isomerase meets at least one of the minimum structural feature and/or minimum functional features of the glucose isomerase of the present invention. Such minimum structural feature is that the glucose isomerase comprises an amino acid sequence, wherein the amino acid sequence of the glucose isomerase is at least 95% identical to and/or at least 95% homologous to an amino acid sequence of SEQ ID NO:1, wherein the amino acid sequence of the glucose isomerase comprises an amino acid substitution at one or more amino acid positions, wherein the one or more amino acid positions is/are each and independently selected from the group consisting of SEQ ID NO: 1 amino acid positions 10, 33, 34, 35, 53, 59, 89, 90, and 95. Such minimum functional feature is one or any combination of any one of characteristics (A), (B), (C), (D), (E) and (F) including any further specifications thereof disclosed herein, whereby characteristic (A) is an increased activity, preferably increased Activity, of the polypeptide, preferably of the glucose isomerase, for the conversion of fructose to glucose at a concentration of 50 mM fructose in comparison to the polypeptide, preferably the glucose isomerase, of SEQ ID NO: 1 of at least 1.1-fold such as of 1.1-fold to 1.6-fold, characteristic (B) is an increased activity, preferably increased Activity, of the polypeptide, preferably of the glucose isomerase, for the conversion of fructose to glucose at a concentration of 200 mM fructose in comparison to the polypeptide, preferably the glucose isomerase, of SEQ ID NO: 1 of at least 1.2-fold such as 1.2-fold to 1.6-fold or 1.2-fold to 3.0-fold, characteristic (C) is thermal stability of the polypeptide, preferably the glucose isomerase, expressed as Residual Activity after incubation of the polypeptide at a temperature of 74° C. for 15 minutes, wherein such Residual Activity is at least 30% and up to 100%, characteristic (D) is a $K_M$ value of the polypeptide, preferably the glucose isomerase, of between 100 mM and 190 mM or of between 50 mM and 190 mM, and characteristic (E) is the Soluble Expression Level of the polypeptide, preferably the glucose isomerase, defined as the ratio of the soluble expression level of said polypeptide and the soluble expression level of the polypeptide, preferably the glucose isomerase of SEQ ID NO: 1, of at least 1.04 such as of 1.04 to 1.38 or of 1.04 up to 1.80, and characteristic (F) is an increased Glucose Formation, preferably of at least 1.2-fold up to 5-fold, or of at least 1.5-fold up to 5-fold, or of at least 1.9-fold up to 5-fold, or of at least 1.9-fold up to 3.5-fold, or of at least 2.2-fold up to 3.3-fold. It is within the present invention that for determining the above characteristics (A), (B), (C), (D), (E), and (F) the assays disclosed herein may be used. It is also within the present invention that characteristic (A), i.e. an increased activity, preferably increased Activity, of the polypeptide, preferably of the glucose isomerase, for the conversion of fructose to glucose at a concentration of 50 mM fructose in comparison to the polypeptide, preferably the glucose isomerase, of SEQ ID NO: 1 may be expressed as a relative activity of the polypeptide, preferably the glucose isomerase, as a relative activity of the polypeptide, preferably of the glucose isomerase, for the conversion of fructose to glucose at a concentration of 50 mM fructose in comparison to the polypeptide, preferably the glucose isomerase, of SEQ ID NO: 1. In such case, the indicated value for the increase translates into the respective ratio with the reference being set as "1". For example, an increased activity, preferably increased Activity, of 1.1-fold translates into a relative activity of 1.1:1, and vice versa. The same equally applies to characteristic (B), i.e. an increased activity, preferably increased Activity, of the polypeptide, preferably of the glucose isomerase, for the conversion of fructose to glucose at a concentration of 200 mM fructose in comparison to the polypeptide, preferably the glucose isomerase, of SEQ ID NO: 1. The same equally applies to characteristic (F), i.e. an increased Glucose Formation of the polypeptide, preferably of the glucose isomerase, for the conversion of fructose to glucose at a concentration of 50 mM fructose at 40° C. for 40 minutes in comparison to the polypeptide, preferably the glucose isomerase, of SEQ ID NO: 1.

It is within the present invention that the glucose isomerase of the present invention displays said characteristic (A), characteristic (B), characteristic (C), characteristic (D), characteristic (E), characteristic (F), characteristics (A) and (B), characteristics (A) and (C), characteristics (A) and (D), characteristics (A) and (E), characteristics (A) and (F), characteristics (B) and (C), characteristics (B) and (D), characteristics (B) and (E), characteristics (B) and (F), characteristics (C) and (D), characteristics (C) and (E), characteristics (C) and (F), characteristics (D) and (E), characteristics (D) and (F), characteristics (E) and (F), characteristics (A), (B) and (C), characteristics (A), (B) and (D), characteristics (A), (B) and (E), characteristics (A), (B) and (F), characteristics (B), (C) and (D), characteristics (B), (C) and (E), characteristics (B), (C) and (F), characteristics (C), (D) and (E), characteristics (C), (D) and (F), characteristics (D), (E) and (F), characteristics (A), (B), (C) and (D), characteristics (A), (B), (C) and (E), characteristics (A), (B), (C) and (F), characteristics (A), (C), (D) and (E), characteristics (A), (C), (D) and (F), characteristics (A), (D), (E) and (F), characteristics (B), (C), (D) and (E), characteristics (B), (C), (D) and (F), characteristics (B), (D), (E) and (F), characteristics (C), (D), (E) and (F), or characteristics (A), (B), (C), (D) and (E), characteristics (A), (B), (C), (D) and (F), characteristics (A), (B), (C), (E) and (F), characteristics (A), (B), (D), (E) and (F), characteristics (A), (C), (D), (E) and (F). Preferred embodiments of the glucose isomerase of the present invention are those glucose isomerases that display the characteristics (A) and (C), characteristics (A) and (D), or characteristics (A) and (E), even more preferred embodiments of the glucose isomerase of the present invention are those glucose isomerases that display the characteristics (A) and (D), or (A), (C), and (D), or (A), (C), and (E), or (A), (D) and (E), and most preferably (A) and (D), or (A), (C), and (E).

In an embodiment of the glucose isomerase of the present invention, the amino acid sequence of the glucose isomerase comprises an amino acid substitution at at least two amino acid positions of the amino acid sequence of SEQ ID NO: 1. These at least two amino acid positions are also referred to herein as a pair of two amino acid positions. In an embodiment of the glucose isomerase of the present invention the pair of two SEQ ID NO: 1 amino acid positions is selected from the group consisting of amino acid positions R10 and A33, R10 and L34, R10 and D35, R10 and F53, R10 and I59, R10 and A89, R10 and T90, R10 and T95, A33 and L34, A33 and D35, A33 and F53, A33 and I59, A33 and A89, A33 and T90, A33 and T95, L34 and D35, L34 and F53, L34 and I59, L34 and A89, L34 and T90, L34 and T95, D35 and F53, D35 and I59, D35 and A89, D35 and T90, D35 and T95, F53 and I59, F53 and A89, F53 and T90, F53 and T95, I59 and A89, I59 and T90, I59 and T95, A89 and T90, A89 and T95, and T90 and T95. Further embodiments of the glucose isomerase of the present invention are those where the pair of two amino acid positions is selected from a more limited group, including those more limited groups of pairs of two amino acid positions specifically disclosed herein. It is within the present invention that a glucose isomerase comprises an amino acid substitution at one of these pairs of two amino acid positions of SEQ ID NO: 1.

As disclosed herein, in a further embodiment the glucose isomerase comprises in addition to amino acid substitution at the pair of two amino acid positions of SEQ ID NO: 1 an amino acid substitution at at least one or more additional amino acid positions of SEQ ID NO: 1. Such one or more additional amino acid positions of SEQ ID NO: 1 are individually and independently selected from the group consisting of amino acid positions 10, 33, 34, 35, 53, 59, 89, 90, and 95, each of SEQ ID NO: 1. Further embodiments of the glucose isomerase of the present invention are those where the one or more additional amino acid position is selected from a more limited group, including those more limited groups of additional amino acid positions specifically disclosed herein. It is within the present invention that a glucose isomerase comprises an amino acid substitution at one of these pairs of two amino acid positions of SEQ ID NO: 1 and at one of said additional amino acid sequences. In accordance therewith, the glucose isomerase of the present invention is, each in an embodiment, a glucose isomerase having an amino acid substitution at at least three amino acid positions, namely at the pair of two amino acid position and at one of said additional amino acid positions of SEQ ID NO: 1, a glucose isomerase having an amino acid substitution at at least four amino acid positions, namely at the pair of two amino acid position and at two of said additional amino acid positions of SEQ ID NO: 1, a glucose isomerase having an amino acid substitution at at least five amino acid positions, namely at the pair of two amino acid position and at three of said additional amino acid positions of SEQ ID NO: 1, or a glucose isomerase having an amino acid substitution at at least six amino acid positions, namely at the pair of two amino acid position and at four of said additional amino acid positions of SEQ ID NO: 1. In an embodiment of the glucose isomerase of the present invention wherein the glucose isomerase comprises an amino acid substitution at at least three amino acid positions, the glucose isomerase comprises an amino acid substitution at at least one amino acid position selected from the group consisting of amino acid positions 10, 33, 35, 59 and at least one amino acid positions selected from the group consisting of amino acid positions 53, 89, 90 and 95, each of SEQ ID NO: 1, and preferably one amino acid position selected from the group consisting of amino acid positions 10, 33, 35, and 59 and two amino acid positions selected from the group consisting of amino acid positions 53, 89, 90 and 95, and most preferably one amino acid position at amino acid position 10 and two amino acid positions selected from the group consisting of amino acid positions 89, 90 and 95, each of SEQ ID NO: 1. In an embodiment of the glucose isomerase of the present invention wherein the glucose isomerase comprises an amino acid substitution at at least four amino acid positions, the glucose isomerase comprises an amino acid substitution at at least one amino acid positions selected from the group consisting of amino acid positions 10, 33, 35, and 59 and at least one amino acid position selected from the group consisting of amino acid positions 53, 89, 90 and 95, each of SEQ ID NO: 1, and preferably one or three amino acid position selected from the group consisting of amino acid positions 10, 33, 35, and 59 and one or three amino acid positions selected from the group consisting of amino acid positions 53, 89, 90 and 95, and most preferably one amino acid position at amino acid position 10 and three amino acid positions selected from the group consisting of amino acid positions 53, 89, 90 and 95, each of SEQ ID NO: 1. In an embodiment of the glucose isomerase of the present invention wherein the glucose isomerase comprises an amino acid substitution at at least five amino acid positions, the glucose isomerase comprises an amino acid substitution at at least two amino acid positions selected from the group consisting of amino acid positions 10, 33, 35, and 59 and at least one amino acid positions selected from the group consisting of amino acid positions 53, 89, 90 and 95, each of SEQ ID NO: 1, and preferably two or four amino acid positions selected from the group consisting of amino acid positions 10, 33, 35, and 59 and one or three amino acid positions selected from the group consisting of amino acid positions 53, 89, 90 and 95, and most preferably two amino acid positions at amino acid positions 10 and 33, and three amino acid positions selected from the group consisting of amino acid positions 53, 90 and 95, each of SEQ ID NO: 1. An embodiment of the glucose isomerase of the present invention wherein the glucose isomerase comprises an amino acid substitution at at least four amino acid positions, is a glucose isomerase comprising an amino acid substitution at amino acid positions 10, 89, 90 and 95, each of SEQ ID NO: 1. An embodiment of the glucose isomerase of the present invention wherein the glucose isomerase comprises an amino acid substitution at at least five amino acid positions, is a glucose isomerase comprising an amino acid substitution at amino acid positions 10, 33, 53, 90 and 95, each of SEQ ID NO: 1.

As to specific substitutions disclosed herein it is to be noted that in accordance with common practice in the field of amino acid substitutions the substitution refers to the number of the amino acid position where a substitution is made, with the left number being flanked on both sides by the indication of an amino acid residue with the amino acid residue on the left side being the amino acid residue as present in the non-substituted amino acid sequence and the amino acid residue on the right side being the amino acid residue as present in the substituted amino acid sequence. Accordingly and for illustrative purposes only, substitution R10K indicated that at amino acid position 10 the arginine reside is replaced by lysine.

It is within the present invention that any of the mutations at an amino acid positions of SEQ ID NO: 1 as disclosed herein is one which results, either alone or in any combination, in a protein which is still active as a glucose isomerase, more specifically as a glucose isomerase in accordance with EC 5.3.1.5. Preferably, any of said mutations results, either alone or in any combination, in a glucose isomerase of EC number EC 5.3.1.5 having at least one of characteristics (A), (B), (C), (D), (E) and (F), or any combination of such characteristics, as disclosed herein.

It will be understood that in connection with the glucose isomerase of the present invention apart from the substitutions and mutations, respectively, specifically disclosed herein, preferably the substitutions and mutations, respectively, at the amino acid positions of SEQ ID NO:1 disclosed herein, further and/or different substitution may be made.

It is known how the identity and homology, respectively, of a polymer of amino acid residues is determined. For the purpose and throughout the context of this invention, homology and identity are to be understood as synonyms. Percent identity is calculated as: Sequence Identity [%]=number of Matches/L×100, wherein L is the number of aligned positions, i.e. identities and non-identities (including gaps, if any). Homology, i.e. identity is preferably calculated as identity using BLASTP (see, for example, Stephen F. Altschul, Thomas L. Madden, Alejandro A. Schäffer, Jinghui Zhang, Zheng Zhang, Webb Miller, and David J. Lipman (1997) "Gapped BLAST and PSI-BLAST: a new generation of protein database search programs", Nucleic Acids Res. 25:3389-3402; or Stephen F. Altschul, John C. Wootton, E. Michael Gertz, Richa Agarwala, Aleksandr Morgulis, Alejandro A. Schäffer, and Yi-Kuo Yu (2005) "Protein database searches using compositionally adjusted substitution matrices." FEBS J. 272:5101-5109), preferably with the following algorithm parameters: Matrix: BLOSUM62; Gap Costs: Existence: 11 Extension: 1, Expect threshold: 10 and Word size: 6. Results are filtered for sequences with more than 35% query coverage. BlastP can be accessed online at the NCBI Homepage (blast.ncbi.nlm.nih.gov/Blast.cgi? PROGRAM=blastp&PAGE_TYPE=BlastSearch&LINK_LOC=blasthome). Other program setting can be adjusted as desired, for example using the following settings:

Field "Enter Query Sequence": Query subrange: none
Field "Choose Search Set": Database: non-redundant protein sequences (nr); optional parameters: none
Field "Program Selection": Algorithm: blastp (protein-protein BLAST)
Algorithm parameters: Field "General parameters": Max target sequences: 20000; Short queries: Automatically adjust parameters for short input sequences; Expect threshold: 10; Word size: 6; Max matches in a query range: 0
Algorithm parameters: Field "Scoring parameters": Matrix: BLOSUM62; Gap Costs: Existence: 11 Extension: 1; Compositional adjustments: Conditional compositional score matrix adjustment
Algorithm parameters: Field "Filters and Masking": Filter: none; Mask: none.

In an embodiment, the glucose isomerase of the present invention is an enzyme classified as EC 5.3.1.5 which catalyses the interconversion of aldose sugars and ketose sugars. Such reaction is reversible and, accordingly, the glucose isomerase of the present invention converts glucose into fructose and fructose into glucose.

In accordance with an embodiment of various aspects, the glucose isomerase of the present invention reacts an aldose molecule to a ketose molecule, and a ketose molecule to an aldose molecule.

In accordance with a further embodiment of various aspects, the glucose isomerase of the present invention reacts an aldose molecule selected from the group consisting of D-glucose, D-xylose, D-arabinose, L-arabinose, L-ribose, D-ribose, D-lyxose, D-allose, L-rhamnose and D-mannose. In a further embodiment, the glucose isomerase of the present invention reacts a ketose molecule selected from the group consisting of fructose, D-xylulose, D-ribulose, L-ribulose, D-psicose and L-rhamnulose. In one preferred embodiment, the glucose isomerase of the present invention reacts with fructose to form D-glucose.

As disclosed herein, the present invention is related to a polypeptide having certain functional characteristics as subject to and, respectively, defined in connection with the second, third, fourth, fifth, sixth, seventh, eighth, ninth, tenth, eleventh, twelfth and 13$^{th}$ aspect of the present invention. Preferably, the polypeptide is a polypeptide having glucose isomerase activity, preferably the Activity. More preferably, the polypeptide is a glucose isomerase.

In accordance with the present invention the polypeptide, preferably the glucose isomerase, of the invention as well as the glucose variant of the invention displays various functional features, including an increased activity, preferably increased Activity, in converting fructose into glucose. Such activity is in a preferred embodiment an Activity as defined herein, and an increased activity is in a preferred embodiment an increased Activity, i.e. an increase in Activity with Activity being as defined herein.

It will be acknowledged by a person skilled in the art that the increase in activity of the polypeptide, preferably the glucose isomerase, of the invention as well as of the glucose variant of the invention is expressed in the instant application as a relative value using the respective activity of the glucose polymerase of SEQ ID NO: 1 as reference. Such relative value may thus be expressed in terms of "folds" or relative activity, if the respective activity of the glucose polymerase of SEQ ID NO: 1 is set as "1". Accordingly and as indicated here for illustrative purposes only, an increased activity of the polypeptide, preferably of the glucose isomerase, of the invention of 1.1-fold is equivalent to a relative activity of 1.1:1.

It is within the present invention that the glucose isomerase of the invention is present as full-length enzyme. It is also within the present invention that the glucose isomerase of the invention is present as a fragment. Preferably, the fragment retains glucose isomerase activity, preferably a glucose isomerase Activity as defined and, respectively disclosed herein for the glucose isomerase of the invention.

In a further aspect, the present invention is related to a nucleic acid molecule encoding the glucose isomerase of the present invention. It is generally known to derive such nucleic acid molecule based on the amino acid sequence discloses herein. Preferably, the nucleic acid sequence depends on the expression system used for the expression of the glucose isomerase of the present invention. Preferred expression systems used for the expression of glucose isomerase of the invention are *E. coli*, *Bacillus* sp, *P. pastoris* and *Streptomyces* sp.

In a still further aspect, the present invention is related to a vector containing the nucleic acid molecule encoding the glucose isomerase of the present invention. Preferably, the vector is an expression vector. Suitable vectors for the expression of enzymes have been described in the state of the art.

In a further aspect, the present invention is related to a host organism containing the vector of the invention. Suitable hosts for hosts containing vectors for the expression of enzymes have been described, and preferably, the host organism is *E. coli*, *Bacillus* sp, *P. pastoris* or *Streptomyces* sp., preferably *E. coli* and *P. pastoris*. Also known are methods to incorporate such vector into the host organism.

In another aspect, the present invention is related a method for the expression of a glucose isomerase. Such method comprises cultivating a host organism disclosed in the description, wherein the host organism comprises an expression vector, wherein the expression vector comprises a nucleic acid molecule encoding a glucose isomerase according to the present invention, under conditions which allow expression of said nucleic acid molecule, and harvesting the glucose isomerase.

In another aspect, the present invention relates to the use of a polypeptide, preferably to the use of a glucose isomerase, for preparing glucose. In a preferred embodiment of this aspect, the use of the polypeptide, preferably of the glucose isomerase, is defined as in any one of the embodiments described herein. Preferably, the use of the polypeptide, preferably of the glucose isomerase for preparing glucose is according to the methods of the present invention or to any one of the embodiments defined in relation thereto.

It is within the present invention that the glucose isomerase of each and any aspect of the invention, including any embodiment thereof, is present in one of the following forms: a liquid solution, a dry powder, a freeze-dried powder, in an immobilized form.

TABLE 1

Overview over the SEQ ID NOs

| SEQ ID NO: | Source | Number of mutations in variant | Mutations to SEQ ID NO: 1 |
|---|---|---|---|
| SEQ ID NO: 1 | wild type, from *Streptomyces* sp. SK | 0 | |
| SEQ ID NO: 2 | variant to SEQ ID NO: 1 | 1 | A33I |
| SEQ ID NO: 3 | variant to SEQ ID NO: 1 | 1 | A33N |
| SEQ ID NO: 4 | variant to SEQ ID NO: 1 | 1 | L34F |

TABLE 1-continued

Overview over the SEQ ID NOs

| SEQ ID NO: | Source | Number of mutations in variant | Mutations to SEQ ID NO: 1 |
|---|---|---|---|
| SEQ ID NO: 5 | variant to SEQ ID NO: 1 | 1 | D35C |
| SEQ ID NO: 6 | variant to SEQ ID NO: 1 | 1 | F53L |
| SEQ ID NO: 7 | variant to SEQ ID NO: 1 | 1 | A89V |
| SEQ ID NO: 8 | variant to SEQ ID NO: 1 | 1 | T90S |
| SEQ ID NO: 9 | variant to SEQ ID NO: 1 | 1 | T95R |
| SEQ ID NO: 10 | variant to SEQ ID NO: 1 | 1 | T95Y |
| SEQ ID NO: 11 | variant to SEQ ID NO: 1 | 1 | R10K |
| SEQ ID NO: 12 | variant to SEQ ID NO: 1 | 1 | I59F |
| SEQ ID NO: 13 | variant to SEQ ID NO: 1 | 3 | R10K, F53L, T95Y |
| SEQ ID NO: 14 | variant to SEQ ID NO: 1 | 4 | R10K, F53L, T90S, T95Y |
| SEQ ID NO: 15 | variant to SEQ ID NO: 1 | 5 | R10K, A33N, F53L, T90S, T95Y |
| SEQ ID NO: 16 | variant to SEQ ID NO: 1 | 3 | R10K, F53L, T90S |
| SEQ ID NO: 17 | variant to SEQ ID NO: 1 | 4 | R10K, A89V, T90S, T95Y |
| SEQ ID NO: 18 | variant to SEQ ID NO: 1 | 5 | R10K, A33I, F53L, T90S, T95Y |
| SEQ ID NO: 19 | variant to SEQ ID NO: 1 | 5 | R10K, D35S, F53L, T90S, T95Y |
| SEQ ID NO: 20 | variant to SEQ ID NO: 1 | 4 | R10K, A33N, I59F, T90S |
| SEQ ID NO: 21 | variant to SEQ ID NO: 1 | 5 | R10K, A33I, D35S, I59F, T90S |
| SEQ ID NO: 22 | variant to SEQ ID NO: 1 | 3 | R10K, T90S, T95Y |
| SEQ ID NO: 23 | variant to SEQ ID NO: 1 | 3 | R10K, T90S, T95R |

It will be acknowledged by a person skilled in the art that the terms variants and mutants are used synonymously herein, including in the example part.

The present invention is further illustrated by the examples and the sequence listing from which further features, embodiments and advantages may be taken.

EXAMPLE 1: GENERAL METHODS

Cloning of the wild type glucose isomerase: The glucose isomerase gene from *Streptomyces* sp. SK was codon-optimized for expression in *E. coli* and synthesized by Eurofins MWG Operon, Ebersberg (Germany). The gene was cloned into the expression vectors pLE1A17 and pLE1A27 (both derivatives of pRSF-1b, Novagen, Madison (USA)). The resulting plasmids were used for transformation of *E. coli* BL21(DE3) cells.

Molecular biology methods: Mutants of the glucose isomerase enzymes were created by standard site-directed mutagenesis technologies as known in the state of the art (as referenced, for example, in S. Lutz, U. T. Bornscheuer, Protein Engineering Handbook, Wiley VCH, Weinheim, 2009)

Expression of recombinant glucose isomerases: Overnight cultures were prepared by inoculating Medium I (5 g/L yeast extract, 10 g/L NaCl, 10 g/L tryptone, pH 7, 50 µg/mL kanamycin) with the recombinant glucose isomerase. The culture was incubated overnight at 37° C. and 200 rpm. For the expression culture, Medium II (4.6 g/L yeast extract, 9.3 g/L peptone, 25 mM $Na_2HPO_4*12H_2O$, 25 mM $KH_2PO_4$, 50 mM $NH_4Cl_2$, $Na_2SO_4$, 5 g/L glycerol, 0.5 g/L glucose*$1H_2O$, 2 mM $MgSO_4$, 50 µg/mL kanamycin) was inoculated with the fresh overnight culture so as to reach an optical density at 600 nm of 0.1. Cultures were then grown at 37° C. up to an optical density at 600 nm of 0.8-1.0. Cultures were subsequently induced with 0.1 mM IPTG final concentration, and expression of recombinant glucose isomerases was achieved at 30° C. overnight.

Preparation of glucose isomerase enzyme preparations: Preparation of cell free extract was done by harvesting cells by centrifugation followed by chemoenzymatic lysis. For this, the cells were suspended in a buffer containing 50 mM potassium phosphate buffer pH 7, 1×CelLytic™ B Cell Lysis Reagent (Sigma), 2 mM $Mg^{2+}$ (as $MgCl_2$ or $MgSO_4$), 0.5 mg/mL lysozyme and 20 U/mL nuclease, and incubated for 45 min at 30° C. Cell free extract containing soluble enzyme was separated from the debris by centrifugation for 30 min at 3,270×g and 4° C.

Glucose isomerase Activity measurements: Activity of glucose isomerase was determined in the direction of fructose to glucose isomerisation as described in Assay I and Assay II:

Assay I: Glucose isomerase Activity was assayed by monitoring the formation of glucose from fructose at 40° C. using the following conditions: 50 mM potassium phosphate buffer pH 7, 10 $Mg^{2+}$ (as $MgCl_2$ or $MgSO_4$), 0.2 mL/mL reaction glucose isomerase enzyme preparations (diluted in 50 mM potassium phosphate buffer pH 7 so as to reach a maximum yield of 18%) and 50 or 200 mM fructose concentrations as given. The glucose produced from fructose by the action of glucose isomerase was determined using a discontinuous coupled assay in which the glucose is converted to glucose-6-phosphate by hexokinase. Glucose-6-phosphate and NADP is converted to 6-phospho-gluconate and NADPH by glucose 6-phosphate dehydrogenase. The detection is based on measuring the absorbance of NADPH at 340 nm. The D-GLUCOSE—HK kit (HK/G6P-DH Format) was employed in the microplate format (product no. K-GLUHK-110A or K-GLUHK-220A available from Megazyme International Ireland, Wicklow, Ireland). The assay is performed according to the manufacturer recommendations and the amount of glucose in the sample is quantified using external standards.

Assay II: The reaction for measuring glucose isomerase Activity was conducted by monitoring the formation of glucose from fructose at following conditions: 50 mM potassium phosphate buffer pH 7, 10 mM $MgSO_4$, 0.05 mL/mL reaction glucose isomerase enzyme preparations (diluted in 50 mM potassium phosphate buffer pH 7 so as to reach a maximum yield of 18%), 50-1000 mM fructose concentrations, and 40° C. The reaction was quenched by adding 0.1 mL 0.25 M HCl per mL reaction. The glucose produced from fructose by the action of glucose isomerase was determined using a discontinuous coupled assay in which glucose was converted to gluconolactone by glucose oxidase. Hydrogen peroxide, a by-product of this reaction, was used by horseradish peroxidase to oxidize 2,2'-azino-bis(3-ethylbenzothiazoline-6-sulphonic acid (ABTS), yielding a coloured product, which shows absorbance at 405 nm. A 10 µL aliquot of acid-quenched reaction is mixed with 90 µL of the assay mix containing 50 mM potassium phosphate buffer pH 6, 1 mM ABTS, 5 U/mL glucose oxidase and 1 U/mL horseradish peroxidase. After 60-70 min incubation at 30° C., the absorbance at 405 nm was measured (endpoint measurement). The amount of glucose in the sample is quantified using external standards.

EXAMPLE 2: DETERMINATION OF GLUCOSE ISOMERASE ACTIVITY WITH 200 MM FRUCTOSE AND 50 MM FRUCTOSE

Glucose isomerase enzyme preparations were prepared as described in Experiment 1 and analyzed for glucose isomerase Activity.

Activity of glucose isomerase variant in fructose isomerization was determined at 50 mM and 200 mM fructose, according to Assay I described in Example 1 above. Glucose isomerase Activity was expressed as Volumetric Activity, that is, units of glucose isomerase Activity per unit of bacterial culture volume.

To assess whether changes in Volumetric Activity resulted from altered soluble expression of glucose isomerase variants or from changes in their Activity, the soluble expression of glucose isomerase variants was analyzed. Cell free extracts of glucose isomerase variants, i.e. amounts of cell extracts were normalized based on optical densities of cell cultures, were loaded onto 12% acrylamide gel, resolved in SDS-PAGE and stained with Coomassie Brilliant Blue G-250. Experimental conditions were selected for SDS-PAGE in order to assure proper separation of proteins and allow correct quantification. For each variant, the intensity of the band corresponding to the respective glucose isomerase variant was quantified and compared to the intensity of the band of the wild type glucose isomerase of SEQ ID NO: 1. In this way, relative Soluble Expression Levels of glucose isomerase variants were determined. Glucose isomerase Volumetric Activities were divided by the relative expression levels to obtain Activity normalized to expression level (Normalized Activity).

TABLE 2

Normalized Activity and Soluble Expression Levels of glucose isomerase variants

| SEQ ID NO: | GI Normalized Activity at 50 mM fructose in comparison to SEQ ID NO: 1 | GI Normalized Activity at 200 mM fructose in comparison to SEQ ID NO: 1 | GI Soluble Expression Level |
|---|---|---|---|
| SEQ ID NO: 1 | 1.0 | 1.0 | 1.00 |
| SEQ ID NO: 2 | 1.6 | 1.4 | 0.92 |
| SEQ ID NO: 3 | 1.2 | 1.2 | 1.04 |
| SEQ ID NO: 4 | 1.4 | 1.3 | 0.89 |
| SEQ ID NO: 5 | 1.2 | 1.3 | 1.07 |
| SEQ ID NO: 6 | 1.3 | 1.3 | 0.97 |
| SEQ ID NO: 7 | 1.4 | 1.3 | 0.94 |
| SEQ ID NO: 8 | 1.6 | 1.5 | 0.83 |
| SEQ ID NO: 9 | 1.6 | 1.6 | 0.89 |
| SEQ ID NO: 10 | 1.4 | 1.5 | 0.91 |
| SEQ ID NO: 11 | 1.1 | 1.2 | 1.36 |
| SEQ ID NO: 12 | 1.3 | 1.3 | 0.88 |
| SEQ ID NO: 13 | 1.4 | 1.3 | 1.33 |
| SEQ ID NO: 14 | 2.0 | 1.6 | 1.31 |
| SEQ ID NO: 15 | 2.1 | 1.7 | 1.43 |
| SEQ ID NO: 16 | 1.5 | 1.3 | 1.60 |
| SEQ ID NO: 17 | 1.7 | 1.5 | 1.63 |
| SEQ ID NO: 18 | 2.0 | 1.8 | 1.38 |
| SEQ ID NO: 19 | 2.3 | 1.9 | 1.10 |
| SEQ ID NO: 20 | 1.6 | 1.4 | 1.62 |
| SEQ ID NO: 21 | 2.4 | 2.2 | 0.98 |

EXAMPLE 3: THERMAL STABILITY: RESIDUAL ACTIVITY OF GLUCOSE ISOMERASE VARIANTS AFTER INCUBATION AT 74° C. FOR 15 MIN

Heat-inactivation and Activity measurement: Glucose isomerase preparations, prepared as described in Example 1, were divided into two aliquots. One 60 µL aliquot was incubated at 74° C. for 15 min Denatured protein was separated by centrifugation for 10 min at 4° C. and 3,270×g. The Activity of the supernatant was determined using Assay I with 50 mM fructose as described in Example 1. The other aliquot of each glucose isomerase variant was assayed directly for Activity without heat-inactivation using Assay I with 50 mM fructose. The resulting residual activities are listed in Table 3.

TABLE 3

Thermal stability of glucose isomerase variants

| SEQ ID NO: | Residual Activity in % after 15 min incubation at 74° C. [%] |
|---|---|
| SEQ ID NO: 1 | 79 |
| SEQ ID NO: 13 | 59 |
| SEQ ID NO: 14 | 64 |
| SEQ ID NO: 15 | 42 |
| SEQ ID NO: 16 | 46 |
| SEQ ID NO: 17 | 62 |
| SEQ ID NO: 18 | 41 |
| SEQ ID NO: 19 | 47 |
| SEQ ID NO: 20 | 34 |
| SEQ ID NO: 21 | 30 |

EXAMPLE 4: DENATURATION PROFILES OF GLUCOSE ISOMERASE VARIANTS

Denaturation profiles of glucose isomerase variants were determined by performing heat inactivation at different temperatures followed by Activity measurements. Glucose isomerase preparations, prepared as described in Example 1, were divided into several aliquots. 60 µL aliquots of each glucose isomerase variant was incubated at temperatures in the range 65-85° C. for 15 min Denatured protein was separated by centrifugation for 10 min at 4° C. and 3,270×g. The Activity of the supernatant was determined using Assay I with 200 mM fructose. Another aliquot of each glucose isomerase variant was assayed directly for activity without heat-inactivation using Assay I with 200 mM fructose. The resulting Residual Activities were plotted against heat inactivation temperature. The following Tm50-values were estimated from the denaturation profiles:

TABLE 4

Tm50-values of glucose isomerase variants in 50 mM potassium phosphate buffer pH 7

| SEQ ID NO: | Tm50 value [° C.] |
|---|---|
| SEQ ID NO: 1 | 78 |
| SEQ ID NO: 17 | 76 |

EXAMPLE 5: $K_M$ VALUE

Activity of glucose isomerase variants was determined at different fructose concentrations in the range 50-1000 mM fructose at the following conditions: 10 mM $MgSO_4$, 50 mM potassium phosphate buffer pH 7.0, 40° C., using Assay II as defined herein. The resulting activities were fitted to the Michaelis-Menten equation from which a Michaelis constant $K_M$ for fructose for a given glucose isomerase variant was derived. As can be seen from Table 5, both tested variants show lower $K_M$ for fructose than the wild type glucose isomerase.

TABLE 5

$K_M$-value of glucose isomerase variants

| SEQ ID NO: | $K_M$(fructose) [mM] |
|---|---|
| SEQ ID NO: 1 | 237 |
| SEQ ID NO: 15 | 140 |
| SEQ ID NO: 17 | 152 |

The features of the present invention disclosed in the specification, the claims, the sequence listing and/or the drawings may both separately and in any combination thereof be material for realizing the invention in various forms thereof.

EXAMPLE 6: GLUCOSE FORMATION FROM 50 MM FRUCTOSE OF GLUCOSE ISOMERASE VARIANTS

Expression of recombinant glucose isomerases: Overnight cultures were prepared by inoculating Medium I (5 g/L yeast extract, 10 g/L NaCl, 10 g/L tryptone, pH 7, 50 µg/mL kanamycin) with the recombinant glucose isomerase. The culture was incubated overnight at 37° C. and 200 rpm. For the expression culture, Medium II (4.6 g/L yeast extract, 9.3 g/L peptone, 25 mM $Na_2HPO_4*12H_2O$, 25 mM $KH_2PO_4$, 50 mM $NH_4Cl_2$, $Na_2SO_4$, 5 g/L glycerol, 0.5 g/L glucose*$1H_2O$, 2 mM $MgSO_4$, 50 µg/mL kanamycin) was inoculated with the fresh overnight culture so as to reach an optical density at 600 nm of 0.1. Cultures were then grown at 37° C. up to an optical density at 600 nm of 0.8-1.0. Cultures were subsequently induced with 0.1 mM IPTG final concentration, and expression of recombinant glucose isomerases was achieved at 30° C. overnight.

Preparation of cell free extracts: Preparation of cell free extract was done by harvesting cells by centrifugation followed by chemo-enzymatic lysis. For this, cells from 1 mL expression culture were suspended in 175 µL buffer containing 50 mM potassium phosphate buffer pH 7, 1×CelLytic™ B Cell Lysis Reagent (Sigma), 2 mM $Mg^{2+}$ (as $MgCl_2$ or $MgSO_4$), 0.5 mg/mL lysozyme and 20 U/mL nuclease, and incubated for 45 min at 30° C. Cell free extract containing soluble enzyme was separated from the debris by centrifugation for 30 min at 3,270×g and 4° C.

Glucose formation reaction: Cell free extract was diluted depending on activity in 50 mM potassium phosphate buffer pH 7. A reaction buffer containing 62.5 mM fructose, 12.5 mM MgSO4 and 62.5 mM potassium phosphate buffer pH 7 was incubated at 40° C. for 30 min. The reaction was started by adding 20 µL of the diluted cell free extract to 80 µL of 40° C. reaction buffer. The reaction mixture was incubated at 40° C. After 40 min a 20 µL sample was taken and inactivated by adding 20 µL of 0.25 M HCl. Samples were neutralized by addition of 60 μL 50 mM potassium phosphate buffer pH 7 and centrifuged for 10 min at 13,000 rpm. The glucose content in the supernatant was measured using the D-GLUCOSE—HK kit (HK/G6P-DH Format) (product no. K-GLUHK-110A or K-GLUHK-220A available from Megazyme International Ireland, Wicklow, Ireland). The kit was used in the microplate format according to the manufacturer recommendations and the amount of glucose in the sample is quantified using external standards. Table 6 shows the Glucose Formation of several variants normalized to undiluted cell free extract per 40 min. The variants SEQ ID NO: 15, 18, 22 and 23 produced approximately 2-times more glucose than SEQ ID NO: 1 (Table 6). SEQ ID NO: 14 showed an over 3-fold higher glucose production with the highest glucose formation.

TABLE 6

Glucose Formation of glucose isomerase variants

| SEQ ID NO: | Glucose Formation (mM) per 40 min | Increase of Glucose Formation compared to SEQ ID NO: 1 |
| --- | --- | --- |
| SEQ ID NO: 1 | 52.2 | 1.0 |
| SEQ ID NO: 14 | 170.4 | 3.3 |
| SEQ ID NO: 15 | 114.3 | 2.2 |
| SEQ ID NO: 18 | 114.7 | 2.2 |
| SEQ ID NO: 22 | 103.3 | 2.0 |
| SEQ ID NO: 23 | 97.5 | 1.9 |

The invention claimed is:

1. A polypeptide comprising an amino acid sequence, wherein the amino acid sequence of the polypeptide is at least 95% identical to an amino acid sequence of SEQ ID NO: 1, wherein the amino acid sequence of the polypeptide comprises an amino acid substitution at one or more amino acid positions, wherein each of the one or more amino acid positions is independently selected from the group consisting of SEQ ID NO: 1 amino acid positions 10, 34, 35, 59, 89, and 90.

2. The polypeptide of claim 1, wherein each of the one or more amino acid positions is selected from the group consisting of SEQ ID NO: 1 amino acid positions 10, 89 and 90.

3. The polypeptide of claim 2, wherein the amino acid sequence of the polypeptide further comprises an amino acid substitution at SEQ ID NO: 1 amino acid position 53.

4. The polypeptide of claim 1, wherein the amino acid sequence of the polypeptide comprises amino acid substitutions at SEQ ID NO: 1 amino acid positions (a) 10 and 33, (b) 10 and 35, (c) 10 and 59, (d) 10 and 89, (e) 10 and 90, (f) 10 and 95, (g) 33 and 35, (h) 33 and 59, (i) 33 and 90, (j) 35 and 59, (k) 35 and 90, (l) 35 and 95, (m) 59 and 90, (n) 89 and 90, (o) 89 and 95, or (p) 90 and 95.

5. The polypeptide of claim 4, wherein the amino acid sequence of the polypeptide comprises amino acid substitutions at SEQ ID NO: 1 amino acid positions 90 and 95.

6. The polypeptide of claim 4, wherein the amino acid sequence of the polypeptide comprises amino acid substitutions at SEQ ID NO: 1 amino acid positions 10 and 89.

7. The polypeptide of claim 4, wherein the amino acid sequence of the polypeptide comprises amino acid substitutions at SEQ ID NO: 1 amino acid positions 89 and 90.

8. The polypeptide of claim 4, wherein the amino acid sequence of the polypeptide comprises amino acid substitutions at SEQ ID NO: 1 amino acid positions 89 and 95.

9. The polypeptide of claim 4, wherein the amino acid sequence of the polypeptide comprises amino acid substitutions at SEQ ID NO: 1 amino acid positions (a) 10 and 33, (b) 10 and 89, (c) 10 and 90, (d) 10 and 95, (e) 33 and 90, (f) 89 and 90, (g) 89 and 95, or (h) 90 and 95, and wherein the polypeptide further comprises an amino acid substitution at SEQ ID NO: 1 amino acid position 53.

10. The polypeptide of claim 4, wherein the amino acid sequence of the polypeptide further comprises an amino acid substitution at SEQ ID NO: 1 amino acid position 53.

11. The polypeptide of claim 1, wherein the amino acid sequence of the polypeptide comprises amino acid substitutions at SEQ ID NO: 1 amino acid positions (a) 10 and 33 and 35, (b) 10 and 33 and 59, (c) 10 and 33 and 90, (d) 10 and 33 and 95, (e) 10 and 35 and 59, (f) 10 and 35 and 90, (g) 10 and 35 and 95, (h) 10 and 59 and 90, (i) 10 and 89 and 90, (j) 10 and 89 and 95, (k) 10 and 90 and 95, (l) 33 and 35 and 59, (m) 33 and 35 and 90, (n) 33 and 59 and 90, (o) 33 and 90 and 95, (p) 35 and 59 and 90, or (q) 89 and 90 and 95.

12. The polypeptide of claim 1, wherein the amino acid sequence of the polypeptide comprises amino acid substitutions at SEQ ID NO: 1 amino acid positions 90, 95 and 10.

13. The polypeptide of claim 1, wherein the amino acid sequence of the polypeptide further comprises an amino acid substitution at SEQ ID NO: 1 amino acid position 53.

14. The polypeptide of claim 13, wherein the amino acid sequence of the polypeptide comprises amino acid substitutions at SEQ ID NO: 1 amino acid positions 53 and 90.

15. The polypeptide of claim 1, wherein the amino acid sequence of the polypeptide further comprises an amino acid substitution at SEQ ID NO: 1 amino acid position 95.

16. The polypeptide of claim 15, wherein the amino acid substitution at position T95 of SEQ ID NO: 1 is T95F, T95W, T95Y, T95P, T95R, T95H or T95K.

17. The polypeptide of claim 13, wherein the amino acid substitution at position F53 of SEQ ID NO: 1 is F53A, F53I, F53L, or F53V.

18. The polypeptide of claim 1, wherein the amino acid sequence of the polypeptide comprises amino acid substitutions at SEQ ID NO: 1 amino acid positions 90, 95 and 10, and the polypeptide further comprises an amino acid substitution at an amino acid position selected from the group consisting of SEQ ID NO:1 amino acid positions 89, 33, 34, 35, 59, and 53.

19. The polypeptide of claim 18, wherein the polypeptide comprises an amino acid substitution at SEQ ID NO: 1 amino acid position 89.

20. The polypeptide of claim 18, wherein the polypeptide comprises an amino acid substitution at SEQ ID NO: 1 amino acid position 53.

21. The polypeptide of claim 18, wherein the amino acid sequence of the polypeptide comprises
(a) an amino acid substitution selected from the group consisting of SEQ ID NO: 1 amino acid positions T90S, T90G, T90N, T90M, T90C, and T90Q,
(b) an amino acid substitution selected from the group consisting of SEQ ID NO: 1 amino acid positions T95Y, T95F, T95W, T95P, T95R, T95H, and T95K,
(c) an amino acid substitution selected from the group consisting of SEQ ID NO: 1 amino acid positions R10K and R10H, and
(d) an amino acid substitution selected from the group consisting of SEQ ID NO:1 amino acid positions A89V, A89I, A89L, A33N, A33I, L34F, L34W, L34Y, L34P, D35C, D35S, I59F, I59W, I59Y, I59P, and F53L.

22. The polypeptide of claim 1, wherein the amino acid sequence of the polypeptide comprises substitutions at
SEQ ID NO: 1 amino acid positions 10, 53, and 90; or
SEQ ID NO: 1 amino acid positions 10, 53, and 95; or
SEQ ID NO: 1 amino acid positions 10, 89, 90 and 95; or
SEQ ID NO: 1 amino acid positions 10, 33, 59, and 90; or
SEQ ID NO: 1 amino acid positions 10, 53, 90, and 95; or
SEQ ID NO: 1 amino acid positions 10, 33, 53, 90 and 95; or
SEQ ID NO: 1 amino acid positions 10, 33, 35, 59, and 90; or
SEQ ID NO: 1 amino acid positions 10, 35, 53, 90, and 95.

23. The polypeptide of claim 1,
wherein, if the one or more amino acid position is an amino acid substitution at position R10 of SEQ ID NO: 1, the substitution is R10H or R10K;
wherein, if the one or more amino acid position is an amino acid substitution at position L34 of SEQ ID NO: 1, the substitution is L34F, L34W, L34Y, or L34P;
wherein, if the one or more amino acid position is an amino acid substitution at position D35 of SEQ ID NO: 1, the substitution is D35G, D35N, D35M, D35C, D35S, D35Q or D35T;
wherein, if the one or more amino acid position is an amino acid substitution at position I59 of SEQ ID NO: 1, the substitution is I59F, I59W, I59Y or I59P;
wherein, if the one or more amino acid position is an amino acid substitution at position A89 of SEQ ID NO: 1, the substitution is A89I, A89L, or A89V; and
wherein, if the one or more amino acid position is an amino acid substitution at position T90 of SEQ ID NO: 1, the substitution is T90G, T90N, T90M, T90C, T90S or T90Q.

24. The polypeptide of claim 23, wherein the amino acid sequence of the polypeptide comprises an amino acid substitution at one or more amino acid positions, wherein each of the one or more amino acid positions is independently selected from the group consisting of SEQ ID NO: 1 amino acid positions R10K, A89V, and T90S, and in addition comprises one more amino acid substitution at SEQ ID NO: 1 amino acid position F53L.

25. The polypeptide of claim 1, wherein the amino acid sequence of the polypeptide comprises amino acid substitutions at SEQ ID NO: 1 amino acid positions (a) R10K and A33N, (b) R10K and A33I, (c) R10K and A89V, (d) R10K and T90S, (e) R10K and T95Y, (f) R10K and T95R, (g) A33I and T90S, (h) A33N and T90S, (i) A89V and T90S, (j) A89V and T95Y, (k) A89V and T95R, (l) T90S and T95R, or (m) T90S and T95Y.

26. The polypeptide of claim 1, wherein the amino acid sequence of the polypeptide comprises substitutions at
SEQ ID NO: 1 amino acid positions R10K, T90S and T95Y; or
SEQ ID NO: 1 amino acid positions R10K, F53L, and T90S; or
SEQ ID NO: 1 amino acid positions R10K, F53L, and T95Y; or
SEQ ID NO: 1 amino acid positions R10K, A89V, T90S and T95Y; or
SEQ ID NO: 1 amino acid positions R10K, A33I, I59F, and T90S; or
SEQ ID NO: 1 amino acid positions R10K, A33N, I59F, and T90S; or
SEQ ID NO: 1 amino acid positions R10K, F53L, T90S, and T95Y; or
SEQ ID NO: 1 amino acid positions R10K, A33I, F53L, T90S and T95Y; or
SEQ ID NO: 1 amino acid positions R10K, A33N, F53L, T90S and T95Y; or
SEQ ID NO: 1 amino acid positions R10K, A33I, D35C, I59F, and T90S; or
SEQ ID NO: 1 amino acid positions R10K, A33N, D35C, I59F, and T90S; or
SEQ ID NO: 1 amino acid positions R10K, D35C, F53L, T90S, and T95Y.

27. The polypeptide of claim 1, wherein the amino acid sequence of the polypeptide is at least 95% identical to the amino acid sequence of SEQ ID NO: 15, 17 or 18.

28. The polypeptide of claim 1, wherein the polypeptide is capable of catalyzing the conversion of
(i) an aldose molecule to a ketose molecule, and/or
(ii) a ketose molecule to an aldose molecule.

29. A polypeptide of claim 1, wherein the polypeptide has at least one of the characteristics selected from the group consisting of (A), (B), (C), (D), (E), and (F), wherein characteristic
(A) is an increased activity of at least 1.1-fold up to 3.0-fold of the polypeptide for the conversion of fructose to glucose at a concentration of 50 mM fructose in comparison to the polypeptide of SEQ ID NO: 1;
(B) is an increased activity of at least 1.2-fold up to 3.0-fold of the polypeptide for the conversion of fructose to glucose at a concentration of 200 mM fructose in comparison to the polypeptide of SEQ ID NO: 1;
(C) is thermal stability of the polypeptide expressed as Residual Activity after incubation of the polypeptide at a temperature of 74° C. for 15 minutes, wherein such Residual Activity is at least 30% up to 100% in comparison to the polypeptide of SEQ ID NO: 1;
(D) is a $K_M$ value of the polypeptide which is less than 190 mM;
(E) is a Soluble Expression Level of the polypeptide defined as the ratio of the soluble expression level of said polypeptide and the soluble expression level of the polypeptide of SEQ ID NO: 1 of at least 1.04 up to 1.80; and
(F) is an increased Glucose Formation preferably of at least 1.2-fold up to 5-fold in comparison to the polypeptide of SEQ ID NO: 1.

30. The polypeptide of claim 1, wherein the amino acid sequence of the polypeptide further comprises an amino acid substitution at SEQ ID NO: 1 amino acid position 33.

31. The polypeptide of claim 30, wherein the amino acid substitution at position A33 of SEQ ID NO: 1 is A33I, A33L, A33V, A33G, A33N, A33M, A33C, A33S, A33Q or A33T.

32. The polypeptide of claim 1, wherein the amino acid sequence of the polypeptide comprises amino acid substitutions at SEQ ID NO: 1 amino acid positions 59 and 95.

\* \* \* \* \*